(12) United States Patent
Eby et al.

(10) Patent No.: US 12,005,262 B2
(45) Date of Patent: Jun. 11, 2024

(54) LEADLESS PACEMAKER HAVING ATTACHMENT FEATURE

(71) Applicant: Pacesetter, Inc., Sylmar, CA (US)

(72) Inventors: Thomas B. Eby, Mountain View, CA (US); Benjamin F. James, IV, Canyon Country, CA (US); Kavous Sahabi, Winnetka, CA (US); Travis Lieber, Saugus, CA (US); Arees Garabed, North Hills, CA (US); Craig E. Mar, Fremont, CA (US); Sondra Orts, Sunnyvale, CA (US); Tyler J. Strang, Valencia, CA (US); Jennifer Heisel, Princeton, MN (US); Bernhard Arnar, Minnetrista, MN (US); Daniel Coyle, St. Louis Park, MN (US); Daniel Goodman, Minnetonka, MN (US); Scott Smith, Monticello, MN (US); Scott Kerns, Chanhassen, MN (US); David Rickheim, Bloomington, MN (US); Adam Weber, Eden Prairie, MN (US); Mike Sacha, Champlin, MN (US); Byron Liehwah Chun, San Francisco, CA (US)

(73) Assignee: PACESETTER, INC., Sylmar, CA (US)

( * ) Notice: Subject to any disclaimer, the term of this patent is extended or adjusted under 35 U.S.C. 154(b) by 101 days.

(21) Appl. No.: 17/493,731

(22) Filed: Oct. 4, 2021

(65) Prior Publication Data

US 2022/0023646 A1 Jan. 27, 2022

Related U.S. Application Data

(62) Division of application No. 16/297,392, filed on Mar. 8, 2019, now Pat. No. 11,141,597.

(Continued)

(51) Int. Cl.
*A61N 1/375* (2006.01)
*A61B 17/00* (2006.01)
(Continued)

(52) U.S. Cl.
CPC ........ *A61N 1/3756* (2013.01); *A61B 17/3468* (2013.01); *A61N 1/056* (2013.01);
(Continued)

(58) Field of Classification Search
CPC ...... A61N 1/3756; A61N 1/056; A61N 1/362; A61N 1/378; A61N 2001/0578;
(Continued)

(56) References Cited

U.S. PATENT DOCUMENTS 7,937,148 B2 5/2011 Jacobson
7,945,333 B2 5/2011 Jacobson
(Continued)

FOREIGN PATENT DOCUMENTS

CN 203194732 U 9/2013
CN 105358212 A 2/2016
(Continued)

OTHER PUBLICATIONS

Extended European Search Report from related European Patent Application No. 21201855.0, dated Jan. 25, 2022 (8 pages).
(Continued)

*Primary Examiner* — Brian T Gedeon
*Assistant Examiner* — Joshua Andrew Schum-Houck
(74) *Attorney, Agent, or Firm* — WOMBLE BOND DICKINSON (US) LLP

(57) ABSTRACT

A leadless biostimulator including an attachment feature to facilitate precise manipulation during delivery or retrieval is described. The attachment feature can be monolithically formed from a rigid material, and includes a base, a button, and a stem interconnecting the base to the button. The stem
(Continued)

is a single post having a transverse profile extending around a central axis. The transverse profile can be annular and can surround the central axis. The leadless biostimulator includes a battery assembly having a cell can that includes an end boss. A tether recess in the end boss is axially aligned with a face port in the button to receive tethers of a delivery or retrieval system through an inner lumen of the stem. The attachment feature can be mounted on and welded to the cell can at a thickened transition region around the end boss. Other embodiments are also described and claimed.

20 Claims, 84 Drawing Sheets

Related U.S. Application Data

(60) Provisional application No. 62/712,781, filed on Jul. 31, 2018, provisional application No. 62/666,618, filed on May 3, 2018, provisional application No. 62/641,129, filed on Mar. 9, 2018.

(51) Int. Cl.
*A61B 17/34* (2006.01)
*A61N 1/05* (2006.01)
*A61N 1/362* (2006.01)
*A61N 1/378* (2006.01)
*A61M 25/00* (2006.01)
*A61M 25/01* (2006.01)

(52) U.S. Cl.
CPC ............ *A61N 1/362* (2013.01); *A61N 1/378* (2013.01); *A61B 2017/00477* (2013.01); *A61M 25/0082* (2013.01); *A61M 25/0136* (2013.01); *A61N 2001/0578* (2013.01)

(58) Field of Classification Search
CPC ..... A61B 17/3468; A61B 2017/00477; A61M 25/0082; A61M 25/0136
See application file for complete search history.

(56) References Cited

U.S. PATENT DOCUMENTS

| | | | |
|---|---|---|---|
| 8,010,209 B2 | 8/2011 | Jacobson | |
| 8,352,025 B2 | 1/2013 | Jacobson | |
| 8,457,742 B2 | 6/2013 | Jacobson | |
| 8,504,156 B2 | 8/2013 | Bonner et al. | |
| 8,527,068 B2 | 9/2013 | Ostroff | |
| 8,790,819 B1* | 7/2014 | Freitag | H01M 50/466 434/262 |
| 9,126,032 B2 | 9/2015 | Khairkhahan et al. | |
| 9,216,298 B2 | 12/2015 | Jacobson | |
| 9,283,382 B2 | 3/2016 | Berthiaume et al. | |
| 9,358,400 B2 | 6/2016 | Jacobson | |
| 9,393,427 B2 | 7/2016 | Schmidt et al. | |
| 9,468,773 B1 | 10/2016 | Anderson et al. | |
| 9,480,850 B2 | 11/2016 | Schmidt et al. | |
| 9,492,674 B2 | 11/2016 | Schmidt et al. | |
| 9,700,732 B2 | 7/2017 | Schmidt et al. | |
| 9,795,781 B2 | 10/2017 | Schmidt et al. | |
| 9,993,648 B2 | 6/2018 | Kelly et al. | |
| 10,003,063 B2 | 6/2018 | Aamodt et al. | |
| 10,071,243 B2 | 9/2018 | Kuhn et al. | |
| 10,080,888 B2 | 9/2018 | Kelly et al. | |
| 10,188,425 B2 | 1/2019 | Khairkhahan et al. | |
| 2004/0106959 A1* | 6/2004 | Schmidt | A61N 1/056 607/11 |
| 2004/0215281 A1 | 10/2004 | O'Phelan et al. | |
| 2005/0267555 A1* | 12/2005 | Marnfeldt | A61B 17/3468 607/116 |
| 2009/0082827 A1 | 3/2009 | Kveen et al. | |
| 2012/0095539 A1 | 4/2012 | Khairkhahan et al. | |
| 2012/0109148 A1 | 5/2012 | Bonner et al. | |
| 2012/0165827 A1 | 6/2012 | Khairkhahan et al. | |
| 2012/0172892 A1* | 7/2012 | Grubac | A61N 1/0573 606/129 |
| 2012/0323099 A1 | 12/2012 | Mothilal et al. | |
| 2013/0053921 A1* | 2/2013 | Bonner | A61N 1/37205 607/36 |
| 2013/0116740 A1 | 5/2013 | Bornzin et al. | |
| 2015/0051609 A1* | 2/2015 | Schmidt | A61N 1/3756 606/129 |
| 2015/0073247 A1 | 3/2015 | Gordon et al. | |
| 2015/0283376 A1 | 10/2015 | Ollivier et al. | |
| 2016/0067446 A1* | 3/2016 | Klenk | A61N 1/05 606/129 |
| 2016/0096001 A1 | 4/2016 | Eidenschink et al. | |
| 2016/0213919 A1* | 7/2016 | Suwito | A61N 1/37205 |
| 2016/0315302 A1* | 10/2016 | Aamodt | A61N 1/3756 |
| 2017/0028207 A1 | 2/2017 | Schmidt et al. | |
| 2017/0143980 A1 | 5/2017 | Soltis et al. | |
| 2017/0281261 A1 | 10/2017 | Shuros et al. | |
| 2017/0319847 A1 | 11/2017 | Ho et al. | |
| 2018/0001082 A1 | 1/2018 | Schmidt et al. | |
| 2018/0028805 A1 | 2/2018 | Anderson et al. | |
| 2018/0264274 A1 | 9/2018 | Haasl et al. | |

FOREIGN PATENT DOCUMENTS

| | | |
|---|---|---|
| CN | 106163609 A | 11/2016 |
| EP | 2929910 A1 | 10/2015 |
| EP | 3056157 A2 | 8/2016 |
| EP | 2651502 B1 | 11/2016 |
| EP | 3090779 A1 | 11/2016 |
| WO | 2006045075 A1 | 4/2006 |
| WO | 2007047681 A2 | 4/2007 |
| WO | 2012/082735 A1 | 6/2012 |
| WO | 2013067496 A2 | 5/2013 |
| WO | 2013067496 A3 | 5/2013 |

OTHER PUBLICATIONS

First Office Action from related Chinese Patent Application No. 201980026983.7, dated Sep. 30, 2023 (21 pages including translation).
U.S. Appl. No. 61/422,622, filed Dec. 13, 2010, entitled "Pacemaker Retrieval Systems and Methods," Khairkhahan, et al., 32 pages.
Intention to Grant received for European Application No. 19713276. 4, dated Jul. 16, 2021, 6 pages.
Intention to Grant received for European Application No. 19713276. 4, dated Nov. 2, 2021, 6 pages.
Intention to Grant received for European Application No. 21201855. 0, dated Feb. 10, 2023, 6 pages.
International Preliminary Report on Patentability received for PCT Patent Application No. PCT/US2019/021481, dated Sep. 24, 2020, 20 pages.
International Search Report and Written Opinion received for PCT Patent Application No. PCT/US2019/021481, dated Jul. 31, 2019, 25 pages.

* cited by examiner

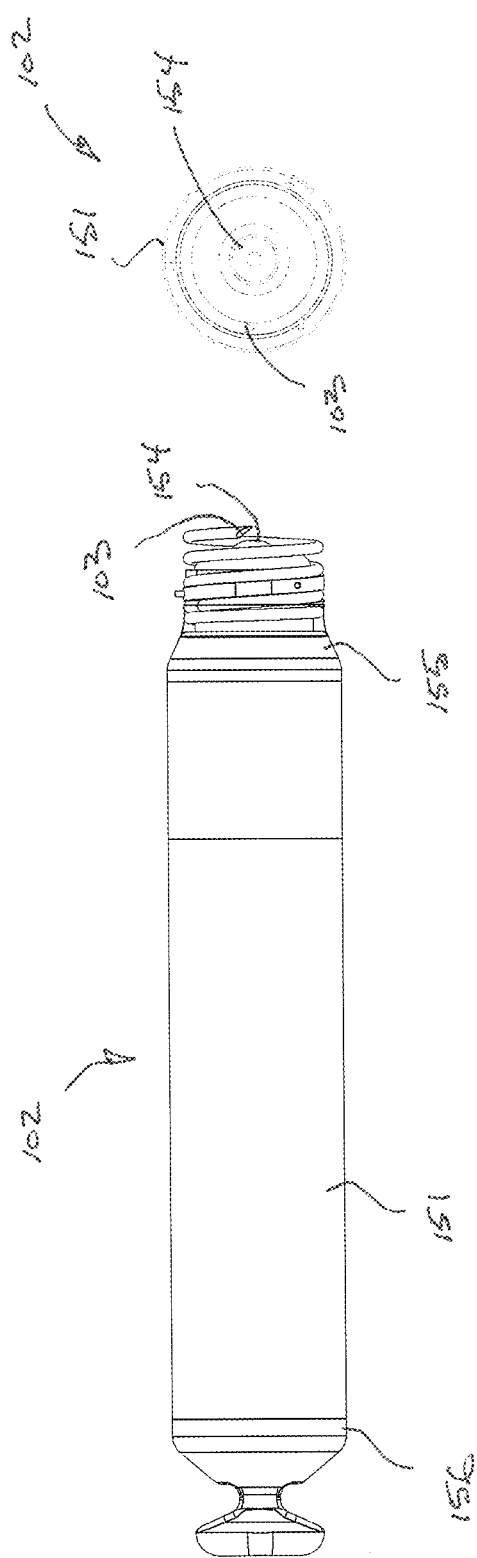

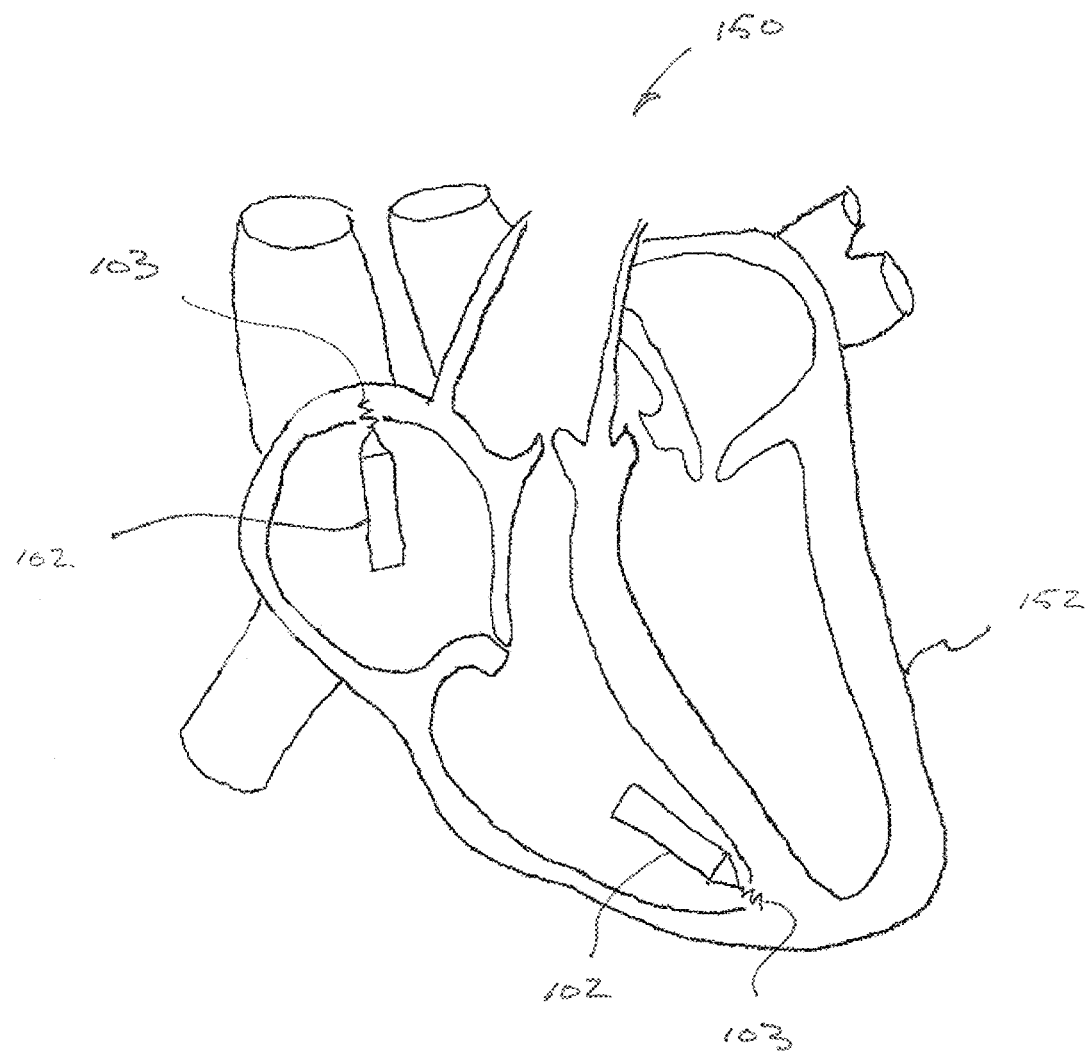
FIG. K

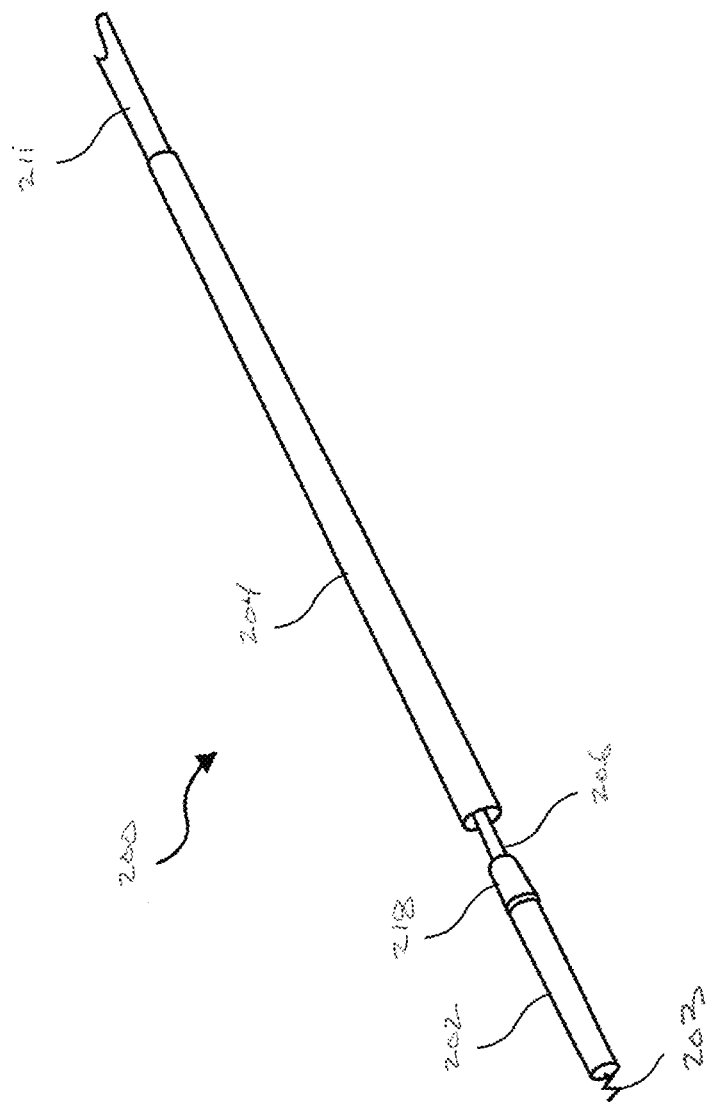

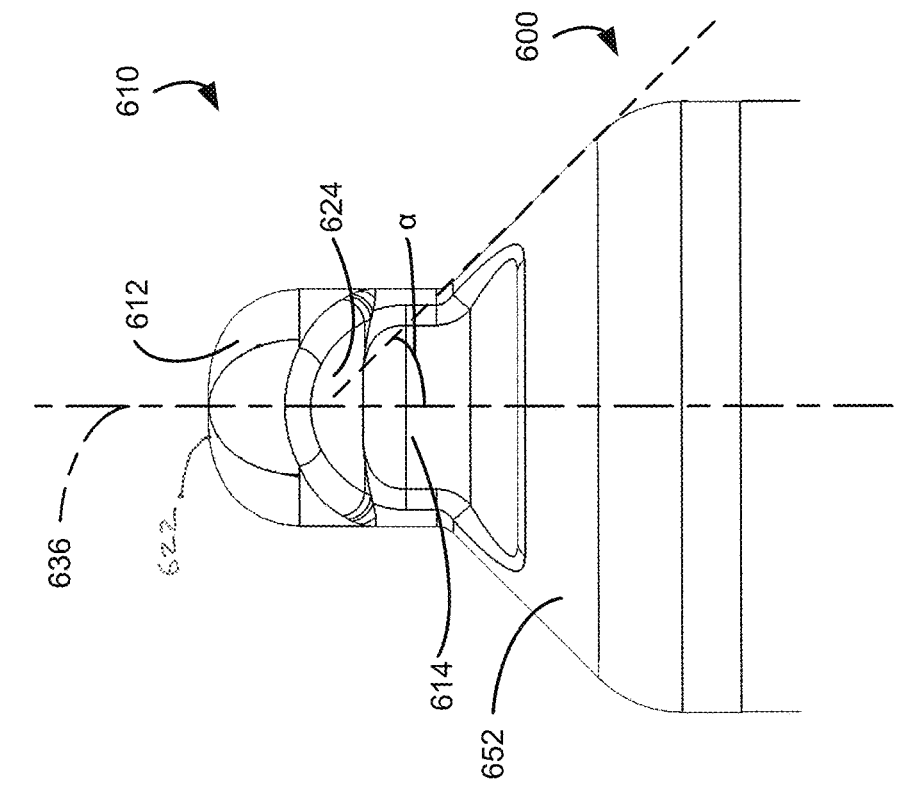
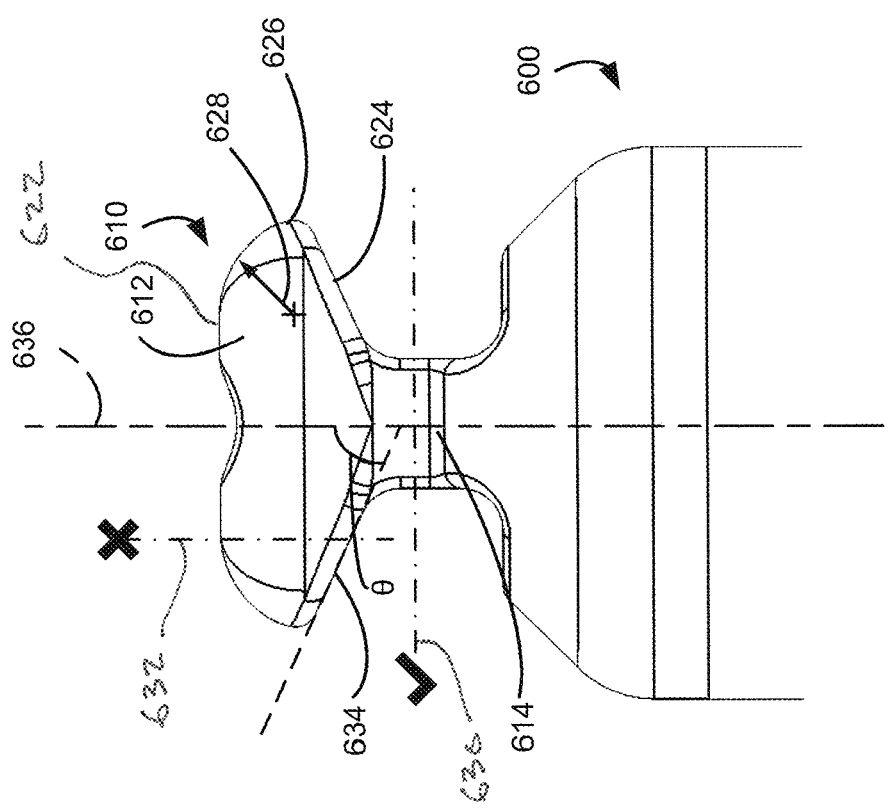

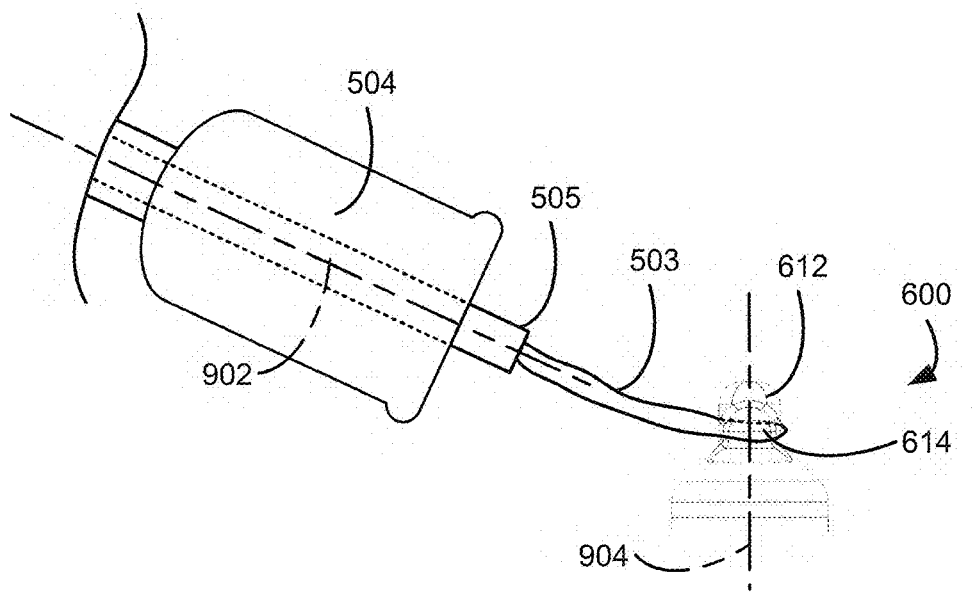
FIG. 9A
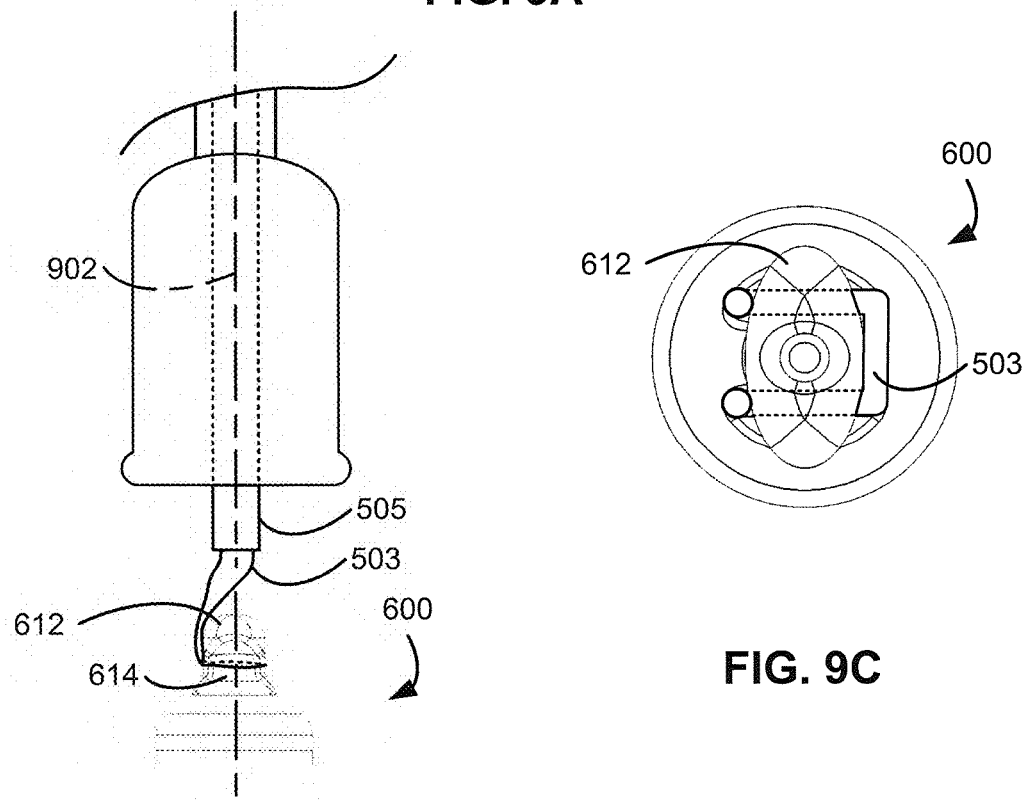
FIG. 9B
FIG. 9C

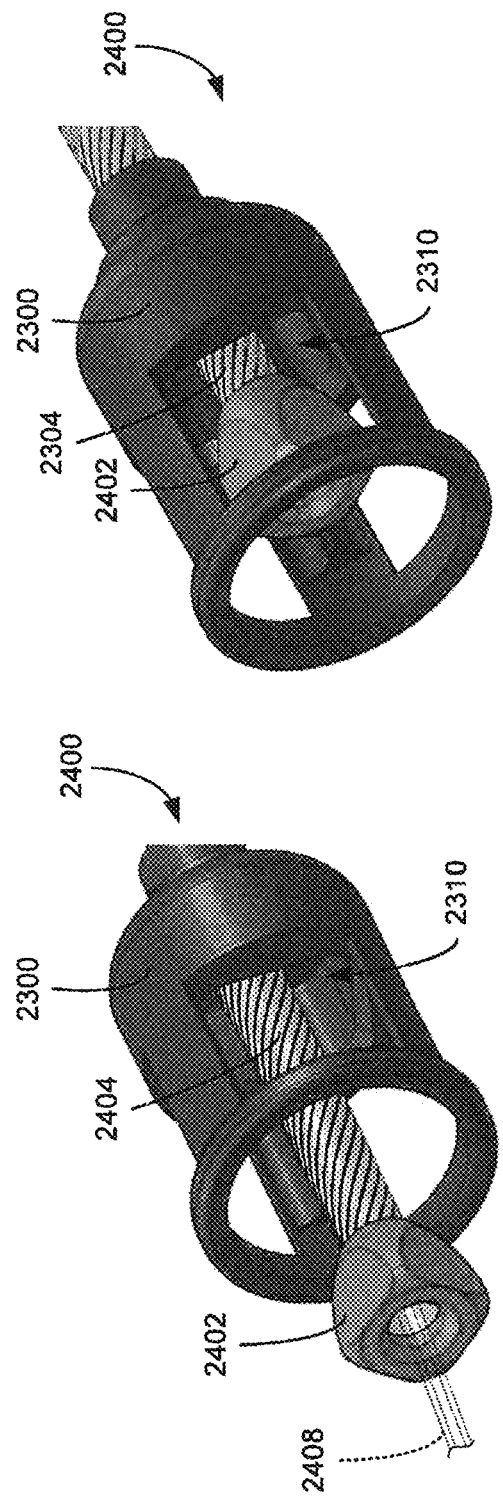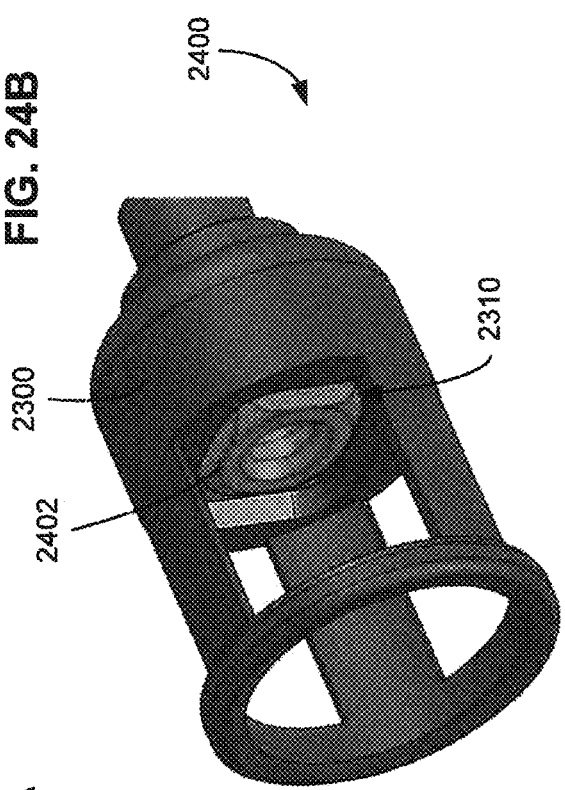
FIG. 24A
FIG. 24B
FIG. 24C

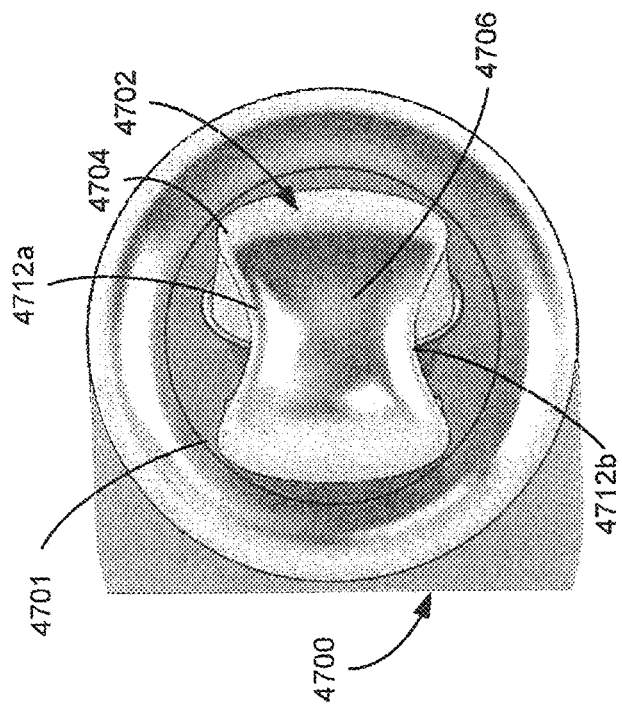
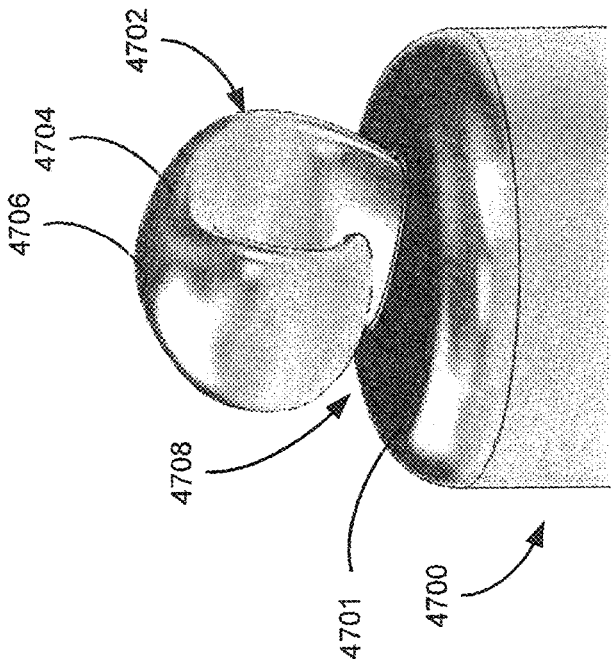
FIG. 47B
FIG. 47A

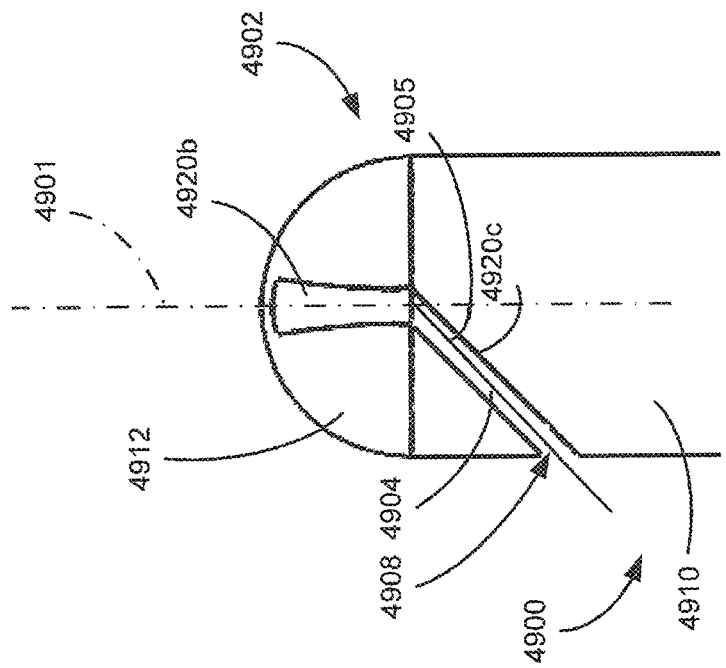
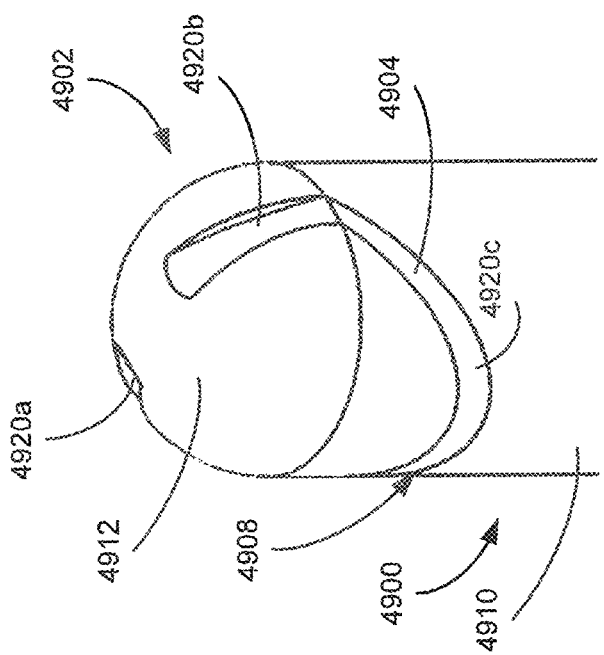
FIG. 49B
FIG. 49A

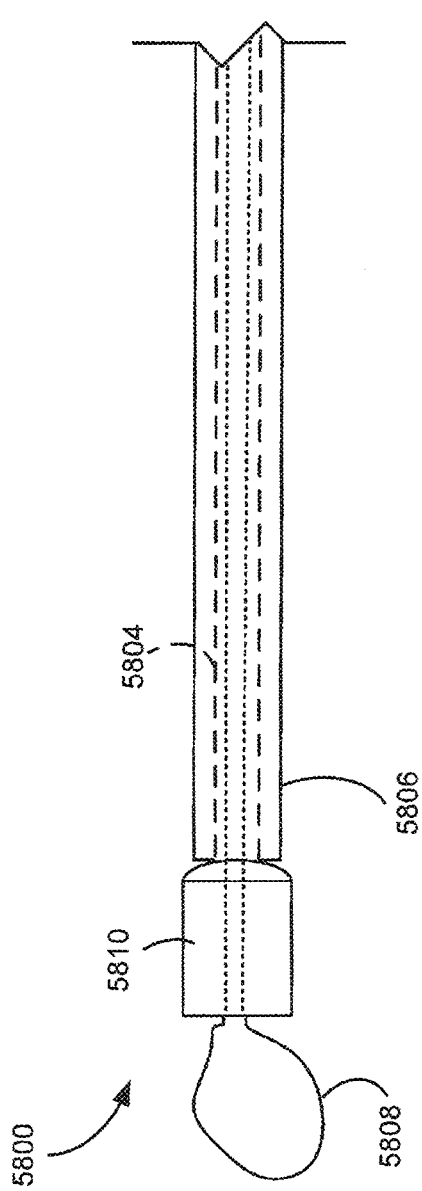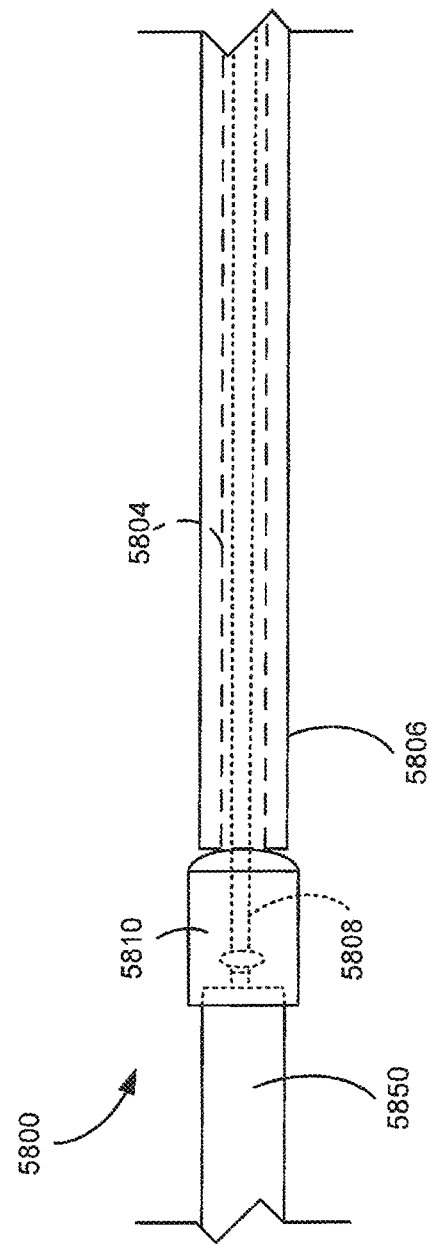

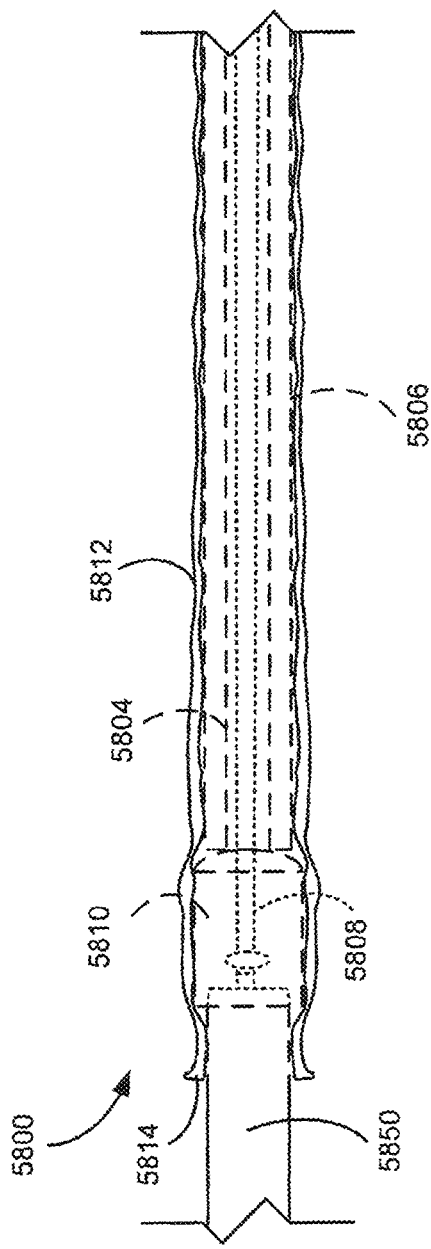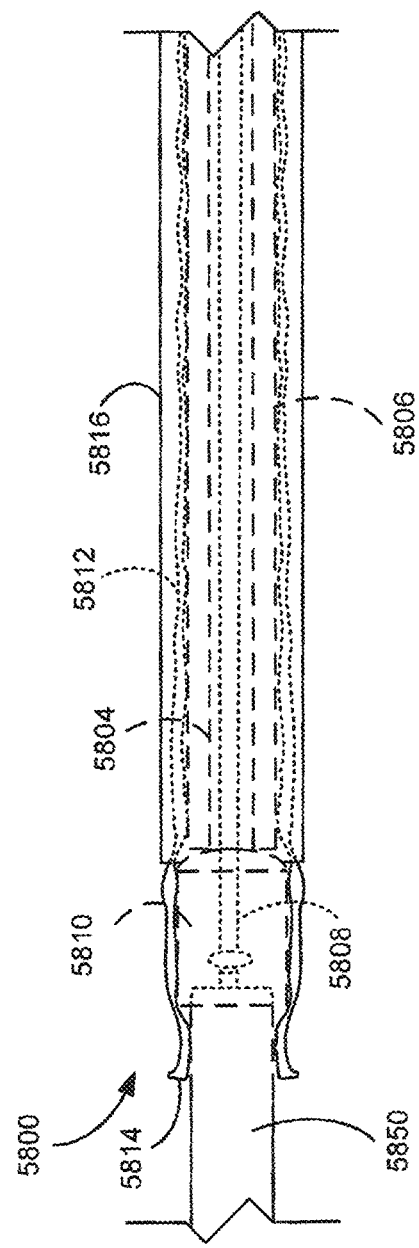

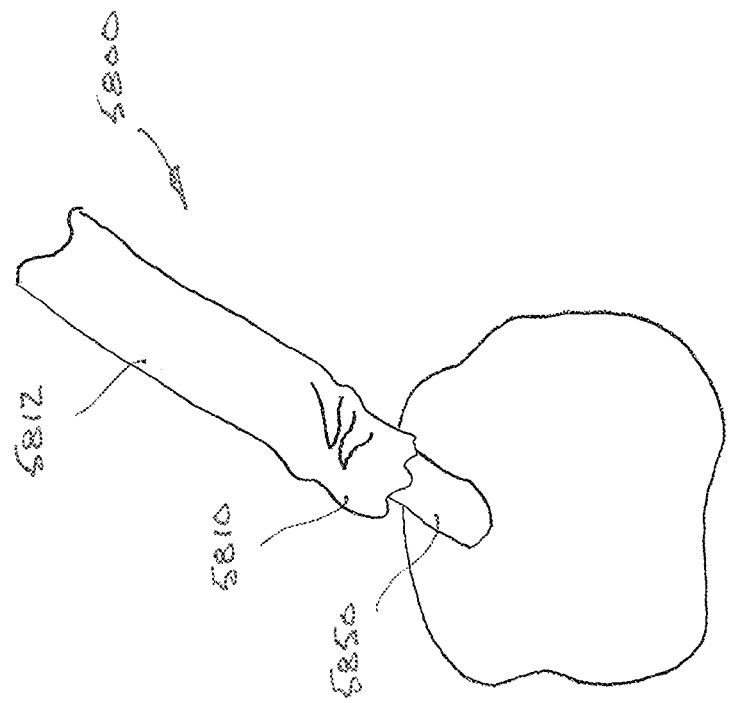
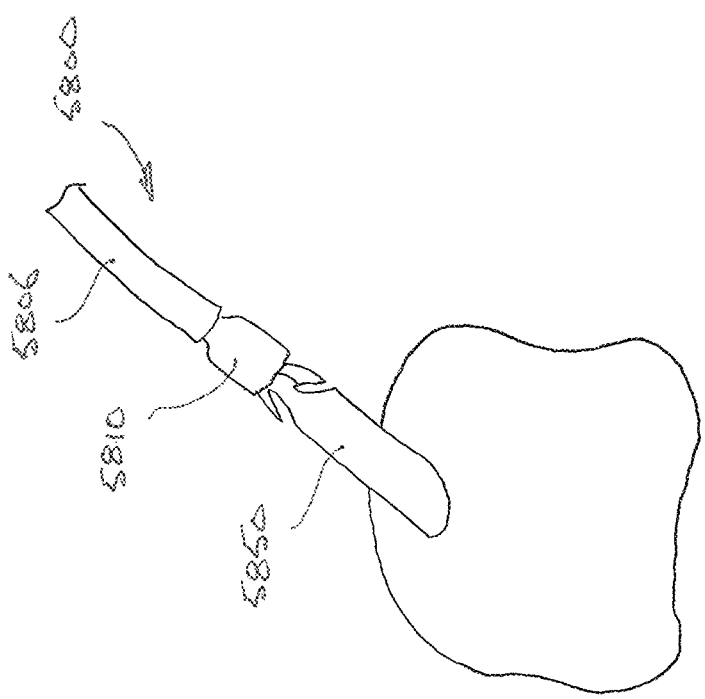

LEADLESS PACEMAKER HAVING ATTACHMENT FEATURE

This application is a divisional of co-pending U.S. patent application Ser. No. 16/297,392, filed on Mar. 8, 2019, which claims the benefit of priority of U.S. Provisional Patent Application No. 62/712,781, filed on Jul. 31, 2018, U.S. Provisional Patent Application No. 62/666,618, filed on May 3, 2018, and U.S. Provisional Patent Application No. 62/641,129, filed on Mar. 9, 2018, and those patent applications are incorporated herein by reference in their entirety to provide continuity of disclosure.

BACKGROUND

Field

The present disclosure relates to leadless cardiac pacemakers and related delivery and retrieval systems and methods. More specifically, the present disclosure relates to leadless cardiac pacemakers and devices and methods for delivering and retrieving such leadless cardiac pacemaker via a catheter-based delivery system.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle." Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more o-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the applications cited below.

Similar to active fixation implantable leads used with conventional pulse generators, leadless pacemakers are typically fixed to an intracardial implant site by an actively engaging mechanism such as a screw or helical member that screws into the myocardium.

SUMMARY

Leadless pacemakers are delivered to an intracardial implant site via a delivery system including catheters, sheaths and/or introducers. Introduction of a leadless pacemaker into the venous system and navigation of the leadless pacemaker through and past delicate tissues and anatomical structures to the implantation site is a complicated task. To achieve this task, manipulation of the sheaths, catheters and introducers relative to each other must often be precise. Similarly, retrieval of previously implanted leadless pacemakers requires precise manipulation of the catheters, sheaths and/or introducers to secure the implanted leadless pacemaker, disengage the leadless pacemaker from the intracardial implant site, and extract the leadless pacemaker through the venous system. The delivery and retrieval may require transmitting torque to the leadless pacemaker from the delivery or retrieval system. Absent sufficient control and precision of the applied torque during the delivery or retrieval process, damage to one or more of the leadless pacemaker, the cardiac tissue of the implant site, and the venous system may result. Accordingly, there is a need in the art for leadless pacemakers, systems, and methods that facilitate precise manipulation of a leadless pacemaker during delivery or retrieval.

In an embodiment, an attachment feature to facilitate precise delivery or retrieval of a leadless pacemaker is provided. The attachment feature can be have a one-piece construction. For example, the attachment feature can be monolithically formed from a rigid material. Accordingly, a delivery or retrieval system can engage the attachment feature and transmit torque to the attachment feature with a reduced likelihood that the attachment feature will experience excessive strain, e.g., twist, and/or fail under the torsional load.

The attachment feature can be a component of the leadless biostimulator. In an embodiment, the leadless biostimulator includes a battery assembly, and the attachment feature is mounted on the battery assembly. The battery assembly can include a cell can containing an electrolyte. The cell can includes an annular wall extending proximally along a central axis, and an end boss extending from the annular wall to a proximal face. The attachment feature can be mounted over the end boss. More particularly, the end boss can be received within an internal cavity of the attachment feature. A tether recess can extend into the proximal face of the end boss. The internal cavity of the attachment feature can extend through the attachment feature, and may be axially aligned with the tether recess. Accordingly, tethers of a delivery or retrieval system can extend through the attachment feature into the tether recess of the cell can. Receiving the tethers in the tether recess can reduce a likelihood that the tethers will press against the proximal face of the cell can and interfere with docking or undocking the leadless pacemaker from the delivery or retrieval system.

The attachment feature can be connected to the cell can by a weld. The attachment feature can include a distal flange, and the distal flange can be mounted on the end boss. More particularly, the weld can attach the distal flange to the cell can. For example, the weld can extend circumferentially along a seam between the distal flange and the cell can. In an embodiment, the weld attaches the distal flange to the cell can at a transition region between an annular wall of the cell can and the end boss. The transition region can be thicker than the annular wall to reduce a likelihood that the weld will cause thermal damage to the electrolyte contained within the cell can.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1B are, respectively, side and end views of an example leadless cardiac pacemaker.

FIG. 1C is a diagrammatic medial-lateral cross section of a patient heart illustrating an example implantation of leadless pacemakers in the patient heart.

FIGS. 2-3 are close-up views of a distal portion of the system of FIG. 1D.

FIGS. 7A-7B are side elevation views of the attachment feature of the leadless pacemaker of FIG. 6.

FIGS. 9A-9C show various views of a retrieval system and the leadless pacemaker of FIG. 6 during retrieval of the leadless pacemaker.

FIGS. 24A-24C are isometric views of a docking system at different stages of a docking operation.

FIGS. 47A and 47B are an isometric and a proximal end view, respectively, of a proximal end of a leadless biostimulator having a second eyelet-type retrieval feature.

FIGS. 49A and 49B are an isometric view and a side elevation view, respectively, of a proximal end of a leadless biostimulator having a slot-type retrieval feature including one slot.

FIGS. 58A-58E are side elevation views of a retrieval system including a flexible sheath during various stages of a retrieval process.

FIGS. 59A-59D are photographs corresponding to the stages of the retrieval process illustrated in FIGS. 58B-58E.

DETAILED DESCRIPTION

Figure 1D:
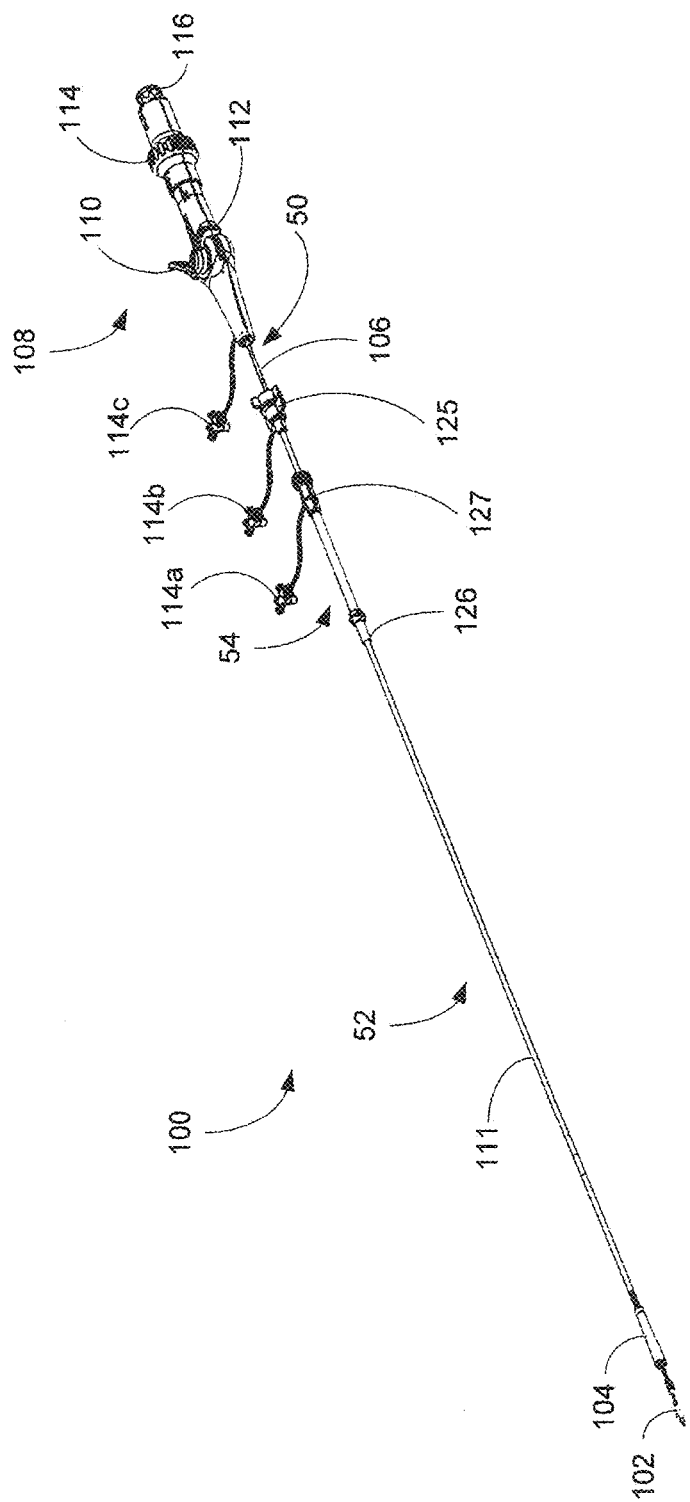
FIG. 1D is one implementation of a system for delivering and/or retrieving a leadless pacemaker.

The present disclosure is directed to a biostimulator, e.g., a leadless pacemaker, and in particular, to improvements in the design of such biostimulators. Such improvements are generally directed to attachment and retrieval features for facilitating delivery and retrieval of biostimulators. Manufacturing and assembly of such biostimulators are also described herein along with docking caps of delivery/retrieval system that may be used to deliver or retrieve biostimulators in accordance with this disclosure. Although the biostimulator is described in the context of implantation within a heart below, the biostimulator may also be used in other applications, such as deep brain stimulation. Thus, reference to the biostimulator as being a leadless cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "proximal" may indicate a first direction along a central axis of a biostimulator. Similarly, "distal" may indicate a second direction opposite to the first direction. Such terms are provided to establish relative frames of reference, however, and are not intended to limit the use or orientation of a biostimulator to a specific configuration described in the various embodiments below.

In one implementation of the present disclosure, a leadless pacemaker is provided having a retrieval feature or button coupled to a housing of the leadless pacemaker by a rigid stem. The retrieval feature can have a transverse, e.g., orthogonal to a longitudinal direction, cross-section that is oval in shape. The oval shape of the button enables the button to be used as a feature for transmitting torque applied to the leadless pacemaker by a docking cap or similar component of a catheter-based delivery/retrieval system. In addition to the oval body, such retrieval features may also include curved and tapered surfaces adapted to encourage proper capture of the leadless pacemaker using a snare about the rigid stem and to promote release of the snare when the retrieval feature is improperly captured. The rigid stem may also be shaped to encourage a predetermined orientation of the leadless pacemaker as the retrieval snare is closed about the rigid stem. Cutouts or similar voids may also be included to facilitate alignment between the retrieval snare, a docking cap, and the leadless pacemaker during docking of the leadless pacemaker after capture. In other implementations, the retrieval feature may have a lobed shape including voids between adjacent lobes, similarly resulting in alignment between the retrieval snare, the docking cap, and the leadless pacemaker during docking of the leadless pacemaker following capture.

In other implementations disclosed herein, the leadless pacemaker includes one or more end components (such as an attachment feature) that is welded or otherwise joined to a housing of the leadless pacemaker. In such implementations, the housing and end components generally include mating surfaces that are adapted to move the weld seam location away from an internal cavity of the housing within which battery material or electronic components may be stored. The surfaces may also provide additional mass adjacent the internal cavity. Such additional mass may, in certain implementations, act as a heat sink or similar structure for absorbing and diverting thermal energy away from the internal. The additional mass may also act to provide structural integrity of the housing, thereby reducing the likelihood of deformation or rupture during assembly and testing.

In yet another implementation of the present disclosure, a docking cap for use with a leadless pacemaker delivery or retrieval system is provided. The docking cap generally defines a cavity within which a proximal attachment feature of a leadless pacemaker may be retained. The docking cap includes an internal surface about which one or more inwardly extending structural features may be disposed. The structural features are arranged such that the attachment feature may be received in the docking cap when the leadless pacemaker is in a first orientation. However subsequent relative rotation between the docking cap and the leadless pacemaker causes the structural feature to interfere with the leadless pacemaker, thereby enabling torque transfer between the docking cap and the leadless pacemaker. Both cage-type implementations, in which the cavity is defined by several disconnected longitudinal members, and socket-type implementations, in which the docking cap is substantially closed, are provided.

Before beginning a detailed discussion of the locking hub and associated method, a general overview of an example leadless pacemaker and catheter-based delivery system is provided as follows.

A. Overview of Leadless Pacemaker and Catheter-Based Delivery and Retrieval Systems FIGS. 1A-1B illustrate an example biostimulator, e.g., a leadless cardiac pacemaker 102. The leadless pacemaker 102 can communicate by conducted communication, representing a substantial departure from conventional pacing systems. The leadless pacemaker can perform cardiac pacing that has many of the advantages of conventional cardiac pacemakers while extending performance, functionality, and operating characteristics.

In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

FIG. 1C illustrates an embodiment of a cardiac pacing system 150 configured to attain these characteristics. The cardiac pacing system 150 includes one or more leadless cardiac pacemakers 102. Each leadless pacemaker is substantially enclosed in a hermetic housing 151 suitable for placement on or attachment to the inside or outside of a cardiac chamber, such as the right atrium and/or right ventricle of the patient heart 152, as can be understood from FIGS. 1A-1B. Attachment of a leadless pacemaker to the cardiac tissue can be accomplished via a helical anchor 103 on an anchor mount 155 extending from a distal end of the leadless pacemaker.

As can be understood from FIGS. 1A-1B, the leadless pacemaker 102 can have two or more electrodes 154, 156 located within, on, or near the housing 151, for delivering pacing pulses to muscle of the cardiac chamber and optionally for sensing electrical activity from the muscle, and for bidirectional communication with at least one other device within or outside the body. For example, the housing 151 can have a longitudinal axis, and the electrode 154 can be a distal pacing electrode mounted on the housing along the longitudinal axis. The housing can contain a primary battery to provide power for pacing, sensing, and communication, which may include, for example bidirectional communication. The housing 151 can optionally contain circuits for sensing cardiac activity from the electrodes 154, 156. The housing 151 may contain circuits for receiving information from at least one other device via the electrodes and contains circuits for generating pacing pulses for delivery via the electrodes. The housing 151 may contain circuits for transmitting information to at least one other device via the electrodes and can optionally contain circuits for monitoring device health. The housing 151 may contain circuits for controlling these operations in a predetermined manner.

In some implementations, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the leadless cardiac pacemaker for pacing the cardiac chamber upon receiving a triggering signal from at least one other device within the body.

Leadless pacemakers or other leadless biostimulators are typically fixed to an intracardial implant site by an actively engaging mechanism or primary fixation mechanism such as a screw or helical member 103 that screws into the myocardium. Examples of such leadless biostimulators are described in the following publications, the disclosures of which are incorporated by reference: (1) U.S. Pat. No. 8,457,742, issued on Jun. 4, 2013, entitled "Leadless Cardiac Pacemaker System For Usage In Combination With An Implantable Cardioverter-Defibrillator"; (2) U.S. Pat. No. 9,358,400 issued on Jun. 7, 2016, entitled "Leadless Cardiac Pacemaker"; (3) U.S. Pat. No. 9,216,298, issued on Dec. 22, 2015, entitled "Leadless Cardiac Pacemaker System with Conductive Communication"; (4) U.S. Pat. No. 8,352,025 issued on Jan. 8, 2013, entitled "Leadless Cardiac Pacemaker Triggered by Conductive Communication"; (5) U.S. Pat. No. 7,937,148 issued on May 3, 2011, entitled "Rate Responsive Leadless Cardiac Pacemaker"; (6) U.S. Pat. No. 7,945,333 issued on May 17, 2011, entitled "Programmer for Biostimulator System"; (7) U.S. Pat. No. 8,010,209, issued on Aug. 30, 2011, entitled "Delivery System for Implantable Biostimulator"; and (8) International Application No. PCT/US2006/040564, filed on Oct. 13, 2006, entitled "Leadless Cardiac Pacemaker and System" and published as WO07043681A2 on Apr. 26, 2007.

In addition to the primary fixation mechanism, such as a helix, some leadless biostimulators may further include a secondary fixation mechanism to provide another feature for keeping the leadless biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the leadless biostimulator from moving around in the body in the case of accidental detachment). Further details on secondary fixation mechanisms can be found in U.S. Pat. No. 8,527,068, issued on Sep. 3, 2013.

Leadless pacemakers or other leadless biostimulators can be delivered to and retrieved from a patient using any of the delivery and retrieval systems described herein. In some implementations of delivery systems, a leadless pacemaker is attached or connected to a delivery system and advanced intravenously into the heart. The delivery system can include features to engage the leadless pacemaker to allow fixation of the leadless pacemaker to tissue. For example, in implementations where the leadless pacemaker includes an active engaging mechanism, such as a screw or helical member, the delivery system can include a docking cap or key configured to engage the leadless pacemaker and apply torque to screw the active engaging mechanism into the tissue. In other implementations, the delivery system includes clips designed to match the shape of a feature on the leadless pacemaker and apply torque to screw the active engaging mechanism into the tissue.

FIG. 1D illustrates a system 100 that may be used for delivery and/or retrieval of a leadless pacemaker 102 into or from a patient. The system 100 can include a deflectable catheter 50, a guide catheter 52, and an introducer sheath 54. As can be understood from FIG. 1D, the deflectable catheter 50 extends through the guide catheter 52 and includes a distal end and a proximal end. The distal end of the deflectable catheter is selectively connectable to the proximal end of the leadless pacemaker 102 and the proximal end of the deflectable catheter includes a handle 108 by which the user may cause the deflectable catheter shaft 106 to distally-proximally displace within the length of the guide catheter and, further, by which the user may actuate the distal end of the deflectable catheter to selectively connect and disconnect from a proximal end of the leadless pacemaker. The deflectable catheter 50 may extend from both the distal and proximal ends of the guide catheter 52.

The guide catheter 52 extends through the introducer sheath 54 and includes a distal end and a proximal end. The distal end of the guide catheter 52 includes a protective pacemaker sheath 104. The proximal end of the guide catheter includes a flush port 114*b* extending from a proximal hub 125. The guide catheter 52 extends from both the distal and proximal ends of the introducer sheath 54. The shaft 111 of the guide catheter 52 may also include one or more sections (not shown) having different durometers such that the reinforcement and corresponding bending resistance of the sections may be modified according to the specific application for which the pacemaker system 100 is being implemented. The introducer sheath 54 includes a distal end 126 and a proximal end. The proximal end of the introducer includes a flush port 114*a* and a hub 127.

As can be understood from FIG. 1D and for purposes of discussion, the system 100 may be considered to include the various components of the deflectable catheter 50, the guide catheter 52 and the introducer 54. For example, the system 100 may be considered to include the pacemaker sheath 104, the guide catheter shaft 111, the pacemaker introducer sheath 54, the handle 108, and the flush ports 114*a*, 114*b*, and 114*c*. The flush ports 114*a*, 114*b*, and 114*c* can be used to flush saline or other fluids through the introducer 54, the guide catheter 52, and the deflectable catheter shaft 106, respectively. The sheath 54 can be advanced distally over the catheter shaft 111 to provide additional steering and support for the delivery catheter during implantation and to surround the pacemaker as it is introduced through a trocar or introducer into the patient.

The handle 108 may further include additional elements to manipulate and actuate elements of the system 100. In general, the handle 108 may include elements directed to, without limitation, one or more of deflecting the deflectable catheter shaft 106, rotating the deflectable catheter shaft 106 (and any implantable medical device, such as the leadless pacemaker 102, coupled to the deflectable catheter shaft 106), extending and retracting the leadless pacemaker 102 (or other implantable medical device) relative to the protective sheath 104, and engaging or disengaging a coupling mechanism, such as a tether or lasso, to a corresponding feature of the leadless pacemaker 102 to couple the leadless pacemaker 102 to the system 100. For example, the handle 108 includes a deflection lever 110 for actuation of the deflectable catheter shaft 106 and a brake 112 for locking the position or otherwise increasing resistance to rotation of the deflection lever 110. The handle 108 further includes a docking shroud 114 that may be rotated to apply torsion to the deflectable catheter shaft 106, thereby rotating the deflectable catheter shaft 106 and the leadless pacemaker 102 when coupled to the deflectable catheter shaft 106. The docking shroud 114 may also translate along the handle 108 to selectively extend and retract the leadless pacemaker 102 from a protective sheath 104 disposed at a distal end of the shaft 111. The handle 108 also includes a release knob 116 that, when rotated, causes engagement or disengagement of the coupling mechanism with the leadless pacemaker 102.

Figure 3:
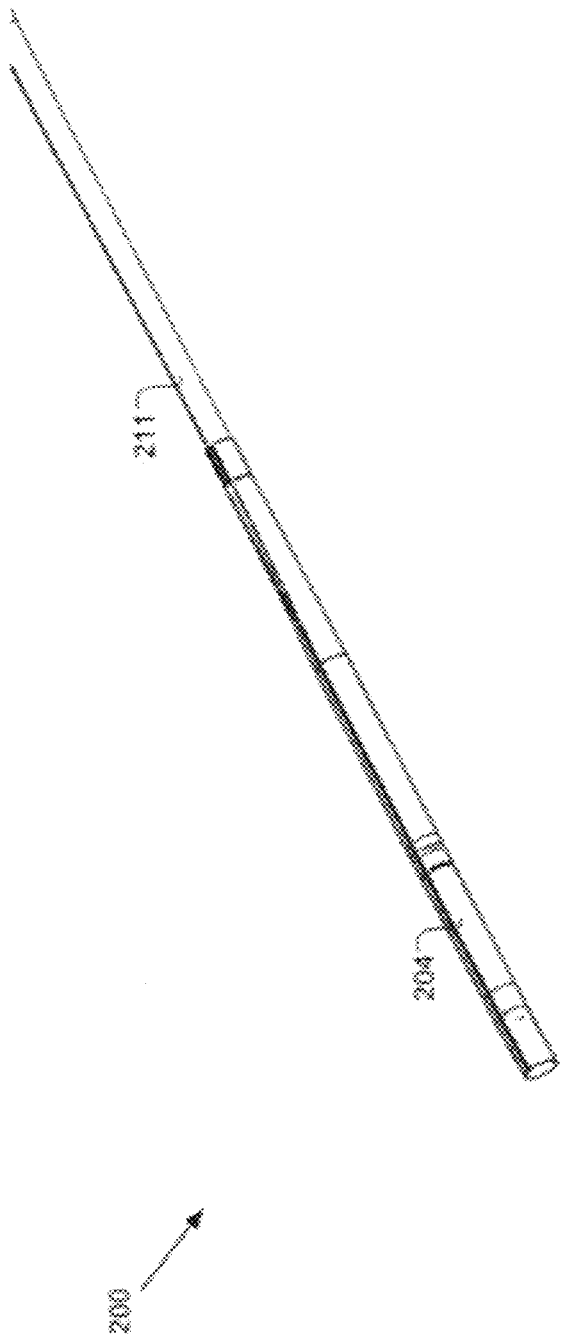

FIG. 2 is a close-up view of a distal portion of a system 200 as used for delivery of a pacemaker 202. The pacemaker 202 of FIG. 2 can include a helix 203 for attachment of the pacemaker to tissue. In FIG. 2, the pacemaker is attached to a docking cap 218 of a catheter shaft 206. The pacemaker sheath 204 is shown pulled back proximally along the catheter shaft 206 and a guide catheter shaft 211 to expose the pacemaker 202 and the helix 203. In FIG. 3, the pacemaker sheath 204 is extended distally along the guide catheter shaft 211 to cover the catheter shaft 206, the pacemaker 202, and the helix 203 to protect the tissue from the sharp edges of the helix 203 during implantation. When the pacemaker sheath 204 is pulled back proximally, as shown in FIG. 2, the pacemaker 202 is in an exposed, delivery configuration. When the pacemaker sheath 204 is advanced distally to protect the pacemaker 202 and the helix 203, as shown in FIG. 3, the pacemaker 202 is in a protected, advancement configuration.

Figure 4A:
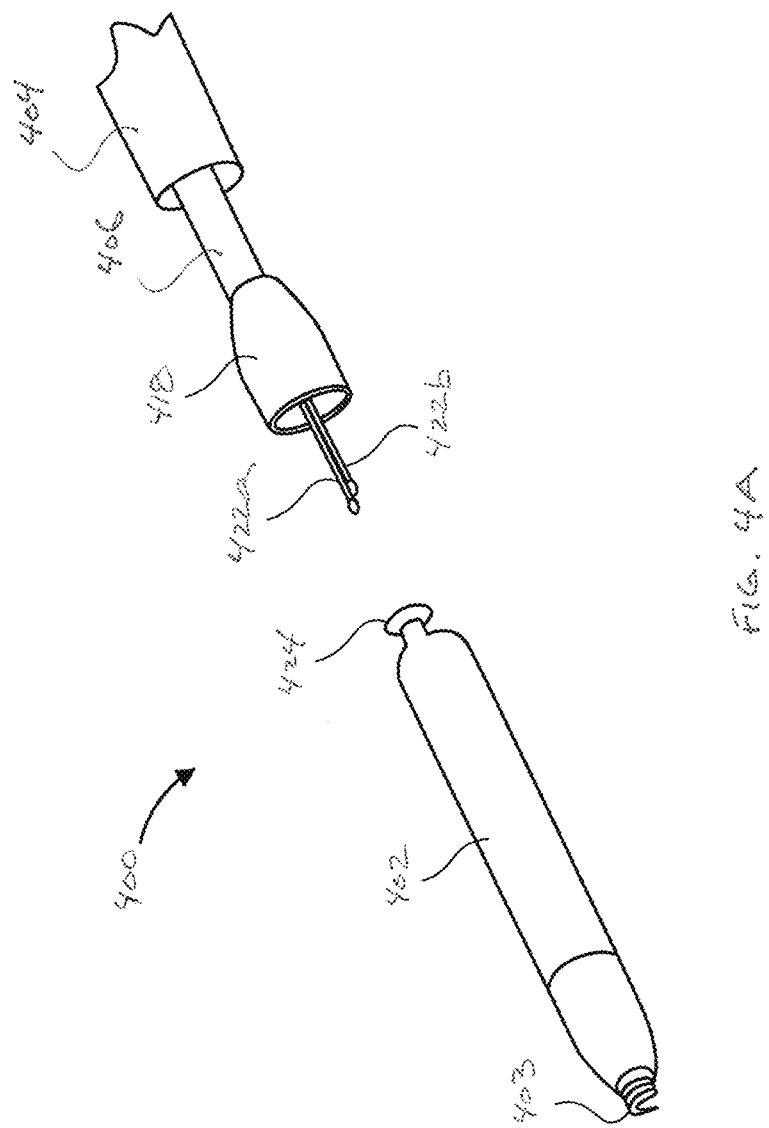
FIGS. 4A-4F are side views of a delivery system approaching, and then attaching to, a pacemaker.

FIG. 4A illustrates a system 400 for delivering a leadless pacemaker, including a pacemaker 402 including a helix 403 and an attachment feature 424, and the system 400 including a pacemaker sheath 404, a catheter shaft 406, a docking cap 418, and tethers 422a, 422b. The tethers 422a, 422b can include wires, shafts, tubes, cords, ropes, strings, or other similar structures that can extend throughout the catheter shaft 406. In some implementations, the tethers 422a, 422b include a shape memory material, such as nitinol. In other implementations, the tethers include stainless steel wires or braids. In FIG. 4A, the pacemaker 402 is not attached to docking cap 418 of the delivery catheter. The process of connecting the pacemaker to the delivery catheter will now be described.

Figure 4B:
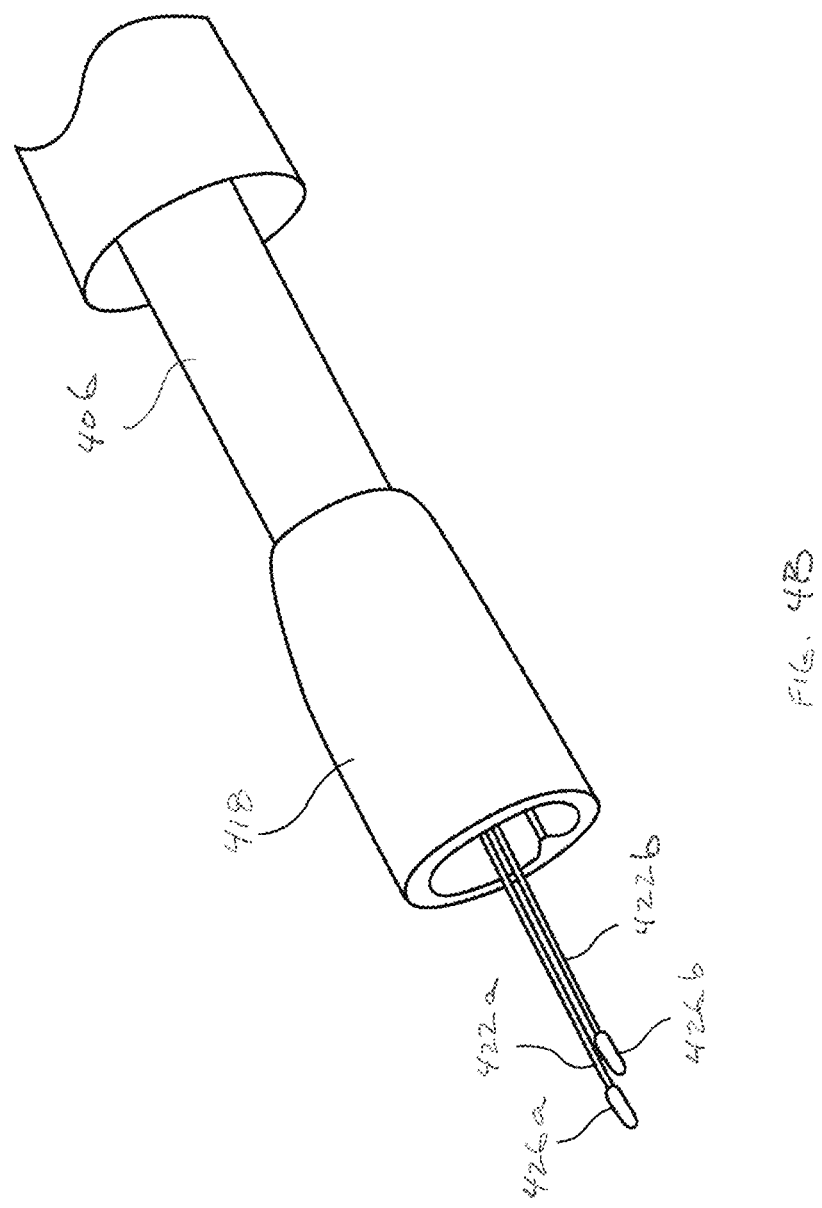

Referring to FIG. 4B, tethers 422a and 422b can include distal features 426a, 426b. The distal features 426a, 426b can be, for example, features on the tethers that protrude radially from the tether, such as bumps, spheres, cylinders, rectangles, or other similar shapes extending outwards from the tethers. In some implementations, the distal features can be expandable, such as balloons or expandable mechanical structures. Generally, the distal features have a cross sectional diameter larger than the cross sectional diameter of the tethers. As shown, in one embodiment, the distal feature 422a can be advanced further from the catheter than the distal feature 422b, so that when the tethers are pushed together, the distal feature 422b rests against the tether 422a. This causes the combined cross sectional diameter of both distal features and tethers to be less than if the distal features were lined up side by side. By way of comparison, in FIG. 4C the distal features 426a, 426b are lined up side by side and therefore have a greater combined cross sectional diameter when pressed together than is shown in FIG. 4B.

Figure 4C:
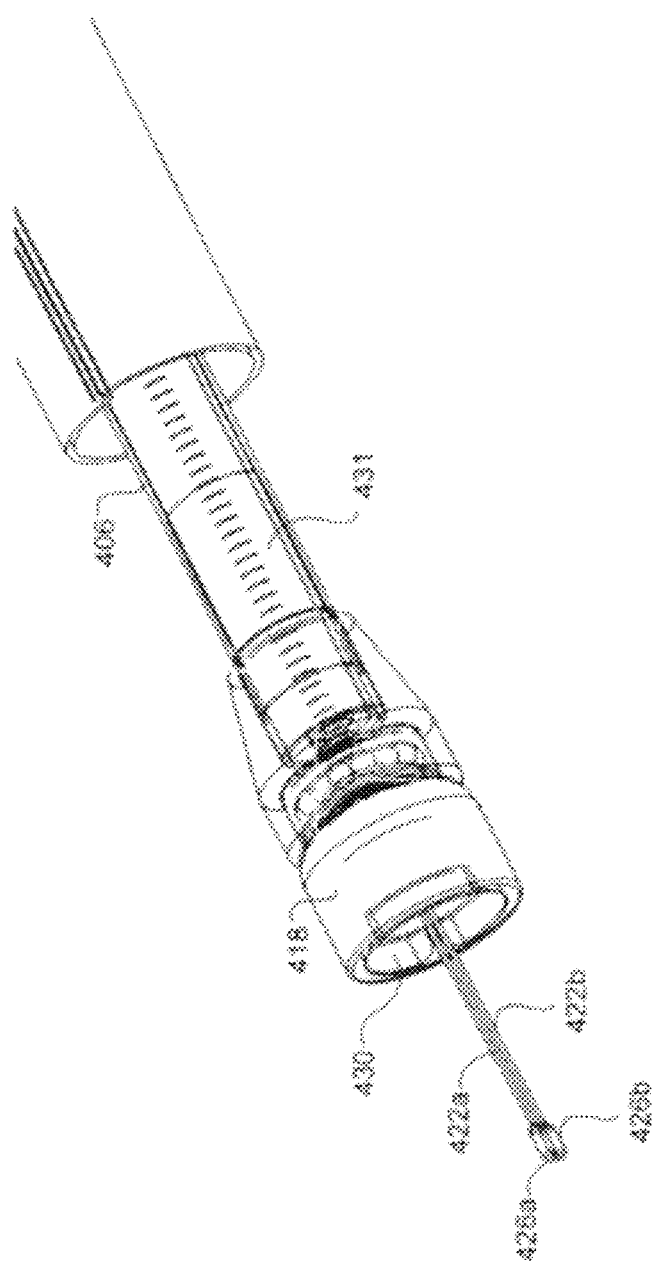
Figure 4D:
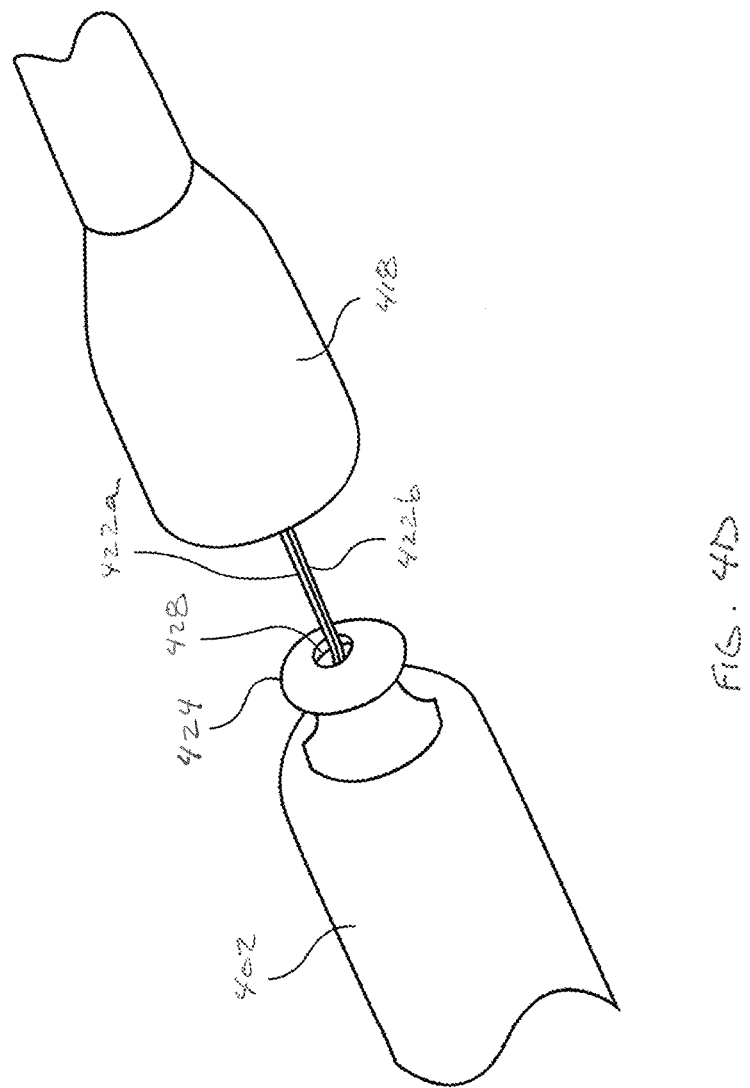
Figure 4E:
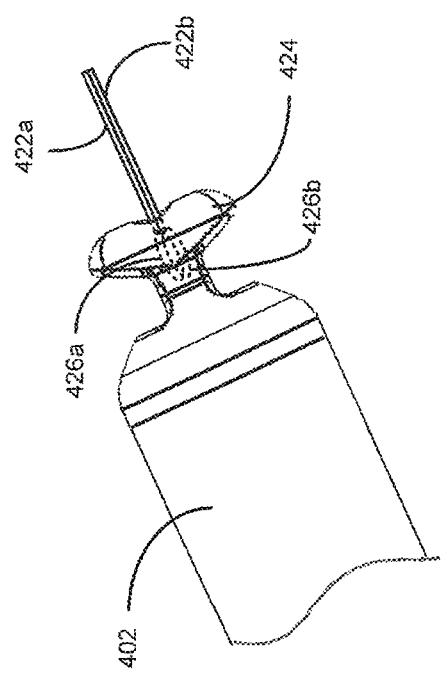
Figure 4F:
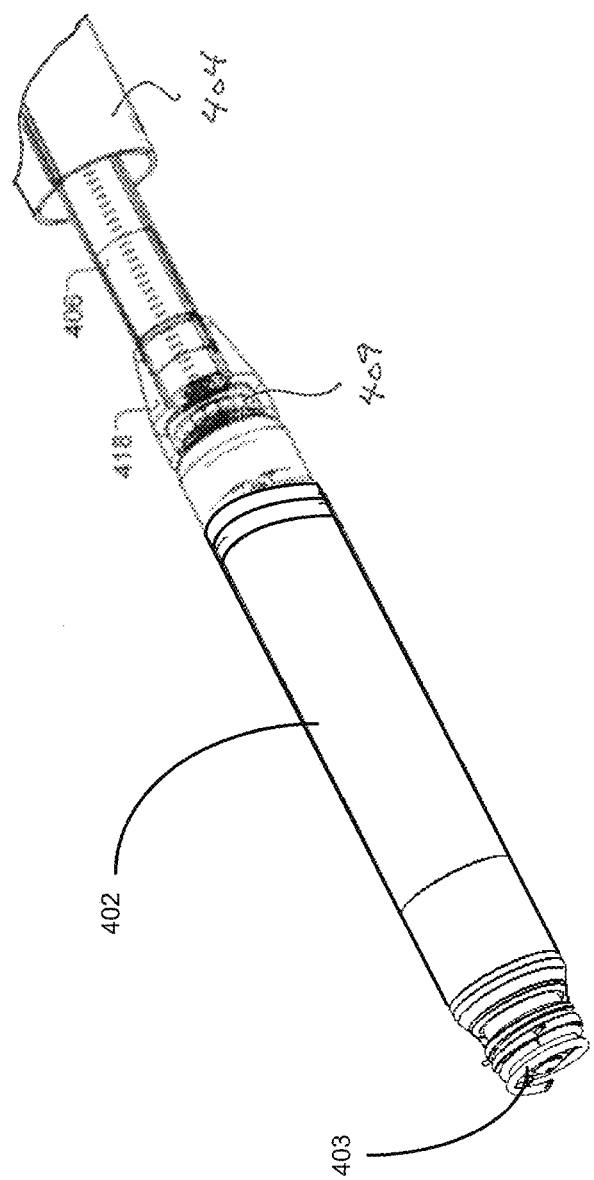

The length of the tethers 422a, 422b and thus the position of the distal features 426a, 426b, can be adjusted so that the distal features 426a, 426b are not aligned in a side by side configuration (e.g., the un-aligned configuration shown in FIGS. 4A-4B). When the tethers and distal features are in this un-aligned configuration, the cross sectional diameter of the distal features is reduced since the distal features are not positioned side by side. The tether distal features 426a, 426b can then be advanced in this un-aligned configuration through a hole 428 of an attachment feature 424 of the leadless pacemaker, as shown in FIGS. 4D-4F. In this implementation, the diameter of the hole 428 should be sufficiently large enough to allow the distal features 426a, 426b of the tethers 422a, 422b to pass when in the un-aligned configuration. Upon passing the distal features through the hole 428, the length of the tethers 422a, 422b can then be adjusted to align the distal features 426a, 426b in the side by side configuration (e.g., as shown in FIGS. 4C and 4E). When the distal features 426a, 426b are positioned side by side, the combined cross sectional diameter of the distal features 426a, 426b becomes larger than the diameter of the hole 428, which essentially locks the tethers 422a, 422b and distal features 426a, 426b in the attachment feature 424 be preventing the distal features 426a, 426b from being able to pass proximally through the hole 428.

Still referring to FIGS. 4C and 4D, the docking cap 418 of the delivery catheter can include a torque slot 430 (shown in FIG. 4C) sized and configured to mate with the attachment feature 424 (shown in FIG. 4D) disposed on a proximal end of the pacemaker 402. The torque slot 430 can be coupled to a torque shaft 431, which runs the length of the delivery catheter extending into the handle (not shown). It should be appreciated that the attachment feature 424 and the torque slot 430 can include any number of shapes, such as square, rectangle, triangle, pentagon, hexagon, cross, "X", etc., so long as attachment feature 432 fits within and can have rotational torque applied to it by to via the slot 430. Once the tethers are locked within the attachment feature 424 (FIGS. 4D-4E), the tethers can be pulled proximally to pull the attachment feature 424 and the pacemaker 402 towards the catheter and to attach the pacemaker 402 to the delivery catheter, thereby engaging the attachment feature 424 with the torque key 432 (as shown in FIG. 4F).

Figure 5A:
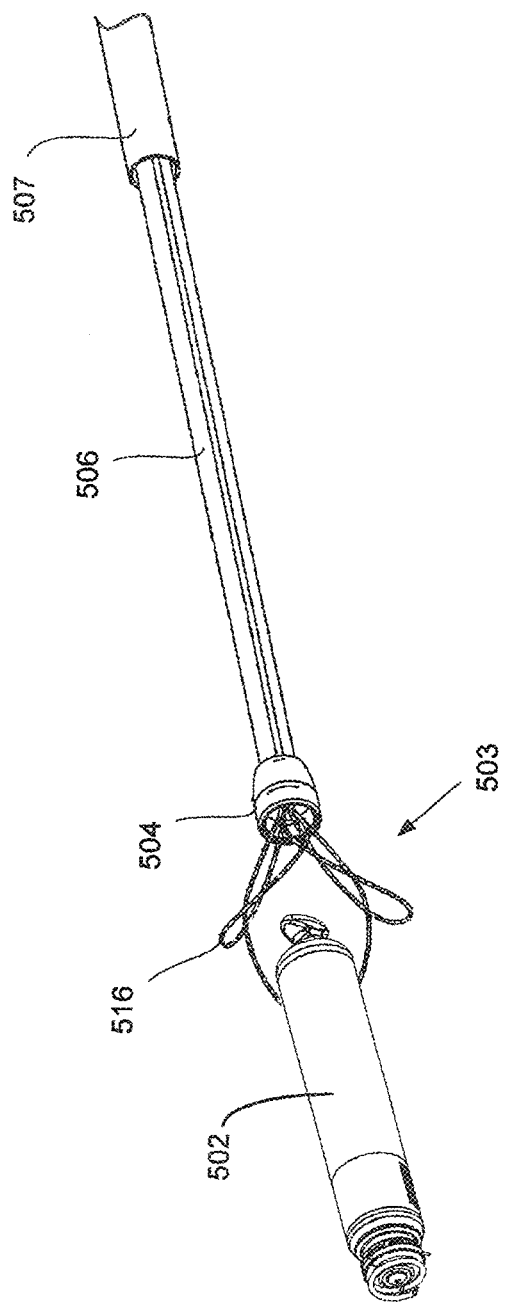
FIGS. 5A-5C show various close-up views of a distal portion of a retrieval catheter system employing alternative capture mechanisms.

FIG. 5A illustrates a close-up view of one embodiment of a distal portion of the system 100 shown in FIG. 1 as used for retrieval of a leadless pacemaker 502. The distal portion of the retrieval catheter can include a snare 503 configured to grasp a leadless cardiac pacemaker or other medical device, and a docking cap 504 configured to allow docking of the leadless pacemaker 502 with the retrieval catheter after engaging the pacemaker 502 with the snare 503. FIG. 5A also illustrates a catheter shaft 506 terminating at the docking cap 504, and a protective sheath 507 positioned along the catheter shaft 506 slightly proximal to the docking cap 504 and the leadless pacemaker 502.

As shown in FIG. 5A, the snare 503 can include at least one loop 516 extending from the catheter shaft 506. As the snare 503 is advanced distally out of the system 100 from the docking cap 504, the loops 516 can expand in size to aid a user in positioning the snare 503 around or in proximity to the pacemaker 502 to be retrieved. In some implementations, as in FIG. 5A, the snare 503 can include multiple loops, such as three loops. However, any number of loops can be used as long as the catheter shaft contains sufficient volume to accommodate the loops.

Figure 5B:
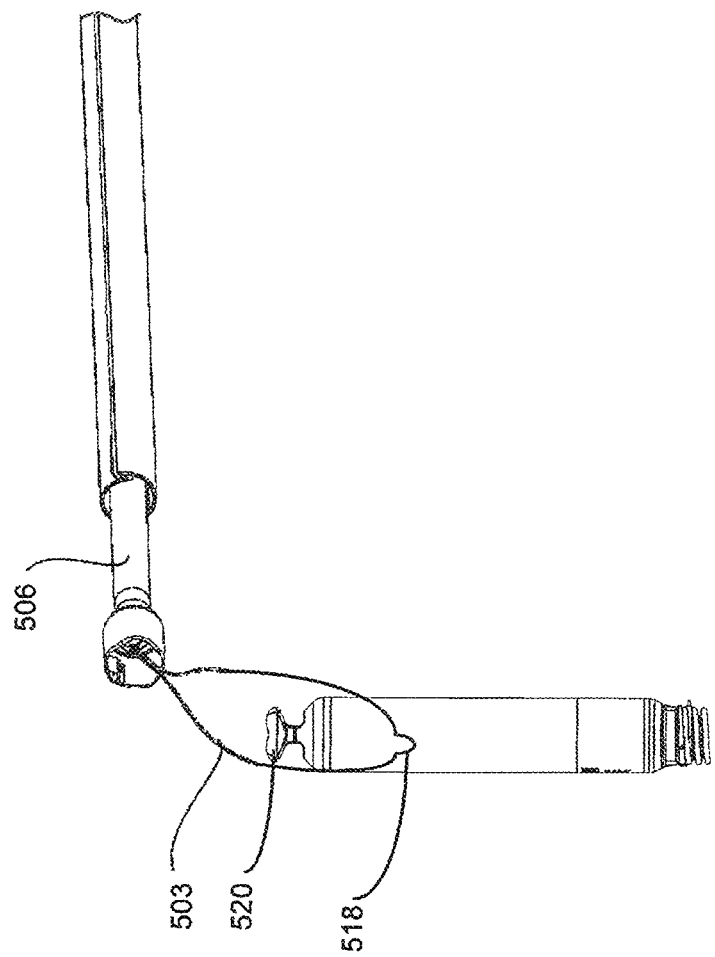

In another embodiment, as shown in FIG. 5B, the snare can include only a single loop. Also shown in FIG. 5B, the loops can include any number of features 518 to aid in grasping a pacemaker or medical device for retrieval. In FIG. 5B, the feature 518 can include, for example, a notch feature. In some implementations, the loops of the snare can be positioned off axis from the center of the catheter shaft to aid in keeping the pacemaker in line with the catheter during removal. For example, in FIG. 5B, the single loop snare 503 can include a notch feature 518 and be positioned off axis from the longitudinal axis of the catheter shaft 506. Since the snare is off axis from the catheter, the snare 503 can be looped around a retrieval feature 520 of the pacemaker by positioning the catheter adjacent to the pacemaker and allowing the loop to come into contact with the housing of the pacemaker. As the catheter is pulled away from the pacemaker, the snare 503 can slide up the pacemaker, and the notch feature 518 can be allowed to engage the retrieval feature 520 of the pacemaker.

Figure 5C:
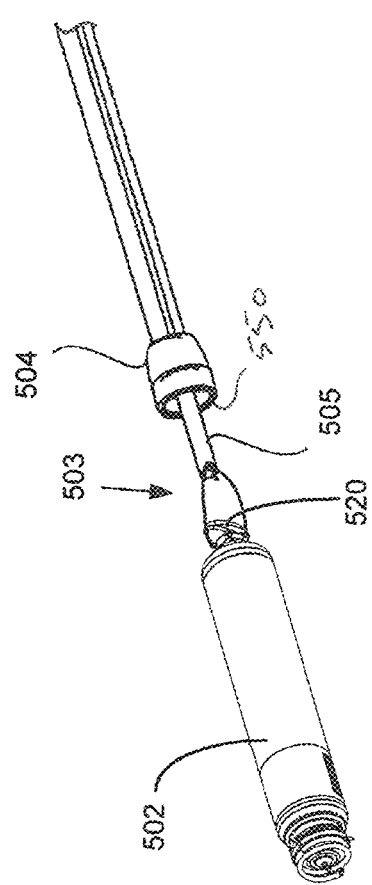

FIG. 5C illustrates the snare 503 grasping a retrieval feature 520 of the leadless cardiac pacemaker 502. In the illustrated embodiment, a snare locking sleeve 505 can be advanced distally over the snare from the docking cap 504 of the catheter. As the snare locking sleeve 505 advances distally along the snare 503, it can cause the loops of the snare 503 to reduce in size, thereby grasping or locking onto the retrieval feature 520 of the pacemaker 502. In some implementations, the snare locking sleeve 505 can also include a torque shaft that runs through the length of the catheter. Details of the torque shaft will be described in more detail below, but generally the torque shaft can be rotated independently of the catheter shaft and coupled to the docking cap 504 of the catheter to apply rotational torque to the docking cap, and thus, to a pacemaker or medical device to be retrieved. In implementations where the snare 503 includes several loops, it may be more likely that one of the loops will grasp the pacemaker than in implementations where the snare 503 includes only a single loop.

Following capture and locking of the snare 502 with the leadless pacemaker 502, the leadless pacemaker may be docked within the docking cap 504. As previously discussed, FIG. 4F illustrates a delivery system in which a leadless pacemaker 402 is retained in a docked position. The configuration illustrated in FIG. 4F may be substantially similar to a configuration in which the leadless pacemaker 402 is docked with a docking cap 418 of a retrieval system. Accordingly, in addition to illustrating docking in a delivery system, FIG. 4F may also be interpreted to illustrate a close-up view of a distal portion of a retrieval catheter with a snare locked onto a retrieval feature (not shown) of the leadless pacemaker 402 (equivalent to 502) and docked within docking cap 418 (equivalent to 504). In some implementations, as will be described in more detail below, the docking cap 418 can include a key or interference feature configured to mate with and engage a corresponding key or feature on the pacemaker 402. In some implementations, the key or slot on the docking cap 418 can match a unique shape or feature of the retrieval feature of the pacemaker 402. Because the key or slot on or in the docking cap 418 can mate with and engage the key or slot on the pacemaker, the retrieval catheter can be configured to apply torque to the pacemaker to unscrew and remove the pacemaker from tissue. FIG. 4F also illustrates a protective sheath 404 positioned slightly proximally to the docking cap 418 along the catheter shaft of the retrieval system.

In an embodiment, the docking cap 502 can have a sharp distal edge 550 to promote detachment of the leadless pacemaker 502 from the implant site. For example, the distal edge of the docking cap 502, which is extended to a location near or abutting a proximal end of the leadless pacemaker 502 when the pacemaker is retracted into the retrieval system, can have an edge that is sharp enough to cut through tissue. By way of example, the sharp distal edge 550 can be located where a pair of faces meet at the distal end of the docking cap 502. One or more of the faces may be oblique to a central axis of the docking cap 502. For example, the outer wall of the docking cap 502 can be parallel to the central axis, or the outer wall can angle inward toward the distal edge to form a cutting edge with the inner wall of the docking cap 502. Similarly, the inner wall can be parallel or angled relative to the central axis. Accordingly, the sharp distal edge 550 can be formed where the faces meet, and the edge can provide a circumferential cutting blade that extends around the central axis. The edge can cut through the tissue under distal advancement forces and/or under torque transmitted through the retrieval system to the docking cap 418. Accordingly, the sharp edge can cut through tissue attached to the leadless pacemaker 402 to excise the implanted device from the patient. When the leadless pacemaker 402 is detached from the target tissue, it may be retrieved from the patient.

As shown in FIG. 4F, the docking cap 418 can include ball bearings 409 which allow the docking cap to be free-rotating from the rest of the catheter shaft. This effectively reduces the removal torque and additional forces from the catheter body. The docking cap 418 can be selectively coupled to a torque shaft (not shown) that extends through the length of the catheter to a torque knob on the handle (described below) or other rotatable portion of the handle coupled to the torque shaft. When the torque shaft is coupled to the docking cap 418, rotation or actuation of the torque knob rotates the torque shaft, thereby rotating the docking cap 418 at the end of the retrieval catheter. In some implementations, the docking cap 418 can include a keyed portion or interference feature so as to apply additional torque to the pacemaker when unscrewing.

Referring back to FIG. 2B, a protective sheath 204 is shown disposed over a leadless cardiac pacemaker and positioned at the distal end of guide catheter shaft 211. As described above, the protective sheath can be configured to slide over the pacemaker to prevent any sharp edges or features of the pacemaker from tearing, damaging, or catching onto tissue during removal of the pacemaker. The protective sheath can be slidable along a longitudinal axis of the catheter so as to allow for covering and uncovering of the pacemaker with the sheath. In some implementations, the protective sheath can include other form factors than illustrated in FIG. 2B. For example, in some retrieval scenarios where vegetative growth over the device is significant, the protective sheath may be of a larger diameter to accommodate the increase in size of the device.

The above description of FIGS. 5A-5C can be used to illustrate one embodiment of a method of retrieving a medical device or leadless cardiac pacemaker from a patient. First, a retrieval catheter can be advanced into a patient until the docking cap of the catheter is in the vicinity of the pacemaker. Next, the snare of the retrieval catheter can be advanced distally outward from the catheter to surround the retrieval feature of the pacemaker. Once the snare is surrounding the retrieval feature of the pacemaker, the snare locking sleeve/torque shaft can be advanced distally along the snare to close the snare, causing the snare to grasp the retrieval feature of the pacemaker. Next, the snare and snare locking sleeve can be pulled proximally towards the docking cap of the catheter so as to engage the proximal end or retrieval feature of the pacemaker. Rotational torque can then be applied by the catheter to the pacemaker via the torque shaft and docking cap to unscrew the pacemaker from the tissue. The protective sheath can be advanced over the pacemaker, and the pacemaker can then be removed from the patient.

B. Leadless Pacemaker Retrieval Features

As previously discussed in the context of FIGS. 1A-1B and 4A-5C, leadless pacemakers in accordance with this disclosure may include an attachment feature. Various implementations of such attachment features are described below in further detail with particular focus on various design features that facilitate the use of the attachment features during the processes of delivery and/or retrieval of the leadless pacemaker. In general, attachment features discussed herein include a fixed retrieval feature or "button" that is robust against the expected forces seen in vivo, that is fatigue resistant, and that provides control over the leadless pacemaker during delivery and retrieval. In general, each of these properties contributes to the overall effectiveness of the attachment feature, thereby reducing the likelihood of improper or incomplete implantation of the leadless pacemaker, breakage or damage to the leadless pacemaker, and, ultimately, potential damage to the patient's heart and associated tissue.

Figure 6:
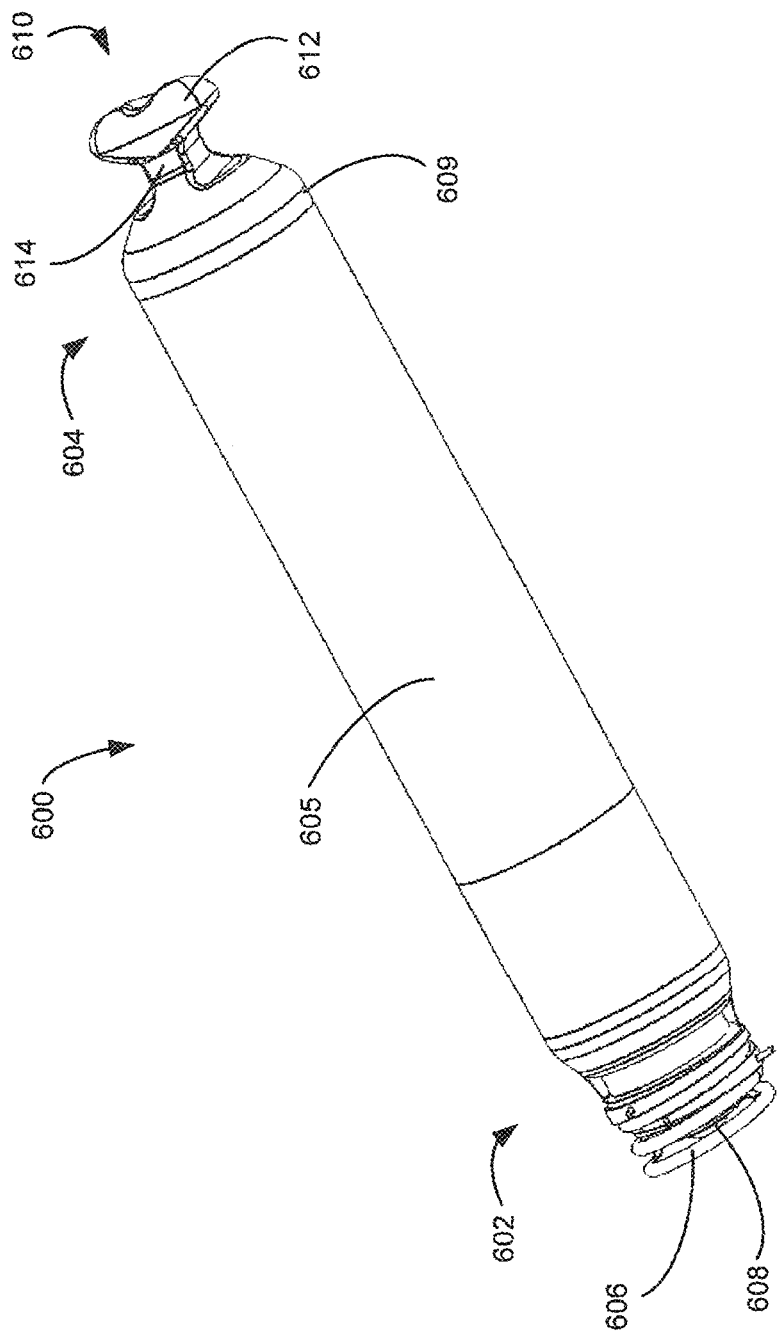
FIG. 6 is an isometric view of one implementation of a leadless pacemaker having an attachment feature.

FIG. 6 is an isometric view of a leadless pacemaker 600 in accordance with the present disclosure. Similar to the leadless pacemaker discussed in the context of FIGS. 1A-5C, the leadless pacemaker 600 may generally include each of a distal end 602, a proximal end 604, and a hermetically sealed housing 605 extending between the distal end 602 and the proximal end 604. The housing 605 generally stores battery material and electronic components for controlling and administering electrical impulses applied by the leadless pacemaker 600. The distal end 602 of the leadless pacemaker 600 includes a fixation mechanism 606, such as a helical screw, for fixing the leadless pacemaker 600 to an interior surface of the heart. The leadless pacemaker 600 may further include electrodes, such as electrodes 608, 609, for delivering electrical impulses to stimulate and pace the heart. The proximal end 604 of the leadless pacemaker 600 includes an attachment feature 610. The attachment feature 610 generally facilitates coupling of the leadless pacemaker 600 to a delivery/retrieval system, such as the delivery and retrieval systems described above in the context of FIGS. 1D-5C, and, in certain implementations, transfer of torque from the delivery/retrieval system to the leadless pacemaker 600.

In certain implementations of the attachment feature 610, torque can be transferred to the attachment feature at a location distal to the proximal end of the attachment feature. For example, with respect to FG. 22A below, the attachment feature 2200 can include torque features 2208a-2208c that engage with a mating torque transmission feature on a delivery or retrieval system to transmit torque applied through the system. It has been discovered, however, that positioning the torque transmission features distally can increase the likelihood that the delivery or retrieval system, e.g., the docking cap 418, will either not engage the torque features or will only partially engage the features. Accordingly, effective torque transmission may be impeded by distally located torque features.

Several of the embodiment described herein include an attachment feature 610 having a torque transmission feature located at a proximalmost location along the feature. For example, the attachment feature 610 can include a retrieval feature 612, which is also referred to herein as a "button." The button 612 can include a torque application point that is at a proximal end. In an embodiment, the torque application point is on the button itself, e.g., at a location that interferes with the docking cap 418. Accordingly, the interference between the docking cap 418 and the button 612 can transmit torque from a delivery or retrieval system to the attachment feature 610. To facilitate the interference, the button 612 can have a non-round profile. For example, a transverse perimeter extending around the button, as described further below, can be a non-round transverse perimeter. The term "non-round" can refer to any profile shape that is not circular. For example, the non-round transverse perimeter can have an oval shape, a polygonal shape, etc. The polygonal shape may be, for example, a triangle, square, pentagon, etc. In an embodiment, the polygonal shape is a normal polygon having sides of equal lengths. For example, the normal polygon may be an equilateral triangle. The non-round transverse perimeter provides a profile having localized regions of increased width or radial distance from the central axis of the attachment feature. For example, in the case of an equilateral triangle, the corners of the triangle provide maxima at which torque may be applied from the docking cap 418 to the button. The docking cap 418 can include a socket having an internal profile that is similarly shaped and sized, such that the docking cap 418 receives the button 612 in the socket. The mating surfaces of the proximally located retrieval feature 612 and the docking cap 418 facilitate effective torque transmission, even when the button is not fully seated within the socket of the docking cap 418.

The button 612 is coupled to the housing 605 by a rigid stem 614. In certain implementations, the button 612 and the rigid stem 614 are integrally formed with the housing 605. In other implementations, the button 612 and the rigid stem 614 may instead be part of a separate end cap that is separately formed form the housing 605 and then attached to the housing 605, such as by a laser welding process.

Figure 7C:
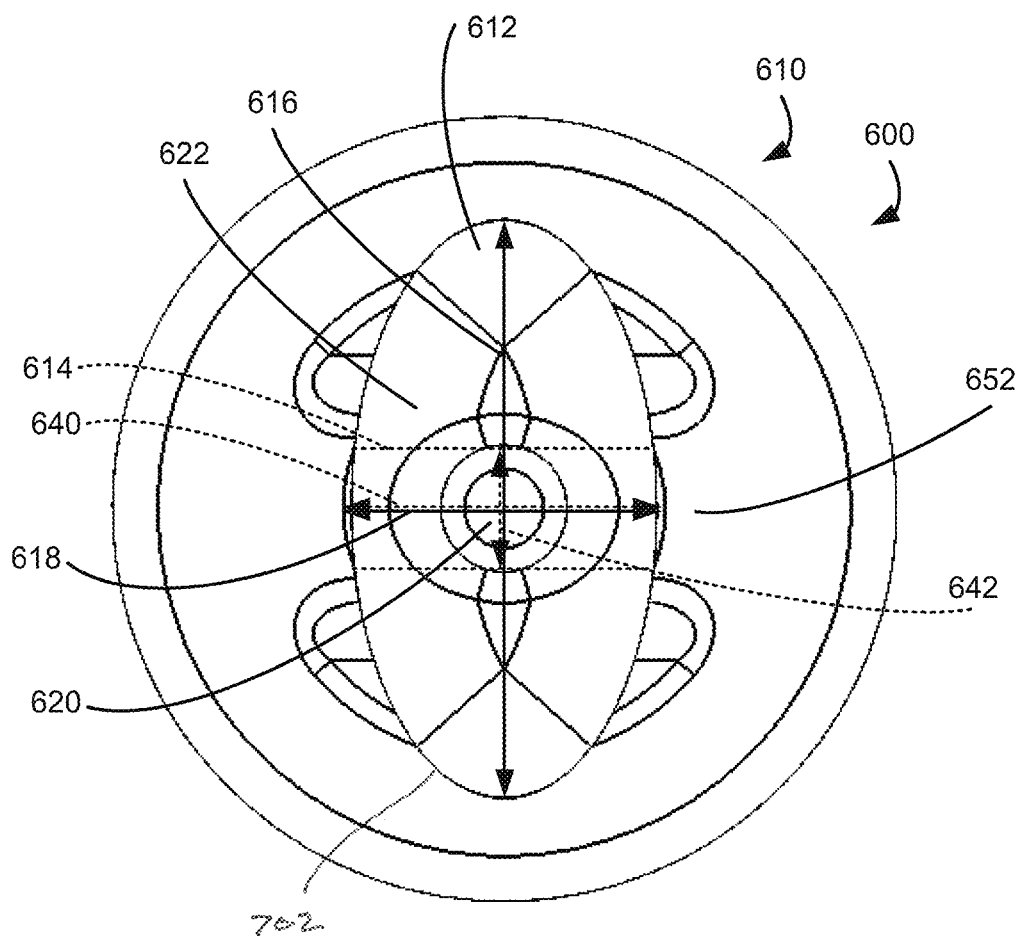
FIG. 7C is a proximal view of the attachment feature of FIGS. 7A-7B.

FIGS. 7A and 7B are side elevation views of the leadless pacemaker 600 and FIG. 7C is a proximal view of the leadless pacemaker 600, each of which are intended to illustrate additional aspects of the attachment feature 610 and its constituents. The button 612 of the leadless pacemaker 600 has a generally oval shape. As indicated in FIG. 7C, the oval shape may be defined by a major axis 616 and a minor axis 618. More particularly, when viewed along the longitudinal axis of the housing, a transverse perimeter 702 of the retrieval feature 612 can have a shape that is oval. The oval shape may be symmetric about one or more of the major axis 616 or the minor axis 618. As shown, the oval transverse perimeter 702 is elliptical and is symmetric about both the major axis 616 and the minor axis 618. In an embodiment, the transverse perimeter 702 is egg-shaped and is symmetric about only one of the major axis 616 and the minor axis 618. In certain implementations, the major axis 616 may be from and including 3 millimeters (0.12 inches) to and including 6 millimeters (0.24 inches) while the minor axis 618 may be from and including 2 millimeters (0.080 inches) to and including 3.5 millimeters (0.140 inches). The button 612 may further include a tether receptacle 620, which is described in more detail below in the context of FIGS. 17-20.

The button 612 may be shaped to minimize acute radii and the corresponding potential of such acute radii to catch and damage cardiac tissue. For example, as most clearly illustrated in FIG. 7A, the button 612 may include a proximal surface 622 that transitions into a distal surface 624 by a radiused transition 626, such that the button 612 has a pillow-top shape. In certain implementations, the radiused transition 626 may have a radius of curvature 628 from and including 0.01 millimeters (0.0004 inches) to and including 1.5 millimeters (0.060 inches) such that the transition between the proximal surface 622 and the distal surface 624 is sufficiently gradual to avoid acute and potentially traumatic radii. As further illustrated throughout FIGS. 7A-7C, other transitions between surfaces of the attachment feature 610 may also be radiused to ensure that the button 612 and the other components of the attachment 610 are generally atraumatic.

The distal surface 624 of the button 612 may also include a taper 634. As illustrated in FIG. 7A, the taper 634 may extend at an angle θ relative to a longitudinal axis 636 defined by the pacemaker 600. In certain implementations, the angle θ may be from and including 0 degrees to and including 45 degrees. For example, in one implementation, the angle θ may be approximately 25 degrees.

The stem 614 may have a substantially rectangular cross-section defined by each of a major stem axis 640 and a minor stem axis 642 (shown in FIG. 7C), the minor stem axis 642 being shorter than the major stem axis 640. For example, as described below, the stem 614 can have a transverse profile having an aspect ratio defined by the stem axes, and the aspect ratio can be greater than 1. Although a rectangular cross-section is primarily discussed here, other shapes having similar axes with differing dimensions may also be used. Moreover, as discussed later in this disclosure, the stem 614 may be formed of multiple "legs" that collectively define a rectangular or similar shape having each of a major and minor stem axis.

The retrieval feature may extend from a tapered body 652 extending from a proximal end of the housing 605. As shown in FIG. 7B, the tapered body 652 may have an angle α relative to the longitudinal axis 636 of the leadless pacemaker 600. In certain implementations, the angle α may be from and including 30 degrees to and including 90 degrees. For example, in one implementation, the angle α may be approximately 45 degrees. Notably, the tapered body 652 may, in certain implementations, blend into the stem 614 or at least a portion of the stem 614. For example, in FIG. 7B, the tapered body 652 is illustrated as blending into the short sides of the stem 614.

The various structures of the attachment feature 604 are generally adapted to facilitate capture of the stem 614 during retrieval operations and, more specifically, to direct a snare to a preferred snare location/orientation 630 (shown in FIG. 7A) about the stem 614 and to orient the leadless pacemaker 600 in a particular direction when captured. The various structures of the attachment feature 604 are further adapted to enable docking of the leadless pacemaker 600 with a docking cap and to facilitate torque transfer between the leadless pacemaker 600 and the docking cap during implantation or retrieval of the leadless pacemaker 600.

As previously discussed, the process of retrieving a leadless pacemaker in accordance with the present disclosure generally includes disposing a retrieval snare about the stem 614 (e.g., along the preferred snare location 630) and closing the snare about the stem 614, thereby providing a firm grasp on the leadless pacemaker 600. The leadless pacemaker 600 may then be drawn into a docking cap or similar component of a catheter-based retrieval system by the attachment feature 604. Once docked or otherwise disposed within the docking cap, torque may be applied to the leadless pacemaker 600, thereby unscrewing it or otherwise dislodging it from the cardiac tissue and enabling removal of the leadless pacemaker 600 from the heart.

The retrieval snare is generally adapted to extend and to be subsequently closed about the stem 614. However, under certain circumstances, the snare may instead be disposed about a lateral portion of the button 612 (i.e., substantially parallel to the longitudinal axis 636, as indicated by the snare location 632 in FIG. 7A) and closed about the lateral portion of the button 612. In certain conventional designs, the closure of the snare about the lateral portion of the button may result in sufficient grasp on the button 612 to at least partially detach the leadless pacemaker from the heart. Nevertheless such retention is tenuous as the snare is generally prone to slip off of the button 612, resulting in spontaneous release of the leadless pacemaker 600. Notably, such a spontaneous release may occur when the leadless pacemaker 600 is partially or fully detached from the cardiac tissue into which it was implanted, potentially leading to the leadless pacemaker 600 becoming embolic or otherwise freed within the heart.

Referring to FIG. 7A, the taper 634 of the button 612 addresses this issue by significantly reducing the likelihood of the button 612 being improperly retained by the snare. Should the snare extend about a lateral portion of the button 612 (such as indicated by the snare location 632) as opposed to around the stem 614, the taper 634 in combination with the radiused transition 626 prevents the snare from retaining the button 612 by causing the snare to slip off the button 612 more readily. As a result, the taper 634 significantly reduces the likelihood that sufficient retention by the snare can be achieved for unscrewing the leadless pacemaker 600 from the implantation location tissue.

Further guidance of the snare about the stem 614 may also be provided in certain implementations by the tapered body 652 (illustrated in FIGS. 7A-7B) that extends from the housing 605 to the stem 614. More specifically, in situations where the snare is disposed about the tapered body 652, closing the snare causes the snare to slide proximally until it reaches the stem 614. Once it reaches the stem 614, further closing of the snare causes the snare to close about the stem 614.

Figure 8A:
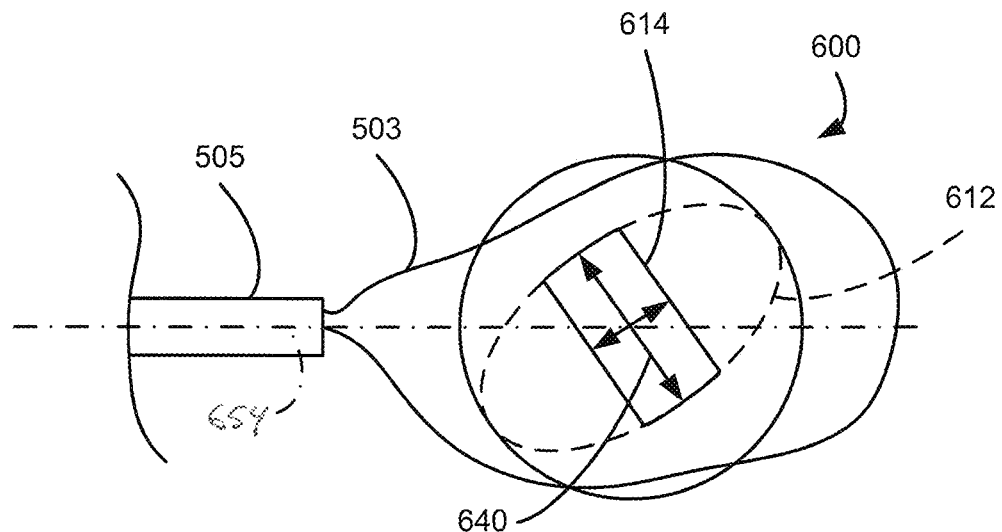
FIGS. 8A-8B are proximal views of the attachment feature of FIGS. 7A-7B during capture using a retrieval snare.
Figure 8B:
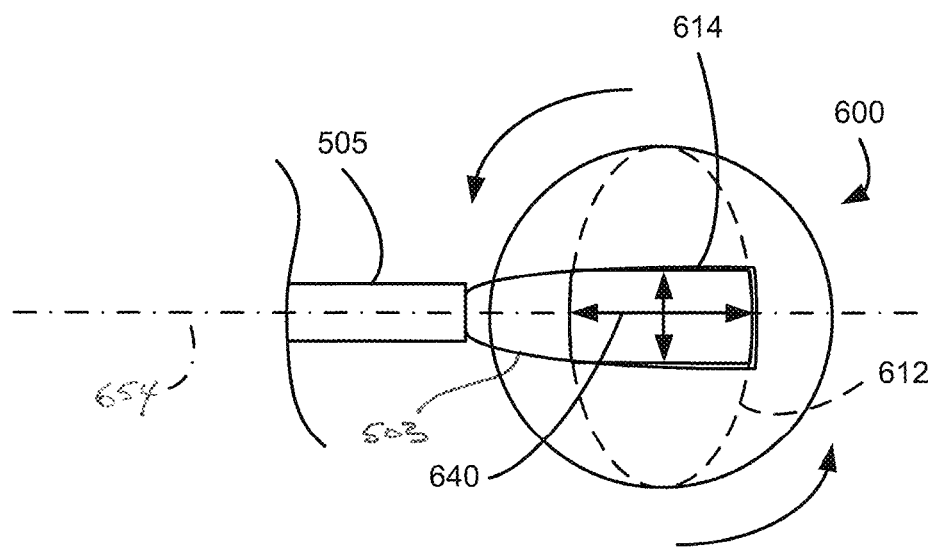

The shape of the stem 614 further facilitates consistent orientation of the leadless pacemaker 600 during retrieval. For example, the rectangular cross-section of the stem 614 generally causes rotation of the leadless pacemaker 600 into a predetermined orientation as the snare is closed. FIGS. 8A and 8B are proximal views of the leadless pacemaker 600 illustrating this concept. In particular, FIG. 8A is a proximal view of the leadless pacemaker 600 prior to closing of a snare 503 about the stem 614 of the leadless pacemaker 600. As shown in FIG. 8A, the orientation of the leadless pacemaker 600 and, in particular, the stem 614 is generally unknown at the time of retrieval and, in most cases, will be offset relative to a longitudinal axis 654 of a snare locking sleeve 505 or similar structure from which the snare 503 extends. However, as illustrated by FIG. 8B, as the snare 503 is closed about the stem 614, the leadless pacemaker 600 may generally be caused to rotate such that the major stem axis 640 is substantially parallel or otherwise aligned with the longitudinal axis 654 of the snare locking sleeve 505. Accordingly, the rectangular shape of the stem 614 facilitates the leadless pacemaker 600 being in a predictable orientation following closure of the snare 503.

An aspect ratio of a transverse profile of the stem 614 can be configured to align the leadless pacemaker 600 during capture, as illustrated with respect to FIGS. 8A-8B. For example, the transverse profile, which can be an annular profile having a central lumen in communication with the tether receptacle 620, can have the aspect ratio defined by a ratio between the major stem axis 640 and the minor stem axis 642. More particularly, the rectangular annulus can have a major width along the major stem axis 640 and a minor width along the minor stem axis 642. A ratio of the major width to the minor width can define the aspect ratio. In an embodiment, the aspect ratio of the major width to the minor width is greater than 1. That is, the major width may greater than the minor width. The higher the aspect ratio, the more likely that the rectangular transverse profile will align the leadless pacemaker 600 during capture. Accordingly, the aspect ratio can be higher than 1.2, e.g., 1.4 or more. In an embodiment, the aspect ratio is 2 or more.

In an embodiment, the major axes and/or minor axes of the stem 614 and the button 612 may be oriented with respect to each other in a predetermined manner. By way of example, the major axis 616 of the button 612 can be orthogonal to the major stem axis 640 of the stem 614. Here, the term "orthogonal" refers to the axes being orthogonal with respect to one another in a top view, as illustrated in FIG. 7C. As described above, the major stem axis 640 can align with the snare locking sleeve 505 during device capture, and thus, the major axis 616 of the button 612 can orient orthogonal to the longitudinal axis 654 during device capture. Accordingly, the aspect ratio of the stem can bias the attachment feature 600 into a configuration in which the snare loop is beneath the distal surfaces 624 of the button 612. The button 612 is unlikely to slip out of the snare loop when the snare is located beneath the ledges of the button 612. Self-orientation of the button 612 in this manner can orient the button 612 such that it retracts into and fills the space of the docking cap 504. This retrieval procedure is described further below with respect to FIGS. 9A-9C. Accordingly, the combined structure of the stem 614 and the button 612 allows the leadless pacemaker to be captured and retracted into the docking cap 504 with a reduced likelihood of either binding or catching on the docking cap 504, or slipping out of the snare.

FIGS. 9A-9C illustrate the general process of snaring the button 612 of the leadless pacemaker 600. In FIG. 9A, the stem 614 of the attachment feature 604 has been looped by a snare 503 extending from a snare locking sleeve 505 that in turn extends through a docking cap 504. As shown in FIG. 9A, at the time of initial capture, the snare locking sleeve 505, docking cap 504, and similar components may be aligned along a first axis 902 and the leadless pacemaker 600 may be aligned along a second axis 904. As the snare 503 is closed around the stem 614, the snare locking sleeve 505 and docking cap 504 align with the leadless pacemaker 600 such that the first axis 902 and the second axis 904 are substantially collinear, as shown in FIG. 9B. As the snare is further closed, the leadless pacemaker 600 is drawn into the docking cap 504.

As further shown in FIG. 9B and FIG. 9C (which is a proximal view of the leadless pacemaker 600), the snare 503 may have to bend around the button 612 as the snare 503 is closed and the leadless pacemaker 600 is drawn into the docking cap 504. Such bending at least partially displaces the snare 503 away from the axes 902, 904 such that as tension is applied to the snare 503 to draw the leadless pacemaker 600 into the docking cap 504, the force applied to the leadless pacemaker 600 may include a component perpendicular to the axes 902, 904. This force component may cause the leadless pacemaker 600 to twist and become misaligned with the docking cap 504. Accordingly, in certain implementations, it may be advantageous to improve the alignment of the snare 503 with the axes 902, 904 when the snare 503 has been closed around the stem 614 of the leadless pacemaker 600.

Figure 10A:
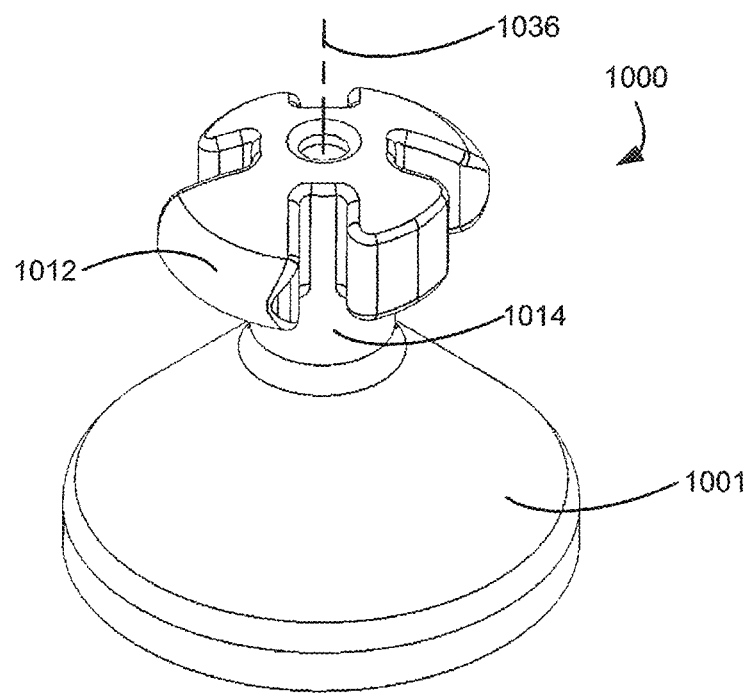
FIGS. 10A-10B are an isometric view and a proximal view, respectively, of a second attachment feature.
Figure 10B:
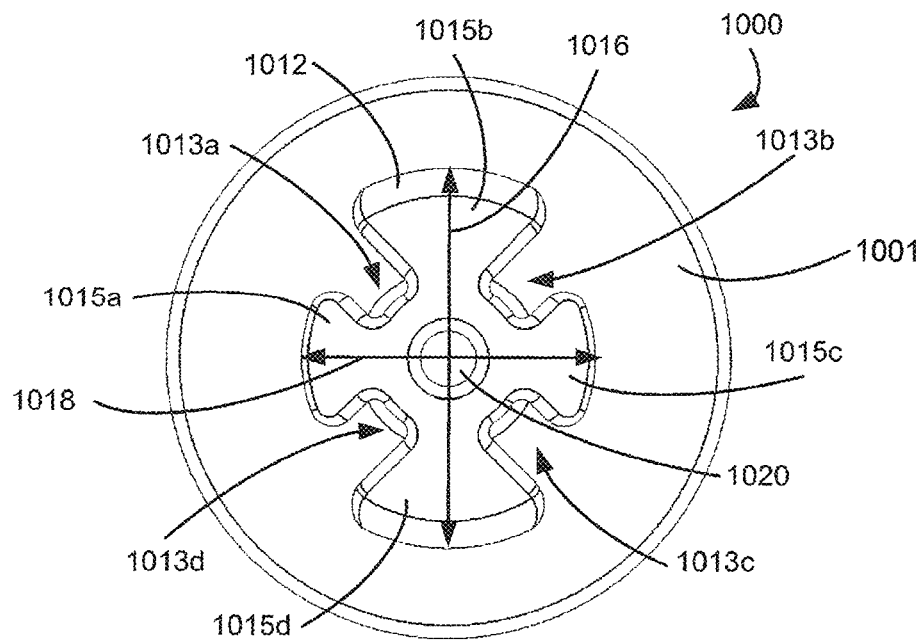

In light of the foregoing, leadless pacemakers according to the present disclosure may include retrieval features (such as buttons) that include cutouts or similar voids adapted to improve alignment of the snare and leadless pacemaker during retrieval of the leadless pacemaker. FIGS. 10A-10B illustrate a first example implementation of such retrieval features. FIG. 10A illustrates an isometric view of an attachment feature 1000 and FIG. 10B is a proximal view of the attachment feature 1000. The attachment feature 1000 generally includes a retrieval feature or button 1012 coupled to an attachment feature body 1001 by a rigid stem 1014. The attachment feature 1000 may be coupled to a housing of a leadless pacemaker, such as by laser welding or another heat joining process, or may be integrally formed with the housing of the leadless pacemaker.

As illustrated in FIGS. 10A and 10B, the attachment feature 1000 generally includes a retrieval feature 1012 or button. The button 1012 has a generally oval perimeter shape that may be defined by a major axis 1016 and a minor axis 1018. The button 612 may further include a tether receptacle 1020. The button 1012 may further include cutouts or voids 1013a-1013d that form notches or otherwise divide the button 1012 into lobes 1015a-1015d. The cutouts/voids 1013a-1013d are generally extend toward a longitudinal axis 1036 of the attachment feature 1000 and are generally sized to receive a retrieval snare 503.

Figure 11B:
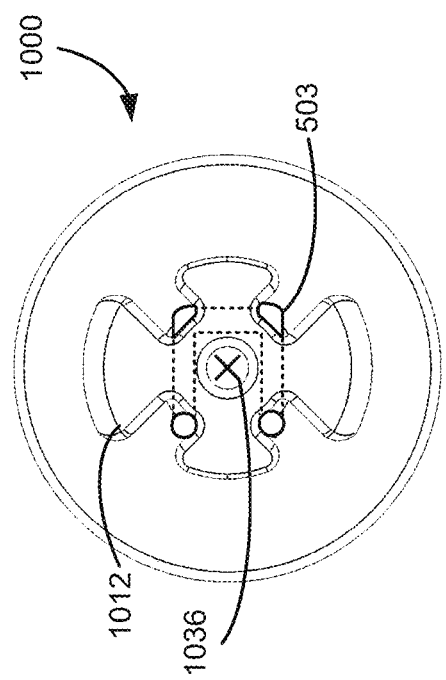
FIGS. 11A-11B show various views of a retrieval system and a leadless pacemaker including the attachment feature of FIGS. 10A-10B during retrieval of the leadless pacemaker.
Figure 11A:
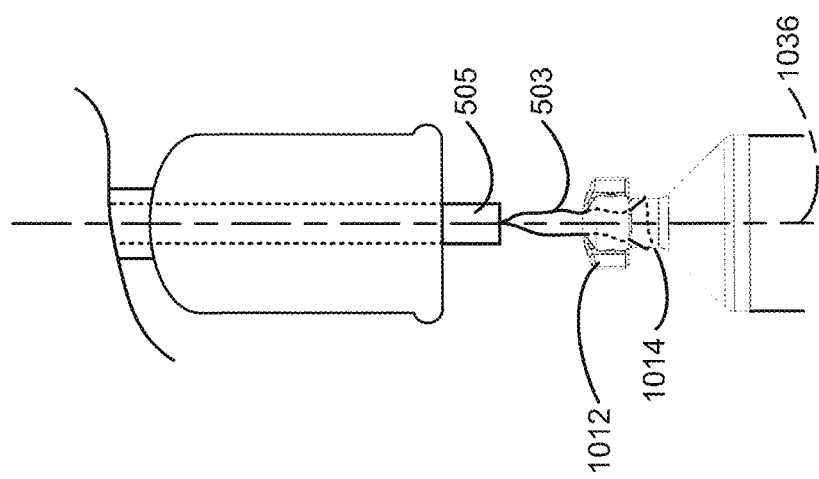

FIG. 11A is a side view of the attachment feature 1000 following capture by a retrieval snare 503. FIG. 11B is a proximal view of the attachment feature 1000 including the retrieval snare 503. As illustrated in FIGS. 11A and 11B, during retrieval the snare 503 slips into the cutouts/voids 1013a-1013d (shown in FIG. 10B) and, as a result, is positioned nearer the longitudinal axis 1036 of the attachment feature 1000 as compared to a button of similar proportions (such as the button 612 of the leadless pacemaker 600 illustrated in FIGS. 6-9C) having a transverse perimeter that is a fully oval shape. In this orientation, the bending of the snare 503 about the button 1012 is minimized, thereby reducing the lateral forces developed on the attachment feature 1000 when tension is applied to the snare 503.

Figure 12A:
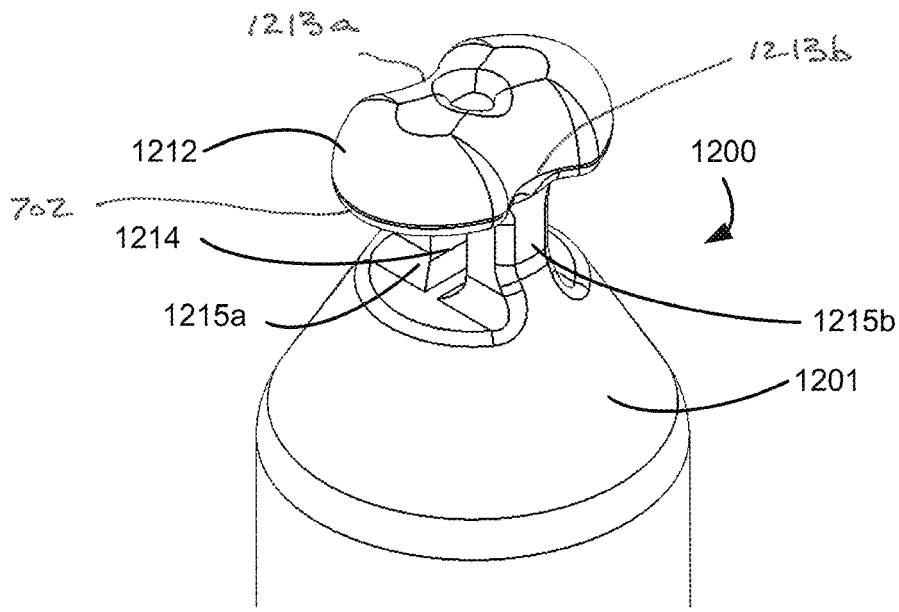
FIGS. 12A-12B are an isometric view and a proximal view, respectively, of a third attachment feature.
Figure 12B:
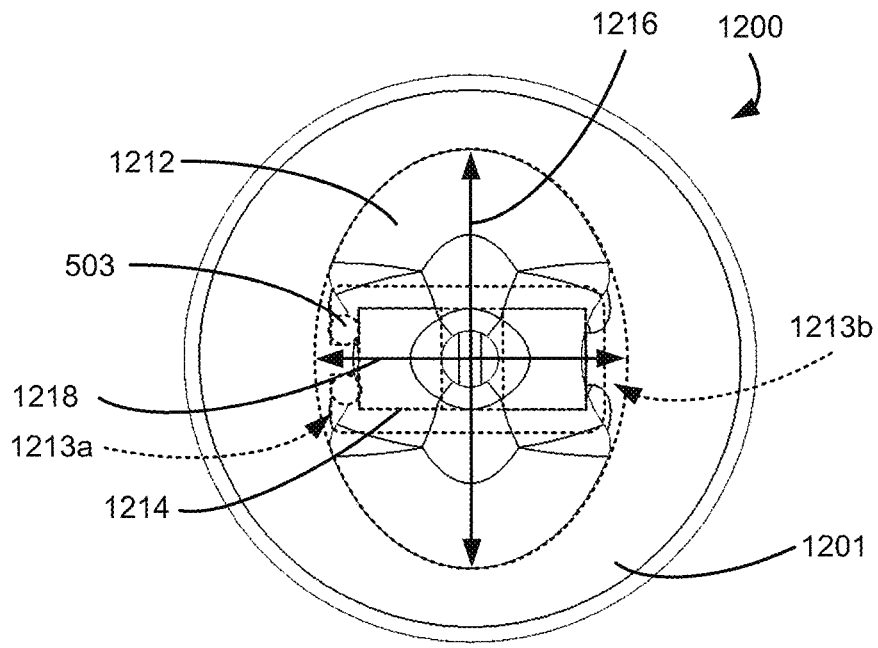

FIGS. 12A-12B are isometric and proximal views of a second attachment feature 1200 that generally includes a retrieval feature 1212 or button and a rigid stem 1214 coupled to a distal side 1201 of the button 1212. The button 1212 has a transverse perimeter 702 that is generally oval-shaped, but for a pair of cutouts 1213a, 1213b (shown in FIG. 12B). The generally oval shape is defined by a major axis 1216 and a minor axis 1218, as illustrated in FIG. 12B. As illustrated in FIG. 12A, the rigid stem 1214 includes two adjacent posts 1215a, 1215b that collectively define a substantially rectangular cross-sectional area.

The pair of cutouts 1213a, 1213b are illustrated in FIGS. 12A-12B as rounded notches disposed on opposite sides of the button 1212 along the minor axis 1218. Notably, the minor axis 1218 further aligns with the rigid stem 1214 coupled to the button 1212. The rigid stem 1214 has a generally rectangular shape that helps achieve predetermined orientations of the leadless pacemaker during retrieval, as described in the context of FIGS. 8A-8B. By doing so, the shape of the rigid stem 1214 further ensures that both sides of the retrieval snare 503 (shown in FIG. 12B in dashed lines) will generally be disposed within one of the cutouts 1213a, 1213b.

The foregoing examples of attachment features generally include cutouts or voids that define lobes of a button or similar retrieval feature. The cutouts/voids improve alignment of the retrieval snare with the attachment feature during the retrieval process. Although primarily discussed above in the context of substantially oval buttons/retrieval features, other shapes are possible.

Figure 13A:
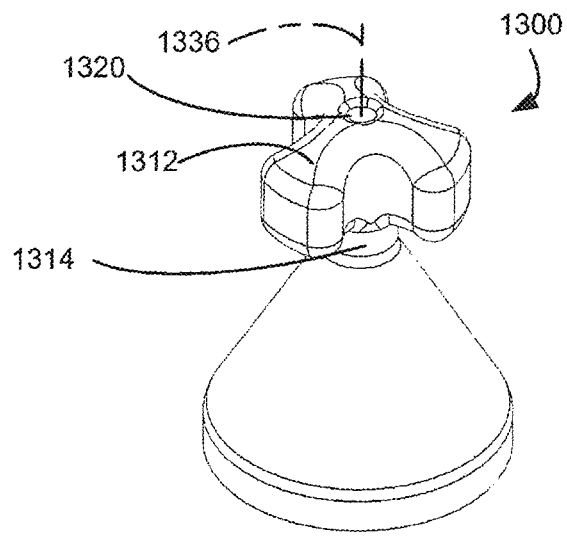
FIGS. 13A-13B are an isometric view and a proximal view, respectively, of a fourth attachment feature.
Figure 13B:
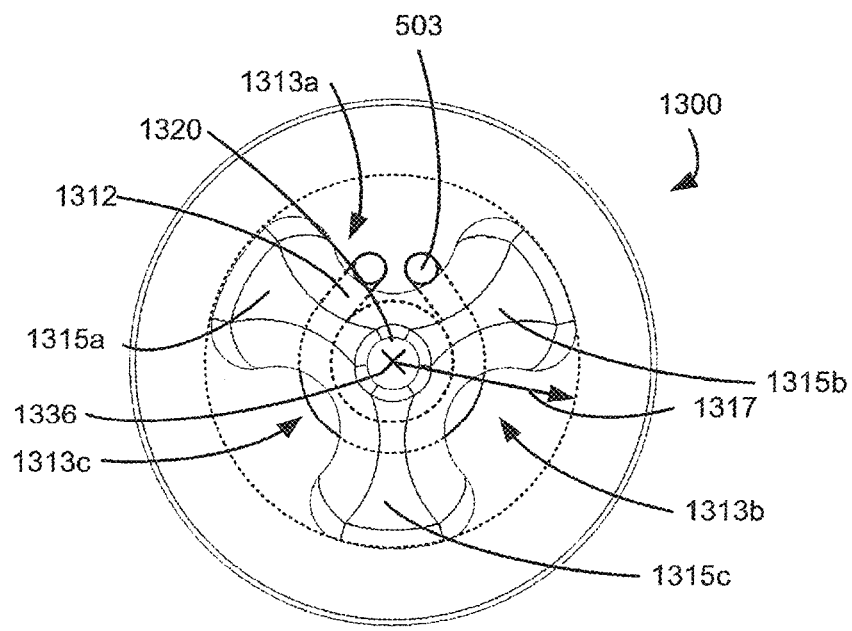

FIGS. 13A-13B are isometric and proximal views of a third attachment feature 1300, which includes a retrieval feature 1312 disposed on a proximal end of a rigid stem 1314. In contrast to the oval buttons of FIGS. 10A-12B, the retrieval feature 1312 is instead of a lobed design in which the retrieval feature 1312 includes three lobes 1315a-1315c. In general, the lobes 1315a-1315c are rotationally symmetric and extend outward to a common radius 1317. Accordingly, between each pair of the lobes 1315a-1315c, a corresponding void/cutout 1313a-1313c is defined. The attachment feature 1300 may further include a receptacle 1320 shaped to receive tethers or similar retention mechanisms of a delivery/retrieval system.

FIG. 13B further includes a snare 503 as may be disposed about the retrieval feature 1312 during retrieval of a leadless pacemaker including the attachment feature 1300. As shown, during retrieval the snare 503 generally wraps about the rigid stem 1314. Because of the lobed design of the retrieval feature 1312, each end of the snare 503 slips into one of the voids 1313a-1313c. In certain cases, both ends of the snare 503 may slip into the same void. As a result of being disposed within the voids 1313a-1313c, the snare is maintained relatively close to a longitudinal axis 1336 of the attachment feature 1300.

Figure 14A:
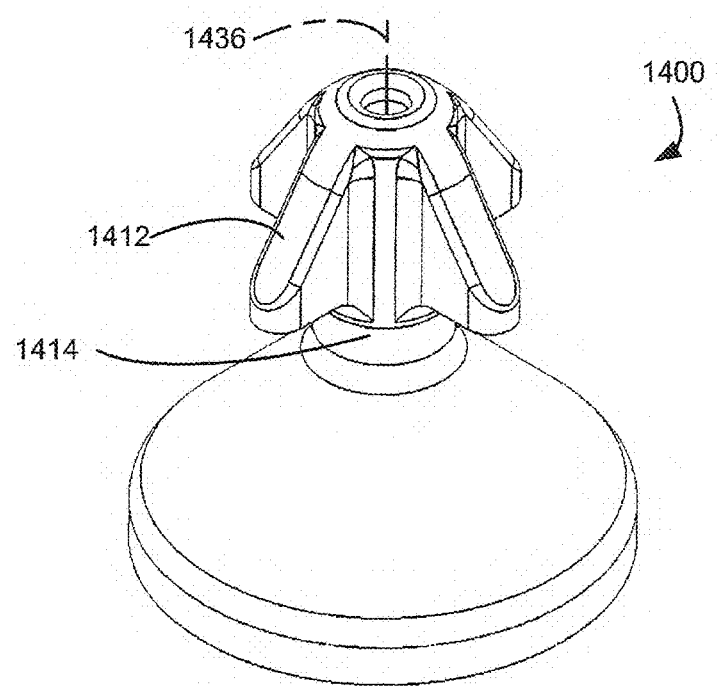
FIGS. 14A-14B are an isometric view and a proximal view, respectively, of a fifth attachment feature.
Figure 14B:
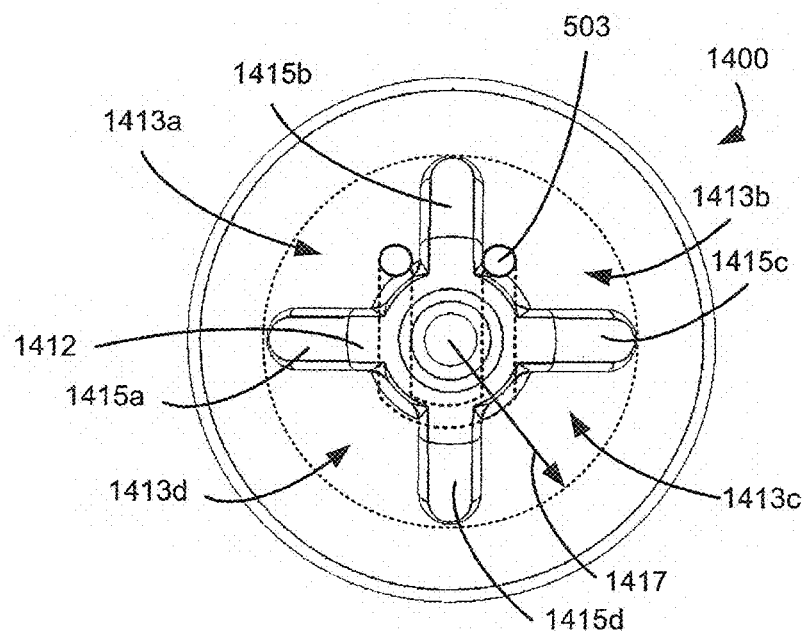

FIGS. 14A-14B are isometric and proximal views of a fourth attachment feature 1400, which includes a retrieval feature 1412 disposed on a proximal end of a rigid stem 1414. In contrast to the oval buttons of FIGS. 10A-12B, the retrieval feature 1412 is instead a lobed design in which the retrieval feature 1412 includes four lobes 1415a-1415d arranged in a harpoon shape. In general, the lobes 1415a-1415d are rotationally symmetric and extend outward to a common radius 1417. Accordingly, between each pair of the lobes 1415a-1415d, a corresponding void/cutout 1413a-1413d is defined.

FIG. 14B further includes a snare 503 as may be disposed about the retrieval feature 1412 during retrieval of a leadless pacemaker including the attachment feature 1400. As shown, during retrieval the snare 503 generally wraps about the rigid stem 1414 and each end of the snare 503 slips into one of the voids 1413a-1413d. As a result, the snare 503 is maintained in proximity to a longitudinal axis 1436 of the attachment feature 1400.

Notably, the lobes 1415A-1415D do not have the bulbous or otherwise curved profiles of previously discussed retrieval features and instead are substantially straight. In light of this, the terms "lobe" and "lobes" as used herein are not intended to be limited to structures having substantially curved cross-sectional profiles or, more generally, any specific cross-sectional shape. Rather, a lobe, as used herein, may be considered any structure of the retrieval feature that extends radially outward and is adapted to position a retrieval snare in proximity to the longitudinal axis of the attachment feature.

Figure 15:
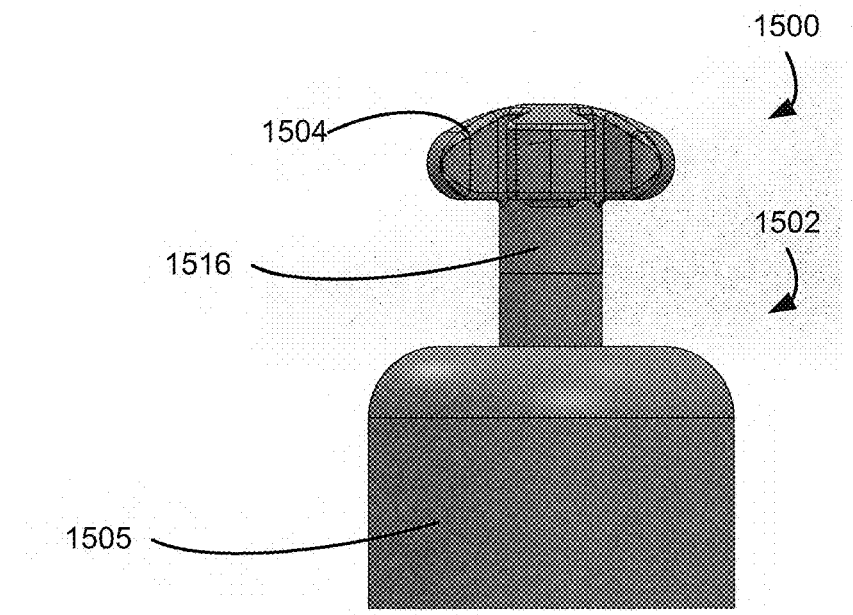
FIG. 15 is a side elevation view of a sixth attachment feature including a one-piece rigid stem.
Figures 16A, 16B:
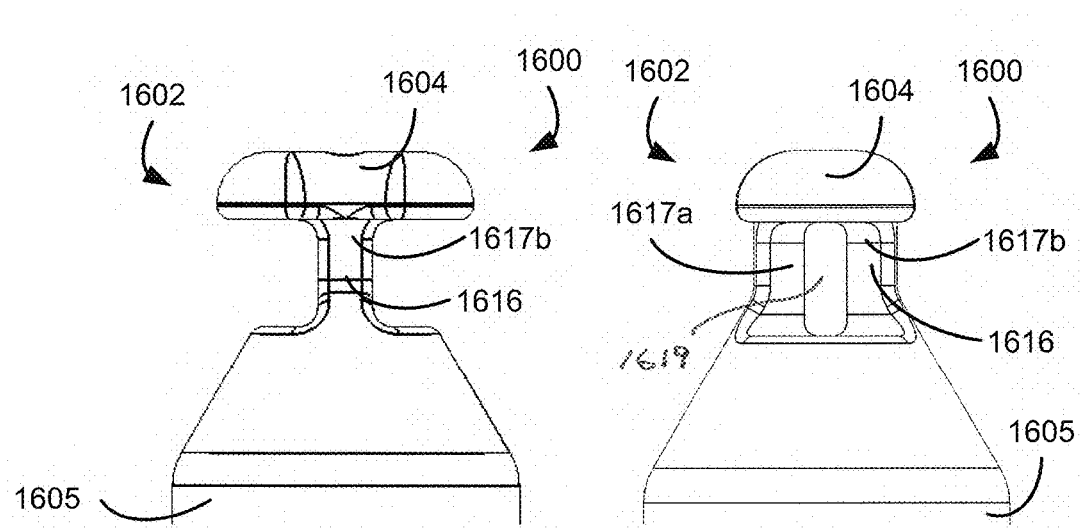
FIGS. 16A-16B are side elevation views of a seventh attachment feature including a two-piece rigid stem.

Other embodiments of leadless pacemakers and, in particular, attachment features of such leadless pacemakers may include other design variations. For example, FIGS. 15-16B illustrate various embodiments of a rigid stem disposed between the retrieval feature/button and the leadless pacemaker housing. The various rigid stems may be used instead of the rigid stem, e.g., 614.

As previously discussed in the context of FIGS. 6-8B, the rigid stem may be a single post having a rectangular cross-section. However, other cross-sectional shapes may be used and implementations of the present disclosure are not limited to any particular cross-sectional shape. For example, FIG. 15 is a side view of a proximal end of a leadless pacemaker 1500 including an attachment feature 1502 coupled to a housing 1505. The attachment feature 1502 further includes a retrieval feature 1504 coupled to a rigid stem 1516 extending between the housing 1505 and the retrieval feature 1504. As shown in FIG. 15, the rigid stem 1516 is a single post having a circular cross-section.

In other implementations, the rigid stem extending between the housing and the retrieval feature may include multiple posts or segments. For example, FIGS. 16A-16B are side views of a proximal end of a leadless pacemaker 1600 including an attachment feature 1602 coupled to a housing 1605. The attachment feature 1602 further includes a retrieval feature 1604 coupled to a rigid stem 1616 extending between the housing 1605 and the retrieval feature 1604. As shown in FIG. 16B, the rigid stem 1616 includes each of a first post 1617a and a second post 1617b offset from the first post 1617a to define a gap 1619. Notably, the first post 1617a and the second post 1617b collectively define a rectangular or other oblong profile to encourage consistent orientation during retrieval, similar to the rectangular rigid stem 614 described in FIGS. 8A-8B.

As previously discussed in the context of FIGS. 4A-4F, delivery of a leadless pacemaker in accordance with this disclosure may include the use of tethers that are used to capture and retain the leadless pacemaker relative to a docking cap or similar component of a catheter-based or similar delivery system. In particular, the tethers are designed such that in a first configuration the tethers may be inserted into a tether receptacle or similar structure of the attachment feature of the leadless pacemaker. Once inserted into the tether receptacle, the tethers are adjusted into a second configuration such that the tethers are unable to be removed from the attachment feature, thereby enabling the tethers to be used to retain the leadless pacemaker within the docking cap. This concept is further illustrated in FIGS. 17-20.

Figure 17:
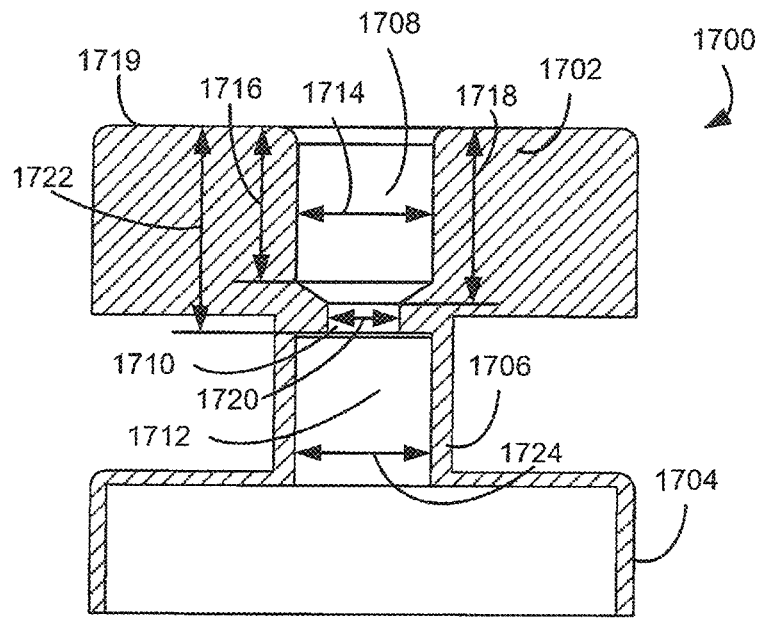
FIG. 17 is a cross-sectional view of an eighth attachment feature illustrating internal cavities for retaining tethers of a delivery/retrieval system.

FIG. 17 is a cross-sectional view of an attachment feature 1700 adapted to receive a tether of a catheter-based delivery system. The attachment feature 1700 generally includes a retrieval feature or button 1702 a body 1704 and a rigid stem 1706 coupling the button 1702 to the body 1704. In the example implementation of FIG. 17, the rigid stem 1706 is a single piece stem. The attachment feature 1700 may include a series of cavities adapted to receive and retain tethers of a delivery system. In general, the cavities include a lead-in bore 1708, a constriction bore 1710, and a retention bore 1712.

The various cavities may have predetermined dimensions to facilitate insertion and retention of tethers. For example, in certain implementations the lead-in bore 1708 may have a diameter 1714 from and including 0.5 millimeters (0.020 inches) to and including 1.5 millimeters (0.060 inches) and a depth 1716 from and including 0.01 millimeters (0.0004 inches) to and including 2 millimeters (0.080 inches). The constriction bore 1710 is generally disposed a distance 1718 from a proximal face 1719 of the attachment feature 1700 and has a diameter 1720. In certain implementations, the predetermined distance from the proximal face 1719 may be from and including 0.01 millimeters (0.0004 inches) to and including 2 millimeters (0.080 inches) and the diameter 1720 may be from and including 0.25 millimeters (0.010 inches) to and including 1 millimeter (0.040 inches). The retention bore 1712 may similarly be disposed a distance 1722 from the proximal face 1719 and may have a diameter 1724. In certain implementations, the distance 1722 from the proximal face 1719 to the retention bore 1712 may be from and including 0.1 millimeters (0.004 inches) to and including 2 millimeters (0.080 inches) and the diameter 1724 of the retention bore 1712 may be from and including 0.5 millimeters (0.020 inches) to and including 1.5 millimeters (0.060 inches).

Figure 18:
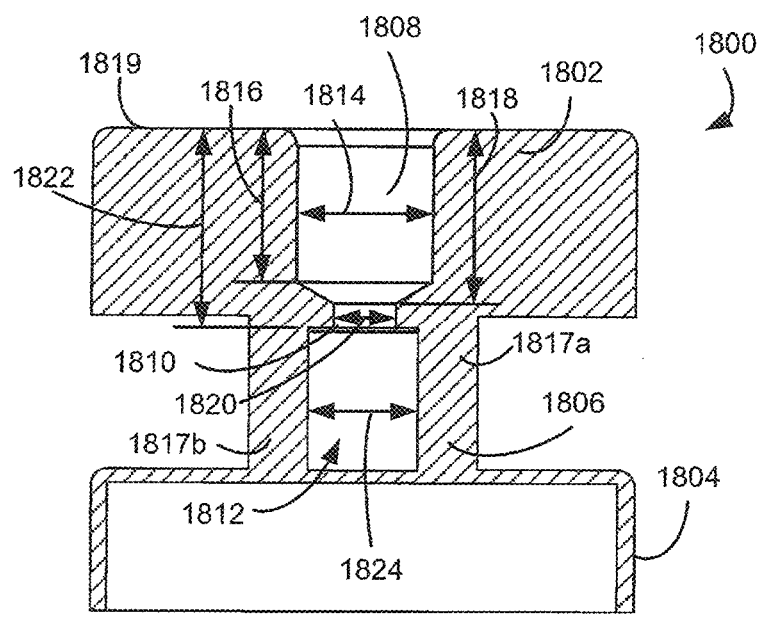
FIG. 18 is a cross-sectional view of a ninth attachment feature illustrating internal cavities for retaining tethers of a delivery/retrieval system.

FIG. 18 is a cross-sectional view of another attachment feature 1800 adapted to receive a tether of a catheter-based delivery system. The attachment feature 1800 generally includes a retrieval feature or button 1802 a body 1804 and a rigid stem 1806 coupling the button 1802 to the body 1804. In the example implementation of FIG. 18, the rigid stem 1806 includes two separate and offset posts 1817a, 1817b. The attachment feature 1800 may include a series of cavities adapted to receive and retain tethers of a delivery system. In general, the cavities include a lead-in bore 1808 and a constriction bore 1810. Instead of the retention bore 1712 illustrated in FIG. 17, the posts 1817A, 1817B of the attachment feature 1800 define a gap 1812 within which the tethers may be retained.

Similar to the attachment feature 1700 of FIG. 17, the various features of the attachment feature 1800 may have predetermined dimensions to facilitate insertion and retention of tethers. For example, in certain implementations the lead-in bore 1808 may have a diameter 1814 from and including 0.5 millimeters (0.020 inches) to and including 1.5 millimeters (0.060 inches) and a depth 1816 from and including 0.01 millimeters (0.0004 inches) to and including 2 millimeters (0.080 inches). The constriction bore 1810 is generally disposed a distance 1818 from a proximal face 1819 of the attachment feature 1800 and has a diameter 1820. In certain implementations, the predetermined distance from the proximal face 1819 may be from and including 0.1 millimeters (0.004 inches) to and including 2 millimeters (0.080 inches) and the diameter 1820 may be from and including 0.5 millimeters (0.020 inches) to and including 1.5 millimeters (0.060 inches). Similar to the retention bore 1712, the gap 1812 between the posts 1817a, 1817b of the attachment feature 1800 may similarly be disposed a distance 1822 from the proximal face 1819 and may have a width 1824. In certain implementations, the distance 1822 from the proximal face 1819 to the gap 1812 may be from and including 0.01 millimeters (0.0004 inches) to and including 2 millimeters (0.080 inches) and the width 1824 of the gap 1812 may be from and including 0.5 millimeters (0.020 inches) to and including 1.5 millimeters (0.060 inches).

Figure 19A:
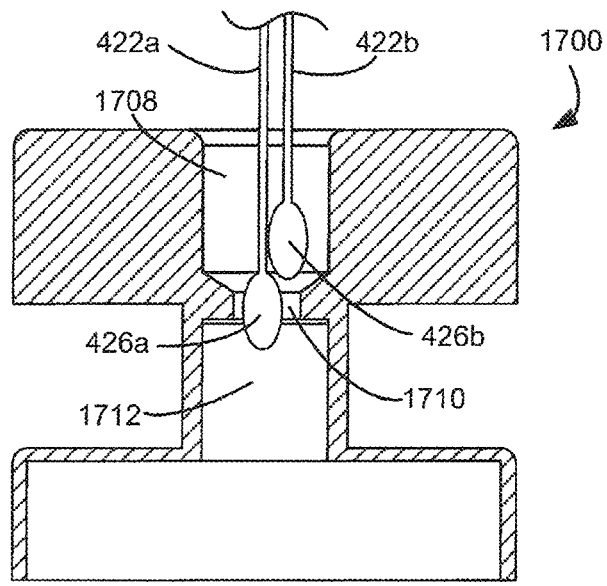
FIGS. 19A-19B are cross-sectional views of the attachment feature of FIG. 17 showing the insertion and retention of tethers within the attachment feature.
Figure 19B:
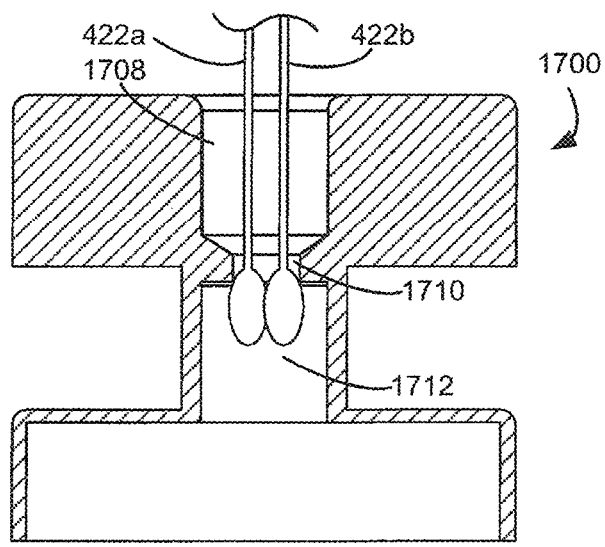

FIGS. 19A-19B illustrate the process of inserting and retaining tethers 422a, 422b in the attachment feature 1700 of FIG. 17. The tethers 422a, 422b can include wires, shafts, tubes, cords, ropes, strings, or other similar structures that can extend throughout a catheter shaft of a delivery system. The tethers 422a, 422b can also include distal features 426a, 426b, which in the illustrate example are in the form of elongated bulbs extending outwards from the tethers 422a, 422b. Generally, the distal features 426a, 426b have a cross-sectional diameter larger than the cross sectional diameter of the tethers 422a, 422b.

As shown in FIG. 19A, the distal features 426a may be advanced further than the distal feature 426b so that when the tethers 422a, 422b are pushed together during insertion of into the attachment feature 1700, the distal feature 422b general abuts the tether 422a. In such a configuration the width of the distal features 426a, 426b and the tethers 422a, 422b is generally less than the combined width of the distal features 426a. 426 combined and, in particular, less than the diameter of the constriction bore 1710. As a result the tethers 422a, 422b and their respective distal features 426a, 426b may be received in the lead-in bore 1708, passed through the constriction bore 1710, and ultimately into the retention bore 1712.

As illustrated in FIG. 19B, once the tethers 422a, 422b and their respective distal features 426a, 426b are inserted into the retention bore 1712, the distal features 426a, 426b may be shifted relative to each other such that they are substantially aligned and their combined width exceeds the diameter of the constriction bore 1710. In certain implementations, the tether 422a may be fixed while the tether 422b may be extended and retracted relative to the tether 422a, for example, by manipulation of a handle or similar device of the delivery system. When aligned, the distal features 426a, 426b interfere with the constriction bore 1710 and, in general, cannot be removed from the retention bore 1712, thereby retaining the attachment feature 1700 and the leadless pacemaker to which the attachment feature 1700 is coupled on the tethers 422a, 422b. Subsequent removal of the attachment feature 1700 from the tethers 422a, 422b may be achieved by shifting the distal features 426a, 426b relative to each other such that they are misaligned. Once misaligned, the distal features 426a, 426b may be slid through the constriction bore 1712 and out of the lead-in bore 1708, thereby releasing the attachment feature 1700 from the tethers 422a, 422b.

Figure 20:
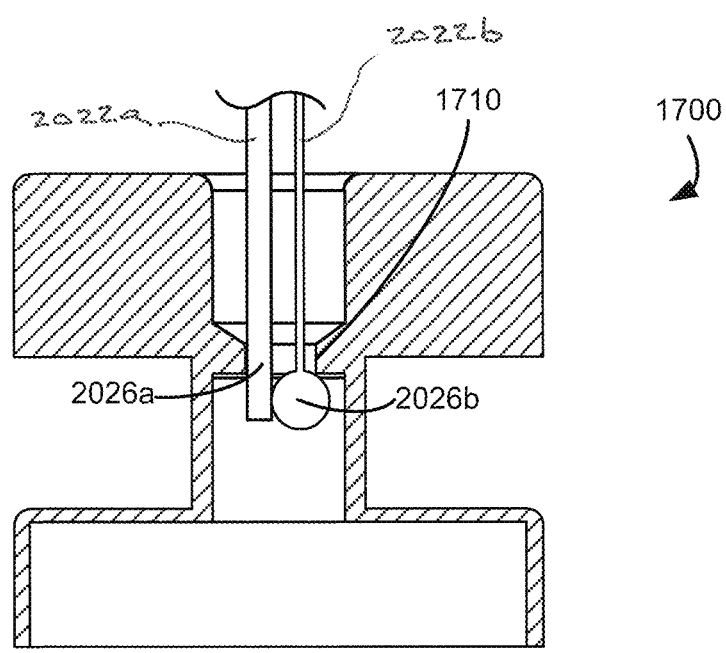
FIG. 20 is a cross-sectional view of the attachment feature of FIG. 17 showing retention of a pin-and-ball tether system within the attachment feature.

FIG. 20 is an alternative implementation in which a pair of tethers 2022a, 2022b are used to retain the attachment feature 1700. In contrast to the tethers 422a, 422b which each included bulbous distal features 426a, 426b, the tether 2022a includes a pin 2026a or similar straight distal feature and the tether 2022b includes a ball 2026b or similarly-shaped distal feature. Similar to the example illustrated in FIGS. 19A-19B, the pin 2026a and ball 2026b are sized such that when disposed adjacent to each other, the combined diameter of the pin 2026a and the ball 2026b exceed the diameter of the constriction bore 1710. However, the pin 2026a and the ball 2026b are movable relative to each other such that the pin 2026a and the ball 2026b may be misaligned. When misaligned, the maximum width between portions of the tethers 2022a, 2022b are less than the constriction bore 1710, such that each of the tethers 2022a, 2022b may be removed from the attachment feature 1700.

One advantage of the ball-and-pin arrangement of FIG. 20 is that it allows for a change in the tether removal process. Referring back to the example implementation illustrated in FIGS. 19A and 19B, the tethers 422a, 422b and their corresponding distal features 426a, 426b are generally removed by misaligning the distal features 426a, 426b and subsequently removing each of the tethers 422a, 422b. When misaligned, for example, the first distal feature 426a may be disposed in a more distal location as compared to the second distal feature 426b and, as a result, the second distal feature 426b is generally aligned with a portion of the first tether 422a. During removal of the second distal feature 426b from the attachment feature, the second distal feature 426b may become jammed by the first tether 422a, particularly if the second distal feature 426b is being removed when the leadless pacemaker is angularly offset relative to the docking cap/catheter from which the tethers extend. In contrast, the pin 2026a of the implementation illustrated in FIG. 20 may be fully retracted from the attachment feature 1700 prior to removal of the ball 2026b and without substantial interference between the pin 2026a and the tether 2022b including the ball 2026b. Notably, the use of a ball shape is intended merely as an example and other shapes are possible. For example, the spherical ball 2026b may instead be replaced with an elongated sphere, a "bullet" shape, or other shape having a transverse dimension, e.g., a diameter, greater than the tether 2022b.

As previously discussed in the context of FIG. 7A, retrieval features/buttons in accordance with the present disclosure may be specifically shaped to reduce the likelihood that the retrieval feature is improperly capture during retrieval using a snare. Such improper capture may occur, for example, when the snare extends about and captures a lobe of the retrieval feature as opposed to the rigid stem disposed between the retrieval feature and the leadless pacemaker housing. As previously noted, one approach to minimizing the likelihood that the retrieval feature is improperly captured is to have a tapered face on the distal side of the retrieval feature. By doing so, the snare is encouraged to slip off of the retrieval feature as it is closed if the snare is disposed about a lobe or similar structure of the retrieval feature. FIGS. 21A-22B illustrate alternative approaches to encourage release of a snare that is not disposed about the rigid stem.

Figures 21A, 21B:
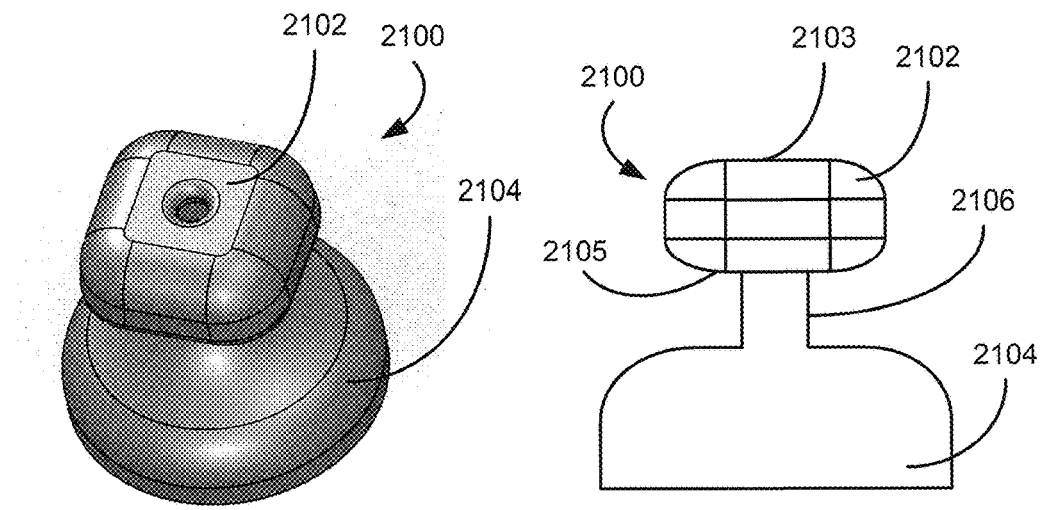
FIG. 21A-21B are isometric and side elevation views, respectively, of a tenth attachment feature.

FIGS. 21A and 21B are an isometric view and a side elevation view, respectively, of an attachment feature 2100 including a retrieval feature 2102 coupled to a base 2104 by a rigid stem 2106. As shown in FIG. 21A, the retrieval feature 2102 is generally in the form of a disc shape with rounded corners and edges. In particular, the retrieval feature 2102 is in the shape of a rounded square prism. The rounded corners and edges of the retrieval feature 2102 generally result in each of a proximal face 2103 and a distal face 2105 that are each at least partially curved/domed. Similar to the distal taper 634 discussed in the context of FIGS. 7A-7B, the rounded edges and corners and curved proximal and distal faces 2103, 2105 of the retrieval feature 2102 generally encourage spontaneous release of a retrieval snare if and when the snare is closed about the retrieval feature 2102 as opposed to around the rigid stem 2106.

Figures 22A, 22B:
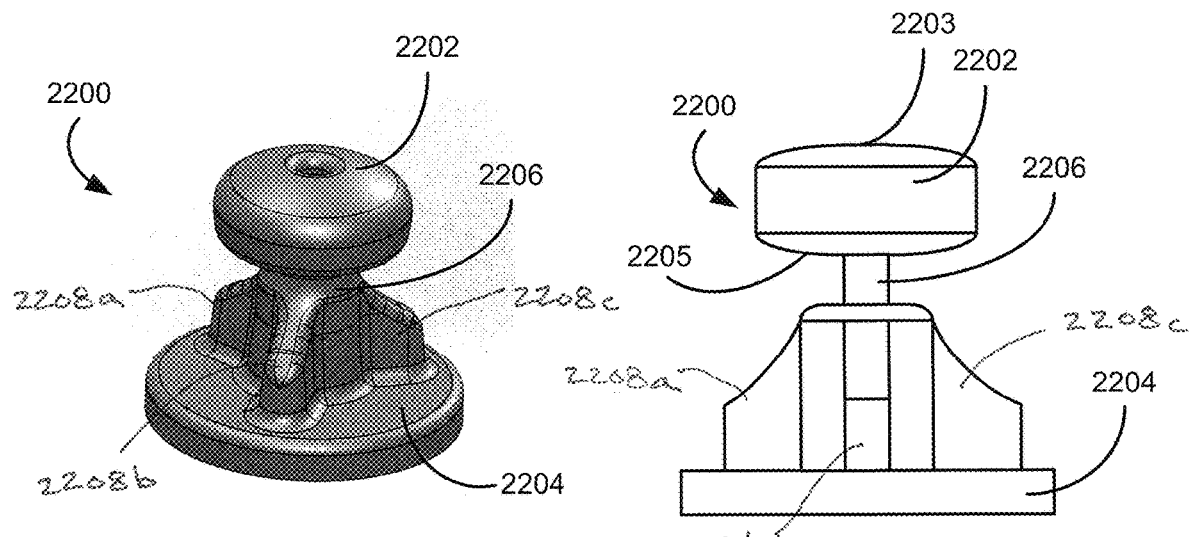
FIG. 22A-22B are isometric and side elevation views, respectively, of an eleventh attachment feature.

FIGS. 22A and 22B are an isometric view and a side elevation view, respectively, of another attachment feature 2200 including a retrieval feature 2202 coupled to a base 2204 by a rigid stem 2206. As shown in FIG. 22A, the retrieval feature 2202 is generally in the form of a circular disc with rounded edges. The rounded edges of the retrieval feature 2202 generally result in each of a proximal face 2203 and a distal face 2205 that are each at least partially curved/domed. The rounded edges and the curved proximal and distal faces 2203, 2205 of the retrieval feature 2202 generally encourage spontaneous release of a retrieval snare if and when the snare is closed about the retrieval feature as opposed to around the rigid stem 2206.

Notably, the circular shape of the retrieval feature 2202 may preclude the retrieval feature 2202 from acting as a torque feature that interacts with a torque key of a docking cap or similar component of a delivery system such that torque may be applied a leadless pacemaker coupled to the attachment feature 2200 (e.g., to facilitate dislodgement of the leadless pacemaker from cardiac tissue). Accordingly, the attachment features in accordance with this disclosure may include one or more torque features distributed about the attachment feature and that are shaped to contact and interact with the docking cap. For example, the attachment feature 2200 includes torque features 2208a-2208c in the form of gussets or webs extending from the rigid stem 2206 to a base structure 2208 of the attachment feature 2200.

Figure 40A:
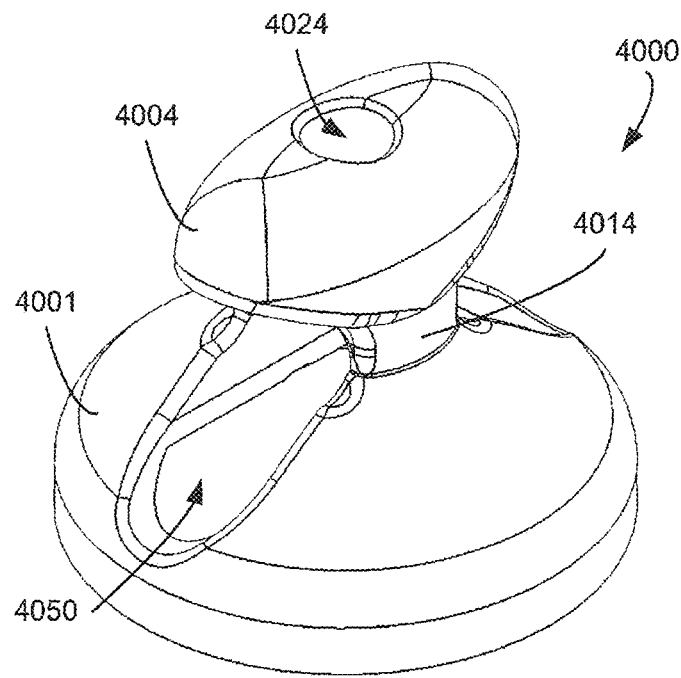
FIGS. 40A-40B are an isometric view and a proximal view, respectively, of a twelfth attachment feature.
Figure 40B:
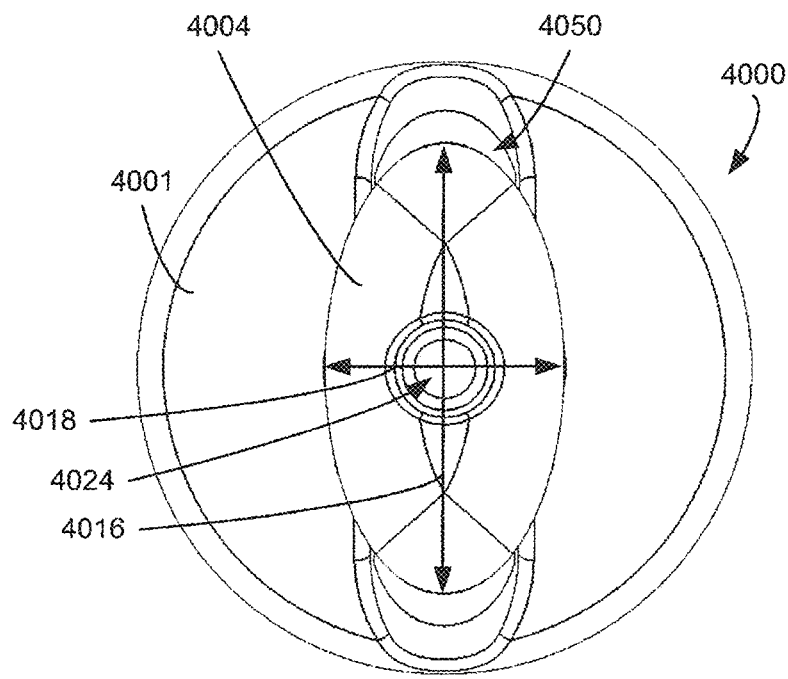
Figure 40C:
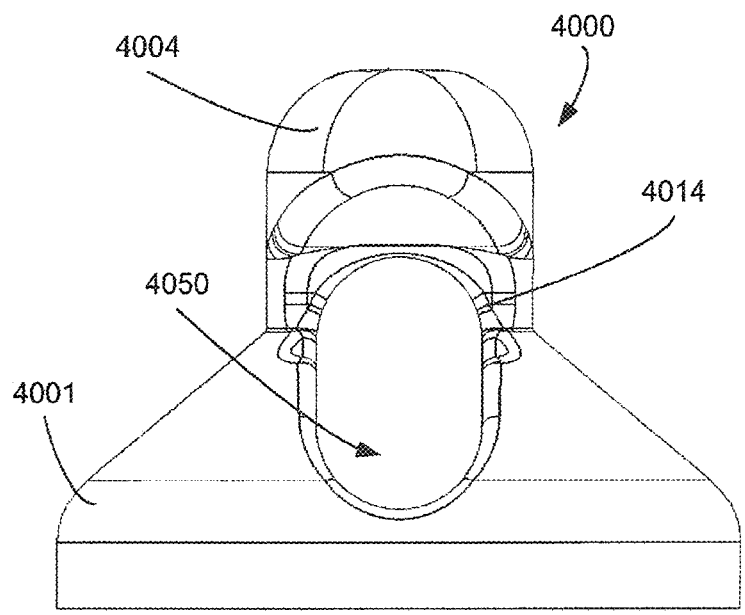
FIGS. 40C-40D are a side elevation view and a cross-sectional side view of the attachment feature of FIGS. 40A-40B.
Figure 40D:
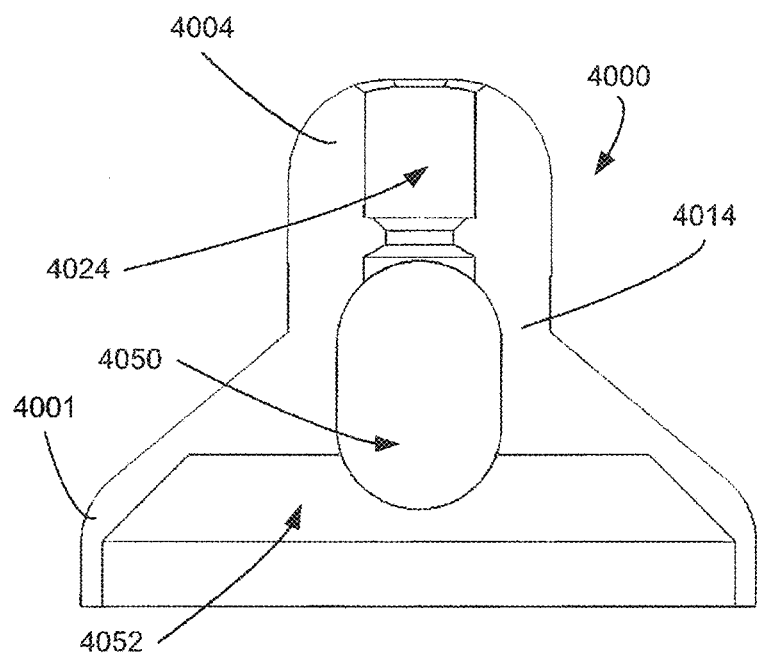

FIGS. 40A-40B are an isometric view and a proximal view, respectively of yet another attachment feature 4000 according to the present disclosure and that may be coupled to a housing of a leadless pacemaker. FIGS. 40C-40D are a side elevation view a side cross-sectional view of the attachment feature 4000.

With reference to FIGS. 40A-40D, the attachment feature 4000 includes an elliptical retrieval feature 4004 coupled to a base 4001 by a rigid stem 4014. The rigid stem 4014 may generally define a rectangular or other oblong profile extending along a minor axis 4018 of the retrieval feature 4004 (shown in FIG. 40B and which is perpendicular to a major axis 4016) to encourage consistent orientation during retrieval, similar to the rectangular rigid stem 614 described in FIGS. 8A-8B.

The attachment feature 4000 may optionally further include a slot 4050 extending parallel to the major axis 4016 to facilitate free passage of blood through and around the attachment feature 4000. Such free passage is particularly beneficial in avoiding clotting or similar buildup that may interfere with insertion or removal of tethers or similar devices into a tether hole 4024 defined through the retrieval feature 4004. As illustrated in FIG. 40D, the slot 4050 may extend through the base 4001 such that it is in communication with an internal volume 4052 of the base 4001. In certain implementations, the slot 4050 may extend substantially in the proximal direction such that the rigid stem 4014 is substantially divided into separate posts, such as in the attachment feature 1600 of FIGS. 16A-16B.

Figure 41A:
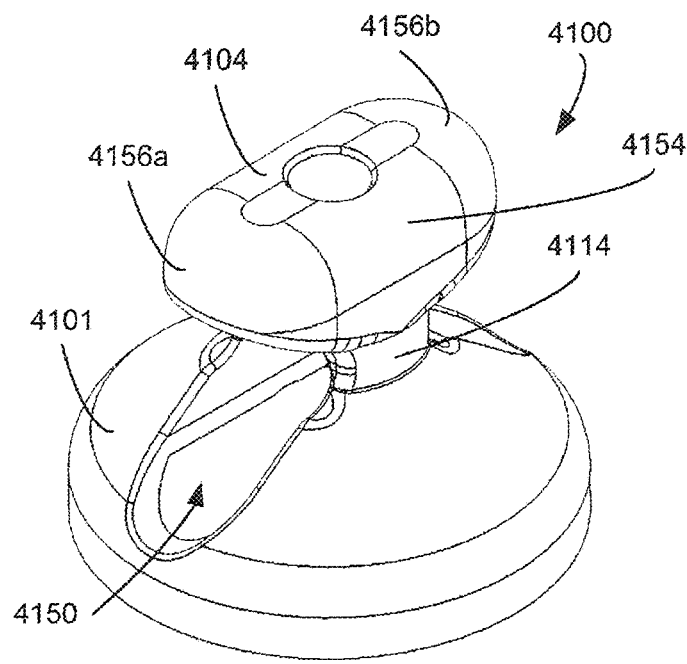
FIGS. 41A-41B are an isometric view and a proximal view, respectively, of a thirteenth attachment feature.
Figure 41B:
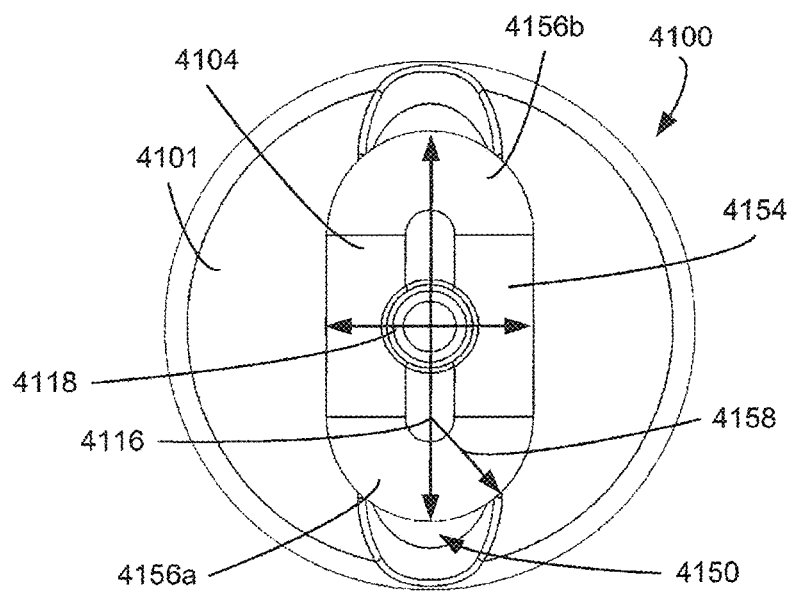

FIGS. 41A-41B are an isometric view and a proximal view, respectively, of another attachment feature 4100 according to the present disclosure. Similar to the attachment feature 4000 of FIGS. 40A-40D, the attachment feature 4100 includes a retrieval feature 4104 coupled to a base 4101 by a rigid stem 4114. The rigid stem 4114 may generally define a rectangular or other oblong profile extending along a minor axis 4118 of the retrieval feature 4104 (shown in FIG. 41B) and which is perpendicular to a major axis 4116 (also shown in FIG. 41B). The attachment feature 4100 optionally further includes a slot 4150 extending along the major axis 4116 and through the rigid stem 4114 to facilitate blood flow through and around the attachment feature 4100. Like the slot 4050 of FIGS. 40A-40D, the slot 4150 extends to a substantially distal extent that it is in communication with an internal volume of the base 4101.

In contrast to the substantially elliptical retrieval feature 4004 of the attachment feature 4000 of FIGS. 40A-40D, the retrieval feature 4104 of the attachment feature 4100 includes a body 4154 extending along the major axis 4116 and terminating in fully radiused end caps 4156a, 4156b. The fully radiused end caps 4156a, 4156b may, in certain implementations, reduce the likelihood of the retrieval feature 4104 damaging or otherwise impinging upon adjacent cardiac tissue. As illustrated in FIG. 41B, the radiused end caps 4156a, 4156b may have a radius 4158 from and including 2 millimeters (0.080 inches) to and including 3.5 millimeters (0.140 inches). Moreover, as illustrated in FIG. 41A, the retrieval feature 4104 may also have a distal "pillow" top or similarly smooth distal face formed by radiusing the edges of the retrieval feature 4104 in the distal direction.

Figure 42A:
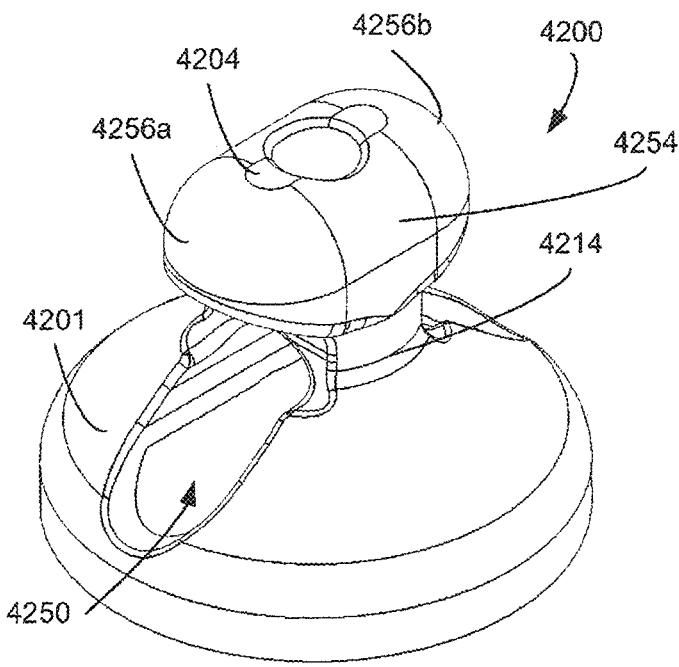
FIGS. 42A-42B are an isometric view and a proximal view, respectively, of a fourteenth attachment feature.
Figure 42B:
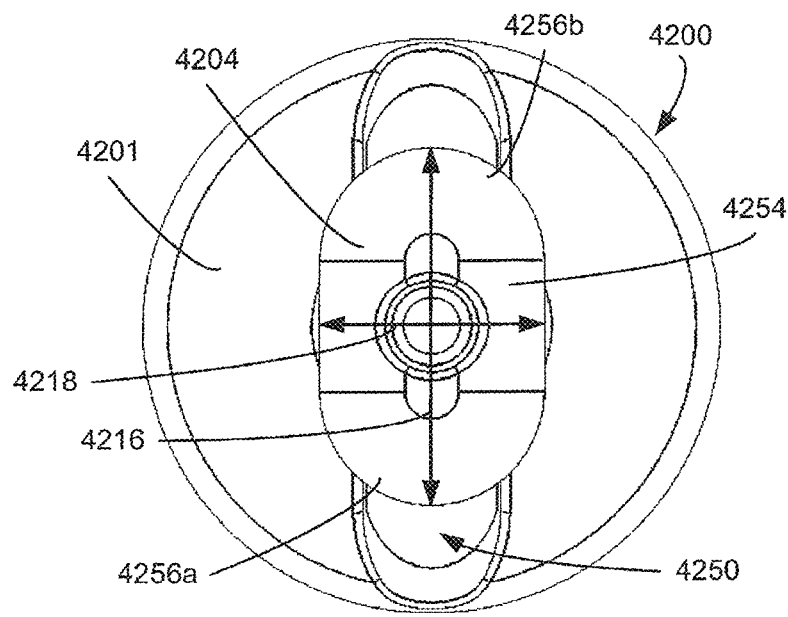

FIGS. 42A-42B are an isometric view and a proximal view, respectively, of another attachment feature 4200 according to the present disclosure. Like the attachment feature 4100 of FIGS. 41A-41B, the attachment feature 4200 includes a retrieval feature 4204 coupled to a base 4201 by a rigid stem 4214 and a slot 4250 extending along the major axis 4216 and through the rigid stem 4214 to facilitate blood flow through and around the attachment feature 4200. The retrieval feature 4204 of the attachment feature 4200 similarly includes a body 4254 extending along the major axis 4216 (shown in FIG. 42B) and terminating in fully radiused end caps 4256a, 4256b. However, the overall length of the retrieval feature 4204 is less than that of the retrieval feature 4104 of FIGS. 41A-41B. Such a reduced major axis 4216 may also reduce or otherwise mitigate the likelihood of the retrieval feature 4204 contacting or otherwise impinging on adjacent cardiac tissue. In certain implementations, the major axis 4216 may be from and including 3 millimeters (0.12 inches) to and including 6 millimeters (0.24 inches) while the minor axis 4218 (shown in FIG. 42B) may be from and including 2 millimeters (0.080 inches) to and including 3.5 millimeters (0.140 inches) provided the minor axis 4218 is less than the major axis 4216.

The foregoing descriptions of attachment features and their respective components are not intended to be limited to the specific examples illustrated herein. Rather, the various concepts, structures, and features of the attachment feature, the retrieval feature/button, the rigid stem, and other components discussed herein may be implemented alone or in any suitable combination. For example, even if not explicitly described or illustrated as doing so, button shapes or design disclosed herein may include a distal tapering face or rounded corners and edges to encourage spontaneous release of snares.

C. Docking Cap for Leadless Pacemaker Delivery and Retrieval

As previously described in the context of FIGS. 2-5C, catheter-based delivery and retrieval systems for leadless pacemakers in accordance with the present disclosure may include docking caps. In general, a docking cap is shaped and adapted to receive a leadless pacemaker and, in particular an attachment feature of a leadless pacemaker during at least one of delivery and retrieval of the leadless pacemaker.

In certain implementations, the docking cap is rotatable such that torque may be applied to a retained leadless pacemaker by rotating the docking cap. During delivery, such torque may be used to implant the leadless pacemaker, for example by engaging cardiac tissue with a helical fixation screw or similar structure disposed on a distal end of the leadless pacemaker.

Retrieval of a leadless pacemaker or similar implantable medical device generally includes capturing the leadless pacemaker and subsequently docking the captured leadless pacemaker within the docking cap. To do so, a snare, tether, lasso, or similar retrieval mechanism is extended from a retrieval catheter and coupled to an attachment feature of the leadless pacemaker. Once coupled and closed about the attachment feature, the snare or similar feature is proximally retracted, thereby docking the leadless pacemaker within the docking cap. A counter-torque may then be applied to unscrew the leadless pacemaker from the cardiac tissue.

During both implantation and removal, some interference or contact between the docking cap and the retained leadless pacemaker is required for torque transfer to occur. As described below in more detail, such interference may occur between the docking cap and a retrieval feature, such as a button, of the leadless pacemaker. In other implementations, torque features such as ridges, gussets, protrusions, and similar structures other than the retrieval feature may be included in a proximal portion of the leadless pacemaker that are positioned to engage and transfer torque from the docking cap.

Figure 23A:
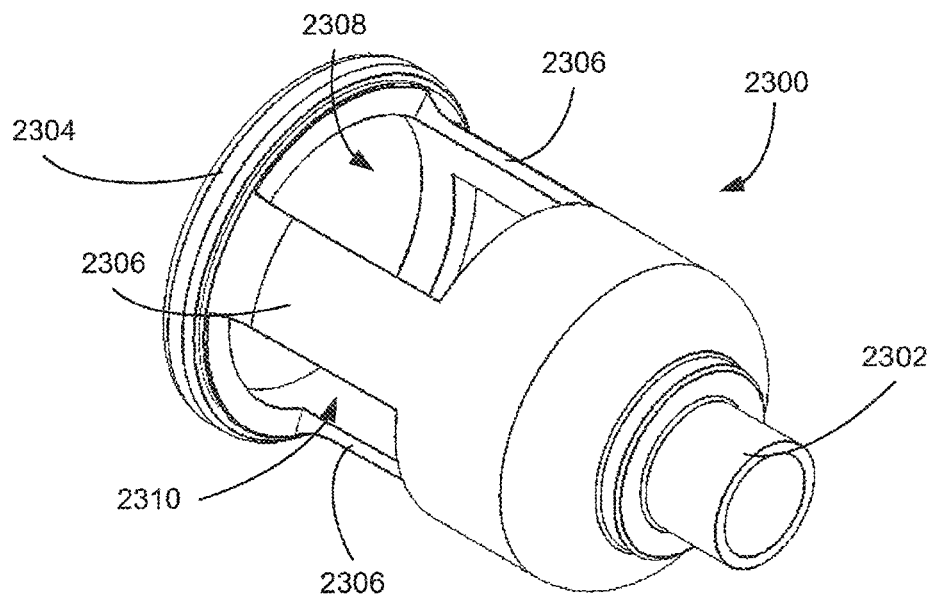
FIGS. 23A-23B are isometric views of a docking cap for use with a retrieval system.
Figure 23B:
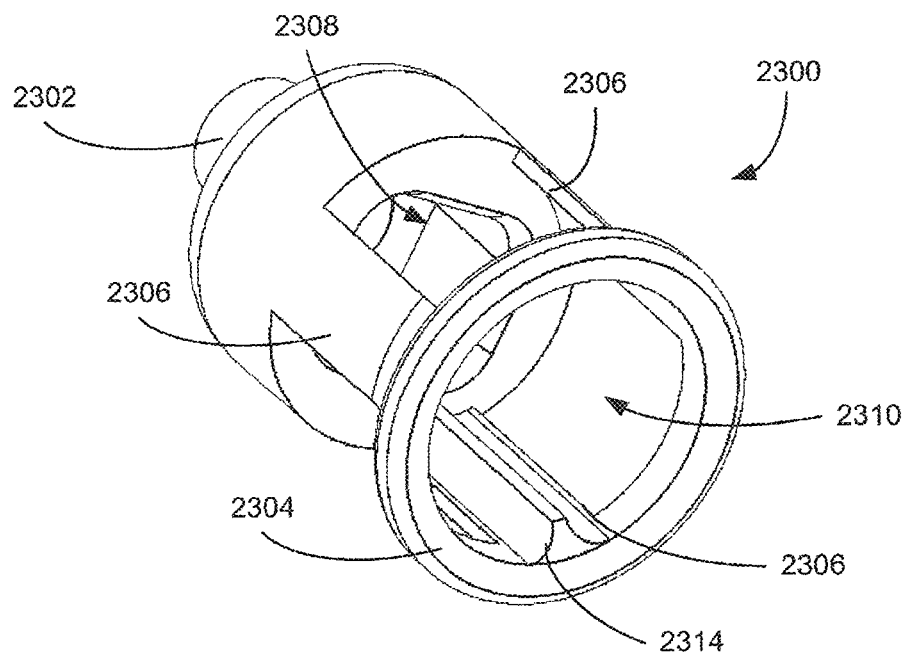
Figure 23C:
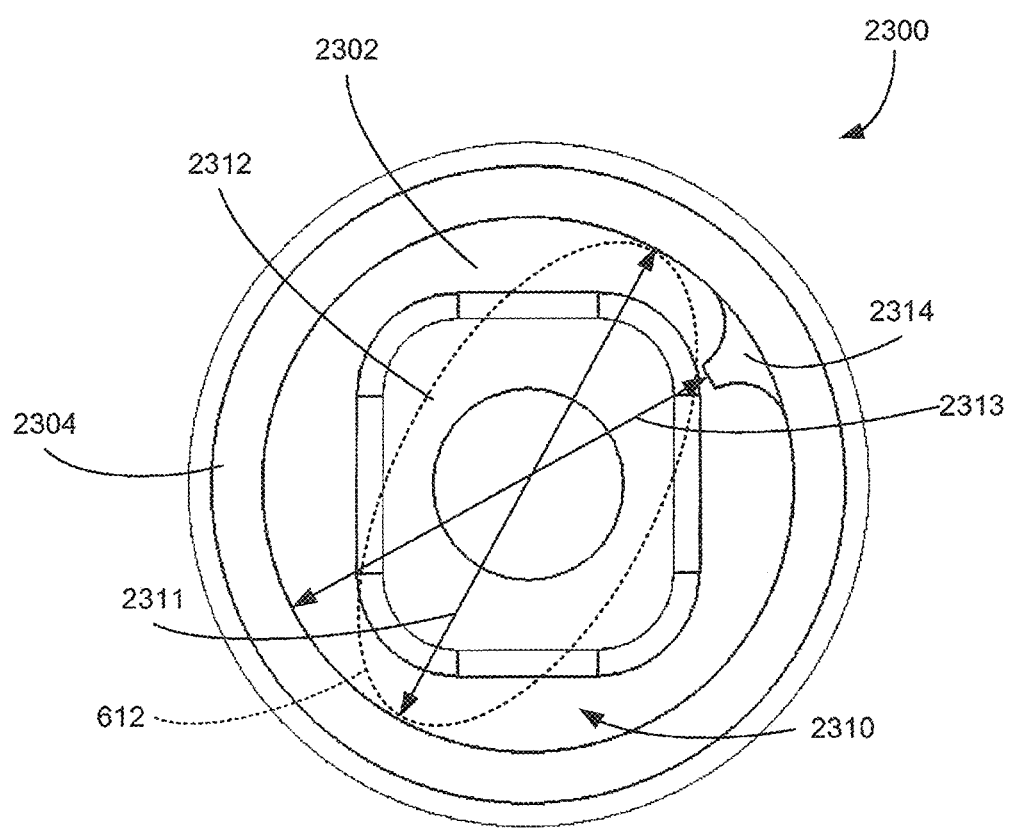
FIG. 23C is a proximal end view of the docking cap of FIGS. 23A-23B.

FIGS. 23A-23B are isometric views of a docking cap 2300 in accordance with the present disclosure. FIG. 23C is a bottom view of the docking cap 2300. In general, the docking cap 2300 forms a cage-like structure defining an internal docking cap volume 2310 adapted to receive the proximal end of a leadless pacemaker or similar implantable medical device. The docking cap 2300 includes a proximal cap end 2302 adapted to be coupled to the retrieval catheter shaft and a distal annulus 2304 disposed opposite the proximal cap end 2302. As shown in FIG. 23C, the proximal cap end 2302 may define a receptacle 2312 shaped to receive a drive gear during retrieval of a leadless pacemaker. In certain implementations, the docking cap 2300 may be formed using at least one of stainless steel (such as 304 stainless steel), titanium, and a polymer, such as polyether ether ketone (PEEK). In certain implementations, the material used to form the docking cap 2300 may be loaded with a radiopaque additive or otherwise visible using fluoroscopy or a similar imaging technique.

As shown in FIG. 23C, the internal docking cap volume 2310 may have an internal diameter 2311. The internal diameter 2311 may be generally selected based on the size and shape of the leadless pacemaker being delivered and/or retrieved using the docking cap. For example, FIG. 23C includes a dashed outline of an oval retrieval feature or button 612, such as the button of the leadless pacemaker 600 illustrated in FIGS. 6-7C, the internal diameter 2311 being approximately equal to or greater than a major axis of the button 612. In other implementations, the internal diameter 2311 may be selected to accept buttons or retrieval features having other shapes and dimensions.

In conventional docking caps, docking of the leadless pacemaker and its retrieval feature is generally limited by the internal diameter 2311 of the internal docking cap volume 2310. However, docking caps according to the present disclosure include longitudinal members 2306 extending between the proximal cap end 2302 and the distal annulus 2304 to define openings, such as opening 2308, between adjacent longitudinal members 2306. The openings 2308 are sufficiently sized to allow the proximal end of a leadless pacemaker and, in particular, the retrieval feature of the leadless pacemaker to pass at least partially through the openings 2308 during the capture and retrieval processes, thereby expanding the effective diameter of the docking cap beyond the internal diameter 2311.

To accommodate the proximal end of the leadless pacemaker and/or the coupling feature of the leadless pacemaker, the longitudinal members 2306 may be disposed about the docking cap 2300 such that the minimum distance between adjacent longitudinal members 2306 is greater than the width of the proximal end of the leadless pacemaker and/or the retrieval feature/button of the leadless pacemaker. Accordingly, while illustrated in FIGS. 23A-23C as including three longitudinal members 2306 and three corresponding openings defined between the longitudinal members, other docking caps in accordance with this disclosure may have more or fewer longitudinal members 2306 and corresponding openings provided they can accommodate the leadless pacemaker of the particular application.

In certain implementations, a torque transmission feature 2314 may be coupled to one of the longitudinal members 2306 and extend into the docking cap volume 2310. The torque transmission feature 2314 is positioned and shaped such that after docking of the leadless pacemaker, rotation of the docking cap 2300 causes the torque transmission feature 2314 to contact the docked leadless pacemaker and transmit torque from the docking cap 2300 to the leadless pacemaker. In certain implementations, the torque transmission feature 2314 may be positioned to interfere with a retrieval feature/button of the leadless pacemaker or one or more corresponding torque features disposed on a proximal portion of the leadless pacemaker housing.

The torque transmission feature 2314 generally reduces the distance across the docking cap volume 2310 as compared to the internal diameter 2311. FIG. 23 includes such a reduced diameter 2313. In implementations in which the docking cap 2300 is adapted to transmit torque to a retrieval feature/button of a leadless pacemaker, the reduced diameter 2313 may generally be less than a major axis of the retrieval feature. As a result, the leadless pacemaker may be docked within the docking cap 2300 when misaligned relative to the reduced diameter 2313. However, once docked, relative rotation between the docking cap 2300 and the retrieval feature 612 may cause contact or interference between the torque transmission feature 2314 and the retrieval feature 612. As a result of such interference, torque may be transmitted between the docking cap 2300 and the retrieval feature 612, thereby enabling screwing/unscrewing of the leadless pacemaker from cardiac tissue.

Figure 23D:
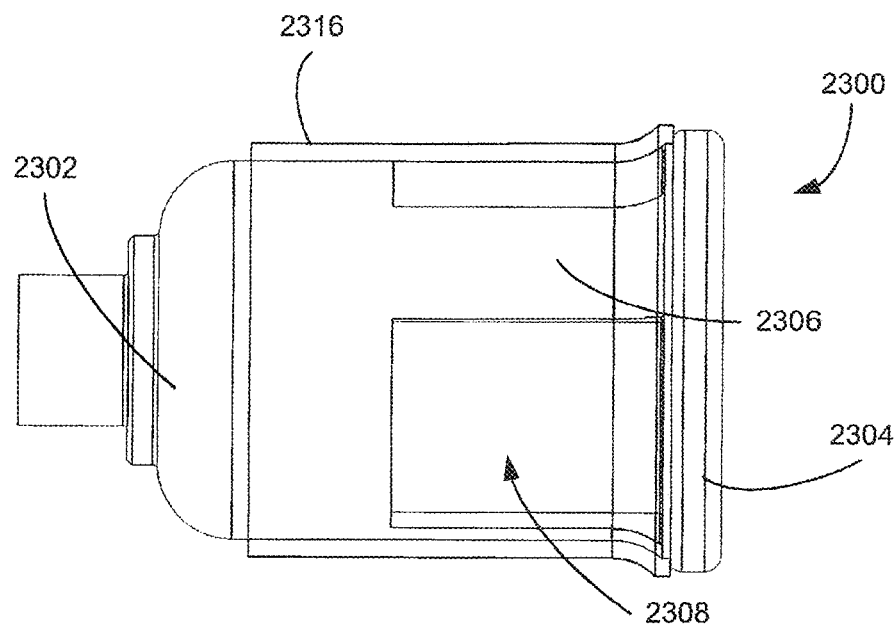
FIGS. 23D-23E are a side view and a side cross-sectional view of the docking cap of FIGS. 23A-23B.
Figure 23E:
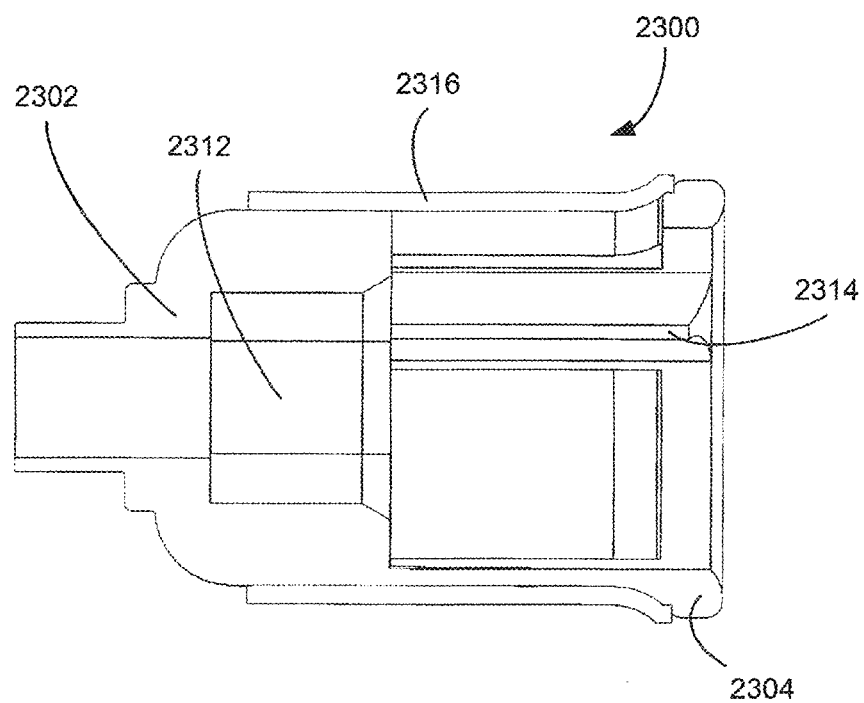

FIGS. 23D and 23E are a side view and a cross-sectional side view, respectively of the docking cap 2300. As shown in FIGS. 23D-23E, the docking cap 2300 may include a sheath 2316 disposed over a portion of the docking cap 2300 including the openings 2308. The sheath 2316 is generally formed from an elastic material. By doing so, the sheath 2316 allows the retrieval feature/button of a leadless pacemaker to extend through the openings 2308 while maintaining inward pressure that biases the retrieval feature into the internal docking cap volume 2310. As a result of the inward biasing provided by the sheath 2316, the retrieval feature is directed away from edges and other features of the docking cap 2300 on which the retrieval feature may become bound up. In addition to assisting during docking of a leadless pacemaker, the inward force provided by the sheath 2316 on the retrieval feature also facilitates alignment of the retrieval feature with the distal annulus 2304 should undocking of the leadless pacemaker be required.

In certain implementations, the sheath 2316 may be formed from one or more of a copolymer, polytetrafluoroethylene (PTFE), and perfluoroalkoxy alkane (PFA) and may have a thickness from and including 0.006 inches to and including 0.020 inches. For example, in one implementation, the sheath 2316 is formed from a fluorinated ethylene propylene (FEP) sheet having a thickness of 0.012 inches that is applied to the docking cap 2300 by heat shrinking the FEP sheet onto the outside surface of the docking cap 2300.

Figure 23F:
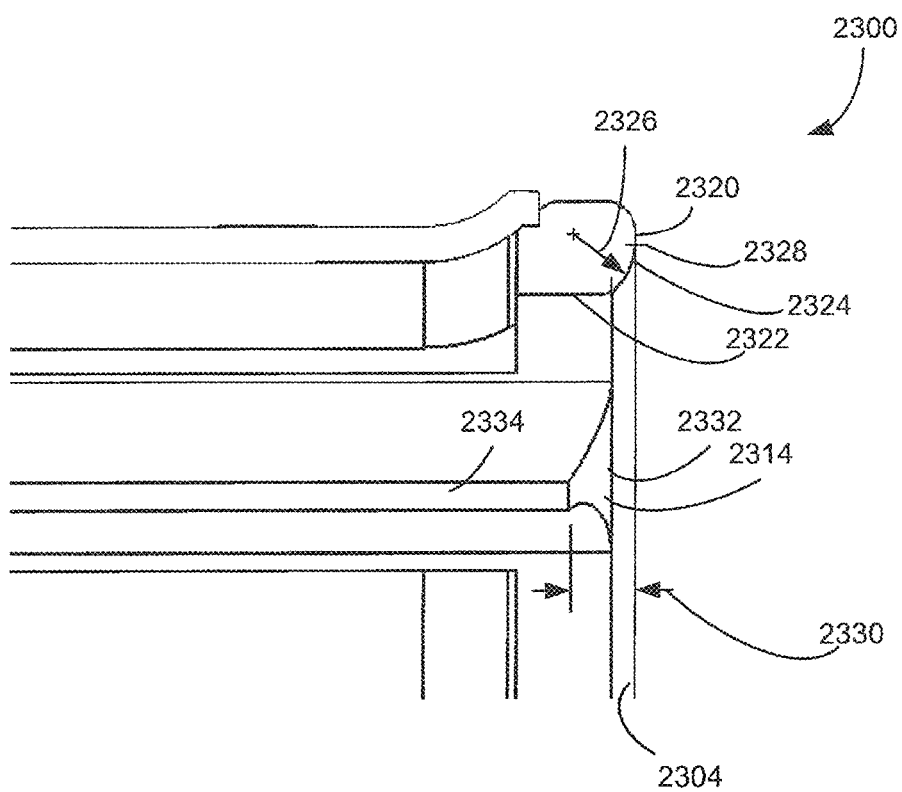
FIG. 23F is a side cross-sectional detail view of the docking cap of FIGS. 23A-23B.

FIG. 23F is a detailed view of the distal annulus 2304 of the docking cap 2300. In certain implementations, to facilitate entry of an implantable medical device, such as a leadless pacemaker, into the docking cap 2300 during the docking process, the distal portion of the distal annulus 2304 may be shaped to reduce edges on which the implantable medical device may become caught. For example, in certain implementations, the distal annulus 2304 may include a distal face 2320 and an internal surface 2322 substantially perpendicular to the distal face 2320. A curved transition 2324 may extend between the distal face 2320 and the internal surface 2322 to guide a captured implantable lead into the docking cap 2300 during the docking process. In certain implementations, the curved transition may have a radius of curvature 2326 from and including 0.017 inches to and including 0.150 inches and an arc length 2328 from and including 0.017 inches to and including 0.035 inches.

To further reduce the likelihood of the leadless pacemaker becoming caught at or near the distal annulus 2304, the torque feature 2314 may also be offset from the distal face 2320 of the distal annulus 2304. For example, the torque feature 2314 may originate from a proximal edge of the curved transition 2324 and include a concave scallop 2332 that terminates in a longitudinal face 2334. The longitudinal face may be entirely longitudinal, e.g., parallel to a longitudinal axis, over a length extending from the concave scallop 2332 to the proximal cap end 2302. Accordingly, in certain implementations, the longitudinal face 2334 may have an offset 2330 from and including 0.065 inches to and including 0.120 inches relative to the distal face 2320.

FIGS. 24A-24C illustrate general operation of a docking system 2400 in accordance with the present disclosure and including the docking cap 2300. The docking system 2400 includes a drive gear 2402 disposed on the end of a torque shaft 2404 or retrieval catheter. The torque shaft 2404 extends through the docking cap 2300 and is translatable relative to the docking cap 2300. The docking cap 2300 may be disposed at a distal end of a catheter shaft and, in certain implementations, may be coupled to the distal end of the catheter shaft using a rotatable coupling such that the docking cap 2300 is able to rotate relative to the catheter shaft.

A retrieval snare 2408 or similar feature (shown in FIG. 24A in dashed lines for clarity) generally extends through the torque shaft 2404 such that the retrieval feature may be used to capture a corresponding attachment feature of a leadless pacemaker or other implantable medical device. To facilitate such capture, the torque shaft 2404 may be extended from the docking cap as illustrated in FIG. 24A.

As shown in FIG. 24B, following capture of the leadless pacemaker, the torque shaft 2404 is retracted into the docking cap 2300 to dock the leadless pacemaker. FIG. 24C illustrates the torque shaft 2404 in a fully retracted position such that the drive gear 2402 is retained within a recess 2310 defined within the docking cap 2300. The recess 2310 is generally sized and shaped such that it interferes, at least partially, with the drive gear 2402. As a result of this interference, torque applied to the torque shaft 2404 when the drive gear 2402 is retained within the recess 2310 is transmitted to the docking cap 2300.

Figure 25:
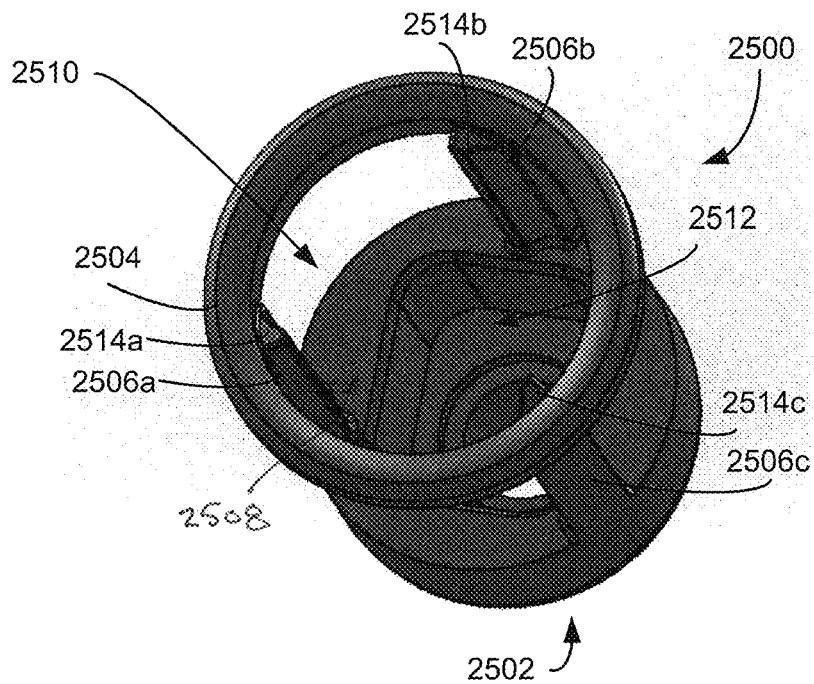
FIG. 25 is an isometric view of a second docking cap according to the present disclosure.

FIG. 25 is an isometric view of another docking cap 2500 in accordance with the present disclosure. In general, the docking cap 2500 forms a cage-like structure defining an internal docking cap volume 2510 adapted to receive the proximal end of a leadless pacemaker or similar implantable medical device. The docking cap 2500 includes a proximal cap end 2502 adapted to be coupled to the retrieval catheter shaft and a distal annulus 2504 disposed opposite the proximal cap end 2502. The proximal cap end 2502 may define a receptacle 2512 shaped to receive a drive gear during retrieval of a leadless pacemaker. The docking cap 2500 further includes longitudinal members 2506a-2506c extending between the proximal cap end 2502 and the distal annulus 2504 to define openings, such as opening 2508, between adjacent longitudinal members 2506.

The docking cap 2500 further includes multiple torque transmission features 2514a-2514c coupled to each of the longitudinal members 2506 that extend into the docking cap volume 2510. The torque transmission features 2514a-2514c are each positioned and shaped such that after docking of the leadless pacemaker, rotation of the docking cap 2500 causes at least one of the torque transmission features 2514a-2514c to contact the docked leadless pacemaker and to transmit torque from the docking cap 2500 to the leadless pacemaker.

Figure 26:
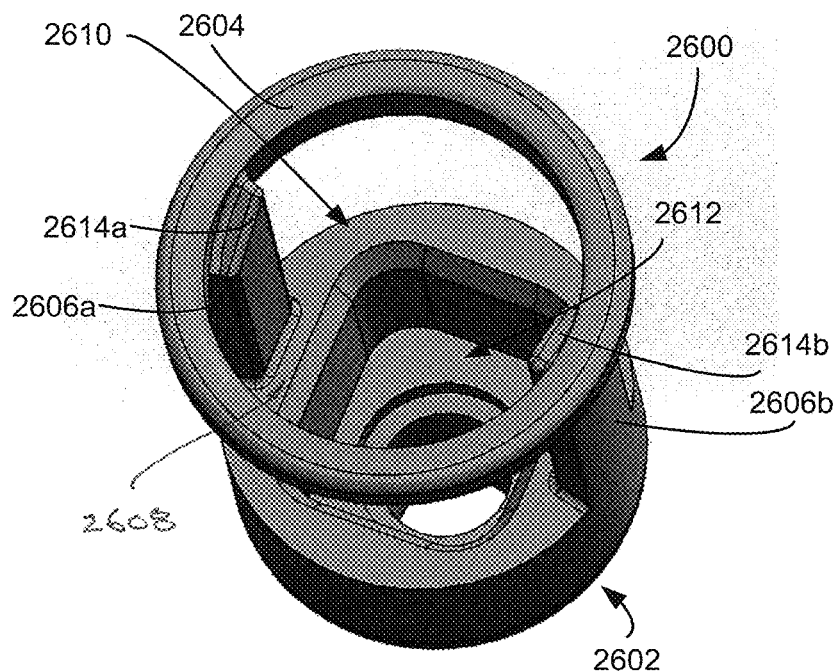
FIG. 26 is an isometric view of a third docking cap according to the present disclosure.

FIG. 26 is an isometric view of yet another docking cap 2600 in accordance with the present disclosure. In general, the docking cap 2600 forms a cage-like structure defining an internal docking cap volume 2610 adapted to receive the proximal end of a leadless pacemaker or similar implantable medical device. The docking cap 2600 includes a proximal cap end 2602 adapted to be coupled to the retrieval catheter shaft and a distal annulus 2604 disposed opposite the proximal cap end 2602. The proximal cap end 2602 may define a receptacle 2612 shaped to receive a drive gear during retrieval of a leadless pacemaker. The docking cap 2600 further includes longitudinal members 2606a-2606b extending between the proximal cap end 2602 and the distal annulus 2604 to define openings, such as opening 2608, between the longitudinal members 2606a-2606b. Each of the longitudinal member 2606a-2606b further includes a respective torque transmission feature 2614a-2614b. More specifically, the torque transmission features 2614a-2614b are generally rectangular protrusions that extend into the docking cap volume 2610.

FIGS. 27A-27D illustrate an alternative docking cap 2700 that may be used in conjunction with leadless pacemakers according to the present disclosure and, in particular, leadless pacemakers, such as the leadless pacemaker 600 of FIG. 6-7C, that include an oval or similarly shaped retrieval feature or button 612. In contrast to the "cage" design illustrated in the implementations of FIG. 23A-26, the implementation of FIGS. 27A-27D is a socket-type design in which the retrieval feature or button 612 of the leadless pacemaker is received within a substantially enclosed cavity of the docking cap 2700.

Figure 27A:
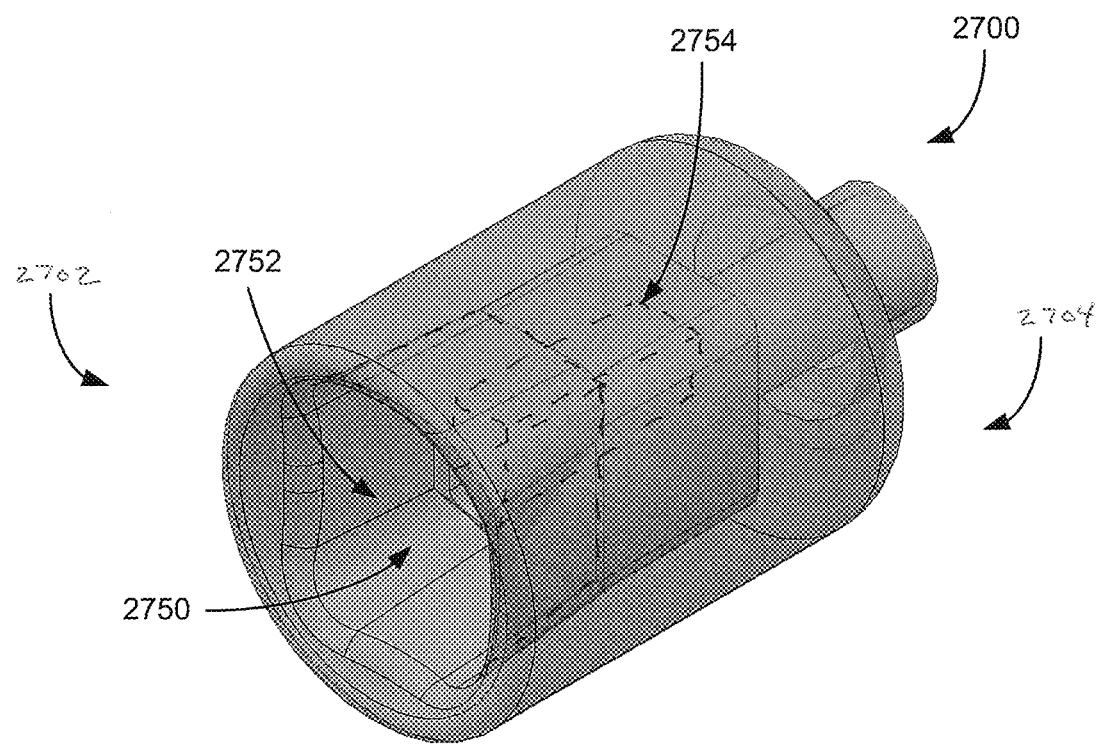
FIGS. 27A-27B are an isometric and proximal end view, respectively, of a fourth docking cap.
Figure 27B:
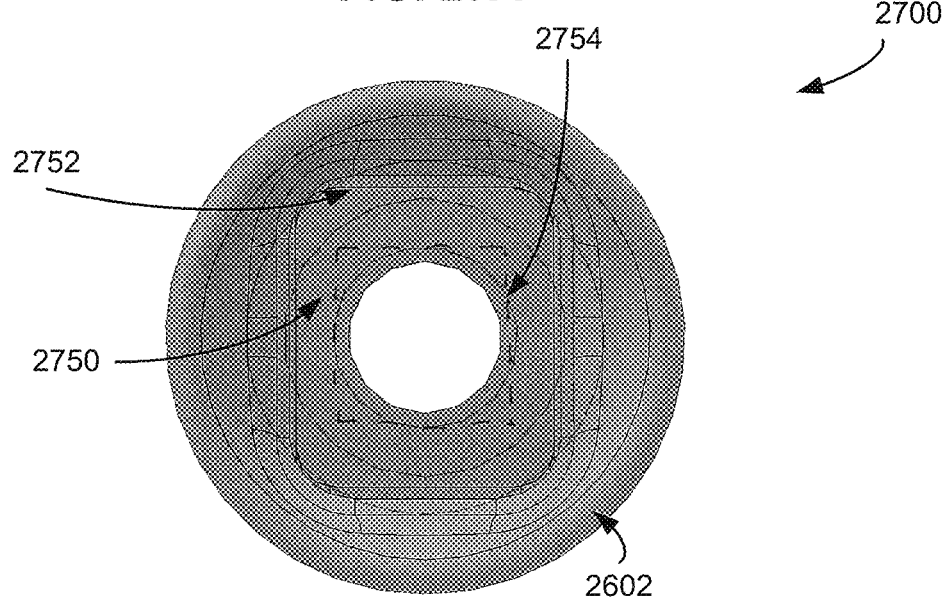

FIGS. 27A and 27B are an isometric and distal view of the docking cap 2700. As illustrated, the docking cap 2700 includes a distal end 2702 and a proximal end 2704. The proximal end 2704 is generally adapted to be coupled to a leadless pacemaker delivery and/or retrieval system. For example, in certain implementations, the proximal end 2704 of the docking cap 2700 may be configured to be coupled to a catheter shaft of the delivery and/or retrieval system.

The docking cap 2700 defines an inner cavity 2750 that may further include a distal cavity section 2752 and a proximal cavity section 2754. The distal cavity section 2752 is generally sized and shaped to receive a proximal end of a leadless pacemaker and, more specifically, an attachment feature of the leadless pacemaker, such as the attachment feature 604 of the leadless pacemaker 600 of FIGS. 6-7C. As illustrated in FIG. 27B, in certain implementations, the distal cavity section 2752 may have a generally square or rectangular shape.

The proximal cavity section 2754 may be sized smaller than the distal cavity section 2752 so as to preclude ingress of the leadless pacemaker into the proximal cavity section 2754. For example, in certain implementations the proximal cavity section 2754 may be sized and shaped to receive other components of the delivery/retrieval system such as a shaft to deliver a snare for capturing an implanted leadless pacemaker. The shaft may further include a drive gear or similar element to apply torque to the leadless pacemaker as previously described in the context of FIGS. 24A-24C.

Figure 27C:
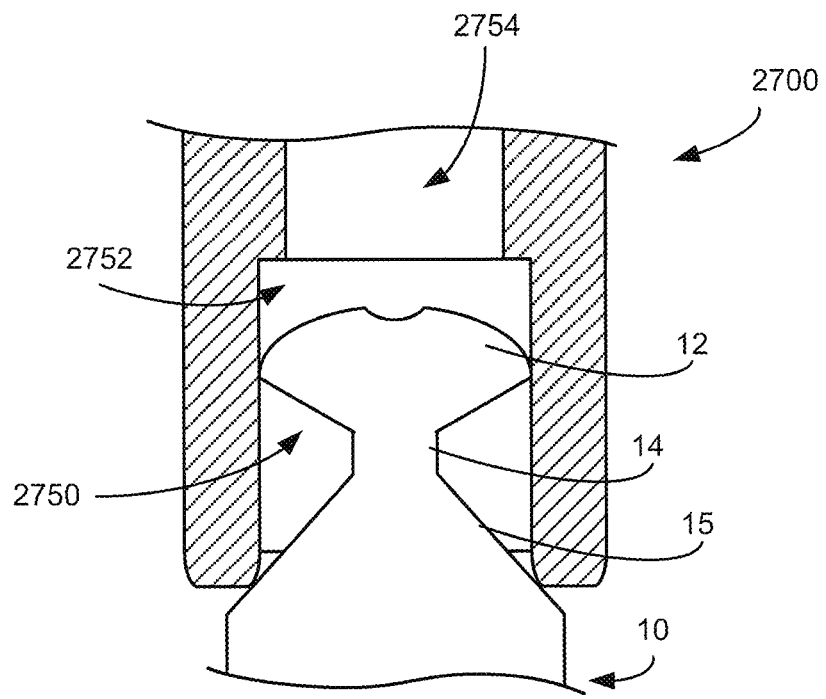
FIGS. 27C-27D are a cross-sectional side view and a proximal view, respectively, of the docking cap of FIGS. 27A-27B including a docked leadless pacemaker.
Figure 27D:
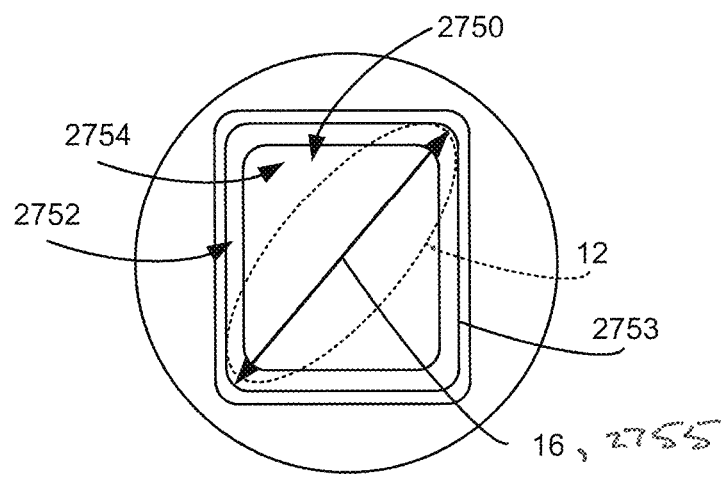

FIGS. 27C-27D illustrate interaction between the docking cap 2700 and a leadless pacemaker 10 when the leadless pacemaker 10 is retained within the distal cavity section 2752 of the docking cap 2700. More specifically, FIG. 27C is a cross-sectional view of the docking cap 2700 with the leadless pacemaker 10 disposed within the distal cavity section 2752 while FIG. 27D is a distal view of the docking cap 2700 indicating the orientation of a button 12 of the leadless pacemaker 10 when disposed within the docking cap 2700.

Referring first to FIG. 27C, the leadless pacemaker 10 is shown retained within the docking cap 2700, which may occur during one of delivery or retrieval of the leadless pacemaker 10. For example, during delivery, tethers or similar retention elements may be inserted into and retained within the button 12 to couple the button 12 with a delivery system including the docking cap 2700. In contrast, during retrieval, a snare or similar retrieval element may be closed around a rigid stem 14 of the leadless pacemaker 10. The snare may then be further closed and retracted into a catheter or shaft of a retrieval system including the docking cap 2700, thereby drawing the leadless pacemaker 10 into the docking cap 2700.

As shown in FIG. 27C, the leadless pacemaker 2700 may generally be disposed within the distal cavity section 2752 of the leadless pacemaker 2700. In certain implementations, the distal cavity section 2752 may include ridges, stops, faces, or similar structural elements to limit the depth of the leadless pacemaker 10 within the distal cavity section 2752. In other implementations, the docking cap 2700 may be shaped such that it interferes with the leadless pacemaker 10 as the leadless pacemaker 10 is drawn into the distal cavity section 2752. For example, as shown in FIG. 27C, the leadless pacemaker 10 includes a proximal tapered section 15 that interferes with the docking cap 2700. Such features of the leadless pacemaker 10 may also facilitate alignment of the leadless pacemaker 10 during docking. For example, the proximal tapered section 15 generally causes the leadless pacemaker 10 to longitudinally align with the docking cap 2700.

FIG. 27D is a proximal view of the docking cap 2700 including a dashed outline indicating the button 12 of the leadless pacemaker 10. As illustrated, the distal cavity section 2752 includes an internal surface 2753 that is generally shaped to interfere with the button 12 while the leadless pacemaker 10 is retained within the docking cap 2700. As a result of such interference, torque may be transferred between the docking cap 2700 and the leadless pacemaker 10 in order to implant (during delivery) or unscrew (during retrieval) the leadless pacemaker 10 from cardiac tissue.

In the docking cap 2700, for example, the internal surface 2753 is substantially rectangular and defines a diagonal 2755 that is approximately equal to the major axis 16 of the button 12. As a result, when the leadless pacemaker 10 is docked within the docking cap 10, rotation of the leadless pacemaker 10 and/or the docking cap 2700 causes the button 12 to interfere with the internal surface 2753, thereby enabling torque transfer between the docking cap 2700 and the leadless pacemaker 10.

As previously noted, socket-style docking caps according to the present disclosure include an internal surface having structural elements shaped and positioned to interfere with corresponding elements of a docked leadless pacemaker. In other words, the structural elements generally allow insertion of the leadless pacemaker in one or more first relative orientations of the docking cap and the leadless pacemaker while preventing insertion in one or more second relative orientations. In order to do so, the structural elements of the internal surface are shaped and positioned such that the distance across the docking cap varies about the internal surface of the distal cavity section. Such variation is generally between a first distance that is greater than the greatest width or major length (e.g., the major axis of an oval button) of the retrieval feature/button and a second length that is less than the major length. Referring to the docking cap 2700 as illustrated in FIG. 27D, for example, the structural elements (e.g., the internal walls of the docking cap 2700) are shaped such that the diagonal across the distal cavity section 2752 is greater than the major axis 16 of the button 12, permitting insertion of the button 12. However, opposite sides of the distal cavity section 2752 are disposed at a distance less than the major axis 16, such that interference occurs when either the leadless pacemaker 10 or the docking cap 2700 are rotated.

Figure 28:
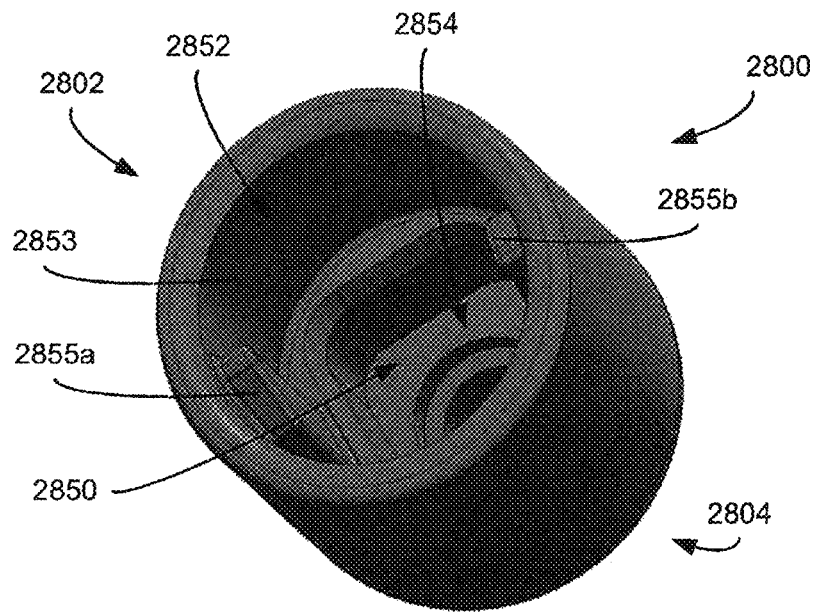
FIG. 28 is an isometric view of a fifth docking cap according to the present disclosure.

FIG. 28 is an isometric view of a second socket-type docking cap 2800 in accordance with the present disclosure. The docking cap 2800 includes a distal end 2802 for receiving a leadless pacemaker and a proximal end 2804 adapted to be coupled to a leadless pacemaker delivery and/or retrieval system. The docking cap 2800 defines an inner cavity 2850 that may further include a distal cavity section 2852 and a proximal cavity section 2854. The distal cavity section 2852 is generally sized and shaped to receive a proximal end of a leadless pacemaker and, more specifically, an attachment feature of the leadless pacemaker.

The distal cavity section 2854 of the docking cap 2800 is substantially cylindrical and includes an internal surface 2853. During use, interference between the docking cap 2800 and a docked leadless pacemaker is achieved by a pair of protrusions 2855a, 2855b extend inwardly from the internal surface 2853. More specifically, the distal cavity section 2854 generally has a diameter that is greater than a major length of a retrieval feature (such as a button) of a leadless pacemaker but the protrusions 2855a, 2855b form a narrowing of the distal cavity section 2854 such that the distance between the protrusions 2855a, 2855b is less than the major length. Accordingly, a leadless pacemaker may be docked when misaligned with the protrusions 2855a, 2855b; however, once docked, rotation of the leadless pacemaker or the docking cap 2800 following such docking will result in interference and torque transfer between the leadless pacemaker and the docking cap.

Figure 29:
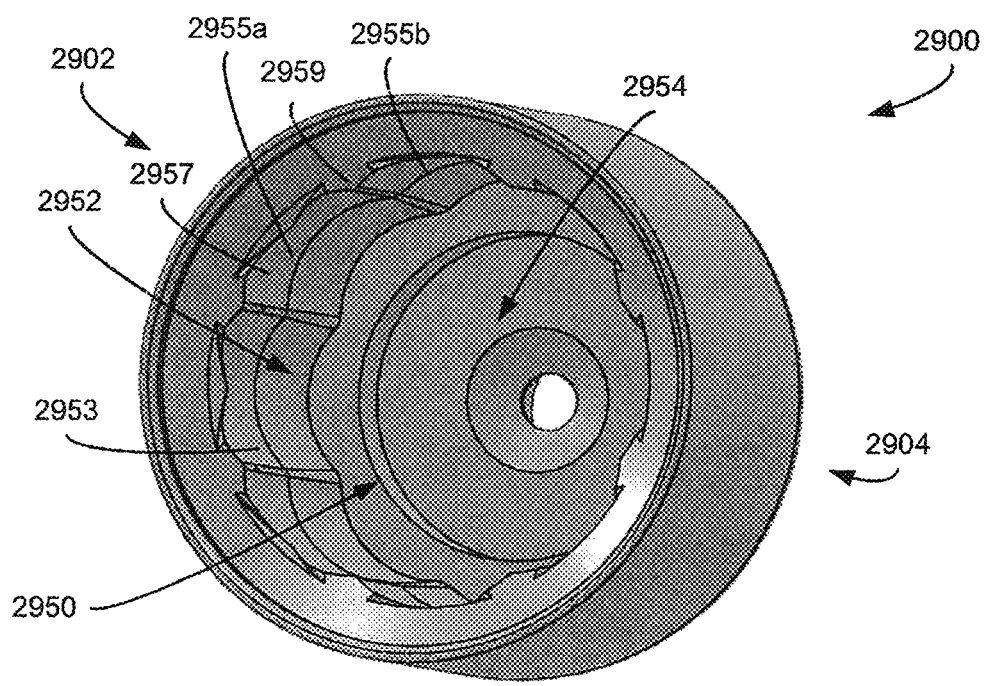
FIG. 29 is an isometric view of a sixth docking cap according to the present disclosure.

FIG. 29 is an isometric view of a third socket-type docking cap 2900 in accordance with the present disclosure. The docking cap 2900 includes a distal end 2902 for receiving a leadless pacemaker and a proximal end 2904 adapted to be coupled to a leadless pacemaker delivery and/or retrieval system. The docking cap 2900 defines an inner cavity 2950 that may further include a distal cavity section 2952 and a proximal cavity section 2954. The distal cavity section 2952 is generally sized and shaped to receive a proximal end of a leadless pacemaker and, more specifically, an attachment feature of the leadless pacemaker.

The distal cavity section 2954 of the docking cap 2900 includes an internal surface 2953. Distributed about the internal surface 2953 are a series of scallops or similar curved surfaces, such as scallops 2955a, 2955b. The scallops are shaped such that each scallop generally includes a trough, such as trough 2957, and adjacent scallops form a peak, such as peak 2959. As shown in FIG. 29, the distribution of the scallops about the internal surface 2953 is symmetrical such that each trough and peak is generally opposite a respective trough or peak disposed on an opposite side of the internal surface 2953.

In general, the scallops are positioned and sized such that the distance between opposite troughs is greater than the major length of the retrieval feature or button of a leadless pacemaker being delivered or retrieved. Similarly, the scallops are also positioned and sized such that the distance between opposite peaks is less than the major length. Accordingly, a leadless pacemaker may be inserted into the docking cap 2900 when oriented such that the major length of the retrieval feature is aligned with a pair of troughs. However, once docked, relative rotation of the leadless pacemaker or docking cap 2900 causes interference between the peaks and the leadless pacemaker, thereby facilitating torque transfer between the leadless pacemaker and the docking cap 2900.

Figure 30:
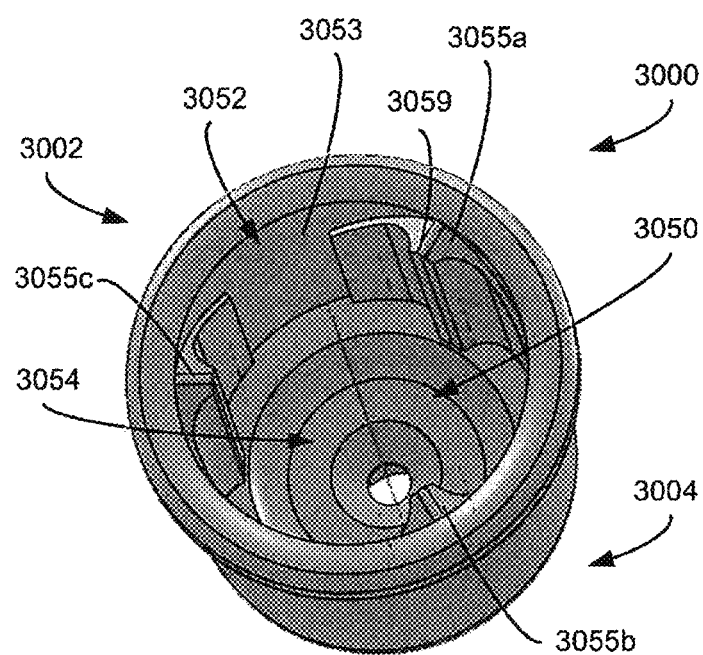
FIG. 30 is an isometric view of a seventh docking cap according to the present disclosure.

FIG. 30 is an isometric view of a fourth socket-type docking cap 3000 in accordance with the present disclosure. The docking cap 3000 includes a distal end 3002 for receiving a leadless pacemaker and a proximal end 3004 adapted to be coupled to a leadless pacemaker delivery and/or retrieval system. The docking cap 3000 defines an inner cavity 3050 that may further include a distal cavity section 3052 and a proximal cavity section 3054. The distal cavity section 3052 is generally sized and shaped to receive a proximal end of a leadless pacemaker and, more specifically, an attachment feature of the leadless pacemaker.

The distal cavity section 3054 of the docking cap 3000 includes an internal surface 3053. Distributed about the internal surface 3053 are a series of torque features 3055a-3055c. The torque features are shaped such that each torque feature 3055a-3055c includes a pair of curved surfaces that join to form a peak, such as peak 3059. For example, the curved surface can project radially inward to the peak 3059. In general, the torque features 3055a-3055c are positioned and sized such that the distance between a peak and an opposite portion of the internal surface 3053 is less than the major length of the retrieval feature or button of a leadless pacemaker being delivered or retrieved. Accordingly, a leadless pacemaker may generally be inserted into the docking cap 3000 provided its retrieval feature is misaligned with one of the peaks. However, once docked, relative rotation of the leadless pacemaker and the docking cap 3000 would cause interference between the nearest peak and the leadless pacemaker, thereby facilitating torque transfer between the leadless pacemaker and the docking cap 3000.

The foregoing examples of socket-type docking caps were generally adapted to interfere with a retrieval feature of a leadless pacemaker. In other implementations, however, the structures of the internal surface of the docking cap may instead be adapted to interfere with a torque feature of the leadless pacemaker other than the retrieval feature. For example, as illustrated in FIGS. 22A-22B, an attachment feature of a leadless pacemaker may include gussets, protrusions, surfaces, or similar structures adapted to interact with a torque feature of a docking cap when a leadless pacemaker is received by and rotated relative to the docking cap.

The socket-type docking caps discussed in FIGS. 27A-30 may also include various features discussed herein with respect to the cage-type docking caps illustrated in FIGS. 23A-26. For example, and without limitation, any docking cap disclosed herein may include a distal face that smoothly transitions into the internal cavity defined by the docking cap, such as illustrated in FIG. 23F. Similarly, any of the internal structural elements adapted to interfere with a docked leadless pacemaker may be offset from the distal face, thereby reducing the likelihood of interference with the leadless pacemaker during docking.

D. Welded Leadless Pacemaker Housing

As previously discussed in the context of FIG. 6, a leadless pacemaker may generally include a hermetic housing, a fixation mechanism (such as a helical screw) and electrodes disposed at a distal end of the hermetic housing, and an attachment feature (such as a button) disposed at a proximal end of the hermetic housing to facilitate delivery and retrieval of the leadless pacemaker.

A significant volume of the leadless pacemaker consists of a battery or battery material and other electronic components housed within a hermetically sealed tube (which may alternatively be referred to a "cell can" or simply a "can"). Such material and components are often thermally sensitive and can degrade if exposed to elevated temperatures. In certain configurations of cell cans, components must be attached at both ends for device functionality. As previously noted, for example, a machined docking feature must be added to the proximal end of the housing to allow for attachment of a delivery and/or retrieval catheter. On the distal end of the cell can, the fixation mechanism and electrodes must be similarly attached. The electrodes must also be coupled to the internal electronics and, in particular, the positive and negative terminals of the battery. In some cases, an external shroud or enclosure tube is also attached to the internal electronics in order to provide further protection.

Attaching components to the ends of the cell can generally requires a manufacturing process, such as laser welding. Often, these processes require highly localized energy application in order to sufficiently heat and melt at least one of the cell can and the component being coupled to the cell can. The heat resulting from such processes can potentially affect the stability of the battery material and electronics within the cell can.

In light of this issue, leadless pacemakers in accordance with this disclosure may include features at one or both ends of the cell can that allow for weld processing (and other similar heat-based processing) of a cell can while limiting the potential degradation of battery material and electronics disposed with the cell can.

Leadless pacemakers according to this disclosure may be assembled by attaching the end components to a first side of the cell can, inserting and connecting the electronic components and battery material within the cell can, and then attaching the end components to the second side of the cell can. In certain cases, one or both of the end components of the first and second side may be attached using adhesives, welding, mechanical coupling, or other approaches to fix the end components to the cell can. Although such implementations may not require welding or similar heat-based processing to affix the end components to the cell can, the features disclosed herein may nevertheless be advantageous due to the structural strength they impart.

The mechanical features described herein strategically position material at an end of the cell can such that the added material reduces or impedes transfer of thermal energy created during attachment of end components to the cell can and its internal components. This reduction of thermal energy transfer protects the internal components by maintaining processing temperatures of the cell can within tolerable ranges for the internal components.

As previously noted, the cell can material added on the faces of the cell can to facilitate thermal transfer of the cell can may also provide structural strength. Such strength may be useful, for example, during cell can battery testing. During such testing, the temperature of the assembled cell being tested may become elevated, leading to expansion of the battery material and corresponding internal cell can stresses. The added structural integrity provided by the cell can design mitigates the risk that the cell will undergo a corresponding expansion, that may lead to potential damage or rupturing of the cell can.

Figure 31A:
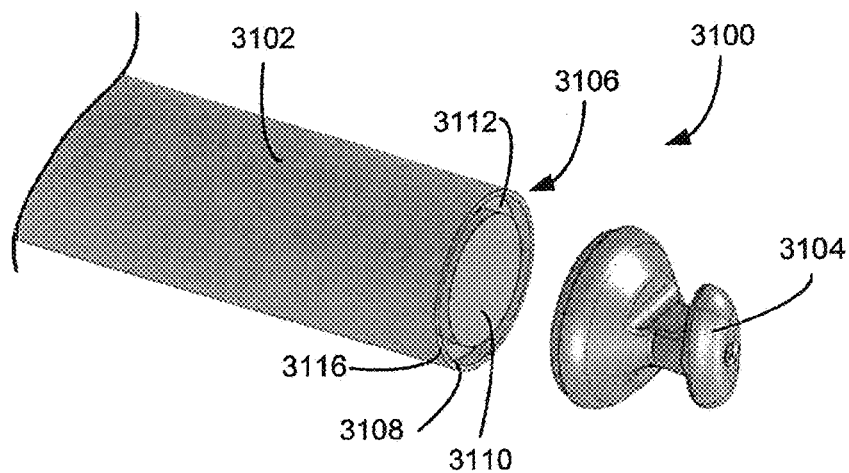
FIGS. 31A-31B are isometric views of a leadless pacemaker including a housing and an attachment feature in a preassembled state.
Figure 31B:
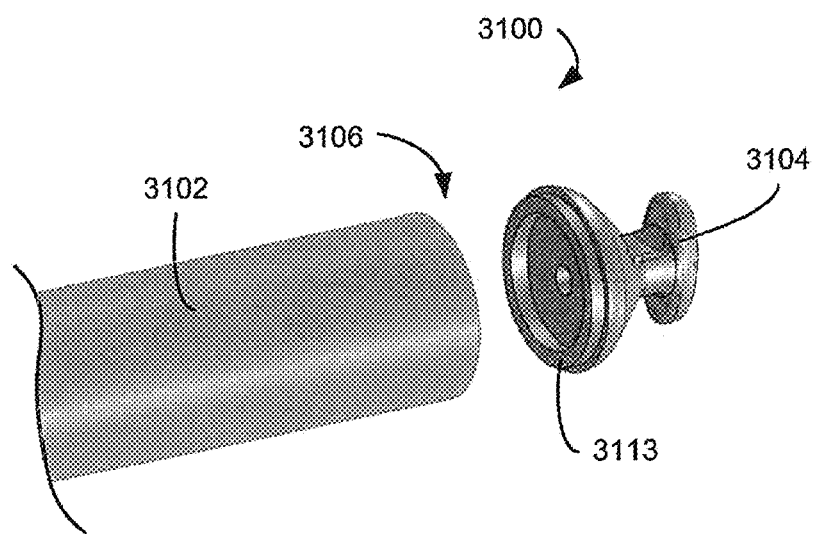

FIGS. 31A-31B are isometric views of a proximal section of a first leadless pacemaker 3100 according to the present disclosure prior to coupling of an attachment feature 3104 to a housing 3102 of the leadless pacemaker 3100.

As shown in FIG. 31A, the housing 3102 includes a proximal end 3106 including a peripheral flange 3108 and a center hub 3110. The peripheral flange 3108 and the center hub 3110 are substantially flush and further define a groove 3112 between them. As shown in FIG. 31B, the attachment feature 3104 generally includes a protrusion 3113 shaped to be received by the groove 3112 during assembly and prior to laser welding or other joining of the attachment feature 3104 to the housing 3102.

Figure 31C:
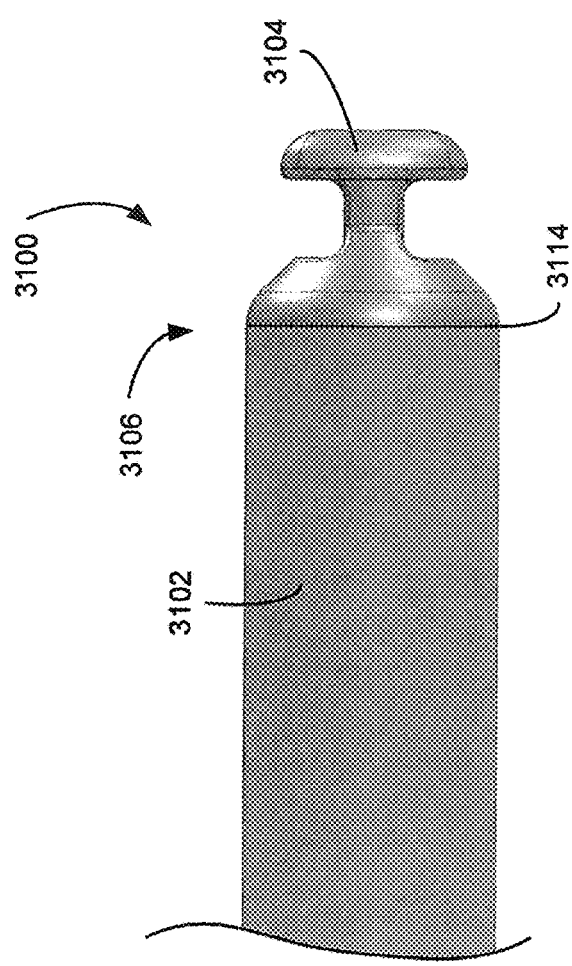
FIG. 31C is a side elevation view of the leadless pacemaker of FIGS. 31A-31B in an assembled state.

FIG. 31C is a side elevation view of the leadless pacemaker 3100 with the attachment feature 3104 inserted into the proximal end 3106 of the housing 3102. During assembly, the attachment feature 3104 and the housing 3102 are coupled along a seam 3114 about which a heat-based joining process, such as laser or other welding, is applied. Accordingly, the peripheral extent of the housing 3102 along the flange 3108 corresponding to a weld seam location 3116 (shown in FIG. 31A).

Figure 32A:
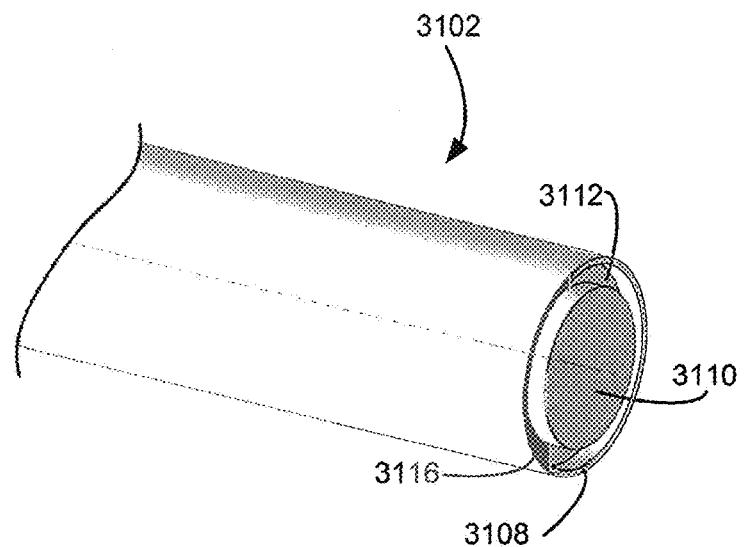
FIGS. 32A-32B are an isometric and cross-sectional side view, respectively of the housing of FIGS. 31A-31C.
Figure 32B:
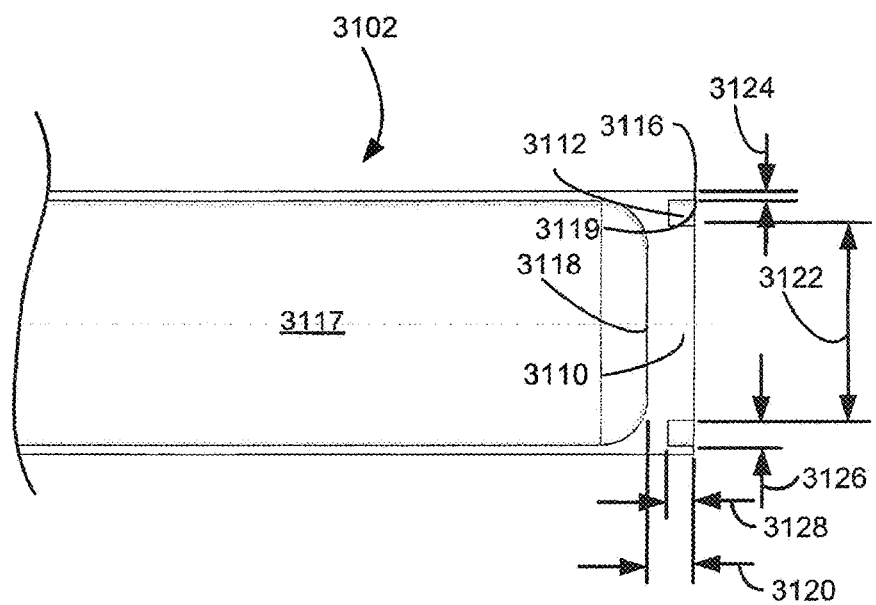

FIG. 32A is an isometric view of a proximal section of the housing 3102, which further illustrates each of the peripheral flange 3108, the center hub 3110 and the groove 3112 defined between the peripheral flange 3108 and the center hub 3110. FIG. 32B is a cross-sectional side view the proximal section of the housing 3102, which further illustrates an internal cavity 3117 of the housing 3102.

During assembly, battery material, electronic components or both may be inserted into the internal cavity 3117. The internal cavity 3117 may include a proximal inner surface 3118 that is longitudinally offset from the proximal face 3119 of the peripheral flange 3108 by a distance 3120. In certain implementations, the distance 3120 may be from and including 0.1 millimeters (0.004 inches) to and including 1 millimeter (0.040 inches). In one example implementation, the distance 3120 may be approximately 0.25 millimeters (0.010 inches).

As further illustrated in FIG. 32B, other elements of the proximal section of the housing 3102 may also adhere to particular dimensional parameters. First, the center hub 3110 may have a diameter 3122 from and including 4 millimeters (0.16 inches) to and including 6.25 millimeters (0.25 inches). In one example implementation, the distance 3122 may be approximately 5.5 millimeters (0.22 inches). The peripheral flange 3108 may have a thickness 3124 from and including 0.1 millimeters (0.004 inches) to and including 0.5 millimeters (0.020 inches). In one example implementation, the thickness 3124 may be approximately 0.25 millimeters (0.10 inches). The groove 3112 may have a width 3126 from and including 0.01 millimeters (0.0004 inches) to and including 0.5 millimeters (0.020 inches) and a depth 3128 from and including 0.01 millimeters (0.0004 inches) to and including 0.5 millimeters (0.020 inches). For example, in one implementation, the width 3126 may be approximately 0.25 millimeters (0.010 inches) and the depth 3128 may be approximately 0.25 millimeters (0.010 inches).

Figure 33:
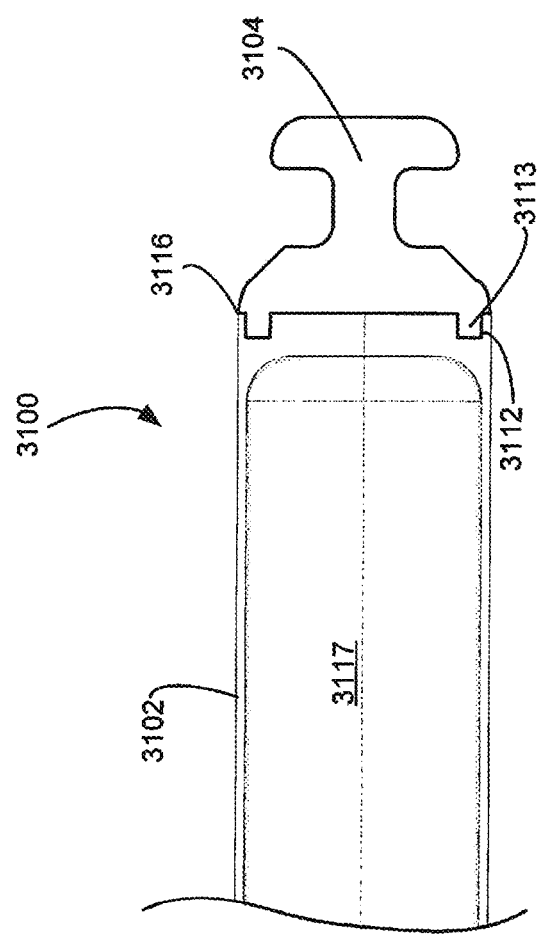
FIG. 33 is a cross-sectional side view of the leadless pacemaker of FIGS. 31A-31C in an assembled state.

FIG. 33 is a cross-sectional side view of the proximal section of the leadless pacemaker 3100 with the attachment feature 3104 coupled to the housing 3102. As illustrated in FIG. 33 the protrusion 3113 of the attachment feature 3104 is received within the groove 3112 of the housing 3102, thereby forming an interface between the attachment feature 3104 and the housing 3102 along the weld seam location 3116.

The leadless pacemaker 3100 illustrated in FIGS. 31A-33 has various advantages. For example, the leadless pacemaker 3100 has a weld seam located away from the battery material and electronics disposed within the internal cavity 3117 of the housing 3102. The interface between the housing 3102 and the attachment feature 3104 further minimizes thermal energy transfer to the internal cavity 3117 by restricting the thermal pathway between the weld seam location 3116 and the internal cavity 3117 to the relatively thin peripheral flange 3108. By positioning the weld seam location 3116 over at least a portion of the attachment feature 3104, thermal energy transfer and dissipation is further facilitated through the attachment feature 3104 and away from the contents of the housing 3102, which may be temperature sensitive. The center hub 3110 also provides added strength to the housing 3102, which may prevent expansion and resulting damage the housing 3102 that may occur due to internal thermal stresses during to processing and/or testing of the leadless pacemaker 3100. The center hub 3110 further functions as a heat sink, thereby providing additional thermal protection of the components contained within the housing 3102. Complimentary pairs of notches, tabs, grooves, or similar features may also be incorporated into the housing 3102 and the attachment feature 3104 to facilitate alignment of the attachment feature 3104 with the housing 3102. In certain implementations, the housing 3102 and the attachment feature 3104 may also include complementary threads or similar structures such that the attachment feature 3104 may be screwed onto the housing 3102.

Figure 34A:
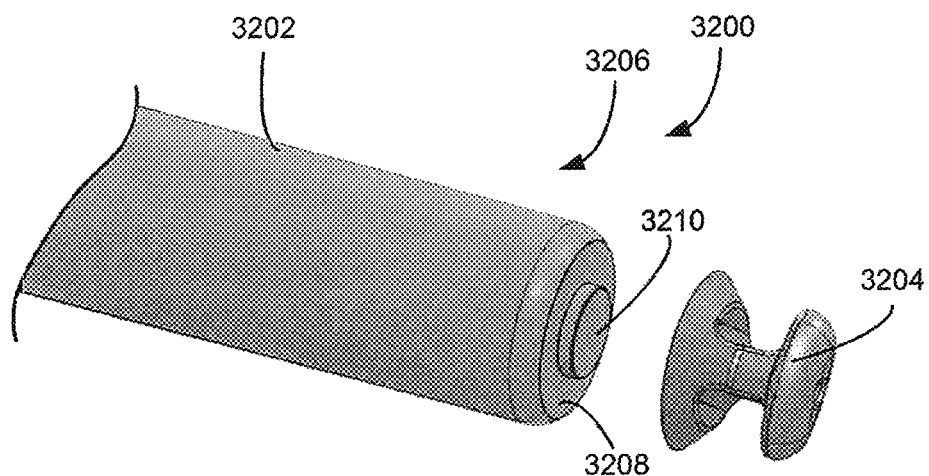
FIGS. 34A-34B are isometric views of a second leadless pacemaker including a housing and an attachment feature in a preassembled state.
Figure 34B:
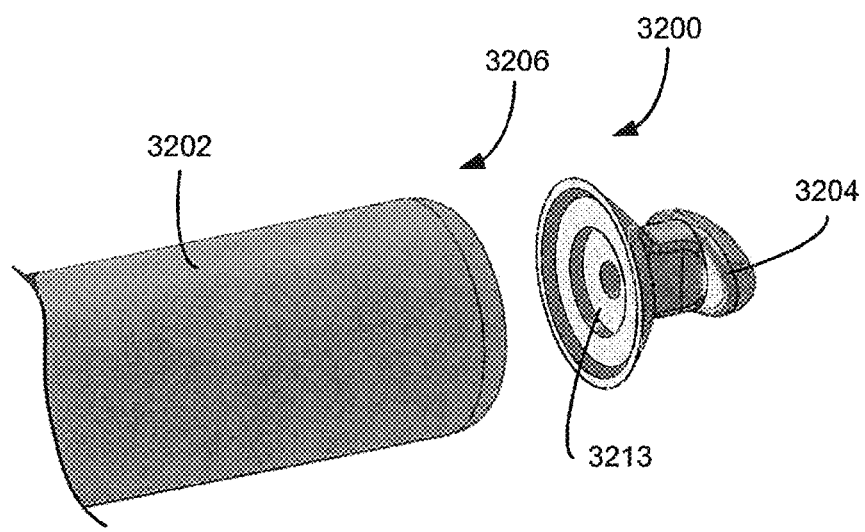

FIGS. 34A-34B are isometric views of a proximal section of a second leadless pacemaker 3200 according to the present disclosure prior to coupling of an attachment feature 3204 to a housing 3202 of the leadless pacemaker 3200.

As shown in FIG. 34A, the housing 3202 includes a proximal end 3206 including a proximal face 3208 from which a center protrusion 3210 extends. As shown in FIG. 34B, the attachment feature 3204 generally includes a cavity 3213 shaped to receive the center protrusion 3210 of the housing 3202 during assembly and prior to laser welding or other joining of the attachment feature 3204 to the housing 3202.

Figure 34C:
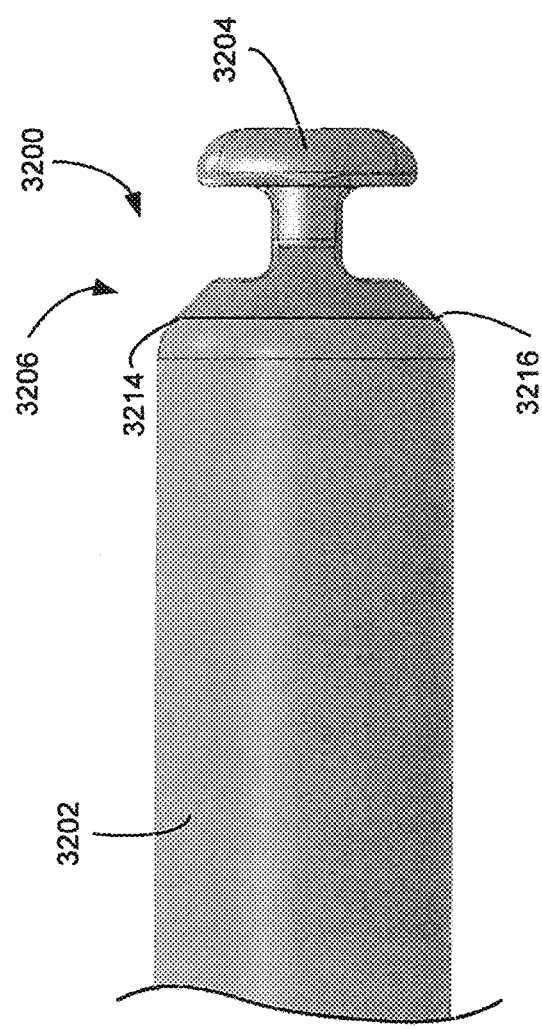
FIG. 34C is a side elevation view of the leadless pacemaker of FIGS. 31A-31B in an assembled state.

FIG. 34C is a side elevation view of the leadless pacemaker 3200 with the attachment feature 3204 abutting the proximal face 3208 (shown in FIGS. 34A-34B) of the housing 3202. The attachment feature 3204 and the housing 3202 are generally coupled along a seam 3214 about which a heat-based joining process, such as laser or other welding, is applied. Accordingly, the peripheral extent of the interface of the attachment feature 3204 and the housing 3202 generally defines a weld seam location 3216.

Figure 35A:
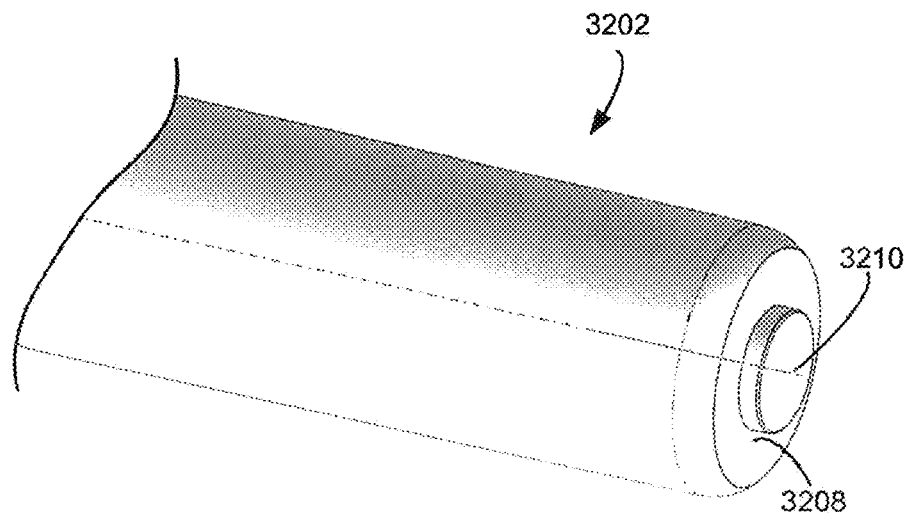
FIGS. 35A-35B are an isometric and cross-sectional side view, respectively of the housing of FIGS. 34A-34C.
Figure 35B:
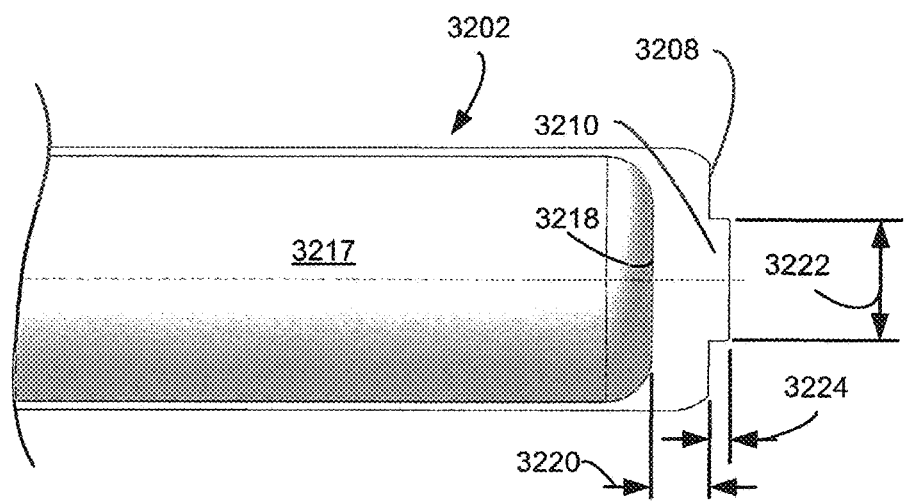

FIG. 35A is an isometric view of a proximal section of the housing 3202, which further illustrates each of the proximal face 3208 and the center protrusion 3210. FIG. 35B is a cross-sectional side view of the proximal section of the housing 3202, which further illustrates an internal cavity 3217 of the housing 3202.

During assembly, battery material, electronic components or both may be inserted into the internal cavity 3217. The internal cavity 3217 may include a proximal inner surface 3218 that is longitudinally offset from the proximal face 3208 by a distance 3220. In certain implementations, the distance 3220 may be from and including 0.1 millimeters (0.004 inches) to and including 1 millimeter (0.040 inches). In one example implementation, the distance 3220 may be approximately 0.25 millimeters (0.010 inches). As further illustrated in FIG. 35B, the center protrusion 3210 may have a diameter 3222 from and including 2 millimeters (0.080 inches) to and including 6 millimeters (0.24 inches) and a thickness 3224 from and including 0.01 millimeters (0.0004 inches) to and including 1 millimeter (0.040 inches).

Figure 36:
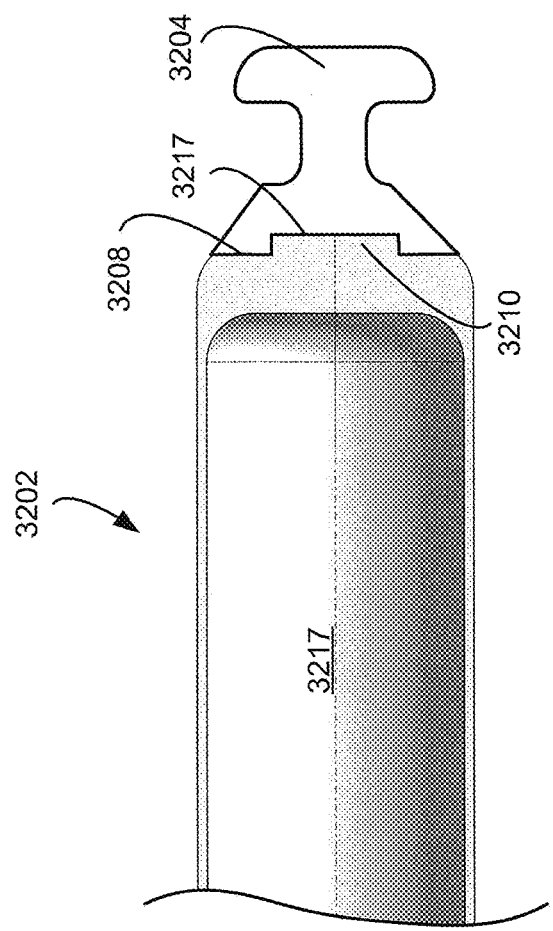
FIG. 36 is a cross-sectional side view of the leadless pacemaker of FIGS. 34A-34C in an assembled state.

FIG. 36 is a cross-sectional side view of the proximal section of the leadless pacemaker 3200 with the attachment feature 3204 coupled to the housing 3202. As illustrated in FIG. 36, the center protrusion 3210 is received within the cavity 3213 of the attachment feature 3204, thereby forming a weld seam location 3216 at the periphery of the interface between the housing 3202 and the attachment feature 3204.

The leadless pacemaker 3200 illustrated in FIGS. 32A-36 has various advantages. For example, the increased mass of the center protrusion 3210 disposed at the proximal end of the housing 3202 mitigates delivery of thermal energy to internal components that may be stored within the housing 3202. Moreover, the increased mass of the center protrusion 3210 displaces the weld seam location 3216 relative to the internal cavity 3217 and any components contained therein. The added material provided by the center protrusion 3210 also adds to the strength of the housing 3202, provides a heat sink for thermal energy imparted onto the housing 3202, and may further include notches, tabs, or similar features that may be used to facilitate alignment of the attachment feature 3204 on the housing 3202.

Figure 37A:
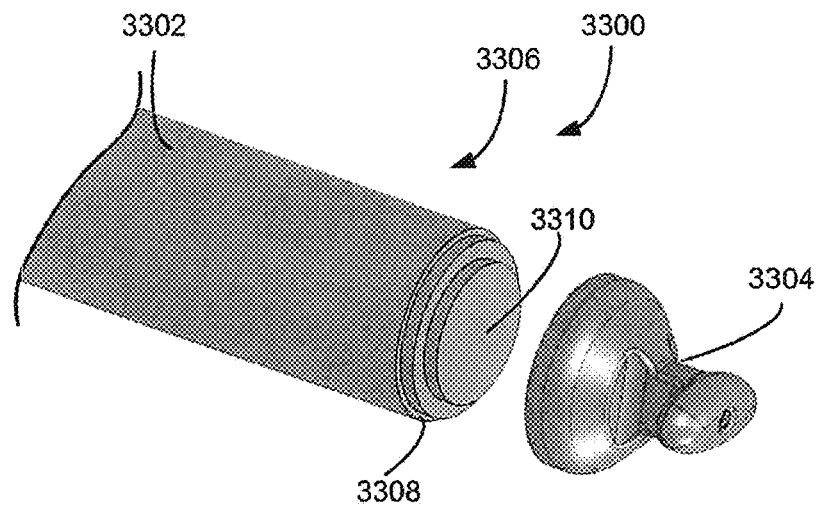
FIGS. 37A-37B are isometric views of a third leadless pacemaker including a housing and an attachment feature in a preassembled state.
Figure 37B:
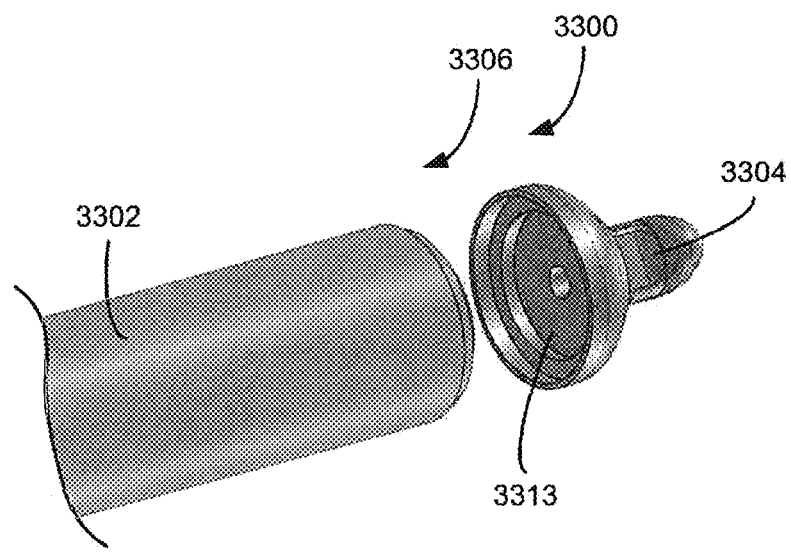

In certain applications, the overall length of a leadless pacemaker may be a critical aspect of its design. For example, a particular length may be required to avoid interference with various intra-cardiac structures and elements. Accordingly, the additional length resulting from the added thickness at the proximal end of the housing illustrated in the example leadless pacemakers of 3100 and 3200 of FIGS. 31A-36 may not be feasible. In such applications, a lower profile design that nevertheless imparts structural and thermal advantages may be desirable. FIGS. 37A-37B illustrate one implementation of such a design.

FIGS. 37A-37B are isometric views of a proximal section of a third leadless pacemaker 3300 according to the present disclosure prior to coupling of an attachment feature 3304 to a housing 3302 of the leadless pacemaker 3300.

As shown in FIG. 37A, the housing 3302 includes a proximal end 3306 including a proximal face 3308 from which a multi-level protrusion 3310 extends. As shown in FIG. 34B, the attachment feature 3304 generally includes a cavity 3313 shaped to receive the multi-level center protrusion 3310 of the housing 3302 during assembly and prior to laser welding or other joining of the attachment feature 3304 to the housing 3302.

Figure 37C:
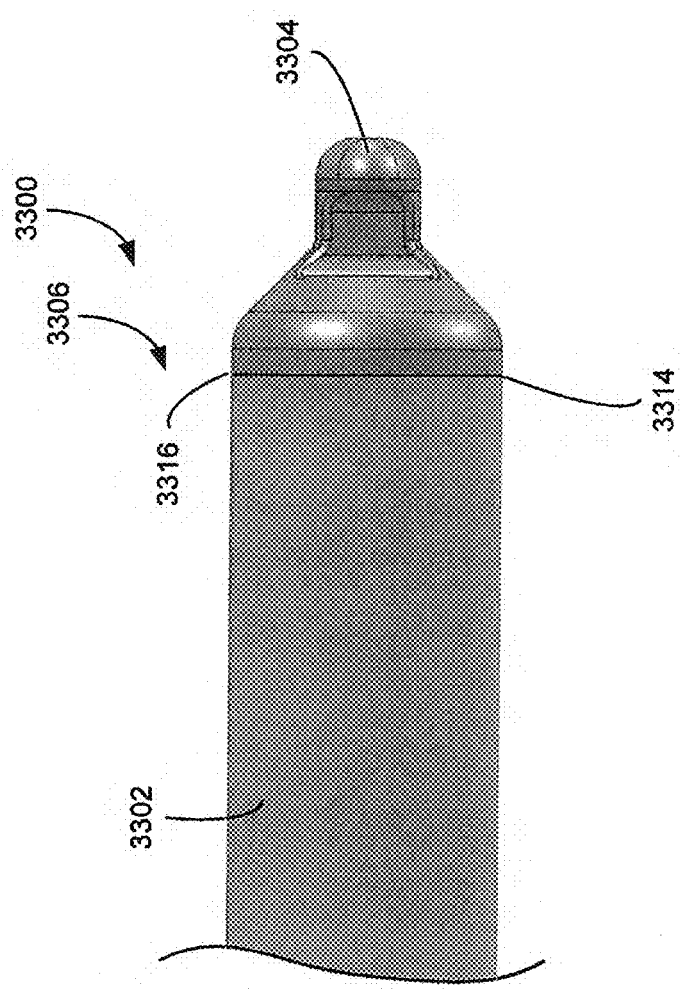
FIG. 37C is a side elevation view of the leadless pacemaker of FIGS. 37A-37B in an assembled state.

FIG. 37C is a side elevation view of the leadless pacemaker 3300 with the attachment feature 3304 disposed such that the multi-level protrusion 3310 is received by the cavity 3313 (each shown in FIGS. 37A-37B) of the attachment feature 3304. When abutting, the attachment feature 3304 and the housing 3302 generally define a seam location 3314 about which heat-based joining, such as laser or other welding, may be applied to couple the attachment feature 3304 to the housing 3302. Accordingly, the peripheral extent of the interface of the attachment feature 3304 and the housing 3302 generally defines a weld seam location 3316.

Figure 38A:
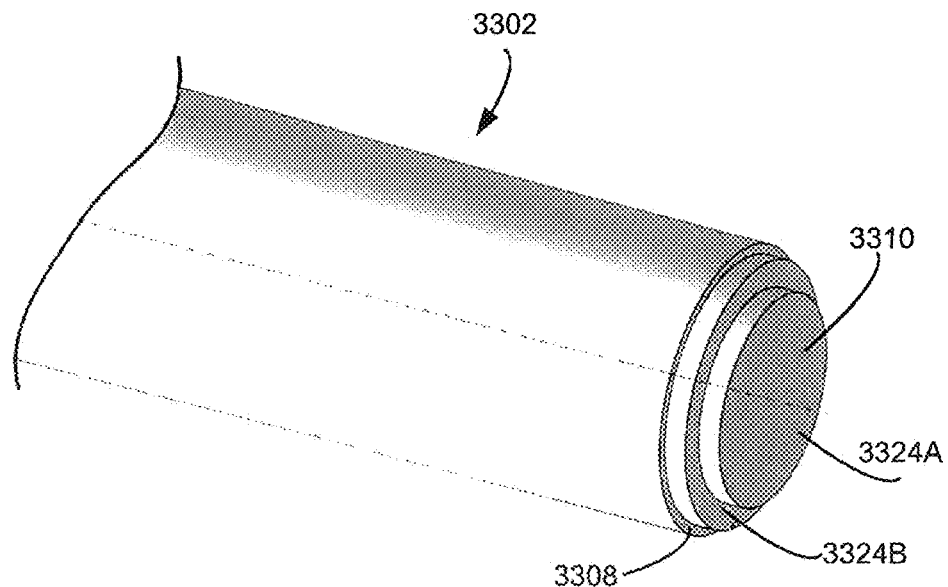
FIGS. 38A-38B are an isometric and cross-sectional side view, respectively of the housing of FIGS. 37A-37C.
Figure 38B:
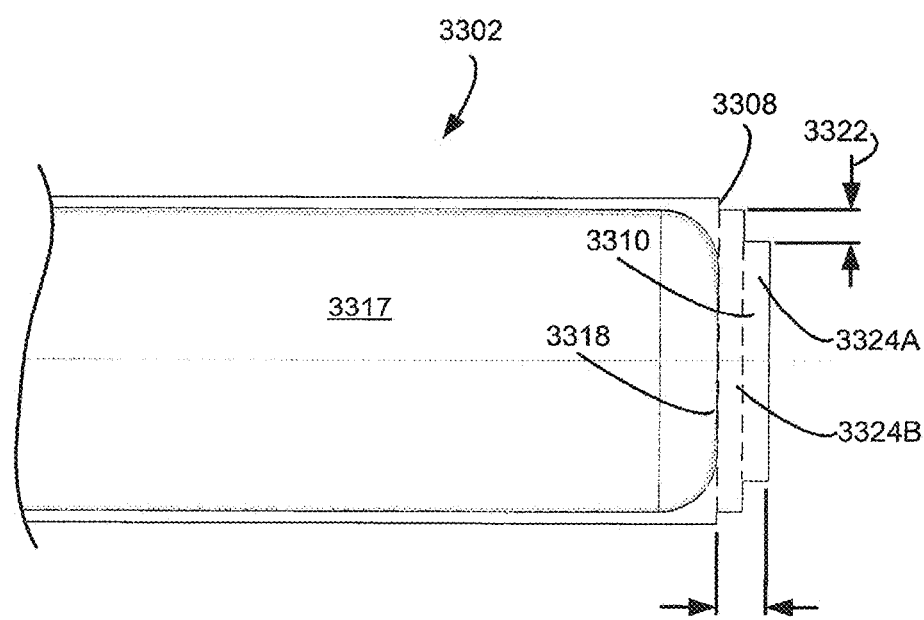

FIG. 38A is an isometric view of a proximal section of the housing 3302, which further illustrates the multi-level protrusion 3310. FIG. 38B is a cross-sectional side view of the proximal section of the housing 3302, which further illustrates an internal cavity 3317 of the housing 3302.

During assembly, battery material, electronic components or both may be inserted into the internal cavity 3317. The internal cavity 3317 may include a proximal inner surface 3318. In contrast to the previous implementations illustrated in FIGS. 31A-36 in which the proximal inner surface was substantially longitudinally offset from the weld seam location, the housing 3302 does not include a significant offset between the proximal inner surface 3318 and a proximal face 3308 from which the multi-level protrusion 3310 extends and about which extends the weld seam for coupling the housing 3302 with the attachment feature 3304. The thermal path between the weld seam location 3316 and the internal cavity 3317 is reduced as compared to the previously discussed implementations, and the added material associated with the multi-level protrusion 3310 provides significant structural benefits. Moreover, the added material causes the multi-level protrusion 3310 to function as a heat sink, drawing thermal energy away from the internal cavity 3317.

Similar to the previous implementations, the housing 3302 may adhere to certain dimensional parameters. For example, the multi-level protrusion 3310 may have an overall height 3320 from and including 0.25 millimeters (0.010 inches) to and including 1.5 millimeters (0.060 inches). In one example implementation, the height 3320 may be approximately 0.75 millimeters (0.030 inches). The multi-level protrusion 3310 may also have different numbers of layers, different thicknesses for each layer, and/or different radii of adjacent layers. For example, the multi-level protrusion 3310 may include from and including two layers to and including three layers, with each layer being from and including 0.01 millimeters (0.0004 inches) to and including 1 millimeter 0.040 inches) thick, and adjacent layers having a radial difference 3322 from and including 0.01 millimeters (0.0004 inches) to and including 1 millimeter (0.040 inches). For example, in one specific implementation, the multi-level protrusion 3310 may include two layers 3324A, 3324B having a thickness of 0.5 millimeters (0.020 inches) and 0.25 millimeters (0.010 inches), respectively. The radial difference 3322 between the adjacent layers 3324A, 3324B may also be approximately 1 millimeter (0.040 inches).

Figure 39:
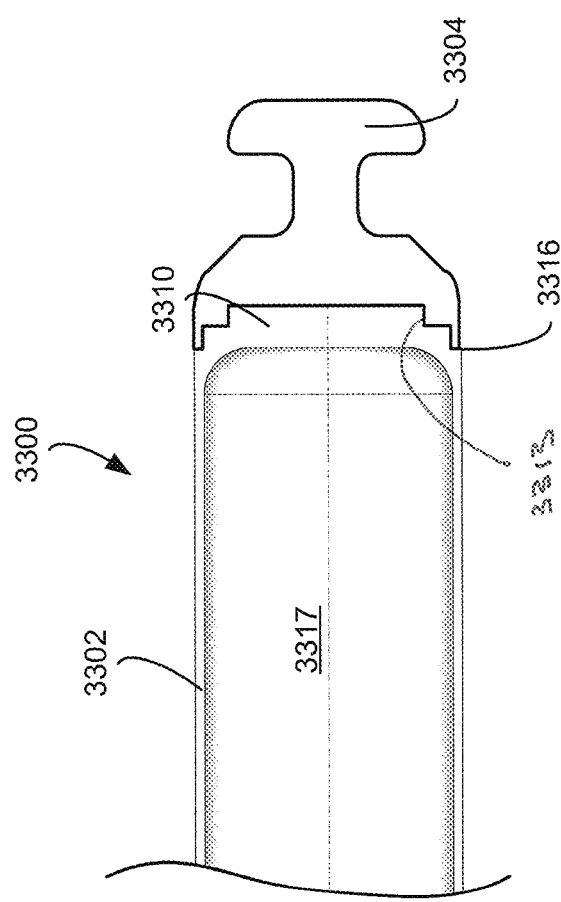
FIG. 39 is a cross-sectional side view of the leadless pacemaker of FIGS. 37A-37C in an assembled state.

FIG. 39 is a cross-sectional side view of the proximal section of the leadless pacemaker 3300 with the attachment feature 3304 coupled to the housing 3302. As illustrated in FIG. 38, the multi-level protrusion 3310 is received within the cavity 3313 of the attachment feature 3304, thereby forming a weld seam location 3316 at the periphery of the interface between the housing 3302 and the attachment feature 3304.

E. Alternative Retrieval Feature Designs

As previously discussed in the context of FIGS. 5A-5C and throughout the foregoing disclosure, a retrieval system may be used in conjunction with leadless biostimulators of the present disclosure to facilitate retrieval of the leadless biostimulators following implantation. The retrieval system includes a series of nested catheters through which one or more snares (or similar retrieval mechanisms) are delivered to the implantation location of the leadless biostimulator. During retrieval, one or more of the snares is looped around a proximal retrieval feature of the leadless biostimulator and cinched or otherwise tightened about the retrieval feature to couple the leadless biostimulator to the retrieval system.

Once coupled in this manner, the proximal end of the leadless biostimulator can be made to enter a docking cap (or similar structure, such as a socket) disposed on a distal end of the retrieval system. Such docking is generally the result of one or both of the docking cap being extended towards the leadless biostimulator and the leadless biostimulator being drawn into the docking cap. When properly docked, the leadless biostimulator is rotationally locked with the docking cap and torque may be applied to the leadless biostimulator to counter rotate the leadless biostimulator and ultimately disengage the leadless biostimulator from the cardiac tissue within which it is implanted.

Among other things, the retrieval feature of the leadless biostimulator significantly dictates the alignment between the leadless biostimulator and the docking cap (or similar retrieval system structure) during docking. Under ideal circumstances, the leadless biostimulator and the docking cap are coaxially aligned prior to docking, thereby facilitating full and easy docking of the leadless biostimulator. However, such coaxial alignment is often impractical due to the difficulty of capturing the leadless biostimulator using the snare of the retrieval system, interference between the geometries of the leadless biostimulator and the retrieval system, and the potential for tissue overgrowth onto the leadless biostimulator. Additionally, the retrieval feature must generally be robust enough to withstand the forces associated with the delivery, implantation, and retrieval processes. For example, during snaring and docking, significant forces are applied to the retrieval feature in various directions. As another example, the retrieval feature may contact or otherwise be impinged upon by tissue during any of delivery, cycling of the heart, or retrieval. Accordingly, the retrieval feature must be sufficiently robust to withstand such forces without breaking off, in whole or in part, and potentially becoming embolic. It is with these considerations in mind, among others, that the following retrieval features were conceived.

Figure 43A:
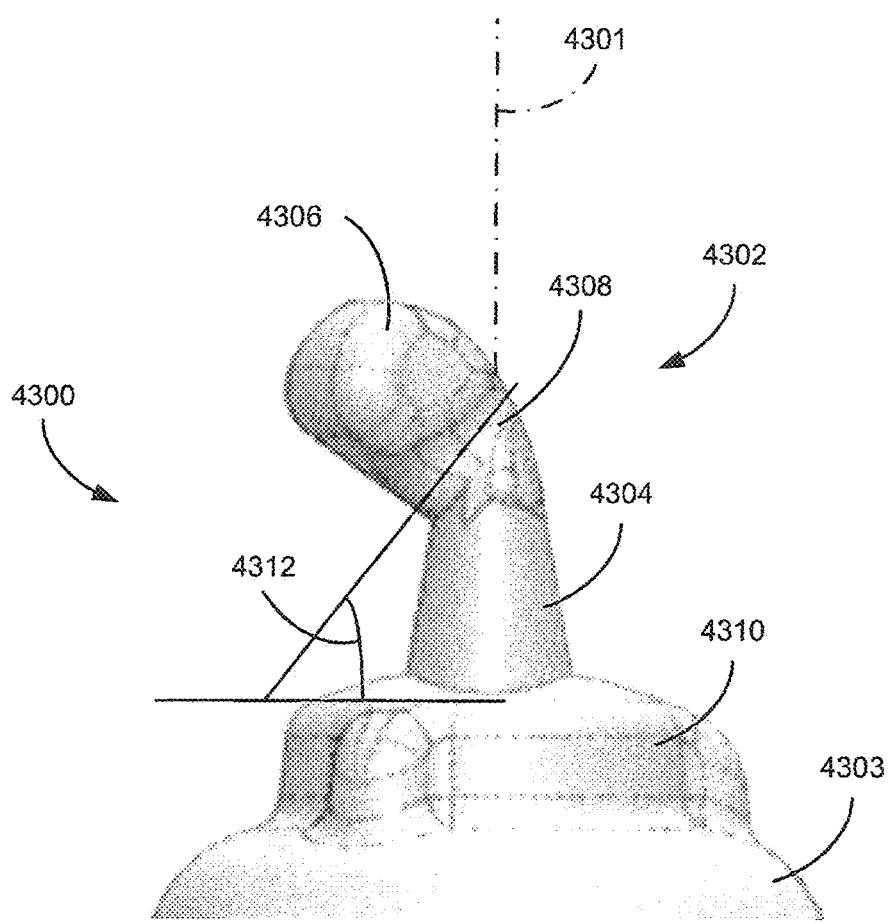
FIGS. 43A-43C are a first side elevation view, a proximal end view, and a second side elevation view of a leadless biostimulator having a club-type retrieval feature.
Figure 43B:
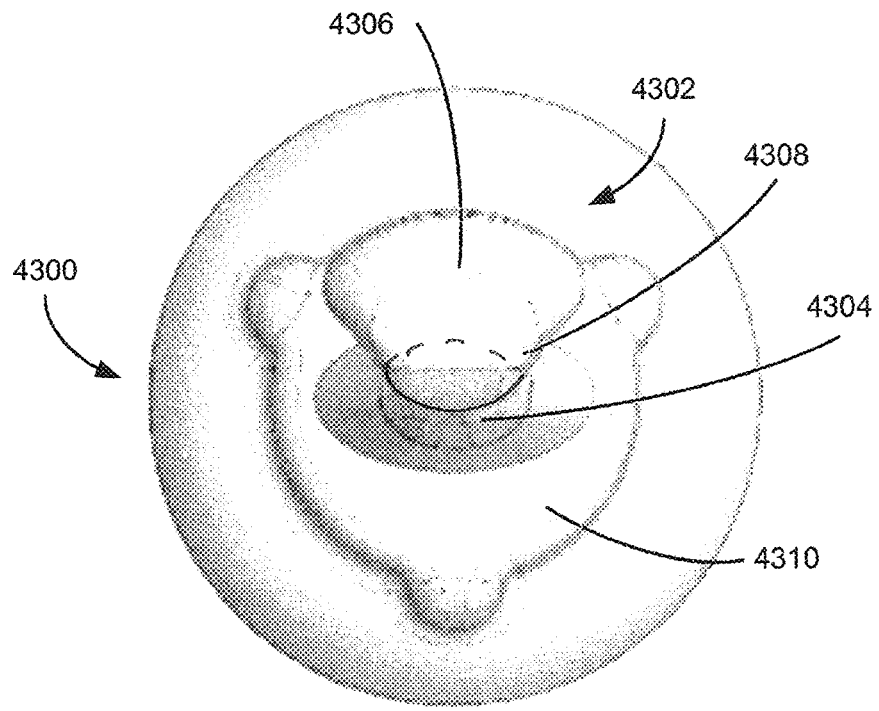
Figure 43C:
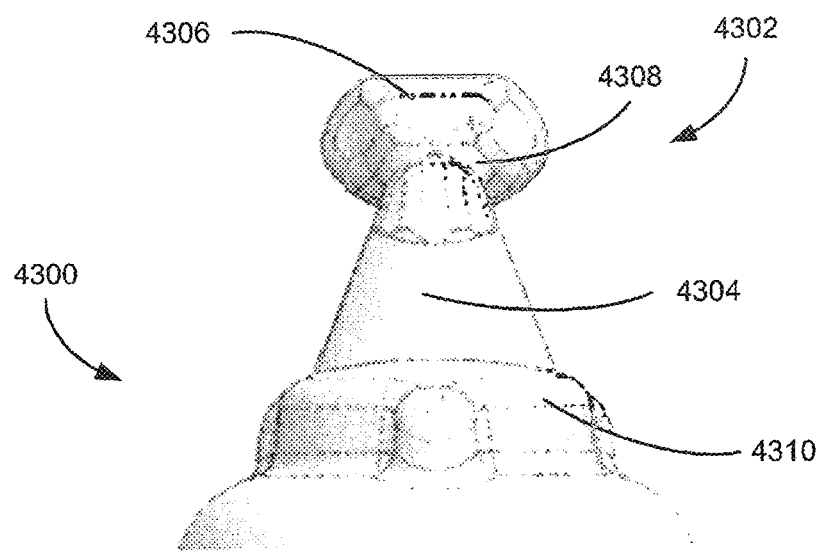

FIGS. 43A-43C illustrate a proximal end of an example biostimulator 4300 including a club-type retrieval feature 4302 in accordance with the present disclosure. More specifically, FIG. 43A is a first side elevation view of the retrieval feature 4302, FIG. 43B is a proximal end view of the retrieval feature 4302, and FIG. 43C is a second side elevation view of the retrieval feature 4302.

The retrieval feature 4302 is generally disposed on a proximal end of the biostimulator 4300 and is used to facilitate retrieval of the biostimulator 4300 after implantation by interacting with a snare or similar retrieval mechanism of a catheter-based retrieval system. The retrieval feature 4302 generally extends from a base 4310 and includes a proximally extending stem 4304 from which a head 4306 extends. The stem 4304 and the head 4306 are generally formed from a rigid material to minimize the likelihood that either the stem 4304 or the head 4306 will fatigue and break during implantation, cycling of the heart, or retrieval following implantation. As illustrated in FIG. 43A, in certain implementations, the stem 4304 and the head 4306 may be integrally formed with a housing 4303 of the leadless biostimulator 4300.

The stem 4304 and the head 4306 are generally shaped to facilitate capture of the retrieval feature 4302 by a snare of a retrieval system. As shown in FIG. 43A, the stem 4304 may extend along a longitudinal axis 4301 defined by the biostimulator 4300 and the head 4306 may extend obliquely from the stem 4304. The head 4306 expands from the stem 4304 such that a narrowed neck 4308 is formed between the stem 4304 and the head 4306. More particularly, the head 4306 can expand outwardly from the neck 4308 such that the head 4306 has a head cross-section that is greater than a neck cross-section of the neck 4308.

Figure 44A:
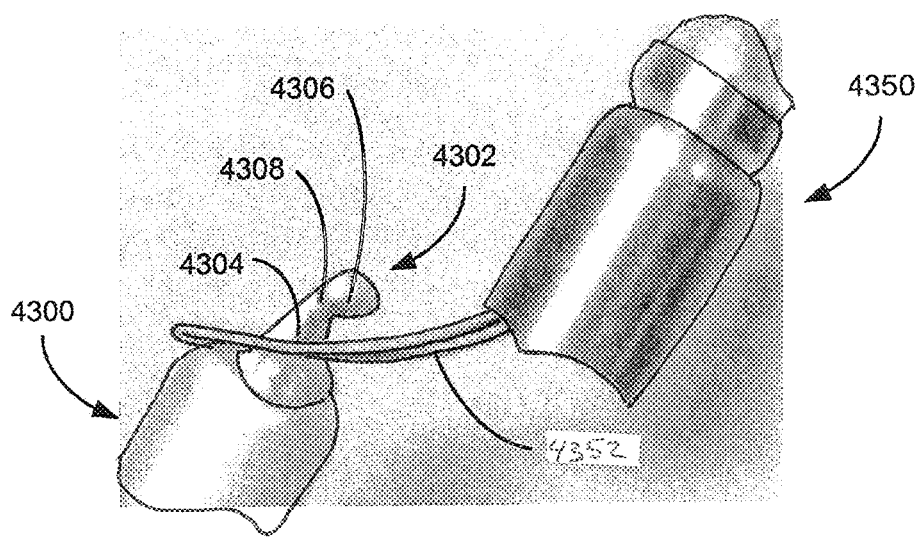
FIGS. 44A-44H are photographs illustrating a docking process of the leadless biostimulator of FIGS. 43A-43C.
Figure 44B:
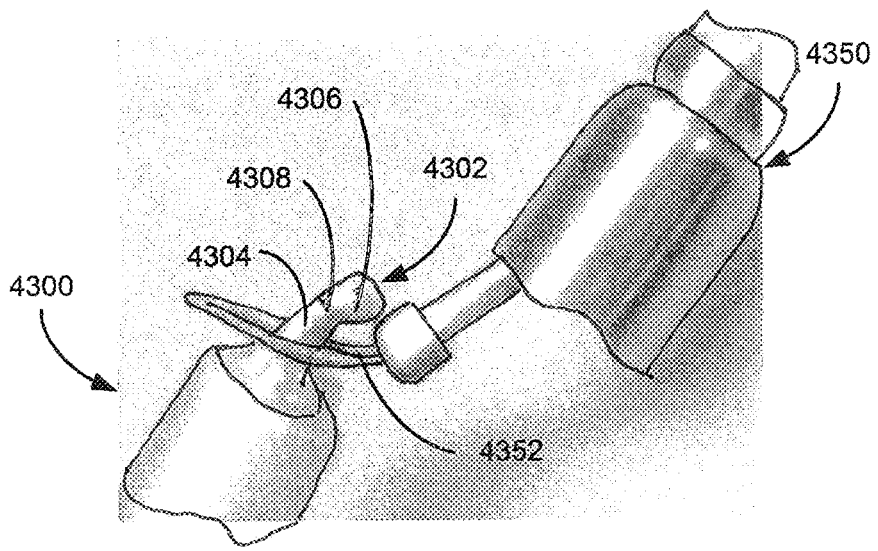
Figure 44C:
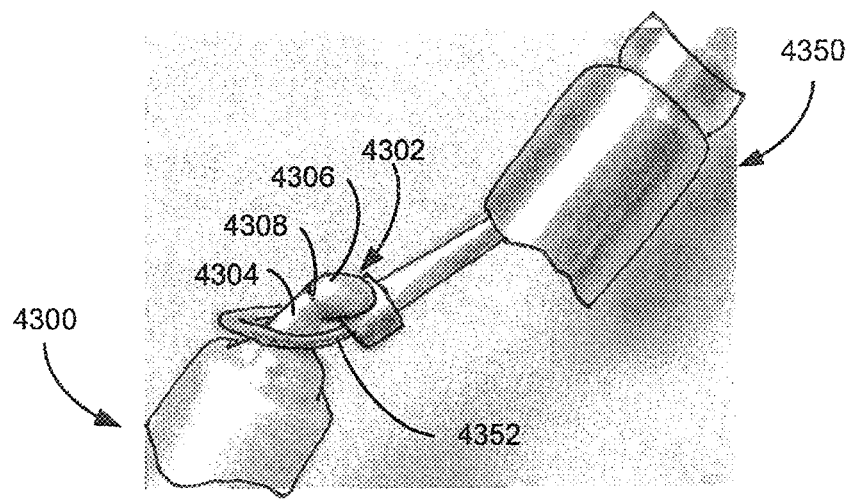
Figure 44D:
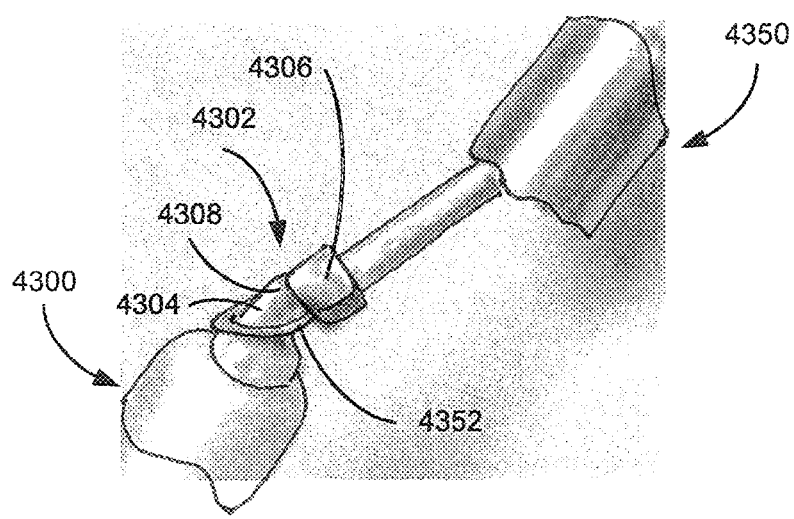
Figure 44E:
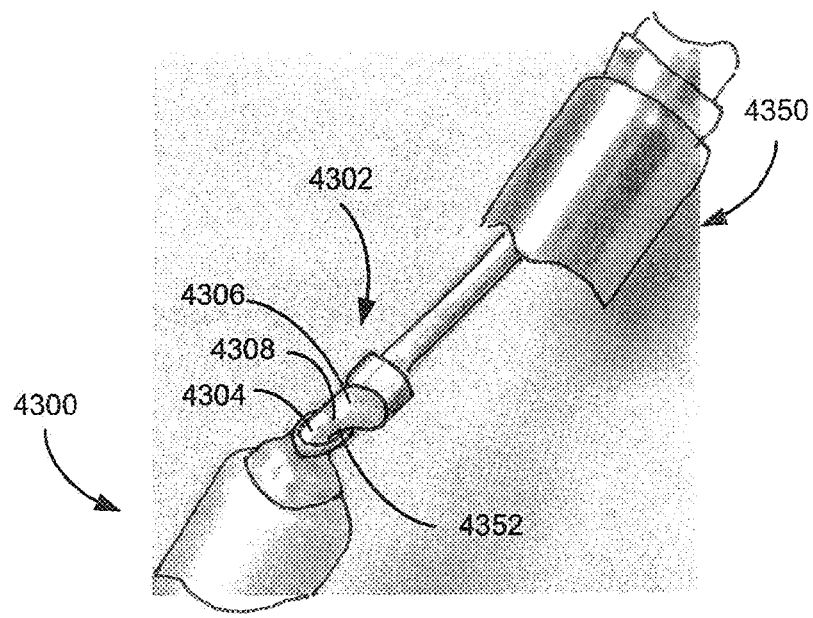
Figure 44F:
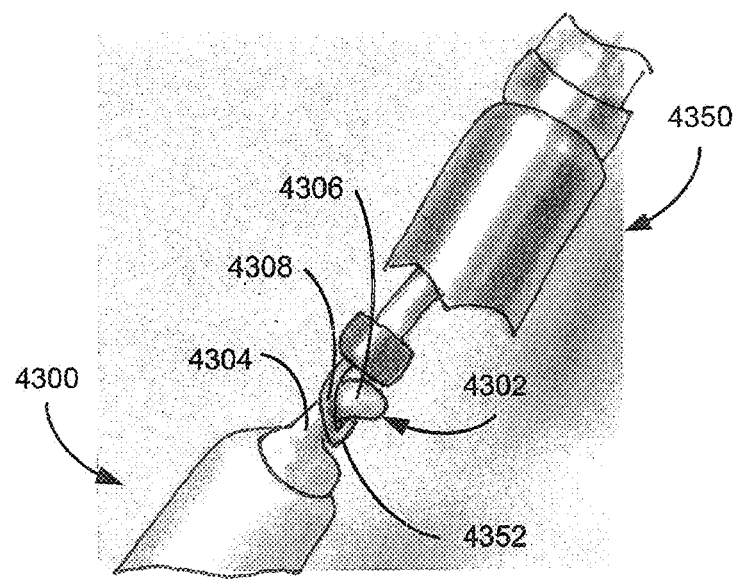
Figure 44G:
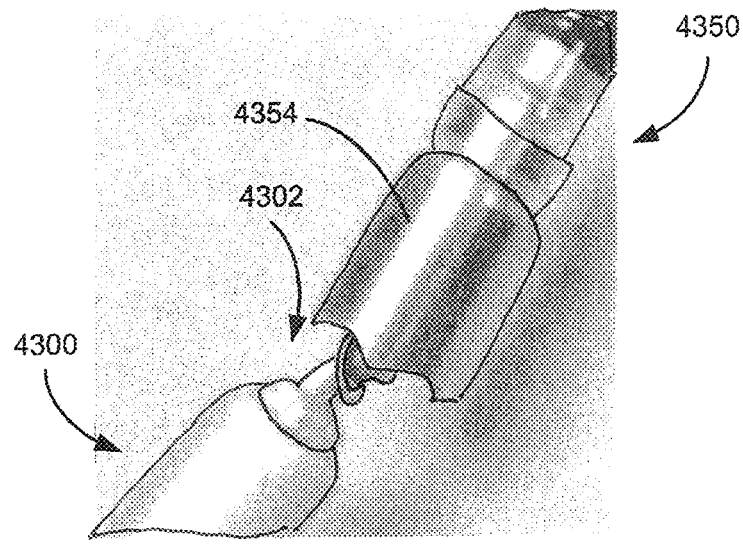
Figure 44H:
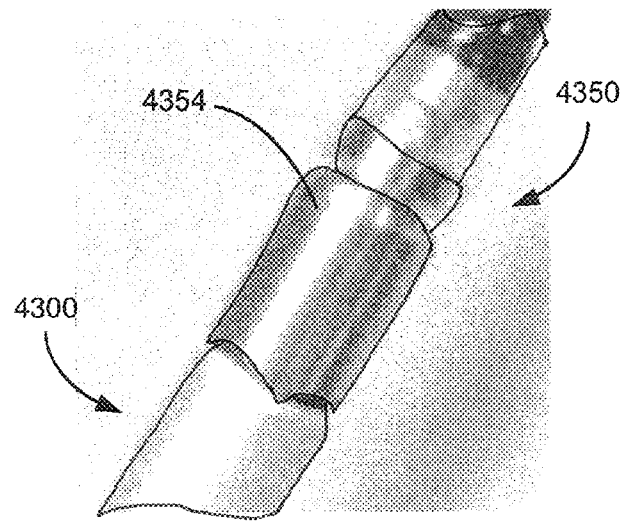

The process of capturing the retrieval feature 4302 using a retrieval system 4350 is illustrated in FIGS. 44A-44H, which are photographs illustrating a general docking process. As shown in FIG. 44A, the snare 4352 of the retrieval system 4350 is first extended and positioned about the retrieval feature 4302. Once the retrieval feature 4302 is disposed within the loop of the snare 4352, the snare 4352 is cinched about the retrieval feature 4302, as shown in FIGS. 44B-44D. As the snare 4352 is further cinched, the snare 4352 moves proximally along the retrieval feature 4302 and is eventually positioned at the neck 4308 of the retrieval feature 4302, as shown in FIG. 44F. When positioned and cinched about the neck 4308, the expanded/bulbous shaped of the head 4306 prevents the cinched snare 4352 from further travelling in the proximal direction. As a result, the retrieval feature 4302 and the snare 4352 remain in a substantially constant position relative to each other unless the snare 4352 is loosened by the user and repositioned. Moreover, and as further described below, the stem 4304, the head 4306, and the neck 4308 are generally shaped such that, when cinched, the snare 4352 and, as a result, other components of the retrieval system 4350 are in a predetermined position and orientation relative to the retrieval feature 4302 to facilitate docking of the leadless biostimulator 4300. For example, and as illustrated in FIGS. 44G-44H, the retrieval feature 4302 may be shaped such that when captured by the snare 4352, a docking cap 4354 or similar structure of the retrieval system 4350 may be in a predetermined alignment (e.g., a substantially coaxial alignment) with the retrieval feature 4302. The predetermined alignment may be such that when the docking cap is translated relative to the retrieval feature 4302, the docking cap extends over the retrieval feature 4302, as illustrated FIG. 44H.

As previously noted, the stem 4304, the head 4306, and the neck 4308 formed between the stem 4304 and the head 4306 may include various features that facilitate location of the snare as the snare is cinched. Referring back to FIGS. 43A-43C, the stem 4304 may have an elliptical cross-section (most clearly visible in FIG. 43B) and a proximal taper (most clearly visible in FIG. 43C), each of which facilitates movement of the snare into a predetermined orientation at the neck 4308 when the snare is cinched. Similar to rigid stem 612 discussed in the context of FIGS. 8A-8B, the elliptical cross-section of the stem 4304 causes the leadless biostimulator 4300 to assume an angular orientation relative to the snare as the snare is cinched about the stem 4302. A similar effect may be achieved by any cross-sectional shape having major and minor axes of different lengths, such as a rectangular cross-section. However, the elliptical shape of the stem 4302 illustrated in FIGS. 43A-43C may be preferable to minimize potential snagging of the snare about the stem 4302 and to eliminate edges of the retrieval feature 4302 such that the retrieval feature 4302 has a substantially atraumatic profile. The stem 4304 may also be tapered, e.g., proximally tapered, such that as the snare is cinched about the stem 4304, the snare is guided proximally to the neck 4308. Although illustrated in combination, implementations of the present disclosure may include either or both of the elliptical cross-section and the taper.

In certain implementations, the head 4306 may be disposed at an obtuse angle relative to the base 4310 to reduce the likelihood of the head 4306 becoming hooked or snagged or otherwise causing trauma to cardiac tissue. To further reduce the likelihood of trauma caused by the head 4306, the head 4306 may have a substantially rounded or bulbous shape with no or minimal edges. Such a rounded shape may, for example, reduce the likelihood of trauma in the event the head 4306 repeatedly contacts cardiac tissue as the heart cycles. The expanded/bulbous shape of the head 4306 relative to the stem 4304 and the neck 4308 also prevents the snare from spontaneously releasing from the retrieval feature 4302 once the snare has been cinched about the neck 4308.

As previously noted, the stem 4304 and the head 4306 are joined at the neck 4308, which forms a narrowed portion of the retrieval feature 4302 about which the snare is cinched. In certain implementations, the neck 4308 may simply be formed by the junction of the stem 4304 and the head 4306. In other implementations, the neck 4308 may include a groove, indentation, or similar cut-out feature such that the neck 4308 is narrower than the stem 4304. The stem 4304 and the head 4306 may also be oriented relative to each other such that the neck 4308 is disposed at a predetermined angle relative to the base 4310 that promotes docking of the retrieval feature 4302 within the docking cap or of the retrieval system. For example, during testing, it was observed that orienting the neck 4308 at an angle 4312 (shown in FIG. 43A) of approximately 60 degrees relative to the base 4310 facilitated retrieval by providing a balance between the ease with which the retrieval feature 4302 is captured by the snare of the retrieval system and the alignment of the biostimulator 4300 relative to the retrieval system once the snare is cinched about the neck 4308. In other implementations, the angle 4312 between the base 4310 and the neck 4308 may be from and including approximately 30 degrees to and including approximately 90 degrees.

Figure 45A:
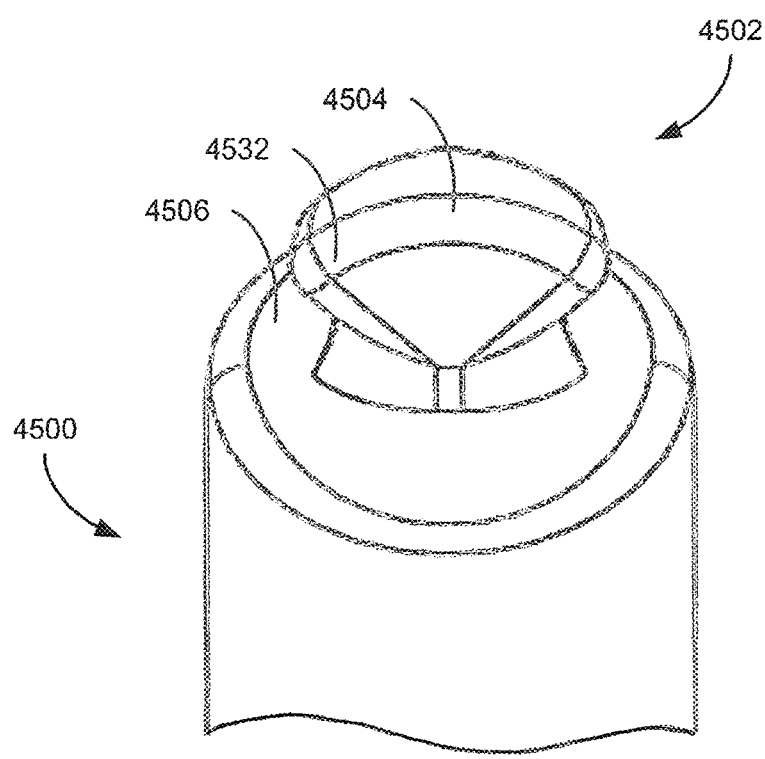
FIGS. 45A-45C are a proximal isometric view, a side elevation view, and a proximal end view, respectively of a leadless biostimulator having an alternative club-type retrieval feature.
Figure 45C:
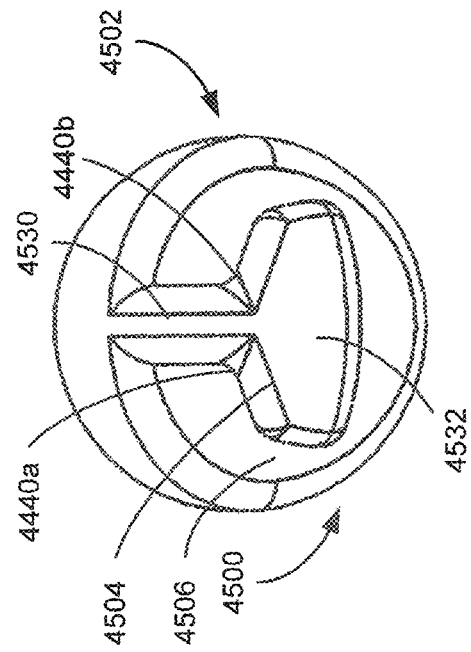
Figure 45B:
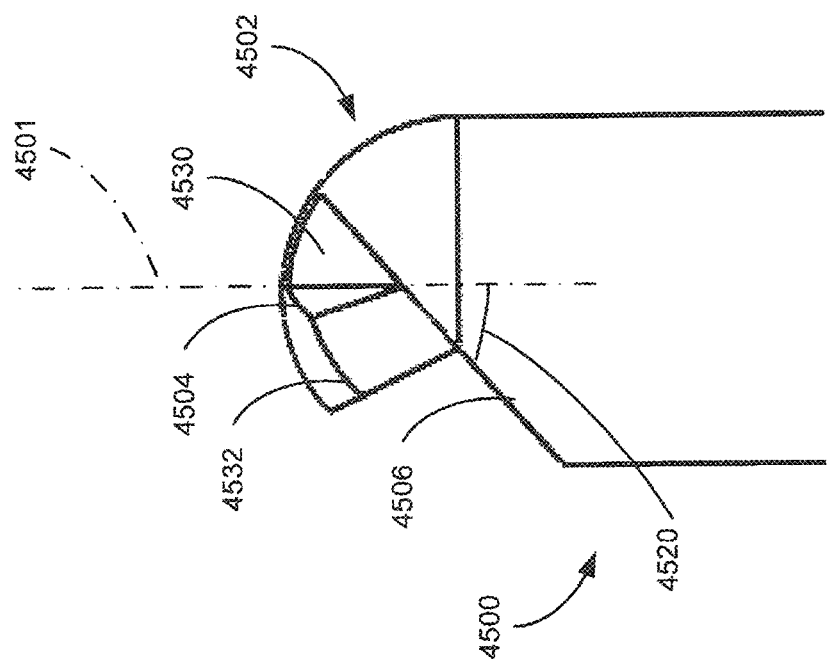

FIGS. 45A-45C illustrate an alternative implementation of a leadless biostimulator 4500 according to the present disclosure. Specifically, FIG. 45A is a proximal isometric view of the proximal end of the leadless biostimulator 4500 while FIGS. 45B-45C are side elevation and proximal end views of the leadless biostimulator 4500, respectively. Similar to the leadless biostimulator 4300 of FIGS. 43A-43C, the leadless biostimulator 4500 generally includes a club-type retrieval feature 4502 adapted to facilitate retrieval of the leadless biostimulator 4500 following implantation.

The retrieval feature 4502 of the biostimulator 4500 includes a t-shaped head 4504 that extends from an oblique proximal surface 4506 of the biostimulator 4500. For purposes of this discussion, the head 4504 is described as include a first or stem member 4530 and a second or cross member 4532 (most clearly illustrated in FIG. 45C). As illustrated in FIG. 45B, the oblique proximal surface 4506 may extend at an angle 4520 of approximately 60 degrees relative to a longitudinal axis 4501 of the biostimulator 4500. In other implementations, the angle 4520 may instead be from and including approximately 45 degrees to and including 75 degrees.

During retrieval, the snare of the retrieval system is made to extend over the head 4504. As the snare is cinched, the snare is guided by the oblique proximal surface 4506 about the head 4504. Similar to the neck 4308 of the biostimulator 4300 of FIGS. 43A-43C, the angle of the oblique proximal surface 4506 maintains the snare in a favorable orientation relative to the leadless biostimulator 4500 to facilitate proper capture. More specifically, as the snare is cinched, it is guided by the oblique proximal surface about the head 4504 such that the snare loops around the head 4504. When fully captured, the snare wraps about the head 4504 and extends in a substantially longitudinal direction through each corner 4440a, 4440b defined between the stem 4530 and the cross member 4532 of the head 4504.

Figure 46A:
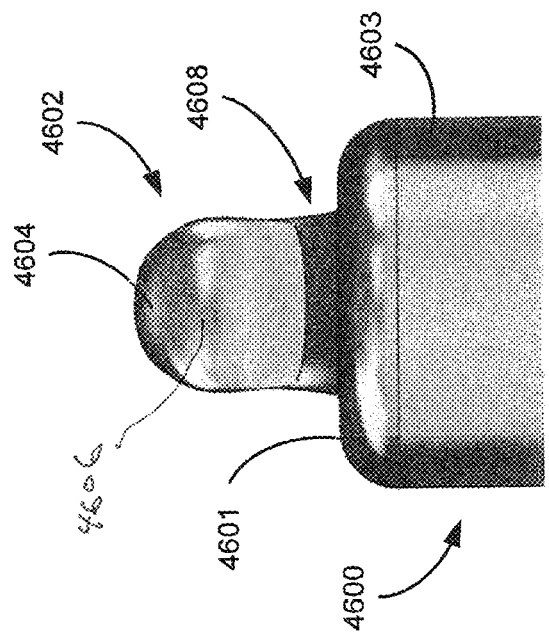
FIGS. 46A and 46B are a first and second side elevation view, respectively, of a proximal end of a leadless biostimulator having an eyelet-type retrieval feature.
Figure 46B:
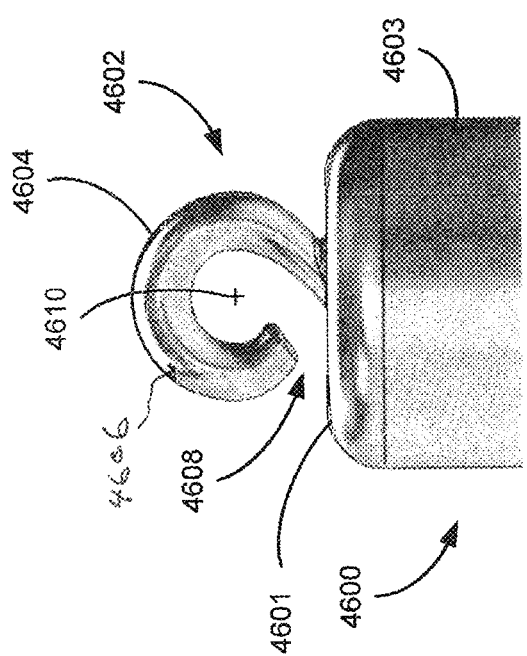

FIGS. 46A-46B illustrate a proximal end of a leadless biostimulator 4600 having an alternative retrieval feature 4602, which is generally referred to herein as an eyelet-type retrieval feature 4602. Specifically, FIGS. 46A-46B are each side elevation views of the retrieval feature 4602. In contrast to the previous implementations discussed herein, the retrieval feature 4602 includes a hook or eyelet 4604 extending from a proximal end 4601 of a housing 4603 of the leadless biostimulator 4600. The curved eyelet 4604 can extend to an eyelet end.

The eyelet 4604 includes a proximal curved portion, such as the curved surface 4606, shaped to define an opening 4608 to the eyelet 4604. More particularly, the eyelet end at least partially defines the opening 4608, which opens into the eyelet. The opening 4608 is sized to receive the snare of the leadless biostimulator retrieval system. During retrieval of the leadless biostimulator 4600, the snare of the retrieval system may be inserted through the opening 4608 such that the snare is contained within the eyelet 4604. The snare may then be cinched about the eyelet 4604 to capture the leadless biostimulator 4600. Once captured, a docking cap or similar feature of the retrieval system may be extended over the eyelet 4604 to fully secure the leadless biostimulator 4600 relative to the retrieval system such that the leadless biostimulator 4600 may be unscrewed from or otherwise removed from the cardiac tissue within which it is implanted.

The curved eyelet 4604 can extend about an eyelet center 4610. In the implementation of FIGS. 46A-46B, the opening 4608 is disposed distal to the center 4610 (shown in FIG. 46A) of the eyelet 4604. More generally, however, the opening 4608 may be positioned lateral to the eyelet center 4610 or distal to the center 4610. Positioning the opening 4608 in such a way, provides various advantages. First, during the retrieval process and after capture of a retrieval feature of a leadless biostimulator, the snare is generally pulled and manipulated in a substantially proximal direction. Accordingly, by positioning the opening 4608 away from the proximal end of the eyelet 4604, the likelihood of spontaneous release of the eyelet 4604 is significantly diminished. By positioning the opening 4608 distal the center 4610 of the eyelet 4604, the opening 4608 is shielded by the eyelet 4604. Such shielding generally prevents the edges of the opening 4608 from contacting or otherwise interacting with cardiac tissue both during and after implantation. For example, the opening 4608 is less likely to interact with adjacent cardiac tissue and have fibrous tissue form about the retrieval feature 4602, which may preclude insertion of a retrieval snare within the eyelet 4604. Moreover, even if tissue were to grow into and obstruct the opening 4608, the retrieval snare may be pulled proximally or otherwise manipulated to cut through the tissue and, once such cutting is completed, the snare would simply enter the eyelet 4604.

As shown in FIGS. 46A-46B, the eyelet 4604 may have a substantially rounded shape that generally lacks any sharp edges or corners. Similar to the retrieval feature 4302 of the leadless biostimulator 4300, such rounded edges reduce the likelihood of trauma caused by the eyelet 4604 during repeated cycling of the heart. Moreover, by having a substantially rounded shape, the eyelet 4604 provides flexibility regarding the positioning of the retrieval snare during capture. More specifically, the snare is permitted to slide or otherwise move within the eyelet 4604 as it is cinched, thereby allowing the snare to move into a substantially coaxial position with the leadless biostimulator 4600 without risk of the snare becoming disengaged from the eyelet 4604 due to the positioning of the opening 4608.

FIGS. 47A-47B are an isometric and proximal view, respectively, of a leadless biostimulator 4700 having a retrieval feature 4702 including an alternative eyelet 4704. Similar to the eyelet 4604 of the leadless biostimulator 4600, the eyelet 4704 includes a proximal curved surface 4706 that extends from the leadless biostimulator 4700 and defines an opening 4708 disposed distal the center of the eyelet 4704. As illustrated in FIG. 47B, the proximal curved surface 4706 may be shaped to include indentations 4712a, 4712b or similar lateral guiding surfaces. Indentations 4712a, 4712b can be a pair of laterally inward indentations. The indentations 4712a, 4712b function similarly to the cutouts 1213a, 1213b of the biostimulator 1200 illustrated in FIGS. 12A-12B. Specifically, the indentations 4712a, 4712b generally guide the snare of the retrieval system as it is cinched such that the snare is disposed in a substantially coaxial direction with the leadless biostimulator 4700 when the latter is captured by the snare, thereby facilitating docking of the leadless biostimulator 4700 with a docking cap or similar structure of the retrieval system.

Figure 48B:
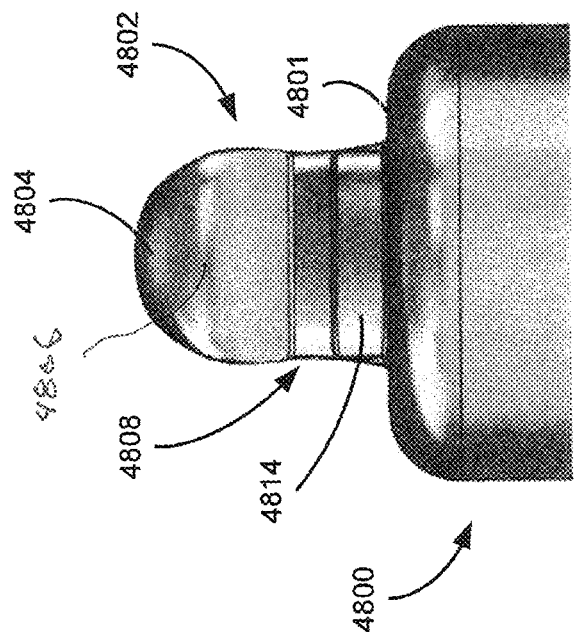
FIGS. 48A and 48B are a first and second side elevation view, respectively, of a proximal end of a leadless biostimulator having a third eyelet-type retrieval feature.
Figure 48A:
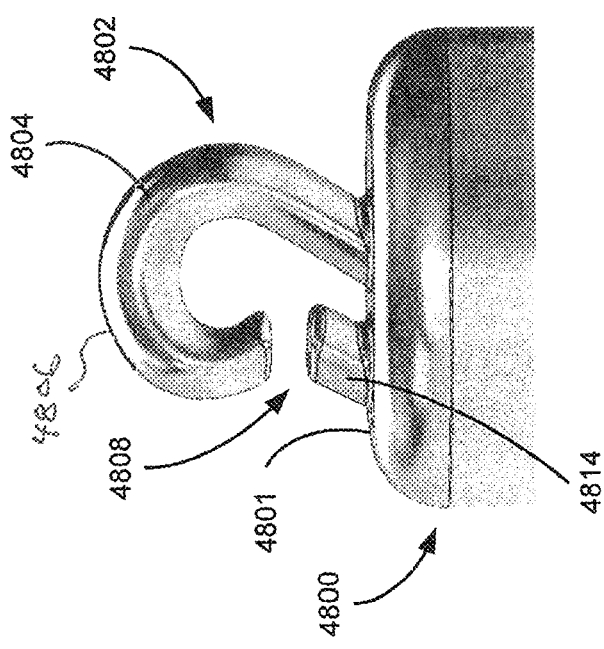

FIGS. 48A-48B are side elevation views of a leadless biostimulator 4800 having a retrieval feature 4802 including yet another alternative eyelet 4804. Similar to the eyelet 4604 of the leadless biostimulator 4600, the eyelet 4804 includes a proximal curved surface 4806 that extends from a proximal surface 4801 of the leadless biostimulator 4800 and extends to define an opening 4708 disposed distal a center of 4810 of the eyelet 4804. In contrast to the opening 4608 of the leadless biostimulator 4600, however, the opening 4808 of the leadless biostimulator 4808 is further defined by a projection 4814 extending proximally from the proximal face 4801 of the leadless biostimulator 4800. As a result, the opening 4808 is disposed in a substantially lateral orientation but is offset from the proximal face 4801 to facilitate capture of the retrieval feature 4802 by the snare. Also, as illustrated, each of the eyelet 4804 and the projection 4814 may be angled inwardly on opposite sides of the opening 4808 to guide a snare of a retrieval system into the eyelet 4804 during the retrieval process.

FIGS. 49A-49B are isometric and side elevation views of a proximal end of another leadless biostimulator 4900 in accordance with the present disclosure. Similar to the previously discussed implementations, the leadless biostimulator 4900 includes a retrieval feature 4902 to facilitate retrieval of the leadless biostimulator 4900 following implantation. The retrieval feature 4902 of the leadless biostimulator 4900 is generally referred to herein as a slotted-type retrieval feature and includes a slot 4904 defined near a proximal end of the leadless biostimulator 4900. During retrieval, the snare of the retrieval system is passed over the proximal end of the leadless biostimulator 4900 and cinched about the leadless biostimulator 4900. As it is cinched, the snare translates proximally along the leadless biostimulator 4900 and enters an opening 4908 of the slot 4904, thereby capturing the leadless biostimulator 4900.

As illustrated in FIGS. 49A-49B, the leadless biostimulator 4900 may further include a domed cap 4912 to facilitate capture and docking of the leadless biostimulator 4900 by a retrieval system. In certain implementations, the domed cap 4912 may be a separate component coupled to a housing 4910 of the leadless biostimulator 4900. Alternatively, the domed cap 4912 may be an integrally formed part of the leadless biostimulator 4900.

Similar to the opening 4608 of the eyelet-type retrieval feature 4602 illustrated in FIGS. 46A-46B, the opening 4908 of the slot 4904 is disposed such that the slot 4904 extends in a substantially proximal direction. By doing so, the opening 4908 is protected from undesirable interaction with cardiac tissue and allows any tissue overgrowth that may occur to be readily cut by the snare as the snare is used to capture the leadless biostimulator 4900. Moreover, the substantially rounded shape of the domed cap 4912, like the proximal curved surface 4606 of the leadless biostimulator 4600, substantially reduces the likelihood of trauma caused by the leadless biostimulator 4900 as the heart cycles with the leadless biostimulator 4900 implanted.

As illustrated in FIGS. 49A-49B, the slot 4904 may generally include multiple segments that are directed in various directions. For example, the slot 4904 includes each of a first segment 4920a and a second segment 4920b that extend along respective sides of the domed cap 4912 and in a primarily proximal direction. The first segment 4920a and the second segment 4920b are connected by an intermediate segment 4920c that extends obliquely relative to a longitudinal axis 4901 of the leadless biostimulator 4900. In such an arrangement, the intermediate segment 4920c facilitates insertion of the snare into the slot 4904 during retrieval. Once inserted into the slot 4904 and cinched, the snare may then be guided into the first and second segment 4920a, 4920b. Similar to the indentations 4712a, 4712b of the leadless biostimulator of FIGS. 47A-47B or the cutouts 1213a, 1213b of the biostimulator 1200 illustrated in FIGS. 12A-12B, the first and second segments 4920a, 4920b of the slot 4924 encourage coaxial alignment between the snare and the leadless biostimulator 4900 as the snare is cinched by disposing segments of the snare closer to the longitudinal axis 4901. In other implementations, such as those illustrated in FIGS. 50A-52B and discussed below, slot segments, such as the first and second segments 4920a, 4920b, may instead be omitted.

As illustrated in FIG. 49B, the intermediate segment of the slot 4920c extends obliquely relative to the longitudinal axis 4901 of the leadless biostimulator 4900. More specifically, the slot 4920c extends at an angle 4905 relative to the longitudinal axis 4901. In certain implementations, the angle 4905 may be from and including approximately 30 degrees to and including 70 degrees relative to the longitudinal axis 4901. In one particular implementation found to be advantageous during testing, the angle 4905 may be approximately 60 degrees.

Figure 50A:
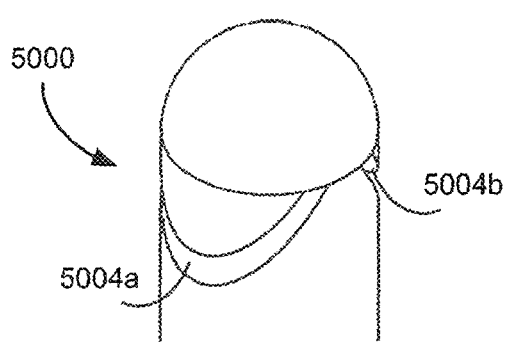
FIGS. 50A-50B are an isometric view and a side elevation view, respectively, of a proximal end of a leadless biostimulator having a slot-type retrieval feature including two slots.
Figure 50B:
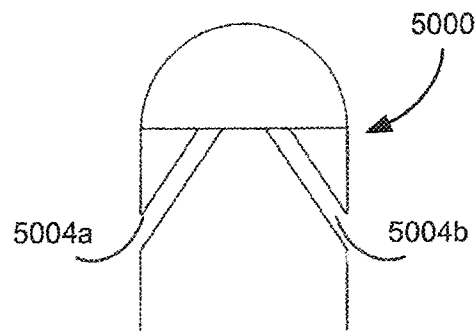
Figure 51A:
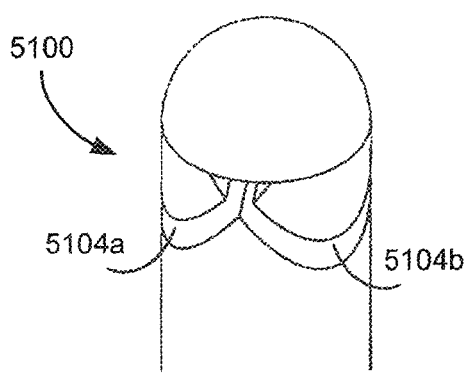
FIGS. 51A-51B are an isometric view and a side elevation view, respectively, of a proximal end of a leadless biostimulator having a slot-type retrieval feature including three slots
Figure 51B:
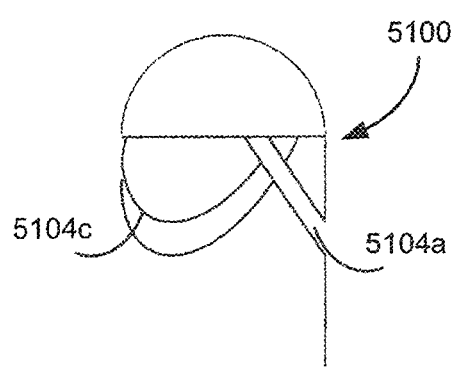
Figure 52A:
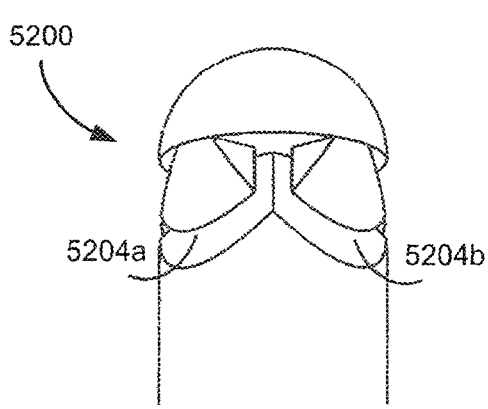
FIGS. 52A-52B are an isometric view and a side elevation view, respectively, of a proximal end of a leadless biostimulator having a slot-type retrieval feature including four slots.
Figure 52B:
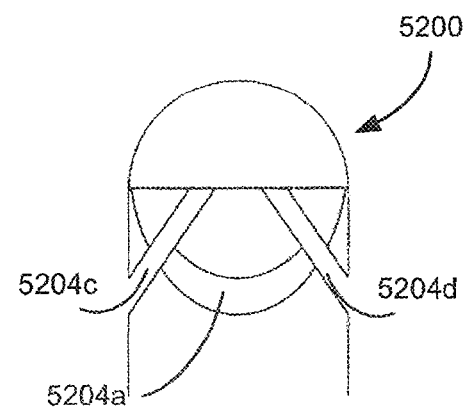

As illustrated in FIGS. 49A-49B, certain implementations of slot-type retrieval features according to the present disclosure may include a single slot. However, in other implementations, multiple slots may be distributed about the leadless biostimulator. More particularly, the slots can be distributed, e.g., evenly distributed, about the housing of the leadless biostimulator. Implementations including multiple slots may facilitate capture of the snare during retrieval by accommodating multiple snare orientations during capture. Examples of multiple slot configurations are illustrated in FIGS. 50A-52B. More specifically, FIGS. 50A-50B are an isometric and side elevation view, respectively, of a leadless biostimulator 5000 including two slots 5004a, 5004b. FIGS. 51A-51B are an isometric and side elevation view, respectively, of a leadless biostimulator 5100 including three slots 5104a, 5104b, 5104c. Finally, FIGS. 52A-52B are an isometric and side elevation view, respectively, of a leadless biostimulator 5200 including four slots 5204a, 5204b, 5204c, 5204d. Similar to the intermediate slot segment 4920c of FIG. 49B, each of the slots illustrated in FIGS. 50A-52B may extend at an angle from and including 15 degrees to and including 70 degrees relative to a longitudinal axis of their respective leadless biostimulators.

Figure 53:
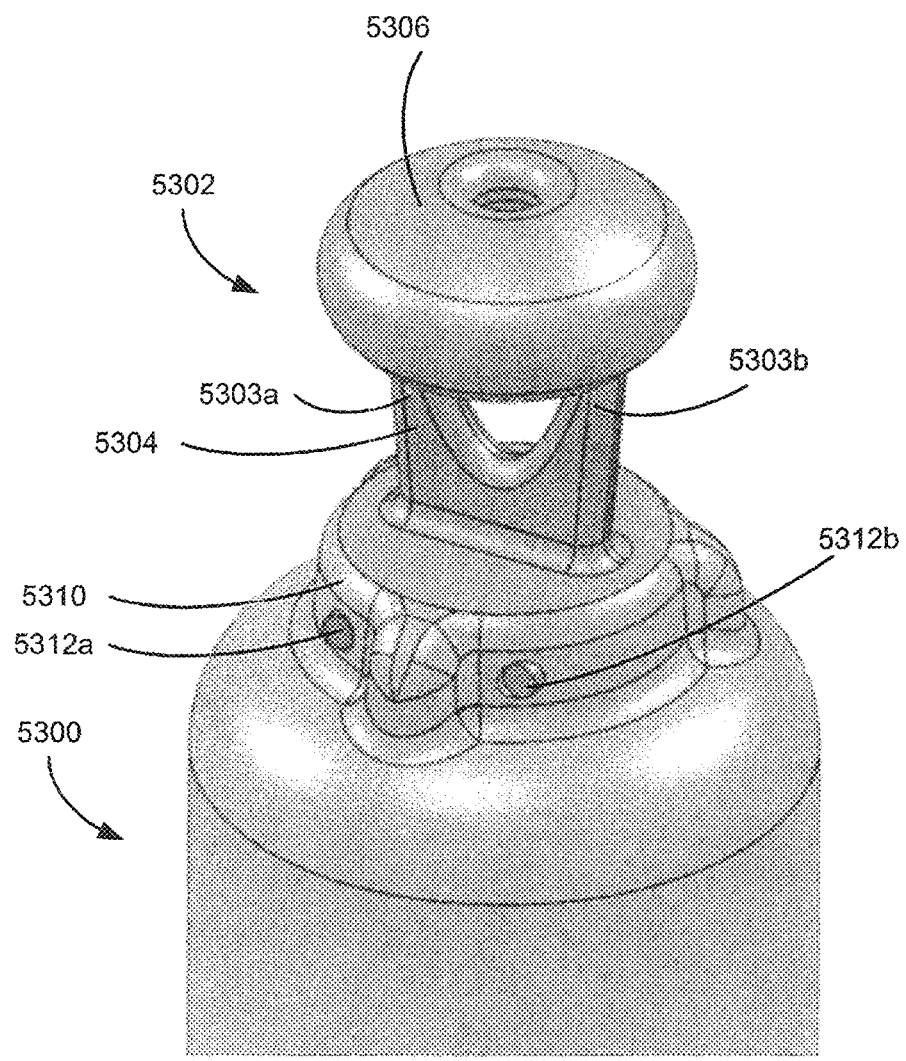
FIG. 53 is an isometric view of a proximal end of a leadless biostimulator including a one-piece flexible retrieval feature.
Figure 54:
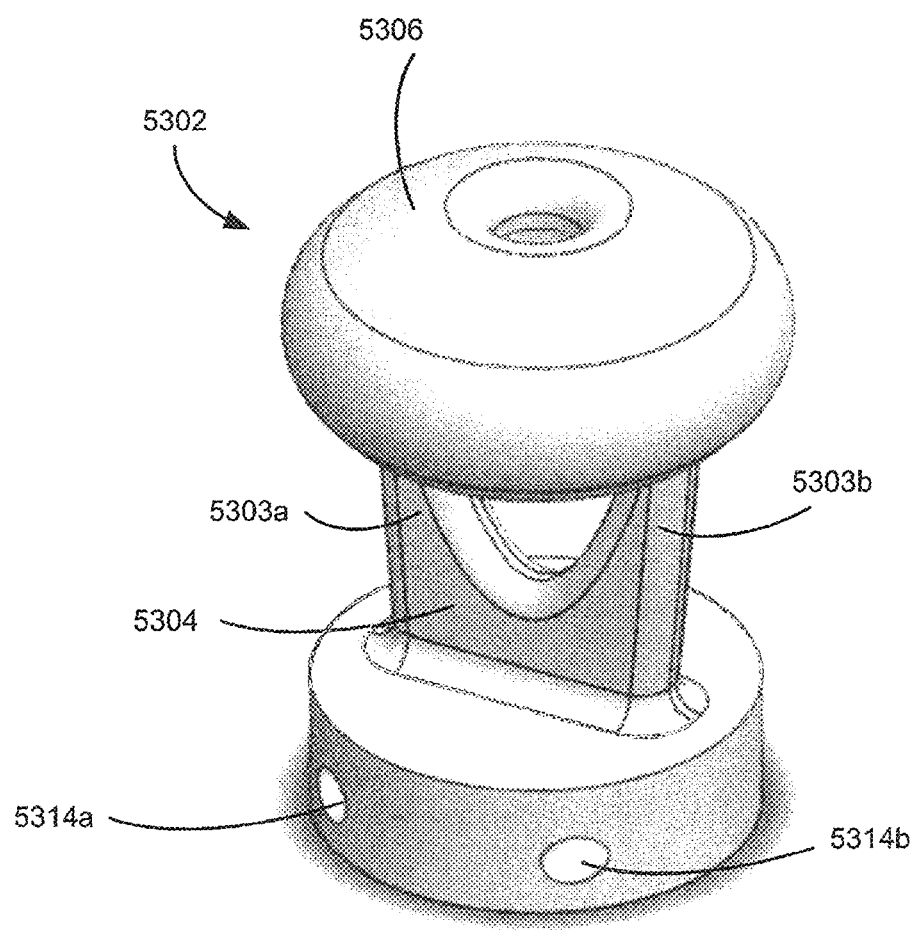
FIG. 54 is an isometric view of the one-piece flexible retrieval feature of FIG. 53.

FIG. 53 is an isometric view of a proximal end of yet another leadless biostimulator 5300 in accordance with the present disclosure. Similar to the previously discussed implementations, the leadless biostimulator 5300 includes a retrieval feature 5302 to facilitate retrieval of the leadless biostimulator 5300 following implantation. A more detailed isometric view of the retrieval feature 5302 is provided in FIG. 54. The retrieval feature 5302 includes a longitudinally extending stem 5304 that is coupled to a rounded button 5306. As described below in more detail, each of the stem 5304 and the rounded button 5306 are formed as a one-piece component from a compressible plastic material. Accordingly, the retrieval feature 5302 is a unitary assembly formed, at least in part, from a flexible material. As illustrated in FIG. 53, the stem 5304 may be formed to have several separate legs coupled to the head 5306. For example, the stem 5304 may have two longitudinally extending legs 5303a, 5303b that facilitate flexibility of the stem 5304 such that the stem 5304 functions as a living hinge. Notably, the shape and orientation of the stem 5304 and the button 5306 illustrated in FIG. 53 are intended only to illustrate one example implementation of a molded retrieval feature in accordance with the present disclosure. In other implementations, other shapes and orientations may be used, including any of the other retrieval features discussed herein.

As illustrated in FIG. 53, the retrieval feature 5302 may be inserted into and coupled to a base 5310 formed into a proximal end 5301 of the leadless biostimulator 5300. The base 5310 can be a proximal base shaped to receive a distal portion of the retrieval feature 5302. For example, as illustrated in FIG. 53, a pair of pins 5312a, 5312b may be inserted through the base 5310 and corresponding holes 5314a, 5314b (shown in FIG. 54) of the retrieval feature 5302 to couple the retrieval feature 5302 to the base 5310. In other implementations, other methods of joining the retrieval feature 5302 to the base 5310 may also be used including, without limitation, adhesives, thermal or ultrasonic welding, or fasteners such as pins.

In general, the material or materials used in implementations of the retrieval feature 5302 balance stiffness to avoid fatigue while enabling compression and flexure as needed to avoid inducing potential trauma if and when the retrieval feature 5302 contact tissue. Accordingly, the retrieval feature 5302 may be formed from a wide range of materials including and without limitation, one or more of polyethyl ether ketone (PEEK), silicone, polyurethane, fluoropolymers (e.g., polytetrafluoroethylene (PTFE) or expanded polytetrafluoroethylene (ePTFE)), and thermoplastic silicone polycarbonate urethane (e.g., Carbosil). Depending on the particular material used, the retrieval feature 5302 may be formed using a variety of processes including but not limited to various methods of at least one of molding or machining.

Implementations of the retrieval feature 5302 may also be formed from multiple materials. For example, the stem 5304 of the retrieval feature 5302 may be formed from a first flexible material, e.g., a first type of polyurethane, having a first durometer while the button 5306 may be formed from a second flexible material, e.g., a second type of polyurethane, having a second durometer different than the first durometer. Similarly, certain portions of the retrieval feature 5302 may include at least one reinforcing structure within the retrieval feature. For example, reinforcing structures or additives can be incorporated into the retrieval feature 5302 to impart particular properties to the retrieval feature. In certain implementations, the reinforcing structure includes at least one fiber, e.g., an aramid fiber. For example, reinforcing fibers may be added into the material from which the retrieval feature 5302 is formed. In other implementations, the retrieval feature 5302 may be formed by overmolding a material onto a substrate or underlying structure. For example, aramid fibers (e.g., Kevlar) may be overmolded into the stem 5304 of the retrieval feature 5302. Alternatively, the fiber(s) can be formed into a loop, e.g., a stand-alone reinforcing loop, within any portion of the retrieval feature 5302. For example, the loop can extend through the retrieval feature 5302.

In certain implementations, the leadless biostimulator includes a radiopaque marker disposed within the retrieval feature. For example, the retrieval feature 5302 may include one or more radiopaque markers formed from one or more of barium sulfate, tantalum, tungsten, or platinum. The radiopaque marker can include additives or embedded structures such that the retrieval feature 3702 is at least partially radiopaque to facilitate viewing of the retrieval feature 5302 using x-ray or other radiographic viewing technologies. For example, in certain implementations a radiopaque powder may be added to the material used to form the retrieval feature 5302. The powder can be mixed with a material that forms the retrieval feature 3702, e.g., a flexible material, during formation of the retrieval feature 3702. Such powders may include, but are not limited to, one or more of barium sulfate, tungsten, or tantalum. In still other implementations, a ribbon, bead, or other structure may be embedded within the retrieval feature 5302. For example, the structural component can be disposed within the retrieval feature 5302 during formation of the feature, e.g., overmolding the retrieval feature 5302 around the radiopaque marker. Such structures may, for example, be formed from one or more of tantalum or platinum, among other radiopaque materials.

By forming the retrieval feature 5302 from a flexible material, such as a flexible plastic, various improvements are realized. For example, the flexible design absorbs impact and, as a result, reduces potential tissue trauma if and when the retrieval feature contacts tissue during implantation, after implantation during cycling of the heart, and during retrieval. The flexibility of the retrieval feature also allows the button 5306 to deflect away from cardiac structures, preventing the button 5306 from becoming snagged or otherwise caught on such structures. Molding the retrieval feature 5302 also reduces the cost and improves overall manufacturing quality as implementing the retrieval feature 5302 as a one-piece molded component reduces process risks and subcomponent failures as may occur with multi-part components.

Figure 55:
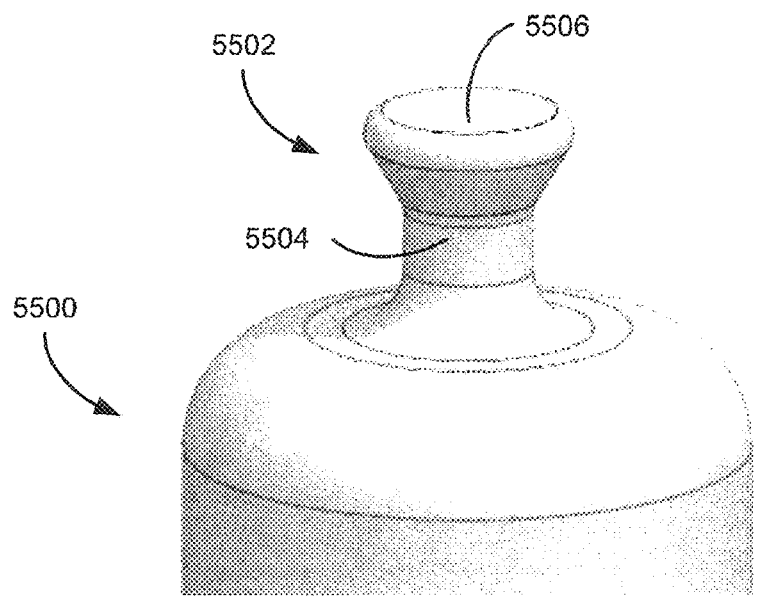
FIG. 55 is an isometric view of a proximal end of a leadless biostimulator including a tapered dome retrieval feature.
Figure 56:
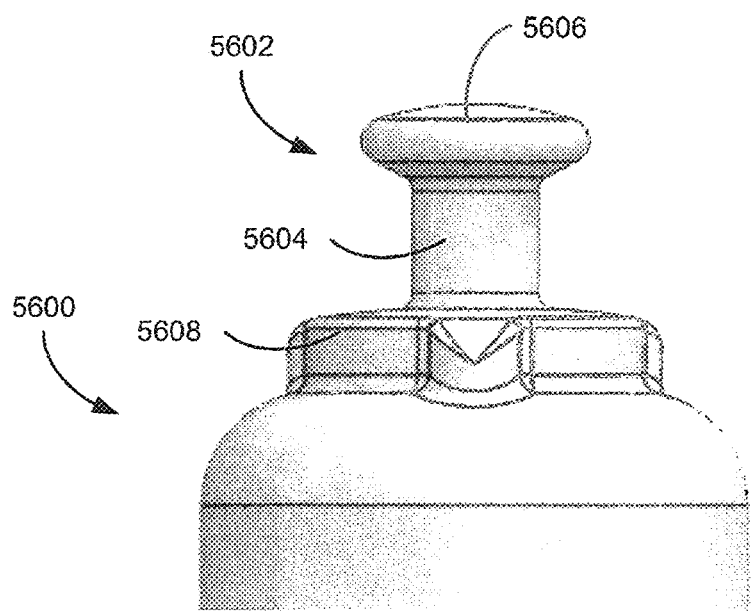
FIG. 56 is an isometric view of a second leadless biostimulator including a tapered dome retrieval feature.

FIGS. 55 and 56 show other examples of retrieval features of the present disclosure. FIG. 55 is an isometric view of a proximal end of a leadless biostimulator 5500 having a retrieval feature 5502 including a stem 5504 and a tapered circular head 5506. FIG. 56 similarly illustrates a proximal end of a leadless biostimulator 5600 having a retrieval feature 5602 including a stem 5604 and a tapered circular head 5606 but further includes a base 5608 from which the stem 5604 extends. The tapered structures illustrated in each of FIGS. 55 and 56 are generally advantageous in preventing the retrieval feature from becoming snared on tissue during delivery, following implantation as the heart cycles, or during retrieval. Accordingly, a similar domed or tapered shape may be implemented in other retrieval features discussed herein to reduce the likelihood of trauma caused by the retrieval features during any of implantation, cycling of the heart, or retrieval.

It should be appreciated that any of the foregoing retrieval features may be shaped or include features to facilitate unscrewing of the respective biostimulator during retrieval. For example, each retrieval feature may have an overall shape or profile that enables insertion of the retrieval feature into a docking cap or similar structure of the retrieval system. When docked, however, rotation of the retrieval feature relative to the docking cap may cause the retrieval feature to abut or otherwise interfere with a corresponding structure of the docking cap such that torque applied to the docking cap is transferred to the leadless biostimulator. For example, similar to the retrieval feature 612 discussed in the context of FIG. 23C, each retrieval feature may be shaped to fit within a cavity of the docking cap when in a first orientation but may interfere with a projection or similar structure within the cavity when rotated. Alternatively, the retrieval features may be shaped to fit within the docking cap in a predetermined orientation in which the retrieval feature is rotationally fixed, as illustrated and discussed in the context of FIG. 27D.

In certain implementations, the retrieval feature may also have a shape that may be readily inserted into a docking cap or similar retrieval structure when in one angular orientation relative to the docking cap but that interferes with an interior surface of the docking cap when rotated into a second angular orientation relative to the docking cap. When in the second angular orientation, the interference between the interior surface and the retrieval structure enables torque to be transferred from the docking cap to the retrieval feature and, as a result, to the leadless biostimulator, thereby facilitating unscrewing or similar disengagement of the leadless biostimulator from the cardiac tissue within which it is implanted.

Figure 57B:
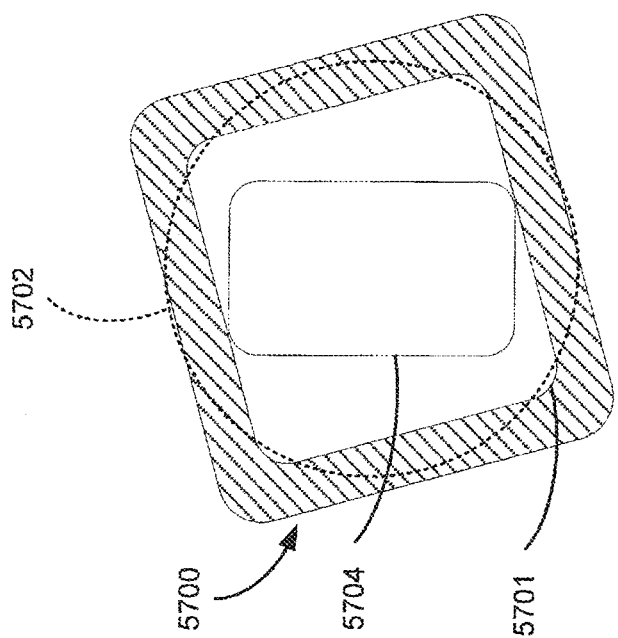
FIGS. 57A-57B are cross-sectional views of a docking cap including a docked leadless biostimulator illustrating interference between the docking cap and a retrieval feature of the leadless biostimulator for purposes of transferring torque therebetween.
Figure 57A:
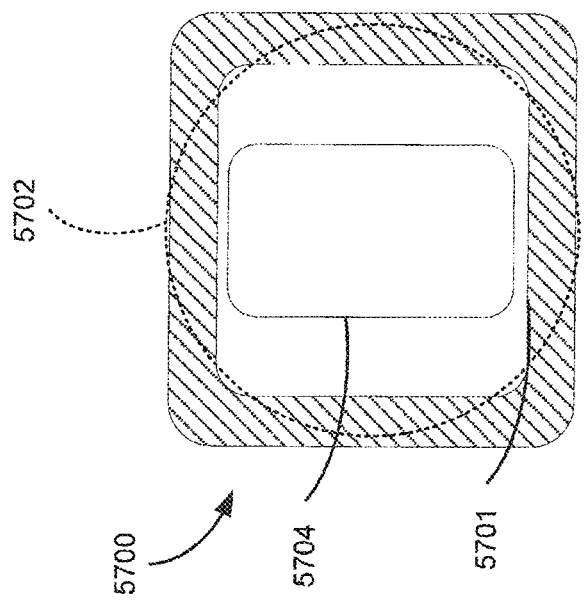

The foregoing principle is illustrated in FIGS. 57A-57B, which are cross-sectional views in a distal direction of a docking cap 5700 within which a leadless biostimulator 5702 is docked. The leadless biostimulator 5702 includes a retrieval feature 5704, which is illustrated as having a rectangular cross-sectional shape. However, the principles illustrated in FIGS. 57A-57B may be implemented with retrieval features having other than rectangular cross-sectional shapes.

FIG. 57A illustrates the leadless biostimulator 5702 and the retrieval feature 5704 in a first angular orientation relative to the docking cap 5700 such that the retrieval feature 5704 does not interfere with an interior wall 5701 of the docking cap 5700. As the angular orientation of the docking cap 5700 and the retrieval feature 5704 changes (such as by applying a torque to the docking cap 5700), the retrieval feature 5704 abuts and interferes with the interior wall 5701, as illustrated in FIG. 57B. Such interference enables the torque applied to the docking cap 5700 to be transmitted to the retrieval feature 5704 and, more generally, to the leadless biostimulator 5700 to facilitate disengagement (e.g., unscrewing) of the leadless biostimulator 5700 from cardiac tissue during retrieval.

F. Retrieval System Including a Flexible Retrieval Sheath

As previously discussed (for example in the context of FIGS. 5A-5C and 44A-44H), retrieval of leadless biostimulators in accordance with the present disclosure generally involves a retrieval system that captures and docks the leadless biostimulator such that torque may be applied to the leadless biostimulator to disengage the leadless biostimulator from the cardiac tissue within which it is implanted. Once disengaged, the captured leadless biostimulator can then be safely removed from the heart and, ultimately, the patient.

The step of applying torque to the leadless biostimulator is particularly critical in the retrieval process and requires reliable torque transfer from the retrieval system to the leadless biostimulator. Such torque transfer generally requires that the leadless biostimulator be sufficiently "locked" to the retrieval system and, in particular, to the catheters and docking structures to which torque is applied by a user of the retrieval system. Absent sufficient torque transfer, the leadless biostimulator may not be extractable using the retrieval system or may not be extractable without significant trauma to the surrounding cardiac tissue. In certain cases, the leadless biostimulator may be not be retrievable without surgical intervention.

In light of the necessity for strong and consistent coupling between the leadless biostimulator and the retrieval system, a locking system is provided herein. The locking system includes a flexible sleeve or sheath that is disposed over a distal portion of the leadless biostimulator once docking has been achieved. A rigid sheath is then positioned over the flexible sleeve, compressing the sleeve against the biostimulator and creating a frictional engagement between the rigid sheath and the leadless biostimulator that effectively locks the leadless biostimulator relative to the retrieval system. As a result of such locking, torque may be efficiently delivered to the leadless biostimulator.

The following discussion and accompanying figures are directed to delivery and implementation of the flexible sheath to provide locking between the leadless biostimulator and the retrieval system. Other aspects of the retrieval system, such as the manner in which the leadless biostimulator is docked with the retrieval system and the general components and functionality of the retrieval system have been previously described in this disclosure.

FIGS. 58A-58E illustrate an example retrieval system 5800 in accordance with the present disclosure at various stages of a retrieval procedure. More specifically, FIGS. 58A-58E are side elevation views of a distal portion of the retrieval system 5800. FIGS. 59A-59D are photographs of an example retrieval procedure and generally correspond to the steps illustrated in FIGS. 58B-58E, respectively.

Referring first to FIGS. 58A-58B, a distal portion of a retrieval system 5800 is illustrated prior to docking of a leadless biostimulator 5850 (FIG. 58A) and immediately after docking of the leadless biostimulator 5850 (FIG. 58B). As shown in FIG. 58A, the retrieval system 5800 generally includes one of more guide and retrieval catheters 5804, 5806 through which a snare 5808 or similar retrieval device is extended to capture the leadless biostimulator 5850. The distal end of the retrieval system 5800 may include a docking cap 5810, socket, or similar structure adapted to receive a proximal portion of the leadless biostimulator 5850 such that, when docked, the leadless biostimulator 5850 is maintained in a substantially coaxial orientation relative to the retrieval system 5800, as illustrated in FIG. 58B and as depicted in the photograph of FIG. 58A. As described above, the docking cap 5810 can have a sharp distal edge.

Notably, for purposes of the sheath-based retrieval system and method described herein, the structure of the leadless biostimulator, the docking cap, and the coupling therebetween may vary and may be in accordance with any implementation of such features disclosed or otherwise discussed herein. So, for example, while FIGS. 58A-58E illustrate the leadless biostimulator 5850 as including a button-type retrieval feature and the retrieval system 5800 as having a single snare, the details discussed below are equally applicable to the implementation depicted in the photographs of FIGS. 59A-59D in which the leadless biostimulator 5850 has a slotted dome retrieval feature and the retrieval system 5800 includes multiple snares.

The retrieval system 5800 can include a flexible sheath 5812 extendable along an inner catheter, e.g., catheter 5806, of the retrieval system 5800. As illustrated in FIG. 58C and depicted in the photograph of FIG. 59B, following docking of the leadless biostimulator 5850, the flexible sheath 5812 is extended distally along the retrieval system 5800 such that a distal end 5814 of the flexible sheath 5812 extends over each of the docking cap 5810 and a proximal portion of the leadless biostimulator 5850. More particularly, the flexible sheath 5812 can envelop exterior surfaces of each of a distal end of the catheter 5806 and a proximal end of the leadless biostimulator 5850. The flexible sheath 5812 can envelop an exterior of the docking cap 5810 in the extended configuration.

In certain implementations, the flexible sheath 5812 may be expandable but may have a natural/resting inner diameter that is less than the outer diameter of either of the docking cap 5810 and the leadless biostimulator 5850. Accordingly, as the flexible sheath 5812 is translated over the docking cap 5810 and the leadless biostimulator 5850, the flexible sheath 5812 may expand to allow insertion of the docking cap 5810 and the leadless biostimulator 5850 into the flexible sheath 5812. However, due to the elasticity of the flexible sheath 5812, the flexible sheath 5812 may apply an inwardly compressive force that creates friction between the flexible sheath 5812 and each of the docking cap 5810 and the leadless biostimulator 5850.

The flexible sheath 5812 may be formed from a variety of biocompatible materials but is generally formed of a material that is highly flexible and resistant to tearing or similar damage during execution of a retrieval process. Accordingly, although other materials may be implemented, in one example implementation the flexible sheath 5812 may include an expandable mesh. For example, the flexible sheath 5812 can be a Nitinol mesh. In an embodiment, a wall-thickness of the flexible sheath 5812 is up to and including 1.5 mil, e.g., up to and including 1.0 mil.

In certain implementations, the flexible sheath 5812 may have a double-walled construction in which the sheet of Nitinol mesh is doubled over on itself. More particularly, the double-wall construction can be formed by folding the expandable mesh back on itself. Such construction generally results in the distal end 5814 of the flexible sheath 5812 being rounded and, as a result, atraumatic. To ensure that such a double-wall construction is not overly bulky, the Nitinol mesh may have a thickness of 1.5 mil or less and, in certain implementations, no greater than 1.0 mil.

The retrieval system 5800 can include a rigid sheath 5816 extendable along at least a portion of the flexible sheath 5812. As illustrated in FIG. 58D and depicted in the photograph of FIG. 59C, once the flexible sheath 5812 is disposed along the length of the retrieval system 5800 and over a proximal portion of the leadless biostimulator 5850, the rigid locking sheath 5816 may be extended along the length of the retrieval system 5800 over the flexible sheath 5812. The inner diameter of the rigid locking sheath 5816 is generally sized to press the flexible sheath 5812 against the exterior surface of the retrieval catheter 5806 and, as a result, to cause frictionally engagement between the flexible sheath 5812 and each of the rigid locking sheath 5816 and the retrieval catheter 5806. In certain implementations, the flexible sheath 5812 and the rigid locking sheath 5816 may each extend substantially along the full length of the retrieval catheter 5806, thereby maximizing the frictional engagement between the flexible sheath 5812 and each of the rigid locking sheath 5816 and the retrieval catheter 5806. The friction from positioning of the rigid locking sheath 5816 along the flexible sheath 5812 further causes the flexible locking sheath 5812 to become longitudinally fixed and increases the compressive force applied by the flexible locking sheath 5812 onto each of the docking cap 5810 and the leadless biostimulator 5850. As a result, the coupling between the docking cap 5810 and the leadless biostimulator 5850 is reinforced by the flexible sheath 5812 and torque transfer between the docking cap 5810 and the leadless biostimulator 5850 when torque is applied to the docking cap 5810 is facilitated.

Figure 58E:
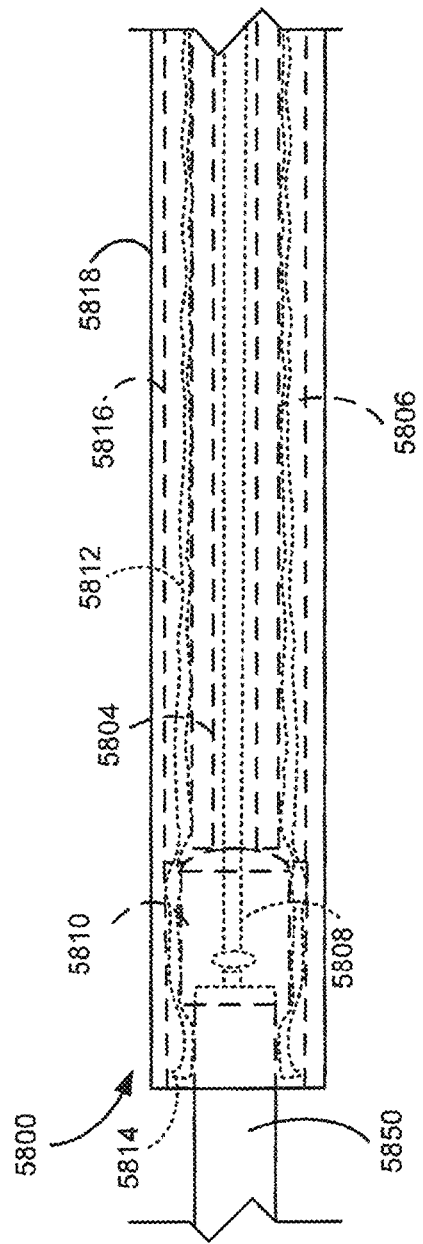
Figure 59D:
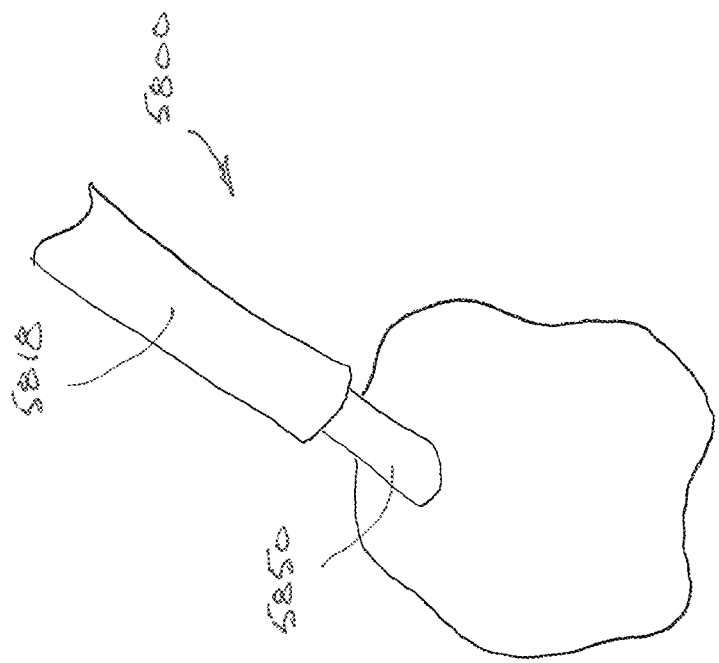
Figure 59C:
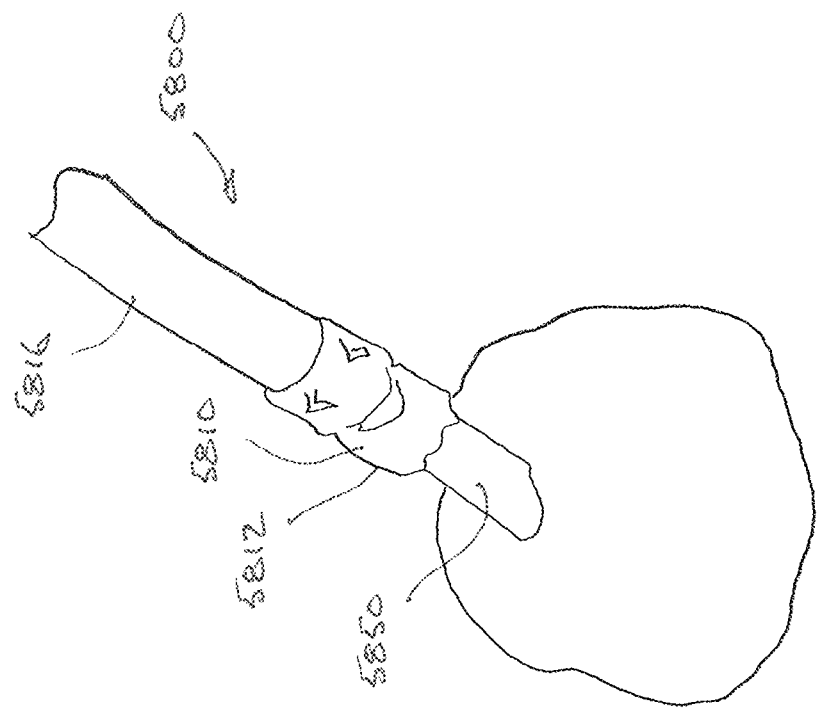

The retrieval system 5800 can include a protective sheath 5818 disposable about each of the flexible sheath 5812 and the rigid sheath 5816. As illustrated in FIG. 58E and the photograph of FIG. 59D, the additional flexible protective sheath 5818 may be disposed about the retrieval system 5800 following application of the rigid locking sheath 5816. For example, the protective sheath 5818 may be used to extend over the leadless biostimulator 5850 prior to torque being applied the leadless biostimulator 5850 to reduce the likelihood that components of the retrieval system or the leadless biostimulator 5850 may contact adjacent tissue. The protective sheath 5818 may also be used to cover or retain the leadless biostimulator 5850 following disengagement of the leadless biostimulator 5850 and during extraction of the leadless biostimulator 5850 to similarly protect adjacent tissue. Accordingly, the protective sheath 5816 can contain the flexible sheath 5812 and the rigid sheath 5816 when the rigid sheath 5816 is extended along at least a portion of the flexible sheath 5812.

While FIGS. 58A-58E illustrate the leadless biostimulator 5850 as being coaxial with the retrieval system 5800, implementations of the flexible sheath 5812, as described herein, improve the tolerance of the retrieval system 5800 to the leadless biostimulator 5850 being offset or otherwise misaligned with the retrieval system 5800 when docked. In other words, the coupling between the retrieval system 5800 and the leadless biostimulator 5850 enable high torque to be transferred to the leadless biostimulator 5850 over a wider range of docking angles. Such flexibility is particularly beneficial in cases where tissue overgrowth, adjacent cardiac tissue, or other conditions generally preclude a coaxial alignment between the retrieval system 5800 and the leadless biostimulator 5850 from being achieved.

Figure 60A:
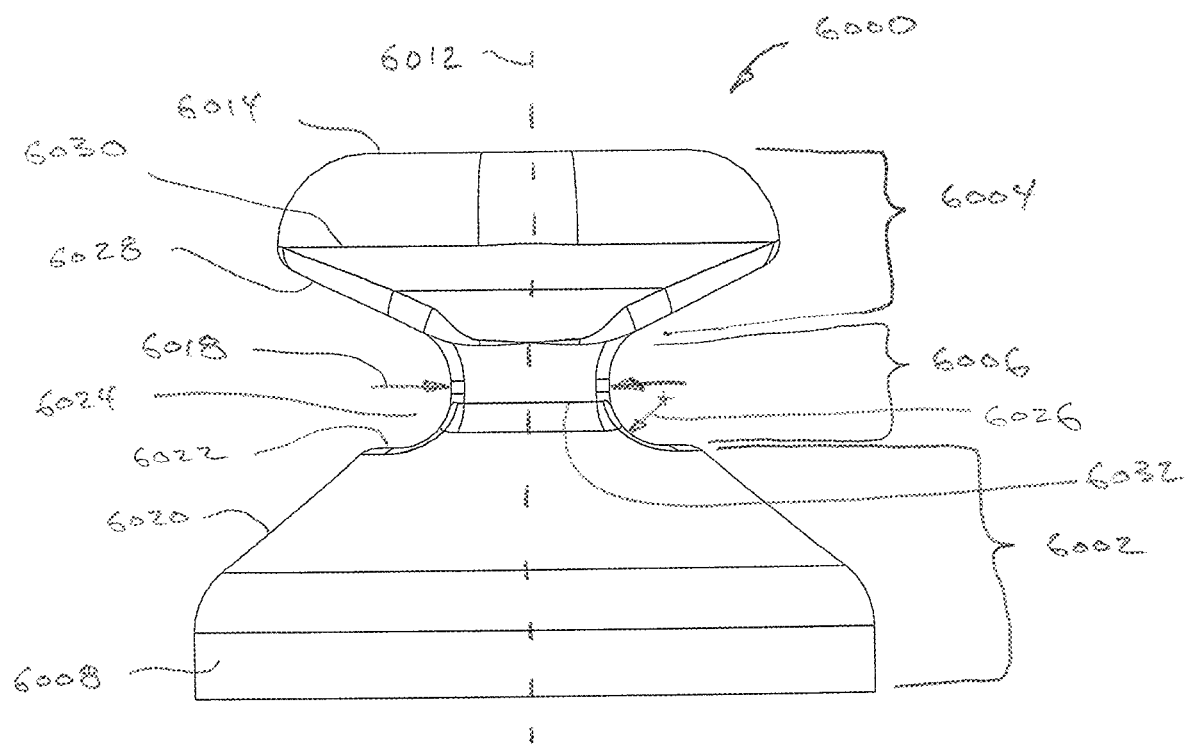
FIGS. 60A-60B are side elevation views of an attachment feature.
Figure 60B:
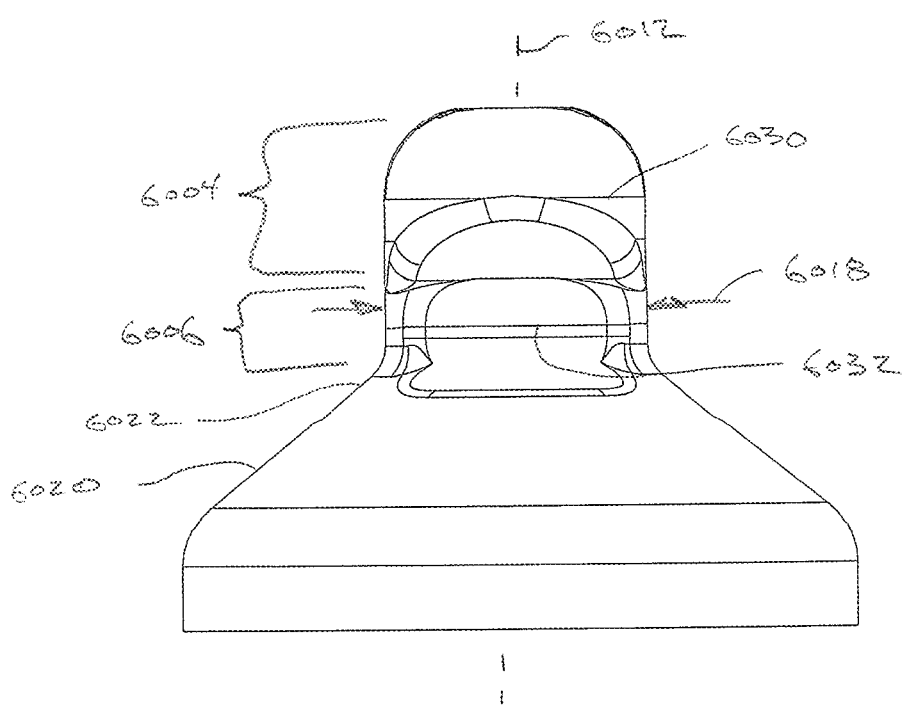

Referring to FIGS. 60A-60B, side elevation views of an attachment feature are shown. In an embodiment, an attachment feature 6000 can be a component of a leadless biostimulator, such as the leadless pacemaker 600 shown in FIG. 6. Accordingly, the features of the attachment feature 6000 can be similar to, and effect the same functionality as, the features described above with respect to the attachment feature 610 or any of the other attachment feature embodiments. The attachment feature 6000 can include a base 6002, a button 6004, and a stem 6006. The attachment feature 6000 can have a one-piece construction. For example, the attachment feature 6000 can be monolithically formed from a rigid material, e.g., titanium, such that the base 6002, the button 6004, and the stem 6006 are all portions of a single structure. As described below, the structure can have the stem 6006 that includes a single post interconnecting the base 6002 to the button 6004 such that the monolithic attachment feature 6000 is strong and stiff. The rigid attachment feature can therefore transmit torque efficiently from a delivery or retrieval system to the leadless pacemaker 600.

In an embodiment, the base includes a distal flange 6008. The distal flange 6008 can be a tubular section of the attachment feature 6000. For example, the distal flange 6008 can have a cylindrical outer surface and may include a flange port 6010 (FIG. 60D) within the outer surface. The flange port 6010 can surround a central axis 6012 that extends in the longitudinal direction through the attachment feature 6000. For example, the distal flange 6008 can have an inner surface extending around the central axis 6012, which defines the flange port 6010.

The button 6004 can be disposed along the central axis 6012. For example, the button 6004 can have a proximal button face 6014 that extends orthogonal to the central axis 6012. In an embodiment, the proximal button face 6014 has a face port 6016 (FIGS. 60C-60D) surrounding the central axis 6012. For example, the button 6004 can have an inner surface extending around the central axis 6012, which defines the face port 6016.

The stem 6006 can be disposed along the central axis 6012 between the base 6002 and the button 6004. In an embodiment, the stem 6006 extends from a distal end at the base 6002 to a proximal end at the button 6004. The stem 6006 portion may be continuous with the base 6002 and button 6004 portions of the attachment feature 6000. Transitions between the portions can be made in various manners. The stem 6006 may have a smaller transverse dimension 6018 than both the base 6002 and the button 6004 in at least one side view. For example, the transverse dimension 6018 of the stem 6006 in the side view of FIG. 60A may be a minimum transverse dimension of the attachment feature 6000. By contrast, the transverse dimension 6018 of the button 6004 and the stem 6006 may be equal and minimum transverse dimensions of the attachment feature 6000 in the side view of FIG. 60B.

One or more of the base 6002 portion or the button 6004 portion of the attachment feature 6000 can transition smoothly into the stem 6006. For example, the base 6002 can include a tapered body 6020 that tapers radially inward from the distal flange 6008 toward the stem 6006. In an embodiment, the distal flange 6008 has a circular transverse profile taken about a plane extending through the flange orthogonal to the central axis 6012, and the stem 6006 has a rectangular transverse profile. A diameter of the circular transverse profile can be greater than a length of a side of the rectangular transverse profile. Accordingly, the base 6002 can have a smaller and smaller circular transverse profile diameter at each point between the distal flange 6008 and an outer proximal end 6022 of the base 6002. The tapered body 6020 may have an angle α relative to the central axis 6012. In certain implementations, the angle α may be from and including 30 degrees to and including 90 degrees. For example, in one implementation, the angle α may be approximately 45 degrees.

The outer surface of the attachment feature 6000 can transition abruptly inward along a transverse face at the outer proximal end 6022 from the tapered body 6020 to the stem 6006 in at least one side view (FIG. 60A). By contrast, the tapered body 6020 may transition gradually into stem 6006 (no discontinuity) at the outer proximal end 6022 in another side view (FIG. 60B).

The abrupt transition between the tapered body 6020 and the stem 6006 may be referred to as a unidirectional notch 6024, when it exists in one side view and not another side view. The attachment feature 6000 may have a bidirectional notch (not shown) in which the notch is evident in both side views. For example, a notch having an inward radius may exist in FIG. 60B. The unidirectional notch 6024 can have a radius such that an outer surface of the stem 6006 is concave inward toward the central axis 6012. The concave inward outer surface can direct a snare to slide inward toward the neck of the stem 6006 when capturing the attachment feature 6000 with a delivery or retrieval system.

As described above, the button 6004 may be shaped to minimize acute radii and the corresponding potential of such acute radii to catch and damage cardiac tissue. For example, the button 6004 may include a proximal surface that transitions from the proximal face 6014 into a distal button face 6028 by a radiused transition. The radiused transition can provide a pillow-top shape to button 6004. More particularly, the radiused transition can have a radius of curvature that makes the proximal end of attachment feature 6000 smooth and reduces a likelihood of trauma to tissue. It will be appreciated that other transitions between surfaces of the attachment feature 6000 may also be radiused to reduce a likelihood of trauma to a patient.

In an embodiment, the distal button face 6028 tapers radially inward from the proximal surface of the button 6004 toward the stem 6006. For example, the distal button face 6028 can include an angled plane that extends from a transverse perimeter 6030 of the button toward the stem 6006. The distal button face 6028 that extends along the angled plane, which is oblique to the central axis 6012, can transition from the transverse perimeter 6030 toward the stem 6006. The transverse perimeter 6030 can be a profile taken along a transverse plane passing through the button 6004 orthogonal to the central axis. In an embodiment, the transverse perimeter 6030 is taken at an outward most point along the outer surface of the button 6004. Accordingly, the transverse perimeter can represent a largest perimeter of any transverse cross-section taken through the button 6004.

Similar to the tapering body 6020, the distal button face 6028 can taper unidirectionally or bidirectionally toward the stem 6006. As shown in FIG. 60A-60B, the distal button face 6028 transitions from the transverse perimeter 6030 near a major axis of the button 6004 along a flat face toward the stem 6006 in one side view (FIG. 60A). By contrast, in another side view (FIG. 60B), the transverse perimeter 6030 of the button 6004 has a same width as the transverse dimension 6018 of the stem 6018, and thus, the outer surface of the attachment feature 6000 extends longitudinally (no taper) along both the button 6004 and the stem 6006. It will be appreciated that the distal button face 6028 could be bidirectional when, for example, the transverse perimeter 6030 is larger than the transverse dimension 6018 in the side view of FIG. 60B. The taper of the distal button face 6028 may extend at an angle θ relative to the central axis 6012. In certain implementations, the angle θ may be from and including 0 degrees to and including 45 degrees. For example, in one implementation, the angle θ may be approximately 25 degrees.

In an embodiment, a transverse profile 6032 of the stem 6006 extends around the central axis 6012. For example, the stem 6006 can be a single elongated rectangular post having a rectangular cross-section that is lofted along the central axis 6012. Alternatively, the stem 6006 can be a single elongated cylindrical post having a circular cross-section that extends along the central axis 6012. Similar unitary post structures can have triangular, elliptical, etc., transverse profiles 6032. As described above with respect to FIG. 7C, the transverse profile 6032 of the stem 6006 may be defined in part by a major stem axis and a minor stem axis, which may have equal (in the case of a square cross-section) or different (in the case of a rectangular cross-section) dimensions.

Figure 60C:
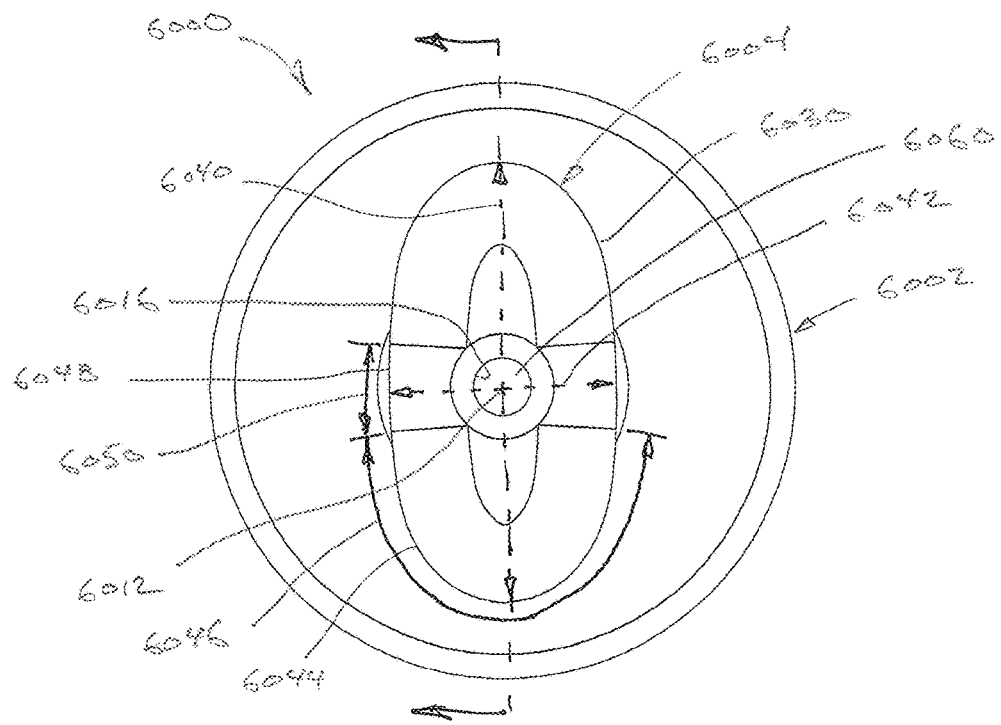
FIG. 60C is a proximal view of the attachment feature of FIGS. 60A-60B.

Referring to FIG. 60C, a proximal view of the attachment feature of FIGS. 60A-60B is shown. The transverse perimeter 6030 of the button 6004 can have an oval shape. For example, the transverse perimeter 6030 can have a major axis 6040 and a minor axis 6042 that differ to define the oval shape. In certain implementations, the major axis 6040 may be from and including 3 millimeters (0.12 inches) to and including 6 millimeters (0.24 inches) while the minor axis 6042 may be from and including 2 millimeters (0.080 inches) to and including 3.5 millimeters (0.140 inches). The oval shape may be symmetric about one or more of the major axis 6040 and the minor axis 6042. For example, as shown in FIG. 60C, the oval shape can be an ellipse, which is symmetric about both axis. The transverse perimeter 6030 could be egg-shaped, and thus, may be symmetric about only one of the axis. The ellipse may have a curved segment 6044 with a curve length 6046, and the curved segment 6044 can be a portion of the ellipse that intersects the major axis 6040. In an embodiment, the ellipse has a straight segment 6048 having a straight length 6050, and the straight segment 6048 intersects the minor axis 6042. In other embodiments, the portion of the oval shape intersecting the major axis 6040 can be straight and the portion intersecting the minor axis 6042 can be curved. Similarly, the oval shape can be straight at both intersections, or curved at both intersections (FIG. 40B). As described above, the oval shape may have an inward inflection point, e.g., an indentation, at one or more of the intersections (FIG. 12B).

In an embodiment, the attachment feature 6000 includes an internal cavity 6060 that is laterally surrounded by the base 6002, the button 6004, and the stem 6006. For example, the internal cavity 6060 can extend along the central axis 6012 from the face port 6016 to the flange port 6010. The internal cavity 6060 can extend through the base 6002, the button 6004, and the stem 6006 in the longitudinal direction from the proximal end of the attachment feature 6000 to the distal end. Accordingly, the internal cavity 6060, provides an opening to receive tethers of a delivery or retrieval system for docking and undocking, as described above.

Figure 60D:
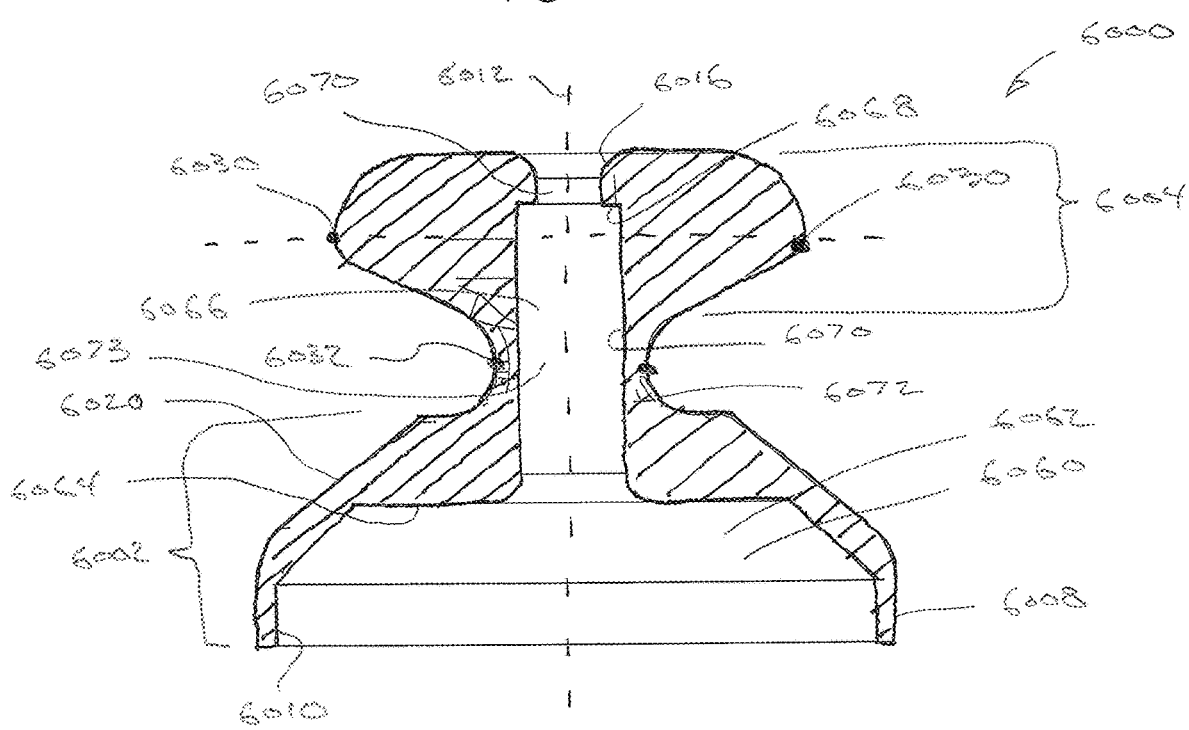
FIG. 60D is a cross-sectional view of the attachment feature of FIGS. 60A-60B, taken about the section line of FIG. 60C.

Referring to FIG. 60D, a cross-sectional view of the attachment feature of FIGS. 60A-60B, taken about the section line of FIG. 60C, is shown. The internal cavity 6060 extending longitudinally through the stem 6006 can produce an annular transverse profile 6032. More particularly, rather than being a solid post, the stem 6006 can have a tubular structure. The tubular stem can have an inner surface 6070 and an outer surface 6072 that are continuous and define an annular wall surrounding the central axis 6012. Accordingly, the stem 6006 can have an inner lumen 6073 that extends longitudinally between the base 6002 and the button 6004. The annular wall can be formed from a rigid material, such as titanium or a glass-filled polymer, to provide strength and rigidity to the attachment feature 6000.

The internal cavity 6060 that extends longitudinally through the attachment feature 6000 and is surrounded in the transverse direction by an inner surface of the attachment feature 6000 can be further defined in terms of cavity portions. For example, a mounting cavity 6062 of the internal cavity 6060 can extend from the distal end of the distal flange 6008 to an inner proximal face 6064 of the base 6002. The mounting cavity 6062 may be a region of the internal cavity 6060 that receives a portion of a cell can, e.g., an end boss of the cell can, as described below. The inner proximal face 6064 can extend orthogonal to the central axis 6012. The inner surface of the attachment feature 6000 surrounding the mounting cavity 6062 can have a similar form to the outer surface of the attachment feature 6000 surrounding the inner surface. For example, a region of the mounting cavity 6062 within the distal flange 6008 can be cylindrical, and a region of the mounting cavity 6062 within the tapered body 6020 can be frustoconical.

The internal cavity 6060 can include a tethering cavity 6066 proximal to the mounting cavity 6062. The tethering cavity 6066 may be a region of the internal cavity 6060 that receives tethers of a delivery or retrieval system during docking or undocking of a leadless pacemaker, as described above. More particularly, the tethering cavity 6066 can have a width greater than a combined width of two tether distal features. The tethering cavity 6066 can extend proximally from the inner proximal face 6064 of the base 6002 to an inner distal face 6068 of the button 6004. The inner distal face 6068 can extend orthogonal to the central axis 6012. The inner surface of the attachment feature 6000 surrounding the tethering cavity 6068 (part of which is inner surface 6070) can be cylindrical.

The internal cavity 6060 can include a passage cavity 6070 proximal to the tethering cavity 6066. The passage cavity 6070 may be a region of the internal cavity 6060 that receives tethers of a delivery or retrieval system during docking or undocking of a leadless pacemaker, as described above. More particularly, the passage cavity 6070 can have a width less than a combined width of two tether distal features. The passage cavity 6070 can extend proximally from the inner distal face 6068 to the face port 6016. The inner surface of the attachment feature 6000 surrounding the passage cavity 6070 may, for example, be cylindrical.

The attachment feature 6000 can have features that contribute to effective long-term use of the leadless pacemaker. For example, one or more of the base 6002, the button 6004, or the stem 6006 may be coated by one or more of an antibacterial coating or an antithrombogenic coating. The antibacterial coating can reduce a likelihood that bacteria will attach to the attachment feature 6000. Accordingly, the antibacterial coating can reduce a likelihood of infection when the leadless pacemaker is implanted at a target tissue location. The antithrombogenic coating can impede the growth and/or deposition of thrombi within the cavities of the attachment feature 6000. Accordingly, the antithrombogenic coating can reduce a likelihood that the cavities will block the entry or retraction of the tether into the attachment feature 6000.

Long-term efficacy of the leadless pacemaker may also be facilitated by making the leadless pacemaker chronically retrievable. The term chronically retrievable can refer to an ability to retrieve the leadless pacemaker using a retrieval system after several, e.g., 3-5, years following implantation. In an embodiment, the leadless pacemaker is chronically retrievable because the attachment feature 6000 includes an internal cavity 6060 having sufficient volume to allow some fibrous tissue to grow within the attachment feature 6000 without impeding the advancement of tether distal features. For example, as described above, the tethering cavity 6066 can have a larger transverse dimension than the passage cavity 6070 to permit the tether distal features to be side-by-side within the tethering cavity 6066 and not the passage cavity 6070. Similarly, the mounting cavity 6060 can have a larger transverse dimension than the tethering cavity 6066 to permit some tissue to be received therein without impeding movement of the tether distal features. By way of example, the mounting cavity 6062 can include a tapered inner surface to maximize the internal volume of the mounting cavity 6062 relative to the tethering cavity 6066.

Figure 61A:
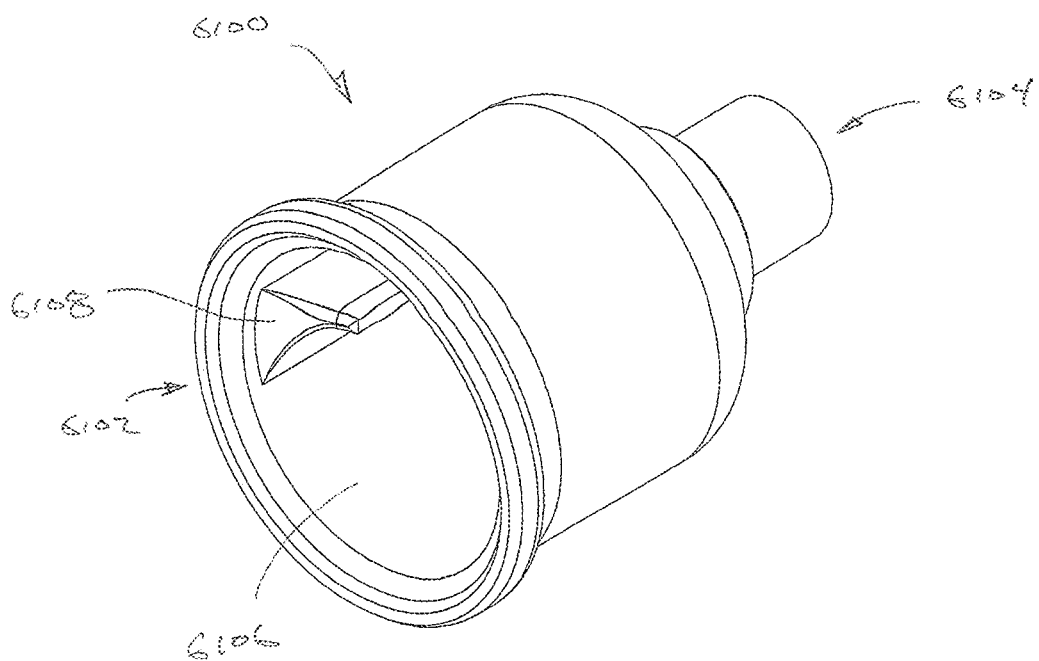
FIG. 61A is an isometric view of a docking cap.

Referring to FIG. 61A, an isometric view of a docking cap is shown. The docking cap 6100 includes a distal end 6102 for receiving a leadless pacemaker and a proximal end 6104 adapted to be coupled to a leadless pacemaker delivery or retrieval system. The docking cap 6100 defines an inner cavity surrounded laterally by an internal surface 6106. As described above, the inner cavity can have a distal cavity section and a proximal cavity section. The distal cavity section can be generally sized and shaped to receive a proximal end of a leadless pacemaker and, more specifically, an attachment feature 6000 of the leadless pacemaker. In an embodiment, a single torque feature 6108 extends radially inward from the internal surface 6106.

Figure 61B:
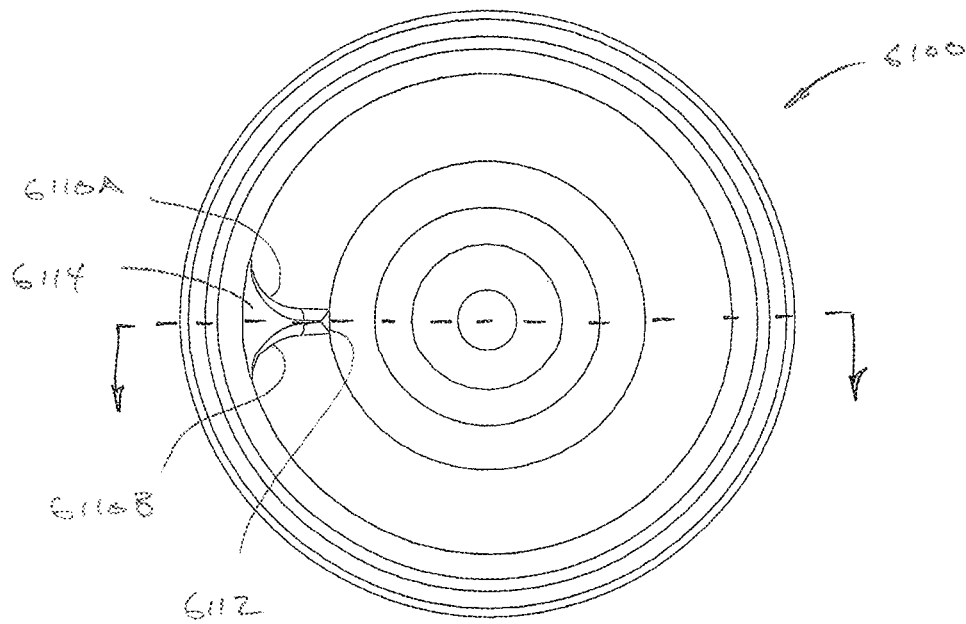
FIG. 61B is a distal end view of the docking cap of FIG. 61A.

Referring to FIG. 61B, a distal end view of the docking cap of FIG. 61A is shown. The torque feature 6108 can be shaped to interfere with the attachment feature 6000 when it is received in the inner cavity of the docking cap 6100. The torque feature 6108 can include a pair of curved surfaces 6110A, 6110B that join to form a peak 6112. The torque feature 6110 can include a distal surface 6114 extending radially inward from the internal surface 6106 to the peak 6112. The distal surface 6114 can slope radially inward along a curved path to the peak 6112. The torque feature 6108 can be sized and positioned to transmit torque to the leadless pacemaker, as described above.

Figure 61C:
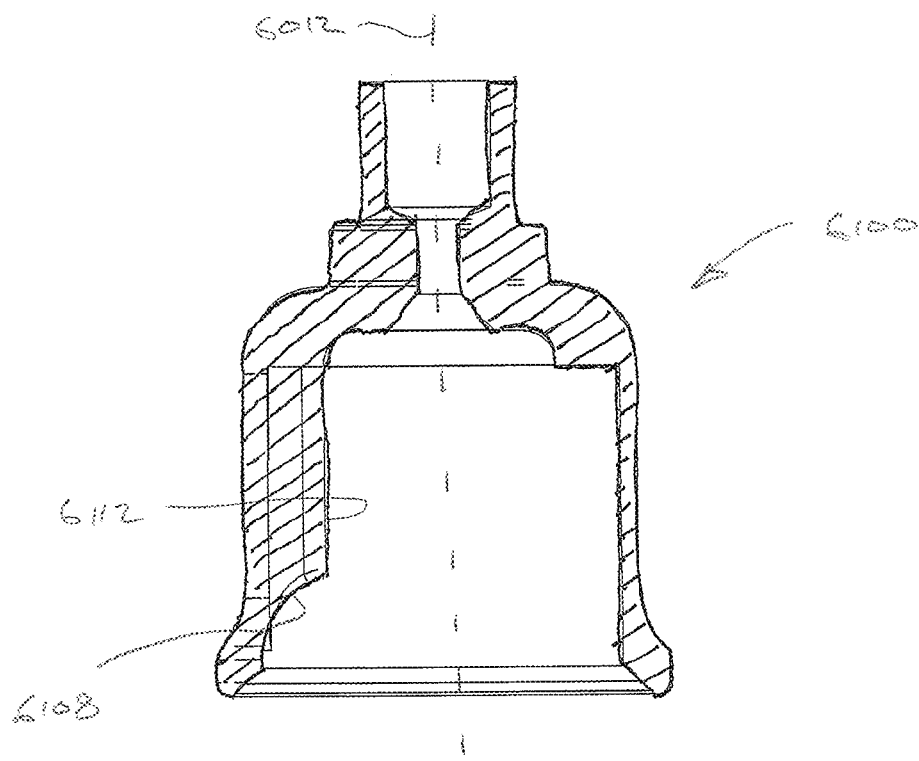
FIG. 61C is a cross-sectional view of the attachment feature of FIG. 61A, taken about the section line of FIG. 61B.

Referring to FIG. 61C, a cross-sectional view of the attachment feature of FIG. 61A, taken about the section line of FIG. 61B, is shown. In an embodiment, the peak 6112 can be a longitudinal face that extends parallel to the central axis 6012. The central axis 6012 of the docking cap 6100 can align with the central axis 6102 of the attachment feature 6000 during delivery or retrieval of the leadless pacemaker.

Figure 62A:
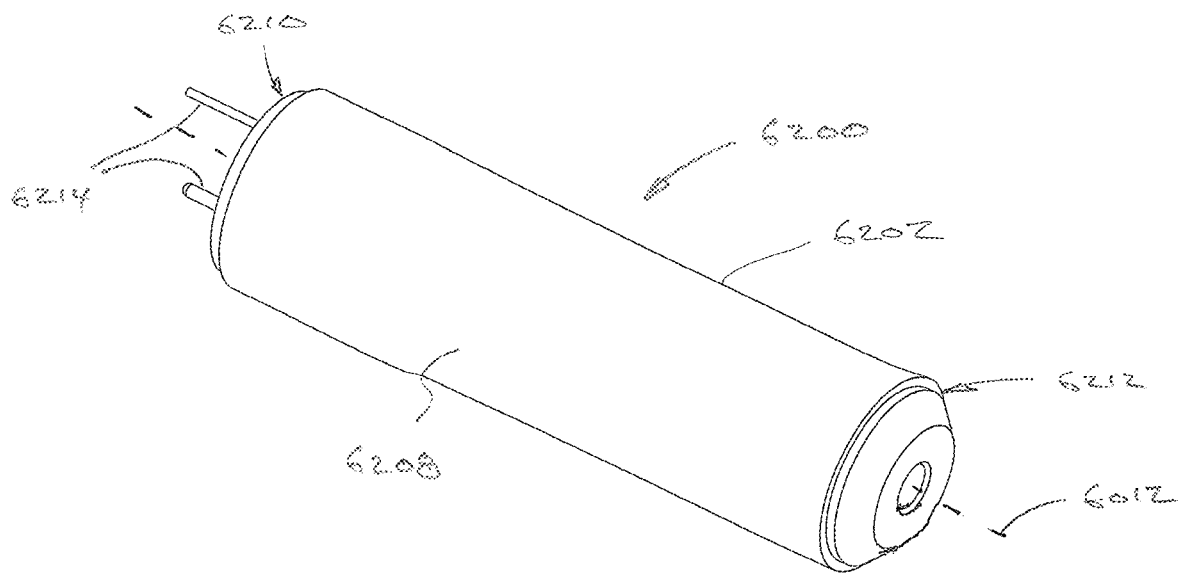
FIG. 62A is an isometric view of a battery assembly.

Referring to FIG. 62A, an isometric view of a battery assembly is shown. At least a portion of the housing 605 of the leadless pacemaker 600 can include a battery assembly 6200. The battery assembly 6200 can have a cell can 6202 that contains an electrolyte 6204 (FIG. 62C). More particularly, the battery assembly can include a separator 6206 (FIG. 62C), which may be a bag containing the electrolyte 6204, and the separator 6206 can be contained within the cell can 6202. In an embodiment, the cell can 6202 is in direct contact with the separator 6206. For example, the cell can 6202 can include an annular wall 6208 having an outer surface facing a surrounding environment and an inner surface in contact with the separator 6206.

The annular wall 6208 can extend proximally along the central axis 6012 (optionally aligned with the central axes of the attachment feature 6100 and docking cap 6200). More particularly, the annular wall can extend longitudinally from a distal battery end 6210 to a proximal battery end 6212. The battery assembly 6200 can include positive and negative terminals 6214 at the distal end 6210. The terminals 6214 can be electrically coupled to the electrolyte 6204 to transfer power from the battery assembly to the internal electronics of the leadless pacemaker 600.

Figure 62B:
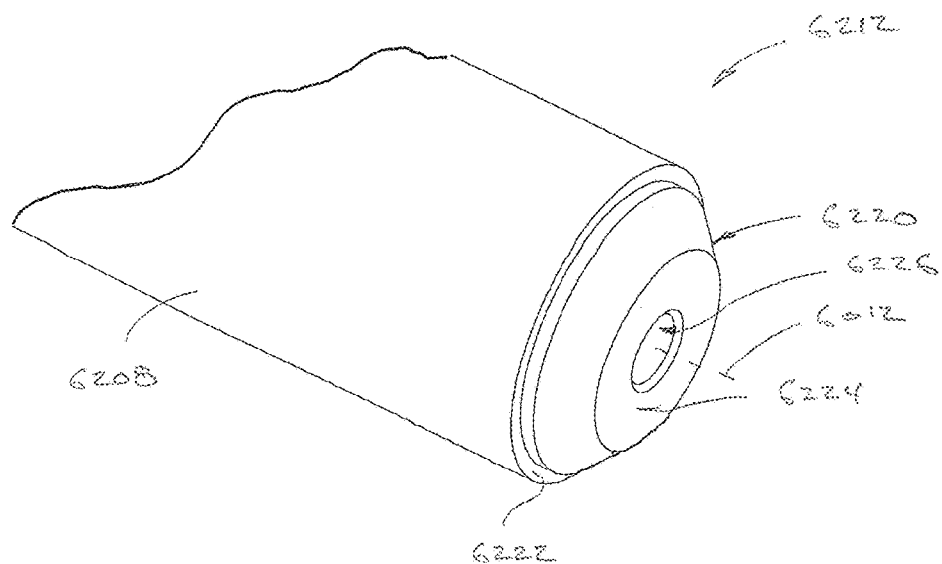
FIG. 62B is a isometric view of a proximal portion of the battery assembly of FIG. 62A.
Figure 62C:
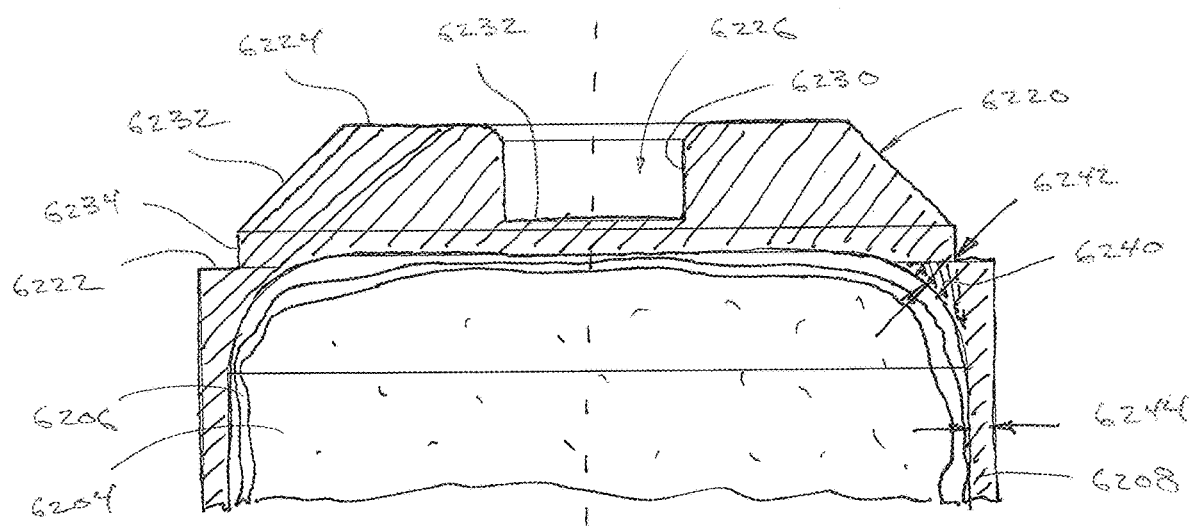
FIG. 62C is a cross-sectional view of the proximal portion of the battery assembly of FIG. 62B.

Referring to FIG. 62B, an isometric view of a proximal portion of the battery assembly of FIG. 62A is shown. The proximal portion includes the proximal end 6212 at which the annular wall 6208 transitions into an end boss 6220. More particularly, the end boss 6220 can extend from a proximal end 6222 of the annular wall 6208 to a proximal face 6224 of the end boss 6220. The proximal face 6224 and the proximal end 6222 can both extend in a transverse direction orthogonal to the central axis 6012. Accordingly, the proximal face 6224 and the proximal end 6222 may be parallel to each other.

Referring to FIG. 62C, a cross-sectional view of the proximal portion of the battery assembly of FIG. 62B is shown. In an embodiment, the end boss 6220 includes a tether recess 6226 extending into the proximal face 6224 along the central axis 6012. The tether recess 6226 can be laterally surrounded by an inner recess surface 6230, which can be a cylindrical or frustoconical (tapered) surface extending distally from the proximal face 6224 to a recess bottom 6232.

The end boss 6220 can be received within the internal cavity 6060 of the attachment feature 6000 during device assembly. For example, the end boss 6220 can facilitate the alignment and attachment of the distal flange 6008 to the annular wall 6208. To ease assembly, the end boss 6220 can include a tapered surface 6232 that tapers distally from the proximal face 6224. For example, an outer surface 6234 of the end boss 6220 can extend longitudinally from the proximal end 6222 of the annular wall 6208, and the tapered surface 6232 can taper radially inward from the outer surface 6234 to the proximal face 6224. The tapered surface 6232 can receive and direct the distal flange 6008 into alignment with the outer surface 6234 when the attachment feature 6000 is mounted on the battery assembly 6200.

In an embodiment, when the attachment feature 6000 is mounted on the cell can 6202 (not shown) the face port 6016 can be axially aligned with the tether recess 6226. For example, the inner lumen 6073 can be axially aligned with the face port 6016 and the tether recess 6226, providing a channel and a path for tethers to travel through the leadless pacemaker 102. The tether recess 6226 can be sized to receive one or more of the distal tether features of the tethers when the leadless pacemaker 102 is engaged by a delivery or retrieval system. For example, a width of the tether recess 6226 can be greater than a combined width of a pair of distal tether features. When the leadless pacemaker 102 is engaged by a pair of tethers, the distal tether features can insert into the tether recess 6226 without bottoming out on the recess bottom 6232. Accordingly, the end boss 6220 having the tether recess 6226 can reduce a likelihood of interference between the tethers and the battery assembly 6200 during tether docking/undocking.

The attachment feature 6000 can be directly attached to the battery assembly 6200. For example, the distal flange 6008 of the base 6002 can be attached to the cell can 6202 by one or more welds at a transition region 6240 between the annular wall 6208 and the end boss 6220. The annular wall 6208 of call can 6202 can be thin, and thus, directly welding the attachment feature 6000 to the battery assembly 6200 includes a risk of compromising the battery chemistry. More particularly, the direct contact between the cell can 6202 and the separator 6206 and/or electrolyte 6204 can lead to thermal damage to the separator 6206 and/or electrolyte 6204 if heat introduced by the welding process is not adequately dissipated. In an embodiment, the transition region 6240 is configured to protect the internal constituents of the battery assembly 6200 from such damage. More particularly, the transition region 6240 can be a region of the cell can 6202 having additional heat sink mass as compared to surrounding regions of the cell can 6202. For example, the transition region 6240 may have a transition thickness 6242 that is thicker than a wall thickness 6244 of the annular wall 6208. The additional heat sink mass of the transition region 6240 can dissipate the heat of a weld, e.g., a laser weld, without causing thermal damage to the electrolyte 6204.

In an embodiment, the weld is applied about a circumference of the battery assembly 6200. For example, when the attachment feature 6000 is mounted on the cell can 6202, the distal end of the distal flange 6008 can abut the proximal end 6222 of the annular wall 6208. The abutment may form a seam that extends around a circumference of the cell can 6202. More particularly, the seam may circumferentially surround the transition region 6240. Accordingly, a laser weld can be formed around the circumference of the cell can 6202 to join the distal flange 6008 to the cell can 6202. The weld can be directed toward the transition region, and thus, the electrolyte 6204 can be protected from thermal damage.

Figure 63:
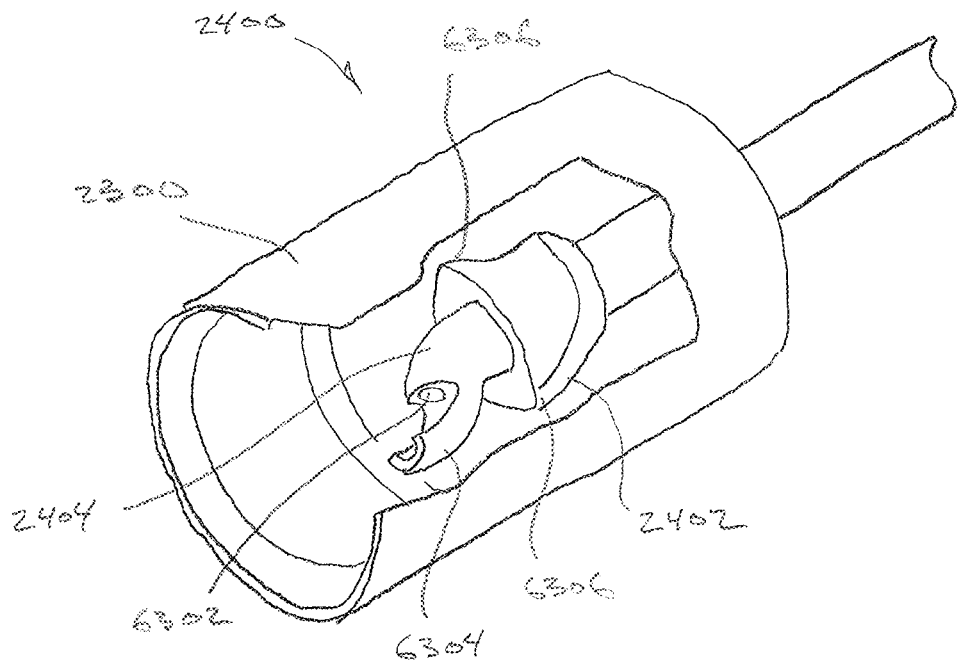
FIG. 63 is an isometric view of a docking system including a drive gear having a curved outer surface.

Referring to FIG. 63, an isometric view of a docking system including a drive gear having a curved outer surface is shown. The docking system 2400 can be an alternative embodiment of the docking system described above with respect to FIGS. 24A-24C, and thus, the features and functionality described above may be incorporated into the docking system 2400 shown in FIG. 63. The docking system 2400 includes a drive gear 2402 disposed on the end of a torque shaft 2404 or retrieval catheter. The torque shaft 2404 extends through the docking cap 2300 and is translatable relative to the docking cap 2300. The docking cap 2300 may be disposed at a distal end of a catheter shaft (not shown) and, in certain implementations, may be coupled to the distal end of the catheter shaft using a rotatable coupling such that the docking cap 2300 is able to rotate relative to the catheter shaft.

The torque shaft 2404 may include an inner lumen 6302 through which the retrieval snare 2408 (not shown) or similar feature extends. As described above, the retrieval snare 2408 may be used to capture a corresponding attachment feature of a leadless pacemaker or other implantable medical device. To facilitate such capture, the torque shaft 2404 may be extended from the docking cap 2300.

The torque shaft 2404 may have an alignment prong 6304 to engage a proximal end of the leadless biostimulator. For example, the alignment prong 6304 may extend radially outward from a central axis of the torque shaft 2404 and then curve forward to a distal end. The alignment prong 6304 can therefore have a curved inner surface that cradles the proximal button face 6014 when the torque shaft 2404 is extended into contact with the docking button 6000.

In an embodiment, the docking system 2400 includes the drive gear 2402 configured to reduce a chance that the drive gear 2402 will jam during retrieval into the recess 2310 of the docking cap 2300. More particularly, a drive gear 2402 having four or more sides that are parallel to the walls of the recess 2310 may bind when retracting the gear into the recess. To reduce the likelihood of such an event, the drive gear 2402 illustrated in FIG. 63 can have less than four lobes or corners, which mate and interfere with corresponding corners of the recess 2310. For example, the drive gear 2402 can have two lobes 6306 to transfer torque to the docking cap 2300 when the lobes engage corresponding internal corners of the recess 2310.

Figure 64:
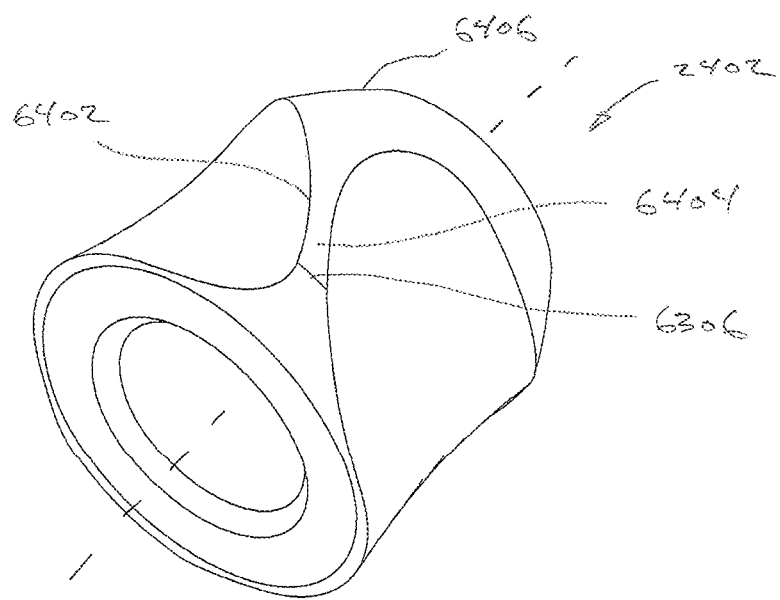
FIG. 64 is an isometric view of a drive gear having a curved outer surface.

Referring to FIG. 64, an isometric view of a drive gear having a curved outer surface is shown. The drive gear 2402 can have a contoured outer surface, e.g., an outer surface having one or more curves, which define one or more spiral features 6402. For example, the drive gear 2402 can have a pair of spiral features 6402 extending spirally about a central axis of the gear. The spirals can have starts that are circularly offset from each other, and can extend around the central axis distally from the starts with a same pitch. A second one of the pair of spiral features 6402 is hidden in FIG. 64. The spiral features 6402 can be spiral flutes, each having an apex or ridge that spirals about the central axis to define a respective lobe 6306 of the gear. The lobes 6306 provide threaded surfaces that can engage and self-orient when the drive gear 2402 is retracted into the recess 2310. To facilitate self-orientation, the drive gear 2402 can include a proximal tapered surface 6406, which flares outward in the distal direction. The starts of the spiral features can be at a distal end of the tapered surface 6406.

Figure 65:
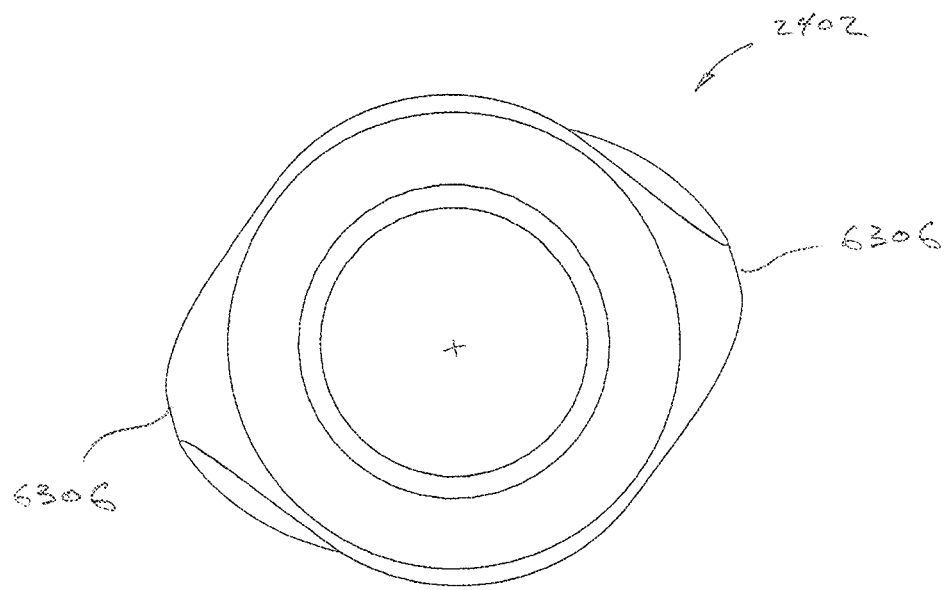
FIG. 65 is an end view of a drive gear having a curved outer surface.

Referring to FIG. 65, an end view of a drive gear having a curved outer surface is shown. The pair of lobes 6306 can be diametrically opposed to each other on opposite sides of the drive gear 2402. A radial width taken across the lobes 6306 and through the central axis of the drive gear 2402 may be greater than the width of the drive gear 2402 at other radial locations. More particularly, the lobes 6306 can have a maximum width of the gear 2402. Accordingly, the lobes can provides points of interference with an internal surface of the recess 2310 of the docking cap 2300.

Following capture of the leadless pacemaker, the torque shaft 2404 is retracted into the docking cap 2300 to dock the leadless pacemaker. As the drive gear 2402 is pulled toward the recess 2310, the proximal tapered surface 6406 can slide over a distal edge of the recess 2310 to center the fluted outer surface relative to the recess. Then, as the spiral flutes engage the distal edge, the flutes can cause the gear to rotate about the central axis under a threaded action as needed to align the lobes 6306 to the recess walls and/or corners. The lobes 6306 can mate with the corners and interfere with the walls to transmit torque to the docking cap 2300. More particularly, the recess 2310 is generally sized and shaped such that it interferes, at least partially, with the drive gear 2402. As a result of this interference, torque applied to the torque shaft 2404 when the drive gear 2402 is retained within the recess 2310 is transmitted to the docking cap 2300.

Figure 66:
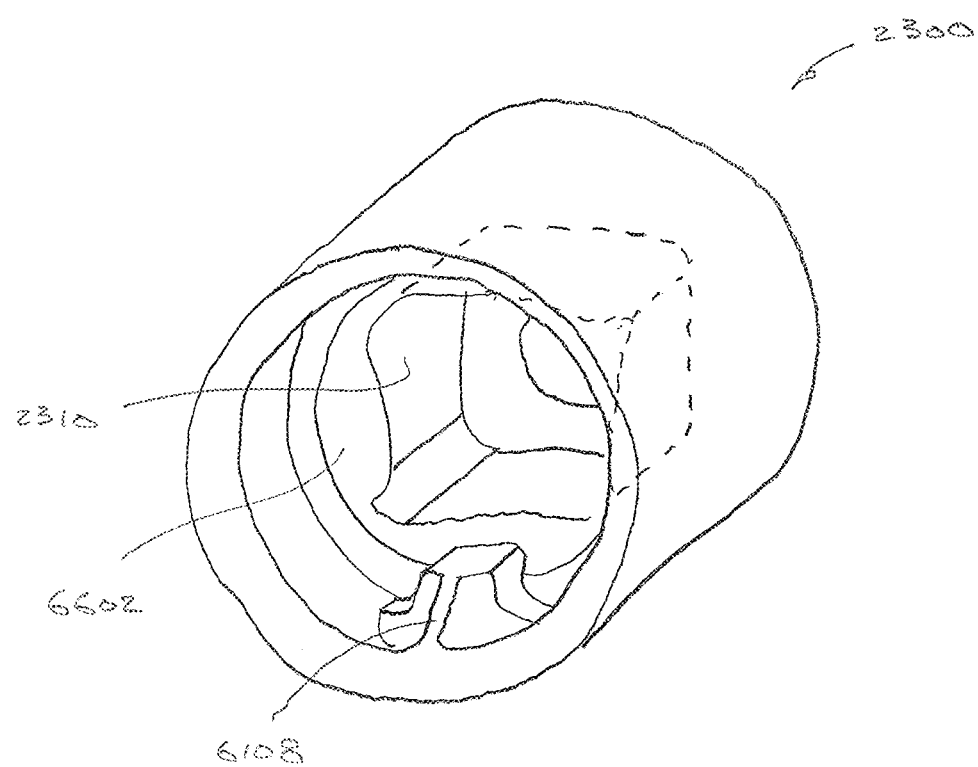
FIG. 66 is an isometric view of a docking cap configured to mate with a drive gear having a curved outer surface.

Referring to FIG. 66, an isometric view of a docking cap configured to mate with a drive gear having a curved outer surface is shown. The docking cap 2300 can have a lead-in configured to match the exterior features of the drive gear 2402. For example, the lead-in can include a tapered inclined plane 6602, tapering radially inward from a distal entry of the docking cap 2300 toward the recess 2310. The tapered surface can transition between the distal docking cavity that receives the docking button of the leadless biostimulator and the socket drive portion of the docking cap 2300 that receives the leadless biostimulator.

In an embodiment, the inclined surface includes a graduated spiral slant cut. More particularly, the inclined surface, rather than being a simple diametrically reducing taper, can have a surface contour that spirals about the central axis of the docking cap 2300. The spiral internal surface can taper inward to match the spiral features of the drive gear 2402. Like the male spiral features of the gear 2402, the female spiral cuts can have a spiral pitch and can extend around the central axis. Accordingly, the internal surface of the docking cap 2300 can guide the exterior surface of the drive gear 2402 to seat and center the drive gear 2402 into the recess 2310 when the torque cable 2404 is retracted proximally. Other features of the docking cap 2300, such as the torque feature 6108, can be similar to those described above, and those previously described features can be incorporated into the docking cap 2300 illustrated in FIG. 66.

Although the foregoing examples are directed primarily to attachment and retrieval features coupled to the proximal end of the housings, features of the foregoing designs may also be incorporated on the distal end of the housing on which electrodes and/or a fixation mechanism may be attached. For example, instead of the attachment feature illustrated in each of the foregoing examples, a cap or similar structure including electrodes or a fixation mechanism may be coupled to a distal end of a leadless pacemaker housing having similar flanges, protrusions, hubs, etc., as in the foregoing examples.

Any of the above mentioned implementations may also include, without limitation, electronic indicators on the delivery/retrieval system (e.g., LEDS or screens) or on adjunct support-screens to communicate status. Finally, the above mentioned systems may also include shaft position indicators via, for example, detents located on the shaft of the deflectable catheter and complementary features for interacting on the detents, the complementary features being located on the guide catheter or even the locking hub. Of course the opposite arrangement is also possible. The position indicator aspects can be used to notify the user of the extent to which the protective sleeve covers the leadless pacemaker.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

Several embodiments are described by way of summary, and not by way of limitation, in the following paragraphs.

In an embodiment, a one-piece attachment feature is provided, and the attachment feature can be a component of a leadless biostimulator. The leadless biostimulator includes an attachment feature including a base. The base includes a distal flange having a flange port surrounding a central axis. The attachment feature includes a button. The button includes a proximal button face having a face port surrounding the central axis. The attachment feature includes a stem. The stem extends between the base and the button. The stem has a transverse profile extending around the central axis. The attachment feature includes an internal cavity extending along the central axis from the face port to the flange port through the stem.

In the embodiment, the attachment feature is monolithically formed from a rigid material. The stem is a single post coupling the base to the button.

In the embodiment, the transverse profile is annular and surrounds the central axis.

In the embodiment, the transverse profile is rectangular. The rectangular transverse profile has an aspect ratio greater than 1.

In the embodiment, the transverse profile has a major stem axis. The button includes a transverse perimeter having a major axis. The major stem axis is orthogonal to the major axis.

In the embodiment, the base includes a tapered body tapering radially inward from the distal flange toward the stem.

In the embodiment, the button includes a transverse perimeter having a non-round shape.

In the embodiment, the non-round shape is a polygonal shape.

In the embodiment, the non-round shape is an oval shape.

In the embodiment, the oval shape is symmetric about one or more of a major axis or a minor axis.

In the embodiment, the oval shape is an ellipse having a curved segment intersecting the major axis and a straight segment intersecting the minor axis.

In the embodiment, the button includes a distal button face tapering radially inward from the transverse perimeter toward the stem.

In the embodiment, the internal cavity includes a tethering cavity extending proximally from an inner proximal face of the base to an inner distal face of the button. The passage cavity extends proximally from the inner distal face to the face port. The tethering cavity has a larger transverse dimension than the passage cavity.

In the embodiment, one or more of the button, the base, or the stem includes an antibacterial coating.

In an embodiment, a battery assembly for a leadless biostimulator includes a cell can containing an electrolyte. The cell can includes an annular wall extending proximally along a central axis. The cell can includes an end boss extending from the annular wall to a proximal face. The end boss includes a tether recess extending into the proximal face along the central axis.

In the embodiment, the cell can includes a transition region between the annular wall and the end boss. A wall thickness of the annular wall is less than a transition thickness of the transition region.

In the embodiment, the end boss includes an outer surface extending longitudinally from the annular wall. The end boss includes a tapered surface tapering radially inward from the outer surface to the proximal face.

In the embodiment, the battery assembly includes a separator containing the electrolyte. The annular wall is in contact with the separator.

In an embodiment, a leadless biostimulator includes a battery assembly. The battery assembly includes a cell can containing an electrolyte. The cell can includes an annular wall extending proximally along a central axis. The cell can includes an end boss extending from the annular wall to a proximal face. The cell can includes a tether recess extending into the proximal face along the central axis. The battery assembly includes an attachment feature mounted on the cell can. The attachment feature includes a button having a face port axially aligned with the tether recess. The attachment feature includes a stem between the button and the end boss. The stem has a transverse profile extending around the central axis.

In the embodiment, the attachment feature is monolithically formed from a rigid material. The stem is a single post.

In the embodiment, the attachment feature includes an internal cavity extending from the face port through the stem. The internal cavity receives the end boss of the cell can.

In the embodiment, the transverse profile of the stem is annular and has an inner lumen axially aligned with the face port and the tether recess.

In the embodiment, the attachment feature includes a distal flange coupled to the cell can by a weld at a transition region between the annular wall and the end boss.

In the embodiment, the weld extends around a circumference of the cell can.

In an embodiment, a leadless biostimulator includes a housing defining a longitudinal axis. The leadless biostimulator includes a retrieval feature disposed at a proximal end of the housing. The retrieval feature includes a stem extending proximally along the longitudinal axis. The retrieval features includes a head extending obliquely from the stem. The retrieval feature includes a neck defined at a junction of the stem and the head. The neck is shaped to receive a snare of a leadless biostimulator retrieval system and has a neck cross-section. The head expands outwardly from the neck such that the head has a head cross-section that is greater than the neck cross-section.

In the embodiment, the stem is proximally tapered.

In the embodiment, the stem has an elliptical cross-section.

In the embodiment, the stem extends from a base of the leadless biostimulator. The base extends perpendicular to the longitudinal axis. The neck is disposed at an angle from and including 30 degrees to an including 90 degrees relative to the base.

In the embodiment, the angle between the neck and the base is approximately 60 degrees.

In the embodiment, the neck further includes an indentation extending about at least a portion of the stem. The snare is received within the indentation.

In an embodiment, a leadless biostimulator includes a housing defining a longitudinal axis. The leadless biostimulator includes a retrieval feature disposed at a proximal end of the housing. The retrieval feature includes a curved eyelet having an eyelet end. The eyelet end at least partially defines an opening into the eyelet. The opening is sized to receive a snare of a leadless biostimulator retrieval system.

In the embodiment, the curved eyelet extends about an eyelet center and the opening is disposed one of lateral to the eyelet center and distal to the eyelet center.

In the embodiment, the eyelet includes a proximal curved portion including a pair of laterally inward indentations.

In the embodiment, the leadless biostimulator includes a protrusion extending proximally from the proximal end of the housing. The opening is defined between the eyelet end of the curved eyelet and the protrusion.

In the embodiment, each of the eyelet end of the curved eyelet and the protrusion are angled inwardly toward the longitudinal axis.

In an embodiment, a leadless biostimulator includes a housing defining a longitudinal axis, and a retrieval feature disposed at a proximal end of the housing. The retrieval feature includes a slot formed within the housing. The slot extends obliquely relative to the longitudinal axis and is sized to receive a snare of a leadless biostimulator retrieval system.

In the embodiment, the slot extends at an angle from and including 15 degrees to and including 70 degrees relative to the longitudinal axis.

In the embodiment, the slot extends at the angle of approximately 60 degrees relative to the longitudinal axis.

In the embodiment, the leadless biostimulator includes a proximal domed cap coupled to the proximal end of the housing.

In the embodiment, the slot is an intermediate slot segment extending between each of a first slot segment and a second slot segment defined by at least one of the housing and a domed cap disposed on the proximal end of the leadless biostimulator. Each of the first slot segment and the second slot segment extend in a substantially proximal direction.

In the embodiment, the first slot segment and the second slot segment are disposed on opposite sides of the at least one of the housing and the domed cap.

In the embodiment, the slot is one of several slots defined by and disposed about the housing. Each of the several slots extend obliquely relative to the longitudinal axis.

In the embodiment, the several slots consist of two, three, or four slots.

In the embodiment, the several slots are evenly distributed about the housing.

In an embodiment, a leadless biostimulator includes a housing defining a longitudinal axis, and a retrieval feature coupled to a proximal end of the housing. The retrieval feature includes a stem extending proximally along the longitudinal axis. The retrieval feature includes a head disposed on a proximal end of the stem. The retrieval feature is a unitary assembly formed, at least in part, from a flexible material.

In the embodiment, the flexible material includes one or more of polyethyl ether ketone (PEEK), silicone, polyurethane, a fluoropolymer, or thermoplastic silicone polycarbonate urethane.

In the embodiment, the stem comprises several separate legs coupled to the head.

In the embodiment, the housing includes a proximal base shaped to receive a distal portion of the retrieval feature.

In the embodiment, the distal portion of the retrieval feature is retained within the proximal base by at least one of an adhesive, welding, or pins.

In the embodiment, the flexible material is a first flexible material and the retrieval feature is further formed from at least one second flexible material.

In the embodiment, the first flexible material has a first durometer and the second flexible material has a second durometer different than the first durometer.

In the embodiment, a radiopaque marker is disposed within the retrieval feature.

In the embodiment, the one or more radiopaque markers are formed from one or more of barium sulfate, tantalum, tungsten, or platinum.

In the embodiment, the radiopaque marker is a powder mixed with the flexible material during formation of the retrieval feature.

In the embodiment, the radiopaque marker is a structural component disposed within the retrieval feature during formation of the retrieval feature.

In the embodiment, the retrieval feature further comprises at least one reinforcing structure disposed within the retrieval feature.

In the embodiment, the reinforcing structure comprises at least one fiber disposed within the retrieval feature.

In the embodiment, the at least one fiber is an aramid fiber.

In the embodiment, the at least one fiber is formed into a loop extending through the retrieval feature.

In the embodiment, the retrieval feature is formed by at least one of molding or machining.

In an embodiment, a retrieval system is provided. The retrieval system can be a system for retrieval of a leadless biostimulator implanted within a patient. The system includes an inner catheter. A distal end of the inner catheter is configured to dock with a proximal end of the leadless biostimulator and to apply torque to the leadless biostimulator when docked. A flexible sheath is extendable along the inner catheter such that the flexible sheath envelops exterior surfaces of each of the distal end of the inner catheter and the proximal end of the leadless biostimulator. A rigid sheath extends along at least a portion of the flexible sheath. Extending the rigid sheath along the flexible sheath when the flexible sheath envelops the exterior surfaces of each of the distal end of the inner catheter and the proximal end of the leadless biostimulator increases frictional engagement between the flexible sheath and each of the distal end of the inner catheter and the proximal end of the leadless biostimulator.

In the embodiment, the flexible sheath includes an expandable mesh formed from a biocompatible material.

In the embodiment, the expandable mesh is a Nitinol mesh.

In the embodiment, the flexible sheath has a wall-thickness up to and including 1.5 mil.

In the embodiment, the flexible sheath has a wall-thickness up to and including 1.0 mil.

In the embodiment, the flexible sheath has a double-wall construction.

In the embodiment, the double-wall construction is formed by folding the expandable mesh back on itself such that the expandable mesh forms a rounded distal end of the flexible sheath.

In the embodiment, the distal end of the inner catheter includes a docking cap shaped to receive the proximal end of the leadless biostimulator and the flexible sheath is configured to envelop an exterior of the docking cap.

In the embodiment, the docking cap includes a sharp distal edge.

In the embodiment, a protective sheath is disposable about each of the flexible sheath and the rigid sheath when the rigid sheath is extended along at least a portion of the flexible sheath.

In the embodiment, a snare is disposed within the inner catheter and extendable relative to the distal end of the inner catheter. The snare is configured to capture the proximal end of the leadless biostimulator.

In an embodiment, a method of retrieving a leadless biostimulator implanted within tissue of a patient includes docking a proximal portion of the leadless biostimulator with a distal end of a catheter. The method includes extending a flexible sheath along the catheter such that the flexible sheath envelops at least a portion of each of the distal end of the catheter and the proximal portion of the leadless biostimulator. The method includes extending a rigid sheath along the flexible sheath such that the flexible sheath is at least partially disposed between the rigid sheath and the catheter. Extending the rigid sheath along the flexible sheath increases frictional engagement between the flexible sheath and each of the distal end of the catheter and the proximal portion of the leadless biostimulator.

In the embodiment, after extending the rigid sheath, a torque is applied to the catheter to disengage the leadless biostimulator from the tissue. At least a portion of the torque is transferred between the distal end of the catheter and the proximal end of the leadless biostimulator by the flexible sheath.

In the embodiment, the flexible sheath includes an expandable mesh formed from a biocompatible material.

In the embodiment, the expandable mesh is a Nitinol mesh having a wall thickness up to and including 1.5 mil.

In the embodiment, the flexible sheath has a double-wall construction formed, at least in part, by folding the expandable mesh back on itself.

In the embodiment, docking the proximal portion of the leadless biostimulator with the distal end of the catheter further includes capturing an attachment feature of the leadless biostimulator using a snare extendable from within the catheter.

In the embodiment, the distal end of the catheter includes a docking cap and docking of the proximal portion of the leadless biostimulator with the distal end of the catheter further includes disposing at least a portion of the attachment feature within the docking cap.

In the embodiment, extending the flexible sheath along the catheter to envelop the portion of the distal end of the catheter includes extending the flexible sheath to envelop an exterior surface of the docking cap.

In the embodiment, a protective sheath is disposed along the rigid sheath such that the protective sheath extends about the distal end of the catheter and the proximal end of the leadless biostimulator.

In the embodiment, the protective sheath is extended before or after the leadless biostimulator is disengaged from the tissue.

In an embodiment, an attachment feature for a leadless biostimulator includes a base including a distal flange having a flange port surrounding a central axis. The attachment feature includes a stem extending proximally from the base. The attachment feature includes a button having a non-round transverse perimeter. The button includes a proximal button face having a face port surrounding the central axis. The attachment feature includes an internal cavity extending along the central axis from the face port to the flange port through the stem.

In the embodiment, the attachment feature is monolithically formed from a rigid material. The stem is a single post coupling the base to the button.

In the embodiment, the non-round transverse perimeter has a polygonal shape.

In the embodiment, the non-round transverse perimeter has an oval shape.

In the embodiment, the oval shape is symmetric about one or more of a major axis or a minor axis.

In the embodiment, the oval shape is an ellipse having a curved segment intersecting the major axis and a straight segment intersecting the minor axis.

In the embodiment, the stem has a transverse profile extending around the central axis.

In the embodiment, the transverse profile is annular and surrounds the central axis.

In the embodiment, the base includes a tapered body tapering radially inward from the distal flange toward the stem.

In the embodiment, the button includes a distal button face tapering radially inward from the transverse perimeter toward the stem.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A battery assembly for a leadless biostimulator, comprising:
   an electrolyte; and
   a cell can containing the electrolyte, wherein the cell can includes an annular wall extending proximally along a central axis, and an end boss extending from the annular wall to a proximal face, wherein an outer surface of the end boss has a smaller diameter than the annular wall, wherein the end boss includes a frustoconical surface tapering radially inward from the outer surface to the proximal face, and wherein the end boss includes a tether recess extending into the proximal face along the central axis.

2. The battery assembly of claim 1, wherein the cell can includes a transition region between the annular wall and the end boss, and wherein a wall thickness of the annular wall is less than a transition thickness of the transition region.

3. The battery assembly of claim 1, wherein the outer surface extends longitudinally from the annular wall.

4. The battery assembly of claim 1 further comprising a separator containing the electrolyte, wherein an inner surface of the annular wall is in contact with the separator.

5. The battery assembly of claim 4, wherein the separator includes a bag.

6. The battery assembly of claim 1, wherein the cell can extends proximally from a distal battery end to a proximal battery end, wherein the end boss is at the proximal battery end, and further comprising one or more terminals at the distal battery end.

7. The battery assembly of claim 1, wherein the proximal face of the end boss is orthogonal to the central axis.

8. The battery assembly of claim 1, wherein the tether recess is surrounded by an inner recess surface extending from the proximal face to a recess bottom, and wherein a proximal diameter of the inner recess surface at the proximal face is equal to or larger than a distal diameter of the inner recess surface at the recess bottom.

9. The battery assembly of claim 8, wherein the inner recess surface is cylindrical.

10. The battery assembly of claim 8, wherein the inner recess surface is tapered.

11. The battery assembly of claim 8 further comprising a transitional edge between the proximal face and the inner recess surface.

12. A leadless biostimulator comprising:
   a battery assembly including a cell can containing an electrolyte, wherein the cell can includes an annular wall extending proximally along a central axis, and an end boss extending from the annular wall to a proximal face, wherein an outer surface of the end boss has a smaller diameter than the annular wall, wherein the end boss includes a frustoconical surface tapering radially inward from the outer surface to the proximal face, and wherein the end boss includes a tether recess extending into the proximal face along the central axis; and
   an attachment feature mounted on the cell can, wherein the attachment feature includes a button having a face port axially aligned with the tether recess.

13. The leadless biostimulator of claim 12, wherein the cell can includes a transition region between the annular wall and the end boss, and wherein a wall thickness of the annular wall is less than a transition thickness of the transition region.

14. The leadless biostimulator of claim 12, wherein the outer surface extends longitudinally from the annular wall.

15. The leadless biostimulator of claim 12, wherein the attachment feature includes a stem between the button and the end boss, and wherein the stem has a transverse profile extending around the central axis.

16. The leadless biostimulator of claim 15, wherein the attachment feature is monolithically formed from a rigid material, and wherein the stem is a single post.

17. The leadless biostimulator of claim 15, wherein the attachment feature includes an internal cavity extending from the face port through the stem, and wherein the internal cavity receives the end boss of the cell can.

18. The leadless biostimulator claim 17, wherein the transverse profile of the stem is annular and has an inner lumen axially aligned with the face port and the tether recess.

19. The leadless biostimulator of claim 12, wherein the attachment feature includes a distal flange coupled to the cell can by a weld at a transition region between the annular wall and the end boss.

20. The leadless biostimulator of claim 19, wherein the weld extends around a circumference of the cell can.

* * * * *